US008956352B2

(12) United States Patent
Mauch et al.

(10) Patent No.: US 8,956,352 B2
(45) Date of Patent: Feb. 17, 2015

(54) CATHETER APPARATUSES HAVING MULTI-ELECTRODE ARRAYS FOR RENAL NEUROMODULATION AND ASSOCIATED SYSTEMS AND METHODS

(75) Inventors: Kevin Mauch, Windsor, CA (US); Mario Alvarado, Santa Rosa, CA (US); Robert Beetel, Mountain View, CA (US); William Chang, Santa Rosa, CA (US); Justin Goshgarian, Santa Rosa, CA (US); Leonila Rivera, Windsor, CA (US); Sukyoung Shin, Santa Rosa, CA (US); Michele Silver, Windsor, CA (US); Sina Som, San Francisco, CA (US); Andrew Wu, Mountain View, CA (US); Denise Zarins, Saratoga, CA (US); Juanita Sanchez-Cole, Santa Rosa, CA (US); Maria G. Aboytes, Palo Alto, CA (US)

(73) Assignee: Medtronic Ardian Luxembourg S.a.r.l., Luxembourg (LU)

( * ) Notice: Subject to any disclaimer, the term of this patent is extended or adjusted under 35 U.S.C. 154(b) by 670 days.

(21) Appl. No.: 13/281,395

(22) Filed: Oct. 25, 2011

(65) Prior Publication Data
US 2012/0143293 A1 Jun. 7, 2012

Related U.S. Application Data

(60) Provisional application No. 61/406,531, filed on Oct. 25, 2010, provisional application No. 61/406,960, filed on Oct. 26, 2010, provisional application No. 61/572,290, filed on Jan. 28, 2011, provisional
(Continued)

(51) Int. Cl.
*A61B 18/14* (2006.01)
*A61B 18/04* (2006.01)
(Continued)

(52) U.S. Cl.
CPC .... *A61B 18/1492* (2013.01); *A61B 2018/00404* (2013.01); *A61B 2018/00434* (2013.01);
(Continued)

(58) Field of Classification Search
USPC .......................................... 606/27, 32–34, 41
See application file for complete search history.

(56) References Cited

U.S. PATENT DOCUMENTS

| 3,935,348 A | 1/1976 | Smith |
| 4,154,246 A | 5/1979 | LeVeen |

(Continued)

FOREIGN PATENT DOCUMENTS

| AU | 2011239313 | 5/2012 |
| AU | 2011239316 | 5/2012 |

(Continued)

OTHER PUBLICATIONS

Allen, E.V., Sympathectomy for essential hypertension, Circulation, 1952, 6:131-140.

(Continued)

*Primary Examiner* — Allen Porter, Jr.

(57) ABSTRACT

Catheter apparatuses, systems, and methods for achieving renal neuromodulation by intravascular access are disclosed herein. One aspect of the present technology, for example, is directed to a treatment device having a multi-electrode array configured to be delivered to a renal blood vessel. The array is selectively transformable between a delivery or low-profile state (e.g., a generally straight shape) and a deployed state (e.g., a radially expanded, generally helical shape). The multi-electrode array is sized and shaped so that the electrodes or energy delivery elements contact an interior wall of the renal blood vessel when the array is in the deployed (e.g., helical) state. The electrodes or energy delivery elements are configured for direct and/or indirect application of thermal and/or electrical energy to heat or otherwise electrically modulate neural fibers that contribute to renal function or of vascular structures that feed or perfuse the neural fibers.

6 Claims, 49 Drawing Sheets

Related U.S. Application Data application No. 61/528,001, filed on Aug. 26, 2011, provisional application No. 61/528,086, filed on Aug. 26, 2011, provisional application No. 61/528,091, filed on Aug. 26, 2011, provisional application No. 61/528,108, filed on Aug. 26, 2011, provisional application No. 61/528,684, filed on Aug. 29, 2011, provisional application No. 61/546,512, filed on Oct. 12, 2011.

(51) Int. Cl.
    *A61B 18/18* (2006.01)
    *A61B 18/00* (2006.01)
    *A61M 25/00* (2006.01)
    *A61M 25/01* (2006.01)

(52) U.S. Cl.
    CPC ..... *A61B2018/1435* (2013.01); *A61M 25/0041* (2013.01); *A61M 25/0133* (2013.01); *A61B 2018/00511* (2013.01)
    USPC .................. 606/41; 606/27; 606/32; 606/33

(56) References Cited

U.S. PATENT DOCUMENTS

| | | |
|---|---|---|
| 4,169,464 A | 10/1979 | Obrez |
| 4,419,819 A | 12/1983 | Dickhudt et al. |
| 4,602,624 A | 7/1986 | Naples et al. |
| 4,649,936 A | 3/1987 | Ungar et al. |
| 4,660,571 A | 4/1987 | Hess et al. |
| 4,706,671 A | 11/1987 | Weinrib |
| 4,709,698 A | 12/1987 | Johnston et al. |
| 4,764,504 A | 8/1988 | Johnson et al. |
| 4,781,682 A | 11/1988 | Patel |
| 4,796,643 A | 1/1989 | Nakazawa et al. |
| 4,819,661 A | 4/1989 | Heil, Jr. et al. |
| 4,860,769 A | 8/1989 | Fogarty et al. |
| 4,921,484 A | 5/1990 | Hillstead |
| 4,957,118 A | 9/1990 | Erlebacher |
| 4,961,377 A | 10/1990 | Bando et al. |
| 4,976,711 A | 12/1990 | Parins et al. |
| 4,995,868 A | 2/1991 | Brazier |
| 4,998,923 A | 3/1991 | Samson et al. |
| 5,002,067 A | 3/1991 | Berthelsen et al. |
| 5,011,488 A | 4/1991 | Ginsburg |
| 5,016,808 A | 5/1991 | Heil, Jr. et al. |
| 5,052,998 A | 10/1991 | Zimmon |
| 5,071,407 A | 12/1991 | Termin et al. |
| 5,133,365 A | 7/1992 | Heil, Jr. et al. |
| 5,156,151 A | 10/1992 | Imran |
| 5,163,928 A | 11/1992 | Hobbs et al. |
| 5,188,602 A | 2/1993 | Nichols |
| 5,188,619 A | 2/1993 | Myers |
| 5,209,723 A | 5/1993 | Twardowski et al. |
| 5,228,442 A | 7/1993 | Imran |
| 5,239,999 A | 8/1993 | Imran |
| 5,249,585 A | 10/1993 | Turner et al. |
| 5,263,492 A | 11/1993 | Voyce |
| 5,263,493 A | 11/1993 | Avitall |
| 5,279,299 A | 1/1994 | Imran |
| 5,296,510 A | 3/1994 | Yamada et al. |
| 5,300,068 A | 4/1994 | Rosar et al. |
| 5,300,099 A | 4/1994 | Rudie |
| 5,308,323 A | 5/1994 | Sogawa et al. |
| 5,318,525 A | 6/1994 | West et al. |
| 5,322,064 A | 6/1994 | Lundquist |
| 5,324,284 A | 6/1994 | Imran |
| 5,327,905 A | 7/1994 | Avitall |
| 5,345,031 A | 9/1994 | Schwartz et al. |
| 5,345,936 A | 9/1994 | Pomeranz et al. |
| 5,354,297 A | 10/1994 | Avitall |
| 5,358,514 A | 10/1994 | Schulman et al. |
| 5,365,926 A | 11/1994 | Desai |
| 5,368,591 A | 11/1994 | Lennox et al. |
| 5,368,592 A | 11/1994 | Stern et al. |
| 5,383,856 A | 1/1995 | Bersin |
| 5,387,233 A | 2/1995 | Alferness et al. |
| 5,397,304 A | 3/1995 | Truckai |
| 5,397,339 A | 3/1995 | Desai |
| 5,399,164 A | 3/1995 | Snoke et al. |
| 5,405,374 A | 4/1995 | Stein |
| 5,411,546 A | 5/1995 | Bowald et al. |
| 5,423,744 A | 6/1995 | Gencheff et al. |
| 5,425,364 A | 6/1995 | Imran |
| 5,441,483 A | 8/1995 | Avitall |
| 5,445,148 A | 8/1995 | Jaraczewski et al. |
| 5,462,545 A | 10/1995 | Wang et al. |
| 5,476,495 A | 12/1995 | Kordis et al. |
| 5,476,498 A | 12/1995 | Ayers |
| 5,477,856 A | 12/1995 | Lundquist |
| 5,484,400 A | 1/1996 | Edwards et al. |
| 5,487,385 A | 1/1996 | Avitall |
| 5,487,757 A | 1/1996 | Truckai et al. |
| 5,497,774 A | 3/1996 | Swartz et al. |
| 5,507,743 A | 4/1996 | Edwards et al. |
| 5,509,909 A | 4/1996 | Moy |
| 5,523,092 A | 6/1996 | Hanson et al. |
| 5,529,820 A | 6/1996 | Nomi et al. |
| 5,545,193 A | 8/1996 | Fleischman et al. |
| 5,545,200 A | 8/1996 | West et al. |
| 5,545,475 A | 8/1996 | Korleski |
| 5,549,661 A | 8/1996 | Kordis et al. |
| 5,554,114 A | 9/1996 | Wallace et al. |
| 5,558,643 A | 9/1996 | Samson et al. |
| 5,564,440 A | 10/1996 | Swartz et al. |
| 5,571,147 A | 11/1996 | Sluijter et al. |
| 5,575,766 A | 11/1996 | Swartz et al. |
| 5,575,810 A | 11/1996 | Swanson et al. |
| 5,582,609 A | 12/1996 | Swanson et al. |
| 5,591,132 A | 1/1997 | Carrie |
| 5,599,345 A | 2/1997 | Edwards et al. |
| 5,609,151 A | 3/1997 | Mulier et al. |
| 5,617,854 A | 4/1997 | Munsif |
| 5,626,576 A | 5/1997 | Janssen |
| 5,628,775 A | 5/1997 | Jackson et al. |
| 5,636,634 A | 6/1997 | Kordis et al. |
| 5,637,090 A | 6/1997 | McGee et al. |
| 5,642,736 A | 7/1997 | Avitall |
| 5,672,174 A | 9/1997 | Gough et al. |
| 5,676,662 A | 10/1997 | Fleischhacker et al. |
| 5,680,860 A | 10/1997 | Imran |
| 5,681,280 A | 10/1997 | Rusk et al. |
| 5,687,723 A | 11/1997 | Avitall |
| 5,688,266 A | 11/1997 | Edwards et al. |
| 5,690,611 A | 11/1997 | Swartz et al. |
| 5,695,506 A | 12/1997 | Pike et al. |
| 5,697,928 A | 12/1997 | Walcott et al. |
| 5,700,282 A | 12/1997 | Zabara |
| 5,707,400 A | 1/1998 | Terry, Jr. et al. |
| 5,709,874 A | 1/1998 | Hanson et al. |
| 5,715,818 A | 2/1998 | Swartz et al. |
| 5,722,401 A | 3/1998 | Pietroski et al. |
| 5,725,512 A | 3/1998 | Swartz et al. |
| 5,727,555 A | 3/1998 | Chait |
| 5,730,127 A | 3/1998 | Avitall |
| 5,730,741 A | 3/1998 | Horzewski et al. |
| 5,741,429 A | 4/1998 | Donadio, III et al. |
| 5,743,903 A | 4/1998 | Stern et al. |
| 5,755,760 A | 5/1998 | Maguire et al. |
| 5,755,761 A | 5/1998 | Obino |
| 5,772,590 A | 6/1998 | Webster, Jr. |
| 5,807,249 A | 9/1998 | Qin et al. |
| 5,807,395 A | 9/1998 | Mulier et al. |
| 5,814,028 A | 9/1998 | Swartz et al. |
| 5,823,955 A | 10/1998 | Kuck et al. |
| 5,827,242 A | 10/1998 | Follmer et al. |
| 5,827,268 A | 10/1998 | Laufer |
| 5,827,272 A | 10/1998 | Breining et al. |
| 5,842,984 A | 12/1998 | Avitall |
| 5,846,355 A | 12/1998 | Spencer et al. |
| 5,860,920 A | 1/1999 | McGee et al. |
| 5,860,974 A | 1/1999 | Abele |
| 5,865,787 A | 2/1999 | Shapland et al. |

(56) References Cited

U.S. PATENT DOCUMENTS

| | | |
|---|---|---|
| 5,865,815 A | 2/1999 | Tihon |
| 5,871,444 A | 2/1999 | Ouchi |
| 5,871,523 A | 2/1999 | Fleischman et al. |
| 5,871,531 A | 2/1999 | Struble |
| 5,873,865 A | 2/1999 | Horzewski et al. |
| 5,879,295 A | 3/1999 | Li et al. |
| 5,882,346 A | 3/1999 | Pomeranz et al. |
| 5,893,885 A | 4/1999 | Webster et al. |
| 5,910,129 A | 6/1999 | Koblish et al. |
| 5,916,214 A | 6/1999 | Cosio et al. |
| 5,931,830 A | 8/1999 | Davis et al. |
| 5,931,848 A | 8/1999 | Saadat |
| 5,935,102 A | 8/1999 | Bowden et al. |
| 5,935,124 A | 8/1999 | Klumb et al. |
| 5,938,694 A | 8/1999 | Jaraczewski et al. |
| 5,941,823 A | 8/1999 | Chait |
| 5,944,710 A | 8/1999 | Dev et al. |
| 5,951,471 A | 9/1999 | de la Rama et al. |
| 5,954,719 A | 9/1999 | Chen et al. |
| 5,957,961 A | 9/1999 | Maguire et al. |
| 5,961,511 A | 10/1999 | Mortier et al. |
| 5,968,085 A | 10/1999 | Morris et al. |
| 5,972,026 A | 10/1999 | Laufer et al. |
| 5,980,516 A | 11/1999 | Mulier et al. |
| 5,983,141 A | 11/1999 | Sluijter et al. |
| 5,987,344 A | 11/1999 | West |
| 5,993,462 A | 11/1999 | Pomeranz et al. |
| 5,997,526 A | 12/1999 | Giba et al. |
| 6,004,269 A | 12/1999 | Crowley et al. |
| 6,004,348 A | 12/1999 | Banas et al. |
| 6,009,877 A | 1/2000 | Edwards |
| 6,012,457 A | 1/2000 | Lesh |
| 6,032,077 A | 2/2000 | Pomeranz |
| 6,042,578 A | 3/2000 | Dinh et al. |
| 6,048,329 A | 4/2000 | Thompson et al. |
| 6,048,338 A | 4/2000 | Larson et al. |
| 6,064,902 A | 5/2000 | Haissaguerre et al. |
| 6,066,134 A | 5/2000 | Eggers et al. |
| 6,071,729 A | 6/2000 | Jeffries et al. |
| 6,074,339 A | 6/2000 | Gambale et al. |
| 6,074,361 A | 6/2000 | Jacobs |
| 6,074,378 A | 6/2000 | Mouri et al. |
| 6,076,012 A | 6/2000 | Swanson et al. |
| 6,078,840 A | 6/2000 | Stokes |
| 6,078,841 A | 6/2000 | Kuzma |
| 6,090,104 A | 7/2000 | Webster, Jr. |
| 6,094,596 A | 7/2000 | Morgan |
| 6,096,036 A | 8/2000 | Bowe et al. |
| 6,099,524 A | 8/2000 | Lipson et al. |
| 6,102,890 A | 8/2000 | Stivland et al. |
| 6,106,522 A | 8/2000 | Fleischman et al. |
| 6,117,101 A | 9/2000 | Diederich et al. |
| 6,125,302 A | 9/2000 | Kuzma |
| 6,129,750 A | 10/2000 | Tockman et al. |
| 6,132,456 A | 10/2000 | Sommer et al. |
| 6,135,999 A | 10/2000 | Fanton et al. |
| 6,146,381 A | 11/2000 | Bowe et al. |
| 6,149,620 A | 11/2000 | Baker et al. |
| 6,161,048 A | 12/2000 | Sluijter et al. |
| 6,161,049 A | 12/2000 | Rudie et al. |
| 6,164,283 A | 12/2000 | Lesh |
| 6,190,356 B1 | 2/2001 | Bersin |
| 6,210,362 B1 | 4/2001 | Ponzi |
| 6,214,002 B1 | 4/2001 | Fleischman et al. |
| 6,219,577 B1 | 4/2001 | Brown, III et al. |
| 6,223,070 B1 | 4/2001 | Chait |
| 6,224,592 B1 | 5/2001 | Eggers et al. |
| 6,228,109 B1 | 5/2001 | Tu et al. |
| 6,246,912 B1 | 6/2001 | Sluijter et al. |
| 6,246,914 B1 | 6/2001 | de la Rama et al. |
| 6,254,588 B1 | 7/2001 | Jones et al. |
| 6,263,224 B1 | 7/2001 | West |
| 6,270,496 B1 | 8/2001 | Bowe et al. |
| 6,273,876 B1 | 8/2001 | Klima et al. |
| 6,273,886 B1 | 8/2001 | Edwards et al. |
| 6,280,441 B1 | 8/2001 | Ryan |
| 6,283,951 B1 | 9/2001 | Flaherty et al. |
| 6,283,960 B1 | 9/2001 | Ashley |
| 6,287,301 B1 | 9/2001 | Thompson et al. |
| 6,292,695 B1 | 9/2001 | Webster, Jr. et al. |
| 6,308,090 B1 | 10/2001 | Tu et al. |
| 6,314,325 B1 | 11/2001 | Fitz |
| 6,322,558 B1 | 11/2001 | Taylor et al. |
| 6,322,559 B1 | 11/2001 | Daulton et al. |
| 6,325,797 B1 | 12/2001 | Stewart et al. |
| 6,364,904 B1 | 4/2002 | Smith |
| 6,385,472 B1 | 5/2002 | Hall et al. |
| 6,405,732 B1 | 6/2002 | Edwards et al. |
| 6,409,742 B1 | 6/2002 | Fulton, III et al. |
| 6,413,255 B1 | 7/2002 | Stern |
| 6,430,426 B2 | 8/2002 | Avitall |
| 6,442,415 B1 | 8/2002 | Bis et al. |
| 6,451,045 B1 | 9/2002 | Walker et al. |
| 6,480,747 B2 | 11/2002 | Schmidt |
| 6,488,679 B1 | 12/2002 | Swanson et al. |
| 6,496,737 B2 | 12/2002 | Rudie et al. |
| 6,500,172 B1 | 12/2002 | Panescu et al. |
| 6,500,174 B1 | 12/2002 | Maguire et al. |
| 6,506,189 B1 | 1/2003 | Rittman, III et al. |
| 6,511,492 B1 | 1/2003 | Rosenbluth et al. |
| 6,514,226 B1 | 2/2003 | Levin et al. |
| 6,514,249 B1 | 2/2003 | Maguire et al. |
| 6,522,926 B1 | 2/2003 | Kieval et al. |
| 6,527,739 B1 | 3/2003 | Bigus et al. |
| 6,529,756 B1 | 3/2003 | Phan et al. |
| 6,530,935 B2 | 3/2003 | Wensel et al. |
| 6,540,734 B1 | 4/2003 | Chiu et al. |
| 6,542,781 B1 | 4/2003 | Koblish et al. |
| 6,546,280 B2 | 4/2003 | Osborne |
| 6,562,031 B2 | 5/2003 | Chandrasekaran et al. |
| 6,562,034 B2 | 5/2003 | Edwards et al. |
| 6,565,562 B1 | 5/2003 | Shah et al. |
| 6,572,612 B2 | 6/2003 | Stewart et al. |
| 6,585,718 B2 | 7/2003 | Hayzelden et al. |
| 6,592,581 B2 | 7/2003 | Bowe |
| 6,602,242 B1 | 8/2003 | Fung et al. |
| 6,605,061 B2 | 8/2003 | VanTassel et al. |
| 6,607,520 B2 | 8/2003 | Keane |
| 6,610,046 B1 | 8/2003 | Usami et al. |
| 6,610,083 B2 | 8/2003 | Keller et al. |
| 6,611,720 B2 | 8/2003 | Hata et al. |
| 6,613,046 B1 | 9/2003 | Jenkins et al. |
| 6,616,624 B1 | 9/2003 | Kieval |
| 6,622,731 B2 | 9/2003 | Daniel et al. |
| 6,623,515 B2 | 9/2003 | Mulier et al. |
| 6,628,976 B1 | 9/2003 | Fuimaono et al. |
| 6,635,054 B2 | 10/2003 | Fjield et al. |
| 6,652,517 B1 | 11/2003 | Hall et al. |
| 6,656,195 B2 | 12/2003 | Peters et al. |
| 6,669,670 B1 | 12/2003 | Muni et al. |
| 6,685,648 B2 | 2/2004 | Flaherty et al. |
| 6,692,490 B1 | 2/2004 | Edwards |
| 6,702,811 B2 | 3/2004 | Stewart et al. |
| 6,711,444 B2 | 3/2004 | Koblish |
| 6,716,207 B2 | 4/2004 | Farnholtz |
| 6,736,835 B2 | 5/2004 | Pellegrino et al. |
| 6,745,080 B2 | 6/2004 | Koblish |
| 6,749,560 B1 | 6/2004 | Konstorum et al. |
| 6,758,830 B1 | 7/2004 | Schaer et al. |
| 6,773,433 B2 | 8/2004 | Stewart et al. |
| 6,780,183 B2 | 8/2004 | Jimenez, Jr. et al. |
| 6,802,840 B2 | 10/2004 | Chin et al. |
| 6,817,999 B2 | 11/2004 | Berube et al. |
| 6,845,267 B2 | 1/2005 | Harrison et al. |
| 6,850,801 B2 | 2/2005 | Kieval et al. |
| 6,869,431 B2 | 3/2005 | Maguire et al. |
| 6,882,886 B2 | 4/2005 | Witte et al. |
| 6,885,888 B2 | 4/2005 | Rezai |
| 6,890,329 B2 | 5/2005 | Carroll et al. |
| 6,893,436 B2 | 5/2005 | Woodard et al. |
| 6,893,438 B2 | 5/2005 | Hall et al. |
| 6,899,711 B2 | 5/2005 | Stewart et al. |
| 6,905,510 B2 | 6/2005 | Saab |
| 6,909,920 B2 | 6/2005 | Lokhoff et al. |

(56) References Cited

U.S. PATENT DOCUMENTS

| | | |
|---|---|---|
| 6,923,808 B2 | 8/2005 | Taimisto |
| 6,926,669 B1 | 8/2005 | Stewart et al. |
| 6,939,346 B2 | 9/2005 | Kannenberg et al. |
| 6,941,953 B2 | 9/2005 | Feld et al. |
| 6,945,956 B2 | 9/2005 | Waldhauser et al. |
| 6,949,097 B2 | 9/2005 | Stewart et al. |
| 6,960,206 B2 | 11/2005 | Keane |
| 6,960,207 B2 | 11/2005 | Vanney et al. |
| 6,972,016 B2 | 12/2005 | Hill, III et al. |
| 7,013,169 B2 | 3/2006 | Bowe |
| 7,013,170 B2 | 3/2006 | Bowe |
| 7,058,456 B2 | 6/2006 | Pierce |
| 7,081,115 B2 | 7/2006 | Taimisto |
| 7,102,151 B2 | 9/2006 | Reinberg et al. |
| 7,104,988 B2 | 9/2006 | Altman et al. |
| 7,110,828 B2 | 9/2006 | Kolberg et al. |
| 7,115,134 B2 | 10/2006 | Chambers |
| 7,115,183 B2 | 10/2006 | Larson et al. |
| 7,137,990 B2 | 11/2006 | Hebert et al. |
| 7,149,574 B2 | 12/2006 | Yun et al. |
| 7,162,303 B2 | 1/2007 | Levin et al. |
| 7,201,738 B1 | 4/2007 | Bengmark |
| 7,211,082 B2 | 5/2007 | Hall et al. |
| 7,221,979 B2 | 5/2007 | Zhou et al. |
| 7,254,451 B2 | 8/2007 | Seifert et al. |
| 7,276,062 B2 | 10/2007 | McDaniel et al. |
| 7,285,119 B2 | 10/2007 | Stewart et al. |
| 7,291,146 B2 | 11/2007 | Steinke et al. |
| 7,311,705 B2 | 12/2007 | Sra |
| 7,367,972 B2 | 5/2008 | Francischelli et al. |
| 7,381,200 B2 | 6/2008 | Katoh et al. |
| 7,390,894 B2 | 6/2008 | Weinshilboum et al. |
| 7,402,151 B2 | 7/2008 | Rosenman et al. |
| 7,435,248 B2 | 10/2008 | Taimisto et al. |
| 7,488,338 B2 | 2/2009 | Eidenschink |
| 7,517,349 B2 | 4/2009 | Truckai et al. |
| 7,520,863 B2 | 4/2009 | Grewe et al. |
| 7,526,343 B2 | 4/2009 | Peterson et al. |
| 7,540,865 B2 | 6/2009 | Griffin et al. |
| 7,542,808 B1 | 6/2009 | Peterson et al. |
| 7,617,005 B2 | 11/2009 | Demarais et al. |
| 7,637,903 B2 | 12/2009 | Lentz et al. |
| 7,647,115 B2 | 1/2010 | Levin et al. |
| 7,647,124 B2 | 1/2010 | Williams |
| 7,653,438 B2 | 1/2010 | Deem et al. |
| 7,682,319 B2 | 3/2010 | Martin et al. |
| 7,706,894 B2 | 4/2010 | Stewart et al. |
| 7,708,704 B2 | 5/2010 | Mitelberg et al. |
| 7,717,948 B2 | 5/2010 | Demarais et al. |
| 7,727,187 B2 | 6/2010 | Lentz |
| 7,729,782 B2 | 6/2010 | Williams et al. |
| 7,747,334 B2 | 6/2010 | Bly et al. |
| 7,763,012 B2 | 7/2010 | Petrick et al. |
| 7,771,410 B2 | 8/2010 | Venturelli |
| 7,771,421 B2 | 8/2010 | Stewart et al. |
| 7,778,703 B2 | 8/2010 | Gross et al. |
| 7,785,289 B2 | 8/2010 | Rios et al. |
| 7,789,877 B2 | 9/2010 | Vanney |
| 7,815,637 B2 | 10/2010 | Ormsby et al. |
| 7,850,685 B2 | 12/2010 | Kunis et al. |
| 7,867,219 B2 | 1/2011 | Chambers |
| 7,881,807 B2 | 2/2011 | Schaer |
| 7,890,188 B2 | 2/2011 | Zhang et al. |
| 7,959,630 B2 | 6/2011 | Taimisto et al. |
| 7,967,816 B2 | 6/2011 | Ocel et al. |
| 7,989,042 B2 | 8/2011 | Obara et al. |
| 8,007,440 B2 | 8/2011 | Magnin et al. |
| 8,007,462 B2 | 8/2011 | Gibson et al. |
| 8,019,435 B2 | 9/2011 | Hastings et al. |
| 1,026,408 A1 | 10/2011 | Ingle |
| 8,043,288 B2 | 10/2011 | Dando et al. |
| 8,062,284 B2 | 11/2011 | Booth |
| 1,031,990 A1 | 12/2011 | Thenuwara et al. |
| 8,092,444 B2 | 1/2012 | Lentz et al. |
| 8,100,859 B2 | 1/2012 | Patterson et al. |
| 8,123,739 B2 | 2/2012 | McQueen et al. |
| 8,124,876 B2 | 2/2012 | Dayton et al. |
| 8,131,371 B2 | 3/2012 | Demarais et al. |
| 8,131,372 B2 | 3/2012 | Levin et al. |
| 8,140,170 B2 | 3/2012 | Rezai et al. |
| 8,145,317 B2 | 3/2012 | Demarais et al. |
| 8,150,518 B2 | 4/2012 | Levin et al. |
| 8,150,519 B2 | 4/2012 | Demarais et al. |
| 8,150,520 B2 | 4/2012 | Demarais et al. |
| 8,172,829 B2 | 5/2012 | Farnholtz |
| 8,175,711 B2 | 5/2012 | Demarais et al. |
| 8,192,428 B2 | 6/2012 | Truckai et al. |
| 8,251,977 B2 | 8/2012 | Partlett |
| 8,257,351 B2 | 9/2012 | Stewart et al. |
| 8,337,492 B2 | 12/2012 | Kunis et al. |
| 8,376,865 B2 | 2/2013 | Forster et al. |
| 8,380,275 B2 | 2/2013 | Kim et al. |
| 8,401,650 B2 | 3/2013 | Simon et al. |
| 8,473,023 B2 | 6/2013 | Worley et al. |
| 8,571,665 B2 | 10/2013 | Moffitt |
| 2001/0005785 A1 | 6/2001 | Sachse |
| 2001/0007070 A1 | 7/2001 | Stewart et al. |
| 2001/0020174 A1 | 9/2001 | Koblish |
| 2001/0023365 A1 | 9/2001 | Medhkour et al. |
| 2001/0031971 A1 | 10/2001 | Dretler et al. |
| 2002/0004631 A1 | 1/2002 | Jenkins et al. |
| 2002/0004644 A1 | 1/2002 | Koblish |
| 2002/0042610 A1* | 4/2002 | Sliwa et al. ............... 606/27 |
| 2002/0062124 A1 | 5/2002 | Keane |
| 2002/0087208 A1 | 7/2002 | Koblish et al. |
| 2002/0128639 A1* | 9/2002 | Pless et al. ............... 606/27 |
| 2002/0139379 A1 | 10/2002 | Edwards et al. |
| 2002/0165532 A1 | 11/2002 | Hill et al. |
| 2002/0183682 A1 | 12/2002 | Darvish et al. |
| 2003/0050681 A1 | 3/2003 | Pianca et al. |
| 2003/0060858 A1 | 3/2003 | Kieval et al. |
| 2003/0074039 A1 | 4/2003 | Puskas |
| 2003/0088244 A1 | 5/2003 | Swanson et al. |
| 2003/0125790 A1 | 7/2003 | Fastovsky et al. |
| 2003/0153967 A1 | 8/2003 | Koblish et al. |
| 2003/0158584 A1 | 8/2003 | Cates et al. |
| 2003/0181897 A1 | 9/2003 | Thomas et al. |
| 2003/0199863 A1 | 10/2003 | Swanson et al. |
| 2003/0204187 A1 | 10/2003 | Hintringer |
| 2003/0216792 A1 | 11/2003 | Levin et al. |
| 2003/0233099 A1 | 12/2003 | Danaek et al. |
| 2004/0010289 A1 | 1/2004 | Biggs et al. |
| 2004/0030375 A1 | 2/2004 | Pierce |
| 2004/0049181 A1 | 3/2004 | Stewart et al. |
| 2004/0082978 A1 | 4/2004 | Harrison et al. |
| 2004/0215186 A1 | 10/2004 | Cornelius et al. |
| 2004/0260278 A1* | 12/2004 | Anderson et al. ............... 606/32 |
| 2005/0004515 A1 | 1/2005 | Hart et al. |
| 2005/0010095 A1 | 1/2005 | Stewart et al. |
| 2005/0033274 A1* | 2/2005 | Pless et al. ............... 606/27 |
| 2005/0080409 A1 | 4/2005 | Young et al. |
| 2005/0187579 A1 | 8/2005 | Danek et al. |
| 2005/0228460 A1 | 10/2005 | Levin et al. |
| 2005/0251125 A1* | 11/2005 | Pless et al. ............... 606/27 |
| 2005/0273006 A1 | 12/2005 | Stewart et al. |
| 2006/0004346 A1 | 1/2006 | Begg |
| 2006/0004352 A1* | 1/2006 | Vaska et al. ............... 606/32 |
| 2006/0074403 A1 | 4/2006 | Rafiee |
| 2006/0095029 A1 | 5/2006 | Young et al. |
| 2006/0100618 A1 | 5/2006 | Chan et al. |
| 2006/0122587 A1 | 6/2006 | Sharareh |
| 2006/0135870 A1 | 6/2006 | Webler |
| 2006/0135953 A1 | 6/2006 | Kania et al. |
| 2006/0142753 A1 | 6/2006 | Francischelli et al. |
| 2006/0200119 A1* | 9/2006 | Vaska et al. ............... 606/32 |
| 2006/0206150 A1 | 9/2006 | Demarais et al. |
| 2006/0241366 A1 | 10/2006 | Falwell et al. |
| 2006/0271111 A1 | 11/2006 | Demarais et al. |
| 2006/0276846 A1 | 12/2006 | Malecki et al. |
| 2007/0067008 A1 | 3/2007 | Scheiner et al. |
| 2007/0083194 A1 | 4/2007 | Kunis et al. |
| 2007/0129720 A1 | 6/2007 | Demarais et al. |
| 2007/0156114 A1 | 7/2007 | Worley et al. |
| 2007/0265687 A1 | 11/2007 | Deem et al. |

(56) References Cited

U.S. PATENT DOCUMENTS

| | | |
|---|---|---|
| 2007/0270779 A1 | 11/2007 | Jacobs et al. |
| 2008/0004658 A1 | 1/2008 | Malecki et al. |
| 2008/0015562 A1 | 1/2008 | Hong et al. |
| 2008/0045921 A1 | 2/2008 | Anderson et al. |
| 2008/0077119 A1 | 3/2008 | Snyder et al. |
| 2008/0086047 A1 | 4/2008 | McDaniel et al. |
| 2008/0097398 A1 | 4/2008 | Mitelberg et al. |
| 2008/0108975 A1 | 5/2008 | Appling et al. |
| 2008/0109011 A1 | 5/2008 | Thenuwara et al. |
| 2008/0140072 A1 | 6/2008 | Stangenes et al. |
| 2008/0177205 A1 | 7/2008 | Rama et al. |
| 2008/0255539 A1 | 10/2008 | Booth |
| 2008/0287918 A1 | 11/2008 | Rosenman et al. |
| 2008/0288039 A1 | 11/2008 | Reddy |
| 2008/0300587 A1 | 12/2008 | Anderson |
| 2008/0319513 A1 | 12/2008 | Pu et al. |
| 2009/0012465 A1 | 1/2009 | Latini |
| 2009/0018534 A1 | 1/2009 | Taimisto et al. |
| 2009/0036948 A1 | 2/2009 | Levin et al. |
| 2009/0149848 A1 | 6/2009 | Werneth et al. |
| 2009/0157048 A1 | 6/2009 | Sutermeister et al. |
| 2009/0163850 A1 | 6/2009 | Betts et al. |
| 2009/0287202 A1 | 11/2009 | Ingle et al. |
| 2009/0306650 A1 | 12/2009 | Govari et al. |
| 2009/0312606 A1 | 12/2009 | Dayton et al. |
| 2010/0030112 A1 | 2/2010 | Anderson et al. |
| 2010/0069882 A1 | 3/2010 | Jennings et al. |
| 2010/0137860 A1 | 6/2010 | Demarais et al. |
| 2010/0137952 A1 | 6/2010 | Demarais et al. |
| 2010/0168740 A1 | 7/2010 | Stewart et al. |
| 2010/0168777 A1 | 7/2010 | Stangenes et al. |
| 2010/0174282 A1 | 7/2010 | Demaris et al. |
| 2010/0179512 A1 | 7/2010 | Chong et al. |
| 2010/0191112 A1 | 7/2010 | Demarais et al. |
| 2010/0204692 A1 | 8/2010 | Stewart et al. |
| 2010/0217184 A1 | 8/2010 | Koblish et al. |
| 2010/0222851 A1 | 9/2010 | Deem et al. |
| 2010/0222854 A1 | 9/2010 | Demarais et al. |
| 2010/0261990 A1 | 10/2010 | Gillis et al. |
| 2010/0324482 A1 | 12/2010 | Farnholtz |
| 2011/0028962 A1 | 2/2011 | Werneth et al. |
| 2011/0034989 A1 | 2/2011 | Al-Marashi et al. |
| 2011/0054464 A1 | 3/2011 | Werneth et al. |
| 2011/0054465 A1 | 3/2011 | Werneth et al. |
| 2011/0112476 A1 | 5/2011 | Kauphusman et al. |
| 2011/0144639 A1 | 6/2011 | Govari |
| 2011/0160719 A1 | 6/2011 | Govari et al. |
| 2011/0270173 A1 | 11/2011 | Gibson et al. |
| 2011/0276024 A1 | 11/2011 | Randolph et al. |
| 2011/0306851 A1 | 12/2011 | Wang |
| 2012/0010607 A1 | 1/2012 | Malecki et al. |
| 2012/0029509 A1 | 2/2012 | Smith |
| 2012/0029510 A1 | 2/2012 | Haverkost |
| 2012/0029513 A1 | 2/2012 | Smith et al. |
| 2012/0035615 A1 | 2/2012 | Koester et al. |
| 2012/0078076 A1 | 3/2012 | Stewart et al. |
| 2012/0101553 A1 | 4/2012 | Reddy |
| 2012/0116382 A1 | 5/2012 | Ku et al. |
| 2012/0116383 A1 | 5/2012 | Mauch et al. |
| 2012/0123406 A1 | 5/2012 | Edmunds et al. |
| 2012/0130289 A1 | 5/2012 | Demarais et al. |
| 2012/0130345 A1 | 5/2012 | Levin et al. |
| 2012/0130368 A1 | 5/2012 | Jenson |
| 2012/0143293 A1 | 6/2012 | Mauch et al. |
| 2012/0172837 A1 | 7/2012 | Demarais et al. |
| 2012/0191083 A1 | 7/2012 | Moll et al. |
| 2012/0197246 A1 | 8/2012 | Mauch |
| 2012/0265066 A1 | 10/2012 | Crow et al. |
| 2012/0277842 A1 | 11/2012 | Kunis |
| 2012/0290053 A1 | 11/2012 | Zhang et al. |
| 2012/0310065 A1 | 12/2012 | Falwell et al. |
| 2012/0310239 A1 | 12/2012 | Stewart et al. |
| 2012/0323233 A1 | 12/2012 | Maguire et al. |
| 2013/0035681 A1 | 2/2013 | Subramaniam et al. |
| 2013/0053876 A1 | 2/2013 | Ogle |
| 2013/0085360 A1 | 4/2013 | Grunewald |
| 2013/0090637 A1 | 4/2013 | Sliwa |
| 2013/0090647 A1 | 4/2013 | Smith |
| 2013/0090649 A1 | 4/2013 | Smith et al. |
| 2013/0090651 A1 | 4/2013 | Smith |
| 2013/0090652 A1 | 4/2013 | Jenson |
| 2013/0096550 A1 | 4/2013 | Hill |
| 2013/0096553 A1 | 4/2013 | Hill et al. |
| 2013/0096554 A1 | 4/2013 | Groff et al. |
| 2013/0123770 A1 | 5/2013 | Smith |
| 2013/0131667 A1 | 5/2013 | Jenson et al. |
| 2013/0165921 A1 | 6/2013 | Sutermeister et al. |
| 2013/0172872 A1 | 7/2013 | Subramaniam et al. |
| 2013/0172879 A1 | 7/2013 | Sutermeister et al. |
| 2013/0172881 A1 | 7/2013 | Hill et al. |
| 2013/0184642 A1 | 7/2013 | O'Donnell et al. |
| 2013/0184703 A1 | 7/2013 | Shireman et al. |
| 2013/0184773 A1 | 7/2013 | Libbus |
| 2013/0253628 A1 | 9/2013 | Chaska |
| 2013/0274614 A1 | 10/2013 | Shimada |
| 2013/0274730 A1 | 10/2013 | Anderson |
| 2013/0274731 A1 | 10/2013 | Anderson |
| 2013/0274737 A1 | 10/2013 | Wang |
| 2013/0282000 A1 | 10/2013 | Parsonage |
| 2013/0282084 A1 | 10/2013 | Mathur |
| 2013/0289686 A1 | 10/2013 | Masson |
| 2013/0304047 A1 | 11/2013 | Grunewald |
| 2013/0304052 A1 | 11/2013 | Rizq |
| 2013/0304061 A1 | 11/2013 | Chang et al. |
| 2013/0304062 A1 | 11/2013 | Chan |
| 2014/0058376 A1 | 2/2014 | Horn |
| 2014/0094787 A1 | 4/2014 | Reynolds |

FOREIGN PATENT DOCUMENTS

| | | |
|---|---|---|
| AU | 2011239320 | 5/2012 |
| CN | 2782017 | 5/2006 |
| CN | 201469401 | 5/2010 |
| CN | 102125460 | 7/2011 |
| CN | 102125725 | 7/2011 |
| CN | 102198015 A | 9/2011 |
| CN | 102274075 A | 12/2011 |
| CN | 102488552 | 6/2012 |
| CN | 202386778 U | 8/2012 |
| CN | 202426649 U | 9/2012 |
| CN | 202537649 U | 11/2012 |
| CN | 202538132 U | 11/2012 |
| CN | 102885648 | 1/2013 |
| CN | 102885648 A | 1/2013 |
| CN | 102885649 A | 1/2013 |
| CN | 202654228 | 1/2013 |
| CN | 202654229 | 1/2013 |
| CN | 202665687 | 1/2013 |
| CN | 102908188 A | 2/2013 |
| CN | 102908189 A | 2/2013 |
| CN | 202761434 | 3/2013 |
| CN | 103027745 | 4/2013 |
| CN | 103027746 | 4/2013 |
| CN | 103027747 | 4/2013 |
| CN | 202843784 | 4/2013 |
| DE | 29909082 | 7/1999 |
| DE | 29909082 U1 | 7/1999 |
| DE | 10252325 | 5/2004 |
| DE | 10257146 | 6/2004 |
| EP | 0132344 | 1/1985 |
| EP | 0132344 | 1/1986 |
| EP | 0348136 | 12/1989 |
| EP | 0352955 | 1/1990 |
| EP | 0510624 | 10/1992 |
| EP | 0512359 | 11/1992 |
| EP | 0542246 | 5/1993 |
| EP | 626818 | 12/1994 |
| EP | 652026 | 5/1995 |
| EP | 664990 | 8/1995 |
| EP | 0680351 | 11/1995 |
| EP | 727184 | 8/1996 |
| EP | 732080 | 9/1996 |
| EP | 0779079 | 6/1997 |
| EP | 0787019 | 8/1997 |

(56) References Cited

FOREIGN PATENT DOCUMENTS

| | | |
|---|---|---|
| EP | 0821602 | 2/1998 |
| EP | 0834289 | 4/1998 |
| EP | 862478 | 9/1998 |
| EP | 0868923 | 10/1998 |
| EP | 0728495 A3 | 4/1999 |
| EP | 0916360 | 5/1999 |
| EP | 0937481 | 8/1999 |
| EP | 944353 | 9/1999 |
| EP | 0951244 | 10/1999 |
| EP | 0984806 | 3/2000 |
| EP | 1042990 | 10/2000 |
| EP | 1233716 | 8/2002 |
| EP | 1233716 A2 | 8/2002 |
| EP | 1326550 | 7/2003 |
| EP | 963191 | 8/2003 |
| EP | 757575 | 9/2003 |
| EP | 873760 | 1/2004 |
| EP | 1374943 | 1/2004 |
| EP | 0778043 | 11/2005 |
| EP | 1656963 | 5/2006 |
| EP | 1042990 | 10/2006 |
| EP | 1733689 | 12/2006 |
| EP | 1768732 | 4/2007 |
| EP | 1787674 | 5/2007 |
| EP | 1802370 | 7/2007 |
| EP | 1824548 | 8/2007 |
| EP | 1827558 | 9/2007 |
| EP | 1857134 | 11/2007 |
| EP | 1968679 | 9/2008 |
| EP | 1009303 | 6/2009 |
| EP | 2208474 | 7/2010 |
| EP | 2263588 | 12/2010 |
| EP | 2340765 | 7/2011 |
| EP | 2389974 | 11/2011 |
| EP | 2398540 | 12/2011 |
| EP | 2445568 | 5/2012 |
| EP | 2519173 | 11/2012 |
| EP | 2558016 | 2/2013 |
| EP | 2598069 | 6/2013 |
| EP | 2664295 | 11/2013 |
| JP | 355137141 | 10/1980 |
| WO | WO-9101772 | 2/1991 |
| WO | WO-9115254 | 10/1991 |
| WO | WO-9215356 | 9/1992 |
| WO | WO-9220291 A | 11/1992 |
| WO | WO-9419039 | 9/1994 |
| WO | WO-9421168 | 9/1994 |
| WO | WO-9513111 | 5/1995 |
| WO | WO-9520416 | 8/1995 |
| WO | WO-9525472 | 9/1995 |
| WO | WO-9600036 | 1/1996 |
| WO | WO-9632980 | 10/1996 |
| WO | WO-9638196 | 12/1996 |
| WO | WO-9717892 | 5/1997 |
| WO | WO-9729800 | 8/1997 |
| WO | WO-9736548 | 10/1997 |
| WO | WO-9748435 | 12/1997 |
| WO | WO 9802201 | 1/1998 |
| WO | WO-9833469 | 8/1998 |
| WO | WO-9843530 | 10/1998 |
| WO | WO-9848885 | 11/1998 |
| WO | WO-9850098 | 11/1998 |
| WO | WO-9852637 | 11/1998 |
| WO | WO-99/00060 | 1/1999 |
| WO | WO-9911313 | 3/1999 |
| WO | WO-9956801 | 11/1999 |
| WO | WO-9962413 | 12/1999 |
| WO | WO 0001313 | 1/2000 |
| WO | WO-0056237 | 9/2000 |
| WO | WO-0067832 | 11/2000 |
| WO | WO-0122897 | 4/2001 |
| WO | WO-0137723 | 5/2001 |
| WO | WO-0137746 | 5/2001 |
| WO | WO-0170114 | 9/2001 |
| WO | WO-0180758 | 11/2001 |
| WO | WO-0230310 | 4/2002 |
| WO | WO-0245608 | 6/2002 |
| WO | WO-02083017 | 10/2002 |
| WO | WO-02087453 | 11/2002 |
| WO | WO-02089687 | 11/2002 |
| WO | WO-02089908 | 11/2002 |
| WO | WO-03082080 A | 10/2003 |
| WO | WO-2004100813 | 11/2004 |
| WO | WO-2005041748 | 5/2005 |
| WO | WO-2005051216 | 6/2005 |
| WO | WO-2005070491 | 8/2005 |
| WO | WO-2005110528 | 11/2005 |
| WO | WO-2006/009588 | 1/2006 |
| WO | WO-2006020920 | 2/2006 |
| WO | WO-2006041881 | 4/2006 |
| WO | WO-2006041881 A2 | 4/2006 |
| WO | WO-2006065949 A2 | 6/2006 |
| WO | WO-2006092000 | 9/2006 |
| WO | WO-2007001981 A2 | 1/2007 |
| WO | WO-2007007981 | 1/2007 |
| WO | WO-2007008954 | 1/2007 |
| WO | WO-2007059277 | 5/2007 |
| WO | WO-2007117359 | 10/2007 |
| WO | WO-2007128064 | 11/2007 |
| WO | WO-2008064399 | 6/2008 |
| WO | WO-2008101244 | 8/2008 |
| WO | WO-2008139347 | 11/2008 |
| WO | WO-2009121017 | 1/2009 |
| WO | WO-2010048676 | 5/2010 |
| WO | WO-2010091701 | 8/2010 |
| WO | WO 2010120835 | 10/2010 |
| WO | WO-2011015218 | 2/2011 |
| WO | WO-2011019838 | 2/2011 |
| WO | WO-2011056311 | 5/2011 |
| WO | WO-2011082279 | 7/2011 |
| WO | WO-2011130534 | 10/2011 |
| WO | WO-2012061159 | 5/2012 |
| WO | WO-2012061161 | 5/2012 |
| WO | WO-2012061164 | 5/2012 |
| WO | WO-2012075156 | 6/2012 |
| WO | WO-2012100095 | 7/2012 |
| WO | WO-2012130337 | 10/2012 |
| WO | WO-2012131107 | 10/2012 |
| WO | WO-2012154219 | 11/2012 |
| WO | WO-2012154796 | 11/2012 |
| WO | WO-2013005667 | 1/2013 |
| WO | WO-2013016203 | 1/2013 |
| WO | WO-2013028993 | 2/2013 |
| WO | WO-2013040201 | 3/2013 |
| WO | WO-2013/055685 | 4/2013 |
| WO | WO-2013049601 | 4/2013 |
| WO | WO-2013055815 | 4/2013 |
| WO | WO-2013055826 | 4/2013 |
| WO | WO-2013058962 | 4/2013 |
| WO | WO-2013101452 | 7/2013 |
| WO | WO-2013106054 | 7/2013 |
| WO | WO2013109318 | 7/2013 |
| WO | WO2013158676 | 10/2013 |
| WO | WO2013158678 | 10/2013 |
| WO | WO2013165920 | 11/2013 |
| WO | WO-2013169340 | 11/2013 |
| WO | WO2013154776 | 12/2013 |

OTHER PUBLICATIONS

Bello-Reuss, E. et al., "Effects of Acute Unilateral Renal Denervation in the Rat," Journal of Clinical Investigation, vol. 56, Jul. 1975, pp. 208-217.

Bello-Reuss, E. et al., "Effects of Renal Sympathetic Nerve Stimulation on Proximal Water and Sodium Reabsorption," Journal of Clinical Investigation, vol. 57, Apr. 1976, pp. 1104-1107.

Bhandari, A. and Ellias, M., "Loin Pain Hemaluria Syndrome: Pain Control with RFA to the Splanchanic Plexus," The Pain Clinc, 2000, vol. 12, No. 4, pp. 323-327.

Curtis, John J. et al., "Surgical Therapy for Persistent Hypertension After Renal Transplantation" Transplantation, 31:125-128 (1981).

Dibona, Gerald F. et al., "Neural Control of Renal Function," Physiological Reviews, vol. 77, No. 1, Jan. 1997, The American Physiological Society 1997, pp. 75-197.

(56) References Cited

OTHER PUBLICATIONS

Dibona, Gerald F., "Neural Control of the Kidney—Past, Present and Future," Nov. 4, 2002, Novartis Lecture, Hypertension 2003, 41 part 2, 2002 American Heart Association, Inc., pp. 621-624.
Janssen, Ben J.A. et al., "Effects of Complete Renal Denervation and Selective Afferent Renal Denervation on the Hypertension Induced by Intrarenal Norepinephrine Infusion in Conscious Rats", Journal of Hypertension 1989, 7: 447-455.
Katholi, Richard E., "Renal Nerves in the Pathogenesis of Hypertension in Experimental Animals and Humans," Am J. Physiol. vol. 245, 1983, the American Physiological Society 1983, pp. F1-F14.
Krum, Henry et al., "Catheter-Based Renal Sympathetic Denervation for Resistant Hypertension: A Mulitcentre Safety and Proof-of Principle Cohort Study," Lancet 2009; 373:1275-81.
Krum, et al., "Renal Sympathetic-Nerve Ablation for Uncontrolled Hypertension." New England Journal of Med, Aug. 2009, 361;9.
Luippold, Gerd et al., "Chronic Renal Denervation Prevents Glomerular Hyperfiltration in Diabetic Rats", Nephrol Dial Transplant, vol. 19, No. 2, 2004, pp. 342-347.
Mahfoud et al. "Treatment strategies for resistant arterial hypertension" Dtsch Arztebl Int. 2011;108:725-731.
Osborn, et al., "Effect of Renal Nerve Stimulation on Renal Blood Flow Autoregulation and Antinatriuresis During Reductions in Renal Perfusion Pressure," Proceedings of the Society for Experimental Biology and Medicine, vol. 168, 77-81, 1981.
Page, I.H. et al., "The Effect of Renal Denervation on Patients Suffering From Nephritis," Feb. 27, 1935;443-458.
Page, I.H. et al., "The Effect of Renal Denervation on the Level of Arterial Blood Pressure and Renal Function in Essential Hypertension," J. Clin Invest. 1934;14:27-30.
Rocha-Singh, "Catheter-Based Sympathetic Renal Denervation," Endovascular Today, Aug. 2009.
Schlaich, M.P. et al., "Renal Denervation as a Therapeutic Approach for Hypertension: Novel Implictions for an Old Concept," Hypertension, 2009; 54:1195-1201.
Schlaich, M.P. et al., "Renal Sympathetic-Nerve Ablation for Uncontrolled Hypertension," N Engl J Med 2009; 361(9): 932-934.
Smithwick, R.H. et al., "Splanchnicectomy for Essential Hypertension," Journal Am Med Assn, 1953; 152:1501-1504.
Symplicity HTN-1 Investigators; Krum H, Barman N, Schlaich M, et al. Catheter-based renal sympathetic denervation for resistant hypertension: durability of blood pressure reduction out to 24 months. Hypertension. 2011;57(5):911-917.
Symplicity HTN-2 Investigators, "Renal Sympathetic Denervation in Patients with Treatment-Resistant Hypertension (The Symplicity HTN-2 Trial): A Randomised Controlled Trial"; Lancet, Dec. 4, 2010, vol. 376, pp. 1903-1909.
USRDS United States Renal Data System 2003 Annual Data Report.
Valente, John F. et al., "Laparoscopic Renal Denervation for Intractable ADPKD-Related Pain", Nephrol Dial Transplant (2001) 16:160.
Wagner, C.D. et al., "Very Low Frequency Oscillations in Arterial Blood Pressure After Autonomic Blockade in Conscious Dogs," Feb. 5, 1997, Am J Physiol Regul Integr Comp Physiol 1997, vol. 272, 1997 the American Physiological Society, pp. 2034-2039.
International Search Report and Written Opinion for International Application No. PCT/US2013/030207, mailed Sep. 23, 2013, 19 pages.
International Search Report and Written Opinion for International Application No. PCT/US2011/057754, mailed Feb. 16, 2012, 13 pages.
International Search Report and Written Opinion for International Application No. PCT/US2011/057756, mailed Jan. 2, 2012, 10 pages.
European Search Report for European Application No. 13159256, Date Mailed: Oct. 17, 2013, 6 pages.
"2011 Edison Award Winners." Edison Awards: Honoring Innovations & Innovators, 2011, 6 pages, <http://www.edisonawards.com/BestNewProduct_2011.php>.
"2012 top 10 advances in heart disease and stroke research: American Heart Association/America Stroke Association Top 10 Research Report." American Heart Association, Dec. 17, 2012, 5 pages, <http://newsroom.heart.org/news/2012-top-10-advances-in-heart-241901>.
"Ardian(R) Receives 2010 EuroPCR Innovation Award and Demonstrates Further Durability of Renal Denervation Treatment for Hypertension." PR Newswire, Jun. 3, 2010, 2 pages, <http://www.prnewswire.com/news-releases/ardianr-receives-2010-europcr-innovation-award-and-demonstrates-further-durability-of-renal-denervation-treatment-for-hypertension-95545014.html>.
"Boston Scientific to Acquire Vessix Vascular, Inc.: Company to Strengthen Hypertension Program with Acquisition of Renal Denervation Technology." Boston Scientific: Advancing science for life—Investor Relations, Nov. 8, 2012, 2 pages, <http://phx.corporate-ir.net/phoenix.zhtml?c=62272&p=irol-newsArticle&id=1756108>.
"Cleveland Clinic Unveils Top 10 Medical Innovations for 2012: Experts Predict Ten Emerging Technologies that will Shape Health Care Next Year." Cleveland Clinic, Oct. 6, 2011, 2 pages. <http://my.clevelandclinic.org/media_relations/library/2011/2011-10-6-cleveland-clinic-unveils-top-10-medical-innovations-for-2012.aspx>.
"Does renal denervation represent a new treatment option for resistant hypertension?" Interventional News, Aug. 3, 2010, 2 pages. <http://www.cxvascular.com/in-latest-news/interventional-news---latest-news/does-renal-denervation-represent-a-new-treatment-option-for-resistant-hypertension>.
"Iberis—Renal Sympathetic Denervation System: Turning innovation into quality care." [Brochure], Terumo Europe N.V., 2013, Europe, 3 pages.
"Neurotech Reports Announces Winners of Gold Electrode Awards." Neurotech business report, 2009. 1 page. <http://www.neurotechreports.com/pages/goldelectrodes09.html>.
"Quick. Consistent. Controlled. OneShot renal Denervation System" [Brochure], Covidien: positive results for life, 2013, (n.l.), 4 pages.
"Renal Denervation Technology of Vessix Vascular, Inc. been acquired by Boston Scientific Corporation (BSX) to pay up to $425 Million." Vessix Vascular Pharmaceutical Intelligence: A blog specializing in Pharmaceutical Intelligence and Analytics, Nov. 8, 2012, 21 pages, <http://pharmaceuticalintelligence.com/tag/vessix-vascular/>.
"The Edison AwardsTM" Edison Awards: Honoring Innovations & Innovators, 2013, 2 pages, <http://www.edisonawards.com/Awards.php>.
"The Future of Renal denervation for the Treatment of Resistant Hypertension." St. Jude Medical, Inc., 2012, 12 pages.
"Vessix Renal Denervation System: So Advanced It's Simple." [Brochure], Boston Scientific: Advancing science for life, 2013, 6 pages.
Asbell, Penny, "Conductive Keratoplasty for the Correction of Hyperopia." Tr Am Ophth Soc, 2001, vol. 99, 10 pages.
Badoer, Emilio, "Cardiac afferents play the dominant role in renal nerve inhibition elicited by volume expansion in the rabbit." Am J Physiol Regul Integr Comp Physiol, vol. 274, 1998, 7 pages.
Bengel, Frank, "Serial Assessment of Sympathetic Reinnervation After Orthotopic Heart Transplantation: A longitudinal Study Using PET and C-11 Hydroxyephedrine." Circulation, vol. 99, 1999,7 pages.
Bettmann, Michael, Carotid Stenting and Angioplasty: A Statement for Healthcare Professionals From the Councils on Cardiovascular Radiology, Stroke, Cardio-Thoracic and Vascular Surgery, Epidemiology and Prevention, and Clinical Cardiology, American Heart Association, Circulation, vol. 97, 1998, 4 pages.
Bohm, Michael et al., "Rationale and design of a large registry on renal denervation: the Global SYMPLICITY registry." EuroIntervention, vol. 9, 2013, 9 pages.
Brosky, John, "EuroPCR 2013: CE-approved devices line up for renal denervation approval." Medical Device Daily, May 28, 2013, 3 pages, <http://www.medicaldevicedaily.com/servlet/com.accumedia.web.Dispatcher?next=bioWorldHeadlines_article&forceid=83002>.

(56) References Cited

OTHER PUBLICATIONS

Davis, Mark et al., "Effectiveness of Renal Denervation Therapy for Resistant Hypertension." Journal of the American College of Cardiology, vol. 62, No. 3, 2013, 11 pages.
Final Office Action; U.S. Appl. No. 12/827,700; Mailed on Feb. 5, 2013, 61 pages.
Geisler, Benjamin et al., "Cost-Effectiveness and Clinical Effectiveness of Catheter-Based Renal Denervation for Resistant Hypertension." Journal of the American College of Cardiology, col. 60, No. 14, 2012, 7 pages.
Gertner, Jon, "Meet the Tech Duo That's Revitalizing the Medical Device Industry." Fast Company, Apr. 15, 2013, 6:00 AM, 17 pages, <http://www.fastcompany.com/3007845/meet-tech-duo-thats-revitalizing-medical-device-industry>.
Golwyn, D. H., Jr., et al. "Percutaneous Transcatheter Renal Ablation with Absolute Ethanol for Uncontrolled Hypertension or Nephrotic Syndrome: Results in 11 Patients with End-Stage Renal Disease." JVIR, 8: 527-533 (1997).
Hering, Dagmara et al., "Chronic kidney disease: role of sympathetic nervous system activation and potential benefits of renal denervation." EuroIntervention, vol. 9, 2013, 9 pages.
Imimdtanz, "Medtronic awarded industry's highest honour for renal denervation system." The official blog of Medtronic Australasia, Nov. 12, 2012, 2 pages, <http://97waterlooroad.wordpress.com/2012/11/12/medtronic-awarded-industrys-highest-honour-for-renal-denervation-system/>.
Kaiser, Chris, AHA Lists Year's Big Advances in CV Research, medpage Today, Dec. 18, 2012, 4 pages, <http://www.medpagetoday.com/Cardiology/PCI/36509>.
Linz, Dominik et al., "Renal denervation suppresses ventricular arrhythmias during acute ventricular ischemia in pigs." Heart Rhythm, vol. 0, No. 0, 2013, 6 pages.
Mabin, Tom et al., "First experience with endovascular ultrasound renal denervation for the treatment of resistant hypertension." EuroIntervention, vol. 8, 2012, 5 pages.
Mahfoud, Felix et al., "Ambulatory Blood Pressure Changes after Renal Sympathetic Denervation in Patients with Resistant Hypertension." Circulation, 2013, 25 pages.
Mahfoud, Felix et al., "Expert consensus document from the European Society of Cardiology on catheter-based renal denervation." European Heart Journal, 2013, 9 pages.
Mahfoud, Felix et al., "Renal Hemodynamics and Renal Function After Catheter-Based Renal Sympathetic Denervation in Patients With Resistant Hypertension." Hypertension, 2012, 6 pages.
Millard, F. C., et al, "Renal Embolization for ablation of function in renal failure and hypertension." Postgraduate Medical Journal, 65, 729-734 (1989).
Ormiston, John et al., "First-in-human use of the OneShotTM renal denervation system from Covidien." EuroIntervention, vol. 8, 2013, 4 pages.
Ormiston, John et al., "Renal denervation for resistant hypertension using an irrigated radiofrequency balloon: 12-month results from the Renal Hypertension Ablation System (RHAS) trial." EuroIntervention, vol. 9, 2013, 5 pages.
Pedersen, Amanda, "TCT 2012: Renal denervation device makers play show and tell." Medical Device Daily, Oct. 26, 2012, 2 pages, <http://www.medicaldevicedaily.com/servlet/com.accumedia.web.Dispatcher?next=bioWorldHeadlines_article&forceid=80880>.
Schlaich, Markus et al., "Renal Denervation in Human Hypertension: Mechanisms, Current Findings, and Future Prospects." Curr Hypertens Rep, vol. 14, 2012, 7 pages.
Schmid, Axel et al., "Does Renal Artery Supply Indicate Treatment Success of Renal Denervation." Cardiovasc Intervent Radiol, vol. 36, 2013, 5 pages.
Schmieder, Roland E. et al., "Updated ESH position paper on interventional therapy of resistant hypertension." EuroIntervention, vol. 9, 2013, 9 pages.
Sievert, Horst, "Novelty Award EuroPCR 2010." Euro PCR, 2010, 15 pages.
Stouffer, G. A. et al., "Catheter-based renal denervation in the treatment of resistant hypertension." Journal of Molecular and Cellular Cardiology, vol. 62, 2013, 6 pages.
Verloop, W. L. et al., "Renal denervation: a new treatment option in resistant arterial hypertension." Neth Heart J., Nov. 30, 2012, 6 pages, <http://www.ncbi.nlm.nih.gov/pmc/articles/PMC3547427/>.
Wilcox, Josiah N., Scientific Basis Behind Renal Denervation for the Control of Hypertension, ICI 2012, Dec. 5-6, 2012. 38 pages.
Worthley, Stephen et al., "Safety and efficacy of a multi-electrode renal sympathetic denervation system in resistant hypertension: the EnligHTN I trial." European Heart Journal, vol. 34, 2013, 9 pages.
Worthley, Stephen, "The St. Jude Renal Denervation System Technology and Clinical Review." The University of Adelaide Australia, 2012, 24 pages.
Zuern, Christine S., "Impaired Cardiac Baroflex Sensitivity Predicts Response to Renal Sympathetic Denervation in Patients with Resistant Hypertension." Journal of the American College of Cardiology, 2013, doi: 10.1016/j.jacc.2013.07.046, 24 pages.
International Search Report, PCT/US02/07661, Aug. 13, 2002, 5 Pages.
International Search Report, PCT/US03/031339, Feb. 18, 2004, 3 Pages.
International Search Report, PCT/US01/044977, Jun. 7, 2002, 6 Pages.
U.S. Appl. No. 95/002,110, filed Aug. 29, 2012, Demarais et al.
U.S. Appl. No. 95/002,209, filed Sep. 13, 2012, Levin et al.
U.S. Appl. No. 95/002,233, filed Sep. 13, 2012, Levin et al.
U.S. Appl. No. 95/002,243, filed Sep. 13, 2012, Levin et al.
U.S. Appl. No. 95/002,253, filed Sep. 13, 2012, Demarais et al.
U.S. Appl. No. 95/002,255, filed Sep. 13, 2012, Demarais et al.
U.S. Appl. No. 95/002,292, filed Sep. 14, 2012, Demarais et al.
U.S. Appl. No. 95/002,327, filed Sep. 14, 2012, Demarais et al.
U.S. Appl. No. 95/002,335, filed Sep. 14, 2012, Demarais et al.
U.S. Appl. No. 95/002,336, filed Sep. 14, 2012, Levin et al.
U.S. Appl. No. 95/002,356, filed Sep. 14, 2012, Demarais et al.
Benito, F., et al. "Radiofrequency catheter ablation of accessory pathways in infants." Heart, 78:160-162 (1997).
Dibona, G.F. "Sympathetic nervous system and kidney in hypertension." Nephrol and Hypertension, 11: 197-200 (2002).
Dibona, G.F., et al. "Neural control of renal function." Physiol Rev, 77:75-197 (1997).
Dubuc, M., et al., "Feasibility of cardiac cryoablation using a transvenous steerable electrode catheter." J Interv Cardiac Electrophysiol, 2:285-292 (1998).
Gelfand, M., et al., "Treatment of renal failure and hypertension." U.S. Appl. No. 60/442,970, filed 2003.
Hall, W. H., et al. "Combined embolization and percutaneous radiofrequency ablation of a solid renal tumor." Am. J. Roentgenol,174: 1592-1594 (2000).
Han, Y.-M, et al., "Renal artery ebolization with diluted hot contrast medium: An experimental study." J Vasc Interv Radiol, 12: 862-868 (2001).
Hanson, J. M., et al. "The transplanted human kidney does not achieve functional reinnervation." Clin. Sci, 87: 13-19 (1994).
Hendee, W. R. et al. "Use of Animals in Biomedical Research: The Challenge and Response." *American Medical Association White Paper* (1988).
Huang et al., "Renal denervation prevents and reverses hyperinsulinemia-induced hypertension in rats." Hypertension 32 (1998) pp. 249-254.
Kompanowska, E., et al., "Early Effects of renal denervation in the anaesthetised rat: Natriuresis and increased cortical blood flow." J Physiol, 531. 2:527-534 (2001).
Lee, S.J., et al. "Ultrasonic energy in endoscopic surgery." Yonsei Med J, 40:545-549 (1999).
Lustgarten, D.L.,et al., "Cryothermal ablation: Mechanism of tissue injury and current experience in the treatment of tachyarrhythmias." Progr Cardiovasc Dis, 41:481-498 (1999).
Medical-Dictionary.com, Definition of "Animal Model," http://medical-dictionary.com (search "Animal Model"), 2005.
Medtronic, Inc., Annual Report (Form 10-K) (Jun. 28, 2011).

(56) References Cited

OTHER PUBLICATIONS

Oliveira, V., et al., "Renal denervation normalizes pressure and baroreceptor reflex in high renin hypertension in conscious rats." Hypertension, 19:II-17-II-21 (1992).

Ong, K. L., et al. "Prevalence, Awareness, Treatment, and Control of Hypertension Among United States Adults 1999-2004." Hypertension, 49: 69-75 (2007) (originally published online Dec. 11, 2006).

Peet, M., "Hypertension and its Surgical Treatment by bilateral supradiaphragmatic splanchnicectomy" Am J Surgery (1948) pp. 48-68.

Renal Denervation (RDN), Symplicity RDN System Common Q&A (2011), http://www.medtronic.com/rdn/mediakit/RDN%20FAQ.pdf.

Schauerte, P., et al. "Catheter ablation of cardiac autonomic nerves for prevention of vagal atrial fibrillation." Circulation, 102:2774-2780 (2000).

Smithwick et al., "Splanchnicectomy for essential hypertension." J. Am. Med. Assn. 152:16 (1953), pp. 1501-1504.

Solis-Herruzo et al., "Effects of lumbar sympathetic block on kidney function in cirrhotic patients with hepatorenal syndrome," J. Hepatol. 5 (1987), pp. 167-173.

Stella, A., et al., "Effects of reversible renal denervation on haemodynamic and excretory functions on the ipsilateral and contralateral kidney in the cat." Hypertension, 4:181-188 (1986).

Swartz, J.F., et al., "Radiofrequency endocardial catheter ablation of accessory atrioventricular pathway atrial insertion sites." Circulation, 87: 487-499 (1993).

Uchida, F., et al., "Effect of radiofrequency catheter ablation on parasympathetic denervation: A comparison of three different ablation sites." PACE, 21:2517-2521 (1998).

Valente, J.F. "Laparoscopic renal denervation for intractable ADPKD-related pain." Nephrol Dial Transplant, 16: 160 (2001).

Weinstock, M., et al., "Renal denervation prevents sodium retention and hypertension in salt sensitive rabbits with genetic baroreflex impairment." Clinical Science, 90:287-293 (1996).

Materials Research Society, "Biomedical Materials and Devices," Symposium helped Nov. 30-Dec. 4, 1987, Boston Massachusetts, USA.

Claudine Jaboro, "An in vivo study of the biocompatibility of classic and novel device materials on the central nervous system", (Jan. 1, 2007), ETD Collection for Wayne State University. Paper AA13310737. <http://digitalcommons.wayne.edu/dissertations/AA13310737>.

Lahiri D. et al. Boron nitride nanotube reinforced polylactide-polycaprolactone copolymer composite: Mechanical properties and cytocompatibility with osteoblasts and macrophages in vitro. Acta Biomater (2010), doi: 10.1016/j.actbio.2010.02.44.

Ahmed, Humera et al., Renal Sympathetic Denervation Using an Irrigated Radiofrequency Ablation Catheter for the Management of Drug-Resistant Hypertension, JACC Cardiovascular Interventions, vol. 5, No. 7, 2012, pp. 758-765.

Avitall et al., "The creation of linear contiguous lesions in the atria with an expandable loop catheter,"Journal of the American College of Cardiology, 1999; 33; pp. 972-984.

Blessing, Erwin et al., Cardiac Ablation and Renal Denervation Systems Have Distinct Purposes and Different Technical Requirements, JACC Cardiovascular Interventions, vol. 6, No. 3, 2013.

ClinicalTrials.gov, Renal Denervation in Patients with uncontrolled Hypertension in Chinese (2011), www.clinicaltrials.gov/ct2/show/NCT01390831.

Excerpt of Operator's Manual of Boston Scientific's EPT-1000 XP Cardiac Ablation Controller & Accessories, Version of Apr. 2003, (6 pages).

Excerpt of Operator's Manual of Boston Scientific's Maestro 30000 Cardiac Ablation System, Version of Oct. 17, 2005 , (4 pages).

Schneider, Peter A.., "Endovascular Skills—Guidewires, Catheters, Arteriography, Balloon Angioplasty, Stents", pp. 70-71, 101 and 188-190 (1998).

Kandarpa, Krishna et al., "Handbook of Interventional Radiologic Procedures", Third Edition, pp. 194-210 (2002).

ThermoCool Irrigated Catheter and Integrated Ablation System, Biosense Webster (2006).

Mount Sinai School of Medicine clinical trial for Impact of Renal Sympathetic Denervation of Chronic Hypertension, Mar. 2013, http://clinicaltrials.gov/ct2/show/NCT01628198.

Opposition to European Patent No. EP2092957, Granted Jan. 5, 2011, Date of Opposition Oct. 5, 2011, 26 pages.

Opposition to European Patent No. EP1802370, Granted Jan. 5, 2011, Date of Opposition Oct. 5, 2011, 20 pages.

Opposition to European Patent No. EP2037840, Granted Dec. 7, 2011, Date of Opposition Sep. 7, 2012, 25 pages.

Oz, Mehmet, Pressure Relief, TIME, Jan. 9, 2012, 2 pages. <www.time.come/time/printout/0,8816,2103278,00.html>.

Prochnau, Dirk et al., Catheter-based renal denervation for drug-resistant hypertension by using a standard electrophysiology catheter; Euro Intervention 2012, vol. 7, pp. 1077-1080.

Purerfellner, Helmut et al., Pulmonary Vein Stenosis Following Catheter Ablation of Atrial Fibrillation, Curr. Opin. Cardio. 20 :484-490, 2005.

Papademetriou, Vasilios, Renal Sympathetic Denervation for the Treatment of Difficult-to-Control or Resistant Hypertension, Int. Journal of Hypertension, 2011, 8 pages.

Holmes et al., Pulmonary Vein Stenosis Complicating Ablation for Atrial Fibrillation: Clinical Spectrum and Interventional Considerations, JACC: Cardiovascular Interventions, 2: 4, 2009, 10 pages.

Purerfellner, Helmut et al., Incidence, Management, and Outcome in Significant Pulmonary Vein Stenosis Complicating Ablation for Atrial Fibrillation, Am. J. Cardiol , 93, Jun. 1, 2004, 4 pages.

Tsao, Hsuan-Ming, Evaluation of Pulmonary Vein Stenosis after Catheter Ablation of Atrial Fibrillation, Cardiac Electrophysiology Review, 6, 2002, 4 pages.

Wittkampf et al., "Control of radiofrequency lesion size by power regulation," Journal of the American Heart Associate, 1989, 80: pp. 962-968.

Zheng et al., "Comparison of the temperature profile and pathological effect at unipolar, bipolar and phased radiofrequency current configurations," Journal of Interventional Cardiac Electrophysiology, 2001, pp. 401-410.

International Search Report and Written Opinion dated Jan. 23, 2012, International Application No. PCT/US2011/057761, 13 pages.

* cited by examiner

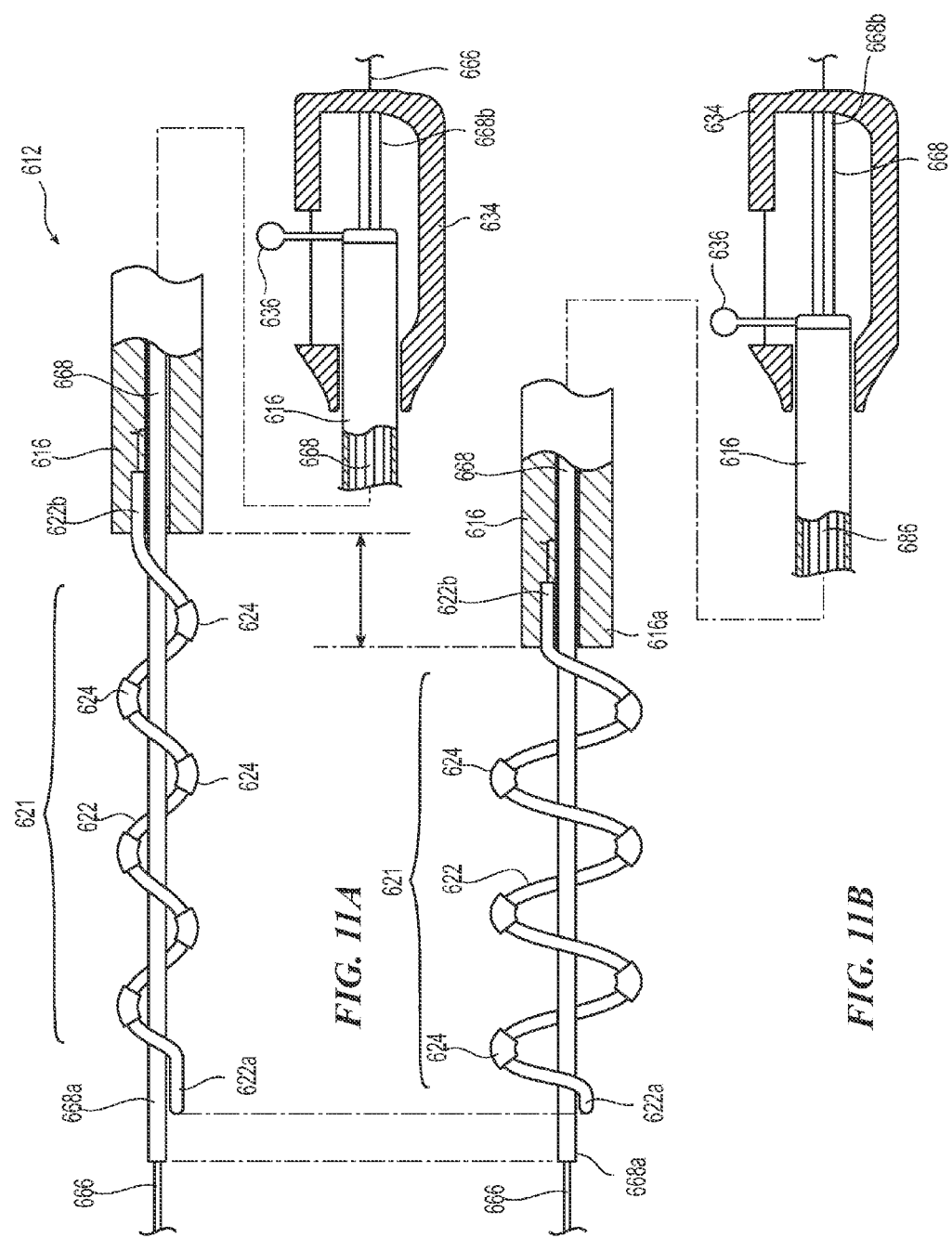

Arterial Vasculature

Venous Vasculature

CATHETER APPARATUSES HAVING MULTI-ELECTRODE ARRAYS FOR RENAL NEUROMODULATION AND ASSOCIATED SYSTEMS AND METHODS

CROSS-REFERENCE TO RELATED APPLICATIONS

The present application claims priority U. S. Provisional Application Ser. No. 61/459,225, filed Dec. 9, 2010.

This application claims the benefit of the following pending applications:

(a) U.S. Provisional Application No. 61/406,531, filed Oct. 25, 2010;

(b) U.S. Provisional Application No. 61/406,960, filed Oct. 26, 2010;

(c) U.S. Provisional Application No. 61/572,290, filed Jan. 28, 2011;

(d) U.S. Provisional Application No. 61/528,001, filed Aug. 26, 2011;

(e) U.S. Provisional Application No. 61/528,086, filed Aug. 26, 2011;

(f) U.S. Provisional Application No. 61/528,091, filed Aug. 26, 2011;

(g) U.S. Provisional Application No. 61/528,108, filed Aug. 26, 2011;

(h) U.S. Provisional Application No. 61/528,684, filed Aug. 29, 2011; and (i) U.S. Provisional Application No. 61/546,512, filed Oct. 12, 2011.

All of the foregoing applications are incorporated herein by reference in their entireties. Further, components and features of embodiments disclosed in the applications incorporated by reference may be combined with various components and features disclosed and claimed in the present application.

TECHNICAL FIELD

The present technology relates generally to renal neuromodulation and associated systems and methods. In particular, several embodiments are directed to multi-electrode radio frequency (RF) ablation catheter apparatuses for intravascular renal neuromodulation and associated systems and methods.

BACKGROUND

The sympathetic nervous system (SNS) is a primarily involuntary bodily control system typically associated with stress responses. Fibers of the SNS innervate tissue in almost every organ system of the human body and can affect characteristics such as pupil diameter, gut motility, and urinary output. Such regulation can have adaptive utility in maintaining homeostasis or in preparing the body for rapid response to environmental factors. Chronic activation of the SNS, however, is a common maladaptive response that can drive the progression of many disease states. Excessive activation of the renal SNS in particular has been identified experimentally and in humans as a likely contributor to the complex pathophysiology of hypertension, states of volume overload (such as heart failure), and progressive renal disease. For example, radiotracer dilution has demonstrated increased renal norepinephrine (NE) spillover rates in patients with essential hypertension.

Cardio-renal sympathetic nerve hyperactivity can be particularly pronounced in patients with heart failure. For example, an exaggerated NE overflow from the heart and kidneys to plasma is often found in these patients. Heightened SNS activation commonly characterizes both chronic and end stage renal disease. In patients with end stage renal disease, NE plasma levels above the median have been demonstrated to be predictive for cardiovascular diseases and several causes of death. This is also true for patients suffering from diabetic or contrast nephropathy. Evidence suggests that sensory afferent signals originating from diseased kidneys are major contributors to initiating and sustaining elevated central sympathetic outflow.

Sympathetic nerves innervating the kidneys terminate in the blood vessels, the juxtaglomerular apparatus, and the renal tubules. Stimulation of the renal sympathetic nerves can cause increased renin release, increased sodium ($Na^+$) reabsorption, and a reduction of renal blood flow. These neural regulation components of renal function are considerably stimulated in disease states characterized by heightened sympathetic tone and likely contribute to increased blood pressure in hypertensive patients. The reduction of renal blood flow and glomerular filtration rate as a result of renal sympathetic efferent stimulation is likely a cornerstone of the loss of renal function in cardio-renal syndrome (i.e., renal dysfunction as a progressive complication of chronic heart failure). Pharmacologic strategies to thwart the consequences of renal efferent sympathetic stimulation include centrally acting sympatholytic drugs, beta blockers (intended to reduce renin release), angiotensin converting enzyme inhibitors and receptor blockers (intended to block the action of angiotensin II and aldosterone activation consequent to renin release), and diuretics (intended to counter the renal sympathetic mediated sodium and water retention). These pharmacologic strategies, however, have significant limitations including limited efficacy, compliance issues, side effects, and others. Accordingly, there is a strong public-health need for alternative treatment strategies.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure.

FIG. 5A-5D illustrate various embodiments of energy delivery elements or devices for use with the treatment assembly of FIGS. 4A and 4B.

FIG. 11A is a broken side view in part section of a treatment device in a delivery state in accordance with another embodiment of the technology.

FIG. 11B is a broken side view in part section of the treatment device of FIG. 11A in a deployed state.

DETAILED DESCRIPTION

Figure 1:
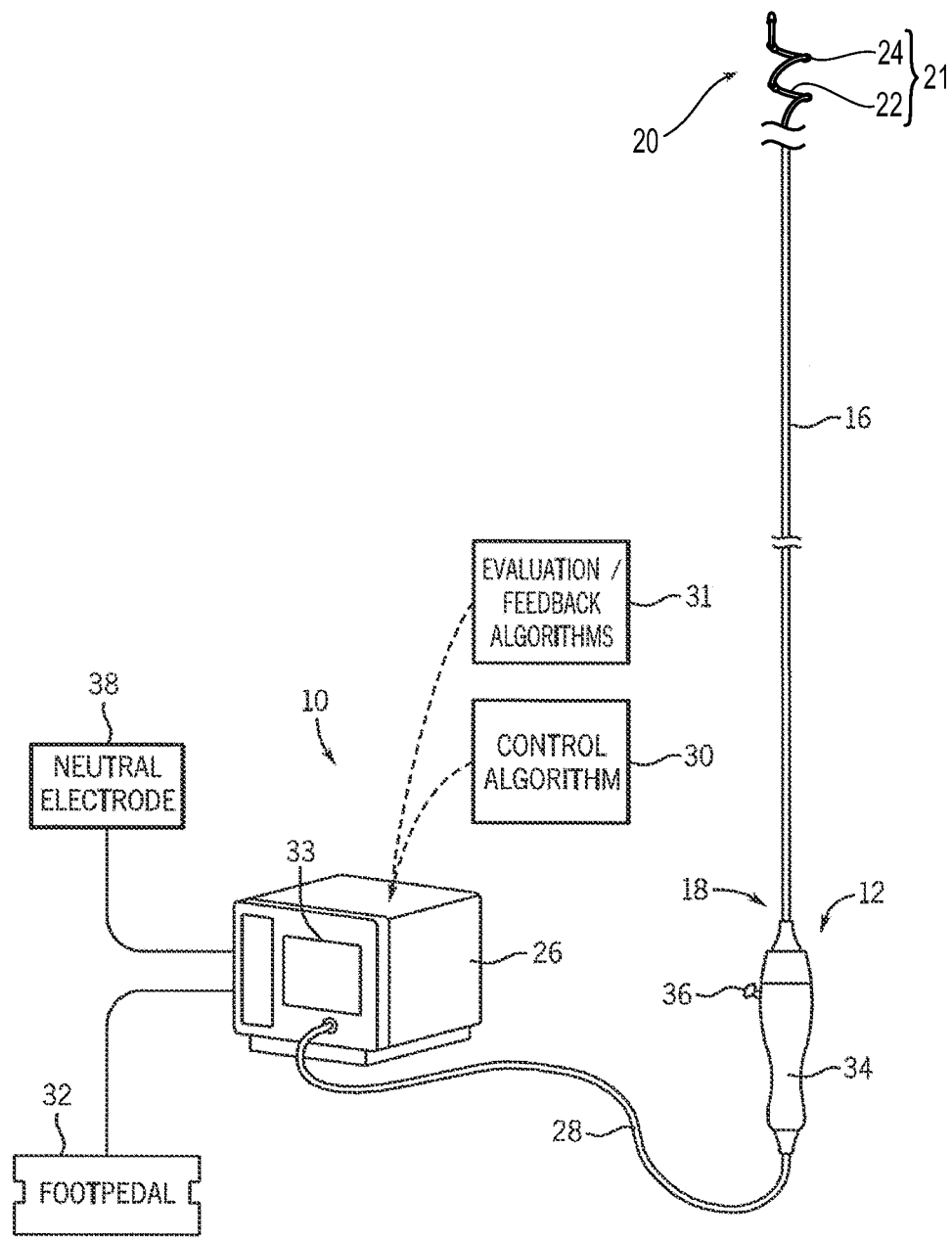
FIG. 1 illustrates an intravascular renal neuromodulation system configured in accordance with an embodiment of the present technology.

The present technology is directed to apparatuses, systems, and methods for achieving electrically- and/or thermally-induced renal neuromodulation (i.e., rendering neural fibers that innervate the kidney inert or inactive or otherwise completely or partially reduced in function) by percutaneous transluminal intravascular access. In particular, embodiments of the present technology relate to apparatuses, systems, and methods that incorporate a catheter treatment device having a multi-electrode array movable between a delivery or low-profile state (e.g., a generally straight shape) and a deployed state (e.g., a radially expanded, generally helical shape). The electrodes or energy delivery elements carried by the array are configured to deliver energy (e.g., electrical energy, radio frequency (RF) electrical energy, pulsed electrical energy, thermal energy) to a renal artery after being advanced via catheter along a percutaneous transluminal path (e.g., a femoral artery puncture, an iliac artery and the aorta, a radial artery, or another suitable intravascular path). The multi-electrode array is sized and shaped so that the electrodes or energy delivery elements contact an interior wall of the renal artery when the array is in the deployed (e.g., helical) state within the renal artery. In addition, the helical shape of the deployed array allows blood to flow through the helix, which is expected to help prevent occlusion of the renal artery during activation of the energy delivery element. Further, blood flow in and around the array may cool the associated electrodes and/or the surrounding tissue. In some embodiments, cooling the energy delivery elements allows for the delivery of higher power levels at lower temperatures than may be reached without cooling. This feature is expected to help create deeper and/or larger lesions during therapy, reduce intimal surface temperature, and/or allow longer activation times with reduced risk of overheating during treatment.

Specific details of several embodiments of the technology are described below with reference to FIGS. 1-32B. Although many of the embodiments are described below with respect to devices, systems, and methods for intravascular modulation of renal nerves using multi-electrode arrays, other applications and other embodiments in addition to those described herein are within the scope of the technology. Additionally, several other embodiments of the technology can have different configurations, components, or procedures than those described herein. A person of ordinary skill in the art, therefore, will accordingly understand that the technology can have other embodiments with additional elements, or the technology can have other embodiments without several of the features shown and described below with reference to FIGS. 1-32B.

As used herein, the terms "distal" and "proximal" define a position or direction with respect to the treating clinician or clinician's control device (e.g., a handle assembly). "Distal" or "distally" are a position distant from or in a direction away from the clinician or clinician's control device. "Proximal"

and "proximally" are a position near or in a direction toward the clinician or clinician's control device.

I. Renal Neuromodulation

Renal neuromodulation is the partial or complete incapacitation or other effective disruption of nerves innervating the kidneys. In particular, renal neuromodulation comprises inhibiting, reducing, and/or blocking neural communication along neural fibers (i.e., efferent and/or afferent nerve fibers) innervating the kidneys. Such incapacitation can be long-term (e.g., permanent or for periods of months, years, or decades) or short-term (e.g., for periods of minutes, hours, days, or weeks). Renal neuromodulation is expected to efficaciously treat several clinical conditions characterized by increased overall sympathetic activity, and in particular conditions associated with central sympathetic over stimulation such as hypertension, heart failure, acute myocardial infarction, metabolic syndrome, insulin resistance, diabetes, left ventricular hypertrophy, chronic and end stage renal disease, inappropriate fluid retention in heart failure, cardio-renal syndrome, and sudden death. The reduction of afferent neural signals contributes to the systemic reduction of sympathetic tone/drive, and renal neuromodulation is expected to be useful in treating several conditions associated with systemic sympathetic over activity or hyperactivity. Renal neuromodulation can potentially benefit a variety of organs and bodily structures innervated by sympathetic nerves. For example, a reduction in central sympathetic drive may reduce insulin resistance that afflicts patients with metabolic syndrome and Type II diabetics. Additionally, osteoporosis can be sympathetically activated and might benefit from the downregulation of sympathetic drive that accompanies renal neuromodulation. A more detailed description of pertinent patient anatomy and physiology is provided in Section IX below.

Various techniques can be used to partially or completely incapacitate neural pathways, such as those innervating the kidney. The purposeful application of energy (e.g., electrical energy, thermal energy) to tissue by energy delivery element(s) can induce one or more desired thermal heating effects on localized regions of the renal artery and adjacent regions of the renal plexus RP, which lay intimately within or adjacent to the adventitia of the renal artery. The purposeful application of the thermal heating effects can achieve neuromodulation along all or a portion of the renal plexus RP.

The thermal heating effects can include both thermal ablation and non-ablative thermal alteration or damage (e.g., via sustained heating and/or resistive heating). Desired thermal heating effects may include raising the temperature of target neural fibers above a desired threshold to achieve non-ablative thermal alteration, or above a higher temperature to achieve ablative thermal alteration. For example, the target temperature can be above body temperature (e.g., approximately 37° C.) but less than about 45° C. for non-ablative thermal alteration, or the target temperature can be about 45° C. or higher for the ablative thermal alteration.

More specifically, exposure to thermal energy (heat) in excess of a body temperature of about 37° C., but below a temperature of about 45° C., may induce thermal alteration via moderate heating of the target neural fibers or of vascular structures that perfuse the target fibers. In cases where vascular structures are affected, the target neural fibers are denied perfusion resulting in necrosis of the neural tissue. For example, this may induce non-ablative thermal alteration in the fibers or structures. Exposure to heat above a temperature of about 45° C., or above about 60° C., may induce thermal alteration via substantial heating of the fibers or structures. For example, such higher temperatures may thermally ablate the target neural fibers or the vascular structures. In some patients, it may be desirable to achieve temperatures that thermally ablate the target neural fibers or the vascular structures, but that are less than about 90° C., or less than about 85° C., or less than about 80° C., and/or less than about 75° C. Regardless of the type of heat exposure utilized to induce the thermal neuromodulation, a reduction in renal sympathetic nerve activity ("RSNA") is expected.

II. Selected Embodiments Of Catheter Apparatuses Having Multi-Electrode Arrays FIG. 1 illustrates a renal neuromodulation system 10 ("system 10") configured in accordance with an embodiment of the present technology. The system 10 includes an intravascular treatment device 12 operably coupled to an energy source or energy generator 26. In the embodiment shown in FIG. 1, the treatment device 12 (e.g., a catheter) includes an elongated shaft 16 having a proximal portion 18, a handle 34 at a proximal region of the proximal portion 18, and a distal portion 20 extending distally relative to the proximal portion 18. The treatment device 12 further includes a therapeutic assembly or treatment section 21 at the distal portion 20 of the shaft 16. As explained in further detail below, the therapeutic assembly 21 can include an array of two or more electrodes or energy delivery elements 24 configured to be delivered to a renal blood vessel (e.g., a renal artery) in a low-profile configuration. Upon delivery to the target treatment site within the renal blood vessel, the therapeutic assembly 21 is further configured to be deployed into an expanded state (e.g., a generally helical or spiral configuration) for delivering energy at the treatment site and providing therapeutically-effective electrically- and/or thermally-induced renal neuromodulation. Alternatively, the deployed state may be non-helical provided that the deployed state delivers the energy to the treatment site. In some embodiments, the therapeutic assembly 21 may be placed or transformed into the deployed state or arrangement via remote actuation, e.g., via an actuator 36, such as a knob, pin, or lever carried by the handle 34. In other embodiments, however, the therapeutic assembly 21 may be transformed between the delivery and deployed states using other suitable mechanisms or techniques.

The proximal end of the therapeutic assembly 21 is carried by or affixed to the distal portion 20 of the elongated shaft 16. A distal end of the therapeutic assembly 21 may terminate the treatment device 12 with, for example, an atraumatic rounded tip or cap. Alternatively, the distal end of the therapeutic assembly 21 may be configured to engage another element of the system 10 or treatment device 12. For example, the distal end of the therapeutic assembly 21 may define a passageway for engaging a guide wire (not shown) for delivery of the treatment device using over-the-wire ("OTW") or rapid exchange ("RX") techniques. Further details regarding such arrangements are described below with reference to FIGS. 9A-17E.

The energy source or energy generator 26 (e.g., a RF energy generator) is configured to generate a selected form and magnitude of energy for delivery to the target treatment site via the energy delivery elements 24. The energy generator 26 can be electrically coupled to the treatment device 12 via a cable 28. At least one supply wire (not shown) passes along the elongated shaft 16 or through a lumen in the elongated shaft 16 to the energy delivery elements 24 and transmits the treatment energy to the energy delivery elements 24. In some embodiments, each energy delivery element 24 includes its own supply wire. In other embodiments, however, two or more energy delivery elements 24 may be electrically coupled to the same supply wire. A control mechanism, such as foot pedal 32, may be connected (e.g., pneumatically connected or electrically connected) to the energy generator 26 to allow the operator to initiate, terminate and, optionally, adjust various operational characteristics of the generator, including, but not limited to, power delivery. The system 10 may also include a remote control device (not shown) that can be positioned in a sterile field and operably coupled to the energy delivery elements 24. The remote control device is configured to allow for selectively turning on/off the electrodes. In other embodiments, the remote control device may be built into the handle assembly 34. The energy generator 26 can be configured to deliver the treatment energy via an automated control algorithm 30 and/or under the control of the clinician. In addition, the energy generator 26 may include one or more evaluation or feedback algorithms 31 to provide feedback to the clinician before, during, and/or after therapy. Further details regarding suitable control algorithms and evaluation/feedback algorithms are described below with reference to FIGS. 20-27.

Figure 2:
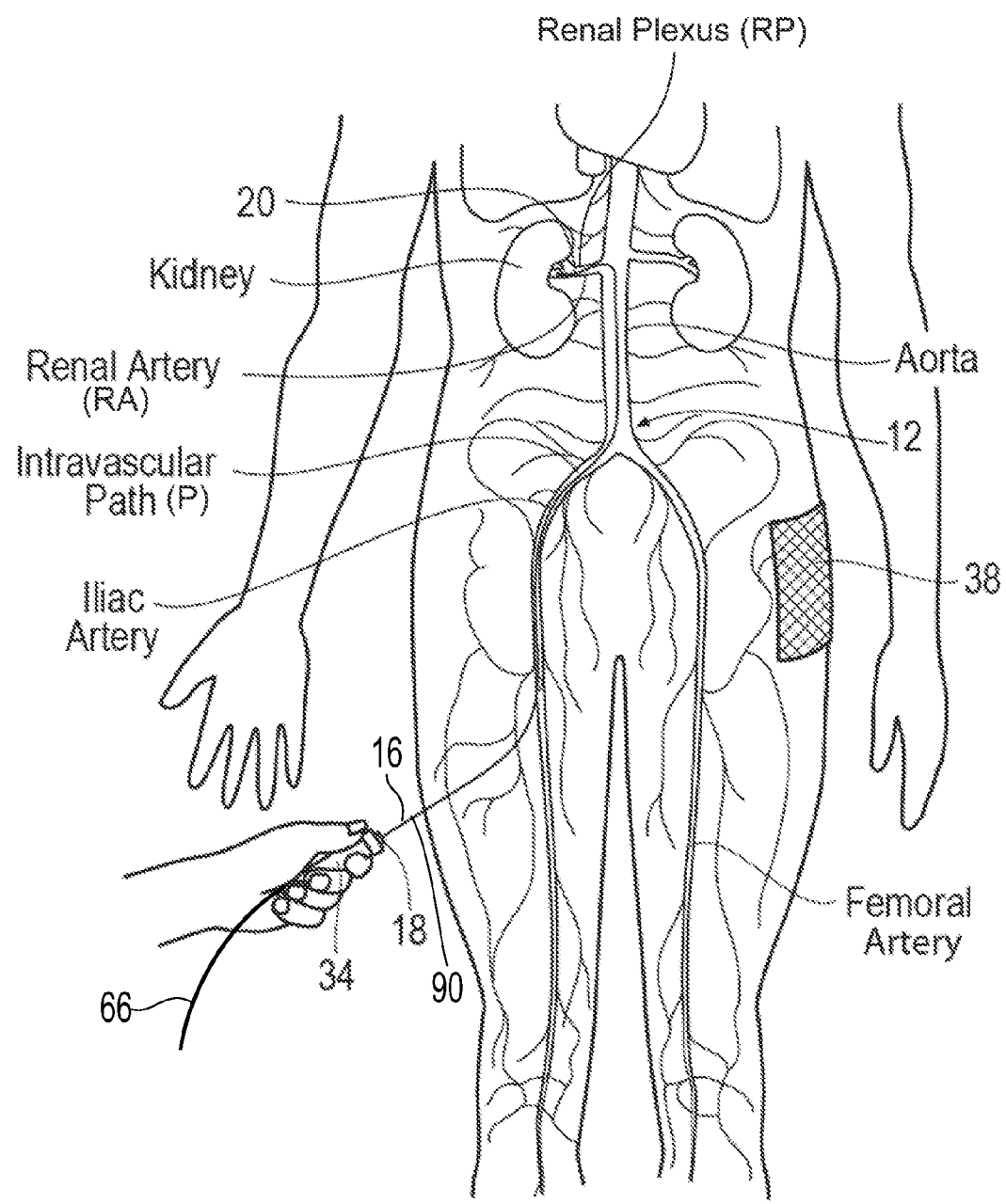
FIG. 2 illustrates modulating renal nerves with a multi-electrode catheter apparatus in accordance with an embodiment of the present technology.

In some embodiments, the system 10 may be configured to provide delivery of a monopolar electric field via the energy delivery elements 24. In such embodiments, a neutral or dispersive electrode 38 may be electrically connected to the energy generator 26 and attached to the exterior of the patient (as shown in FIG. 2). Additionally, one or more sensors (not shown), such as one or more temperature (e.g., thermocouple, thermistor, etc.), impedance, pressure, optical, flow, chemical or other sensors, may be located proximate to or within the energy delivery elements 24 and connected to one or more supply wires (not shown). For example, a total of two supply wires may be included, in which both wires could transmit the signal from the sensor and one wire could serve dual purpose and also convey the energy to the energy delivery elements 24. Alternatively, a different number of supply wires may be used to transmit energy to the energy delivery elements 24.

The energy generator 26 may be part of a device or monitor that may include processing circuitry, such as a microprocessor, and a display. The processing circuitry may be configured to execute stored instructions relating to the control algorithm 30. The monitor may be configured to communicate with the treatment device 12 (e.g., via cable 28) to control power to the energy delivery elements 24 and/or to obtain signals from the energy delivery elements 24 or any associated sensors. The monitor may be configured to provide indications of power levels or sensor data, such as audio, visual or other indications, or may be configured to communicate the information to another device. For example, the energy generator 26 may also be configured to be operably coupled to a catheter lab screen or system for displaying treatment information.

FIG. 2 (with additional reference to FIG. 30) illustrates modulating renal nerves with an embodiment of the system 10. The treatment device 12 provides access to the renal plexus RP through an intravascular path P, such as a percutaneous access site in the femoral (illustrated), brachial, radial, or axillary artery to a targeted treatment site within a respective renal artery RA. As illustrated, a section of the proximal portion 18 of the shaft 16 is exposed externally of the patient. By manipulating the proximal portion 18 of the shaft 16 from outside the intravascular path P, the clinician may advance the shaft 16 through the sometimes tortuous intravascular path P and remotely manipulate the distal portion 20 of the shaft 16. Image guidance, e.g., computed tomography (CT), fluoroscopy, intravascular ultrasound (IVUS), optical coherence tomography (OCT), or another suitable guidance modality, or combinations thereof, may be used to aid the clinician's manipulation. Further, in some embodiments, image guidance components (e.g., IVUS, OCT) may be incorporated into the treatment device 12 itself. After the therapeutic assembly 21 is adequately positioned in the renal artery RA, it can be radially expanded or otherwise deployed using the handle 34 or other suitable means until the energy delivery elements 24 are in stable contact with the inner wall of the renal artery RA. The purposeful application of energy from the energy delivery elements 24 is then applied to tissue to induce one or more desired neuromodulating effects on localized regions of the renal artery and adjacent regions of the renal plexus RP, which lay intimately within, adjacent to, or in close proximity to the adventitia of the renal artery RA. The purposeful application of the energy may achieve neuromodulation along all or at least a portion of the renal plexus RP.

The neuromodulating effects are generally a function of, at least in part, power, time, contact between the energy delivery elements 24 and the vessel wall, and blood flow through the vessel. The neuromodulating effects may include denervation, thermal ablation, and non-ablative thermal alteration or damage (e.g., via sustained heating and/or resistive heating). Desired thermal heating effects may include raising the temperature of target neural fibers above a desired threshold to achieve non-ablative thermal alteration, or above a higher temperature to achieve ablative thermal alteration. For example, the target temperature may be above body temperature (e.g., approximately 37° C.) but less than about 45° C. for non-ablative thermal alteration, or the target temperature may be about 45° C. or higher for the ablative thermal alteration. Desired non-thermal neuromodulation effects may include altering the electrical signals transmitted in a nerve.

In some embodiments, the energy delivery elements 24 of the therapeutic assembly 21 may be proximate to, adjacent to, or carried by (e.g., adhered to, threaded over, wound over, and/or crimped to) a support structure 22. The proximal end of the support structure 22 is preferably coupled to the distal portion 20 of the elongated shaft 16 via a coupling (not shown). The coupling may be an integral component of the elongated shaft 16 (i.e., may not be a separate piece) or the coupling may be a separate piece such as a collar (e.g., a radiopaque band) wrapped around an exterior surface of the elongated shaft 16 to secure the support structure 22 to the elongated shaft 16. In other embodiments, however, the support structure 22 may be associated with the elongated shaft 16 using another arrangement and/or different features.

In still another embodiment, the energy delivery elements 24 may form or define selected portions of, or the entirety of, the support structure 22 itself. That is, as is described in further detail below, the support structure 22 may be capable of delivering energy. Moreover, although in some embodiments the therapeutic assembly 21 may function with a single energy delivery element, it will be appreciated that the therapeutic assembly 21 preferably includes a plurality of energy delivery elements 24 associated with or defining the support structure 22. When multiple energy delivery elements 24 are provided, the energy delivery elements 24 may deliver power independently (i.e., may be used in a monopolar fashion), either simultaneously, selectively, or sequentially, and/or may deliver power between any desired combination of the elements (i.e., may be used in a bipolar fashion). Furthermore, the clinician optionally may choose which energy delivery element(s) 24 are used for power delivery in order to form highly customized lesion(s) within the renal artery having a variety of shapes or patterns.

Figure 3A:
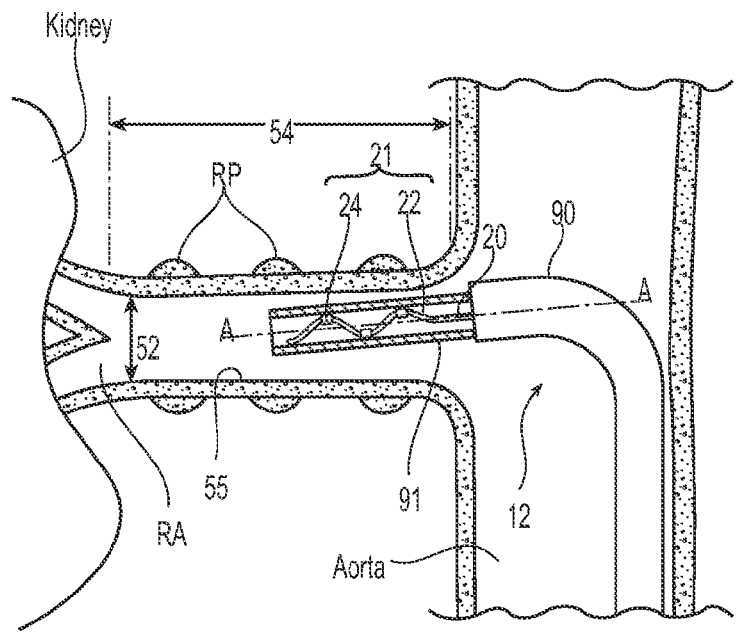
FIG. 3A is a view of a distal portion of a catheter shaft and a multi-electrode array in a delivery state (e.g., low-profile or collapsed configuration) within a renal artery used in conjunction with a guide catheter in accordance with an embodiment of the present technology.
Figure 3B:
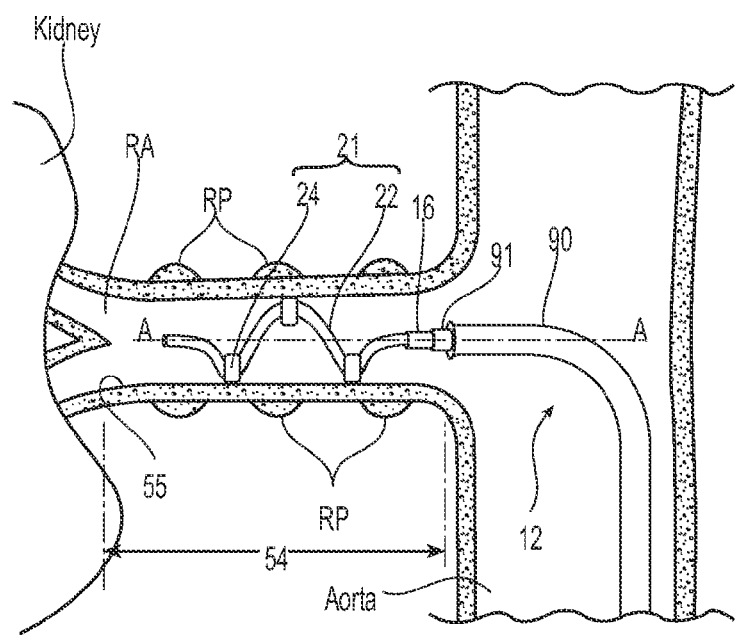
FIG. 3B is a view of the distal portion of the catheter shaft and the multi-electrode array of FIG. 3A in a deployed state (e.g., expanded configuration) within a renal artery in accordance with an embodiment of the technology.
Figure 3C:
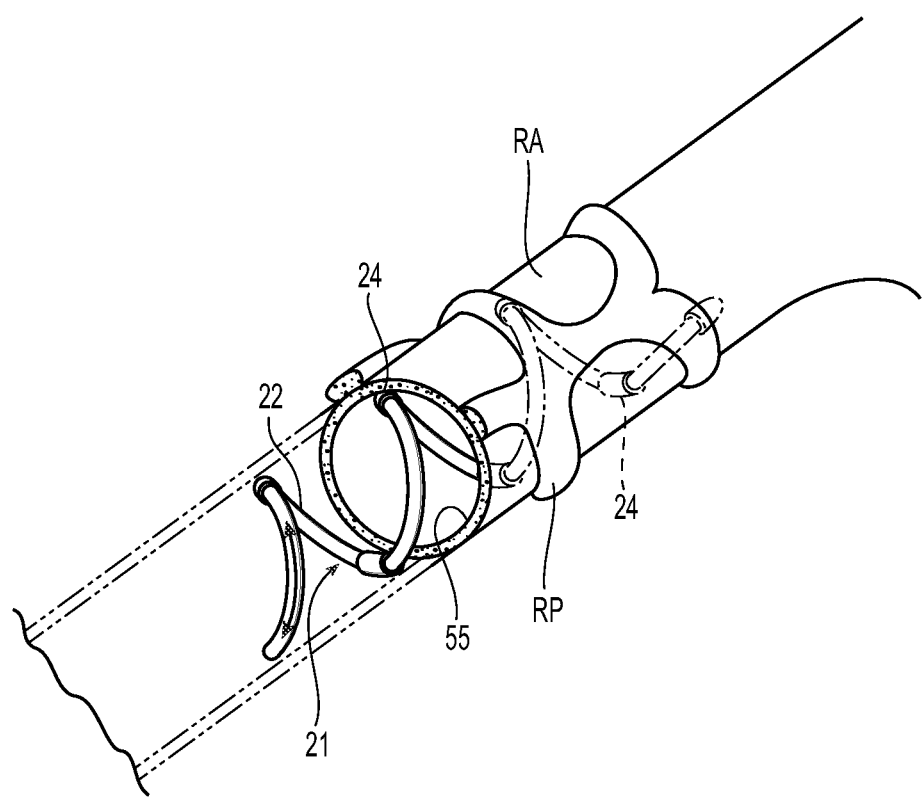
FIG. 3C is a partially cutaway, isometric view of a treatment device in a deployed state within a renal artery in accordance with an embodiment of the technology.

FIG. 3A is a cross-sectional view illustrating one embodiment of the distal portion 20 of the shaft 16 and the therapeutic assembly 21 in a delivery state (e.g., low-profile or collapsed configuration) within a renal artery RA, and FIGS. 3B and 3C illustrate the therapeutic assembly 21 in a deployed state (e.g., expanded or helical configuration) within the renal artery. Referring first to FIG. 3A, the collapsed or delivery arrangement of the therapeutic assembly 21 defines a low profile about the longitudinal axis A-A of the assembly such that a transverse dimension of the therapeutic assembly 21 is sufficiently small to define a clearance distance between an arterial wall 55 and the treatment device 12. The delivery state facilitates insertion and/or removal of the treatment device 12 and, if desired, repositioning of the therapeutic assembly 21 within the renal artery RA.

In the collapsed configuration, for example, the geometry of the support structure 22 facilitates movement of the therapeutic assembly 21 through a guide catheter 90 to the treatment site in the renal artery RA. Moreover, in the collapsed configuration, the therapeutic assembly 21 is sized and shaped to fit within the renal artery RA and has a diameter that is less than a renal artery inner diameter 52 and a length (from a proximal end of the therapeutic assembly 21 to a distal end of the therapeutic assembly 21) that is less than a renal artery length 54. Further, as described in greater detail below, the geometry of the support structure 22 is also arranged to define (in the delivery state) a minimum transverse dimension about its central axis that is less than the renal artery inner diameter 52 and a maximum length in the direction of the central axis that is preferably less than the renal artery length 54. In one embodiment, for example, the minimum diameter of the therapeutic assembly 21 is approximately equal to the interior diameter of the elongated shaft 16.

The distal portion 20 of the shaft 16 may flex in a substantial fashion to gain entrance into a respective left/right renal artery by following a path defined by a guide catheter, a guide wire, or a sheath. For example, the flexing of distal portion 20 may be imparted by the guide catheter 90, such as a renal guide catheter with a preformed bend near the distal end that directs the shaft 16 along a desired path, from the percutaneous insertion site to the renal artery RA. In another embodiment, the treatment device 12 may be directed to the treatment site within the renal artery RA by engaging and tracking a guide wire (e.g., guide wire 66 of FIG. 2) that is inserted into the renal artery RA and extends to the percutaneous access site. In operation, the guide wire is preferably first delivered into the renal artery RA and the elongated shaft 16 comprising a guide wire lumen is then passed over the guide wire into the renal artery RA. In some guide wire procedures, a tubular delivery sheath 1291 (described in greater detail below with reference to FIGS. 16A and 16B) is passed over the guide wire (i.e., the lumen defined by the delivery sheath slides over the guide wire) into the renal artery RA. Once the delivery sheath 1291 (FIG. 16A) is placed in the renal artery RA, the guide wire may be removed and exchanged for a treatment catheter (e.g., treatment device 12) that may be delivered through the delivery sheath 1291 into the renal artery RA. Furthermore, in some embodiments, the distal portion 20 can be directed or "steered" into the renal artery RA via the handle assembly 34 (FIGS. 1 and 2), for example, by an actuatable element 36 or by another control element. In particular, the flexing of the elongated shaft 16 may be accomplished as provided in U.S. patent application Ser. No. 12/545,648, "Apparatus, Systems, and Methods for achieving Intravascular, Thermally-Induced Renal Neuromodulation" to Wu et al., which is incorporated herein by reference in its entirety. Alternatively, or in addition, the treatment device 12 and its distal portion 20 may be flexed by being inserted through a steerable guide catheter (not shown) that includes a preformed or steerable bend near its distal end that can be adjusted or re-shaped by manipulation from the proximal end of the guide catheter.

The maximum outer dimension (e.g., diameter) of any section of the treatment device 12, including elongated shaft 16 and the energy delivery elements 24 of the therapeutic assembly 21 can be defined by an inner diameter of the guide catheter 90 through which the device 12 is passed. In one particular embodiment, for example, an 8 French guide catheter having, for example, an inner diameter of approximately 0.091 inch (2.31 mm) may be used as a guide catheter to access the renal artery. Allowing for a reasonable clearance tolerance between the energy delivery elements 24 and the guide catheter, the maximum outer dimension of the therapeutic assembly 21 is generally less than or equal to approximately 0.085 inch (2.16 mm). For a therapeutic assembly having a substantially helical support structure for carrying the energy delivery elements 24, the expanded or helical configuration preferably defines a maximum width of less than or equal to approximately 0.085 inch (2.16 mm). However, use of a smaller 5 French guide catheter may require the use of smaller outer diameters along the treatment device 12. For example, a therapeutic assembly 21 having a helical support structure 22 that is to be routed within a 5 French guide catheter preferably has an outer dimension or maximum width of no greater than about 0.053 inch (1.35 mm). In still other embodiments, it may be desirable to have a therapeutic assembly 21 with a maximum width substantially under 0.053 inch (1.35 mm) provided there is sufficient clearance between the energy delivery elements and the guide catheter. Moreover, in some embodiments it may be desirable to have an arrangement in which the guide catheter and the therapeutic assembly 21 define a ratio of diameters of about 1.5:1. In another example, the helical structure and energy delivery element 24 that are to be delivered within a 6 French guide catheter would have an outer dimension of no great than 0.070 inch (1.78 mm). In still further examples, other suitable guide catheters may be used, and outer dimensions and/or arrangements of the treatment device 12 can vary accordingly.

After locating the therapeutic assembly 21 at the distal portion 20 of the shaft 16 in the renal artery RA, the therapeutic assembly 21 is transformed from its delivery state to its deployed state or deployed arrangement. The transformation may be initiated using an arrangement of device components as described herein with respect to the particular embodiments and their various modes of deployment. As described in greater detail below and in accordance with one or more embodiments of the present technology, the therapeutic assembly may be deployed by a control member, such as for example a pull- or tension-wire, guide wire, shaft or stylet engaged internally or externally with the support structure of the therapeutic assembly to apply a deforming or shaping force to the assembly to transform it into its deployed state. Alternatively, the therapeutic assembly 21 may be self expanding or deploying such that removal of a radial restraint results in deployment of the assembly. Further, the modality used to transform the therapeutic assembly 21 from the delivery state into the deployed state may, in most embodiments, be reversed to transform the therapeutic assembly 21 back to the delivery state from the deployed state.

Further manipulation of the support structure 22 and the energy delivery elements 24 within the respective renal artery RA establishes apposition of the energy delivery elements 24 against the tissue along an interior wall of the respective renal artery RA. For example, as shown in FIGS. 3B and 3C, the therapeutic assembly 21 is expanded within the renal artery RA such that the energy delivery elements 24 are in contact with the renal artery wall 55. In some embodiments, manipulation of the distal portion 20 will also facilitate contact between the energy delivery elements 24 and the wall of the renal artery. Embodiments of the support structures described herein (e.g., the support structure 22) are expected to ensure that the contact force between the renal artery inner wall 55 and the energy delivery elements 24 does not exceed a maximum value. In addition, the support structure 22 or other suitable support structures described herein preferably provide for a consistent contact force against the arterial wall 55 that may allow for consistent lesion formation.

The alignment may also include alignment of geometrical aspects of the energy delivery elements 24 with the renal artery wall 55. For example, in embodiments in which the energy delivery elements 24 have a cylindrical shape with rounded ends, alignment may include alignment of the longitudinal surface of the individual energy delivery elements 24 with the artery wall 55. In another example, an embodiment may comprise energy delivery elements 24 having a structured shape or inactive surface, and alignment may include aligning the energy delivery elements 24 such that the structured shape or inactive surface is not in contact with the artery wall 55.

As best seen in FIGS. 3B and 3C, in the deployed state, the therapeutic assembly 21 defines a substantially helical support structure 22 in contact with the renal artery wall 55 along a helical path. One advantage of this arrangement is that pressure from the helical structure can be applied to a large range of radial directions without applying pressure to a circumference of the vessel. Thus, the helically-shaped therapeutic assembly 21 is expected to provide stable contact between the energy delivery elements 24 and the artery wall 55 when the wall moves in any direction. Furthermore, pressure applied to the vessel wall 55 along a helical path is less likely to stretch or distend a circumference of a vessel that could thereby cause injury to the vessel tissue. Still another feature of the expanded helical structure is that it may contact the vessel wall in a large range of radial directions and maintain a sufficiently open lumen in the vessel allowing blood to flow through the helix during therapy.

Figure 4A:
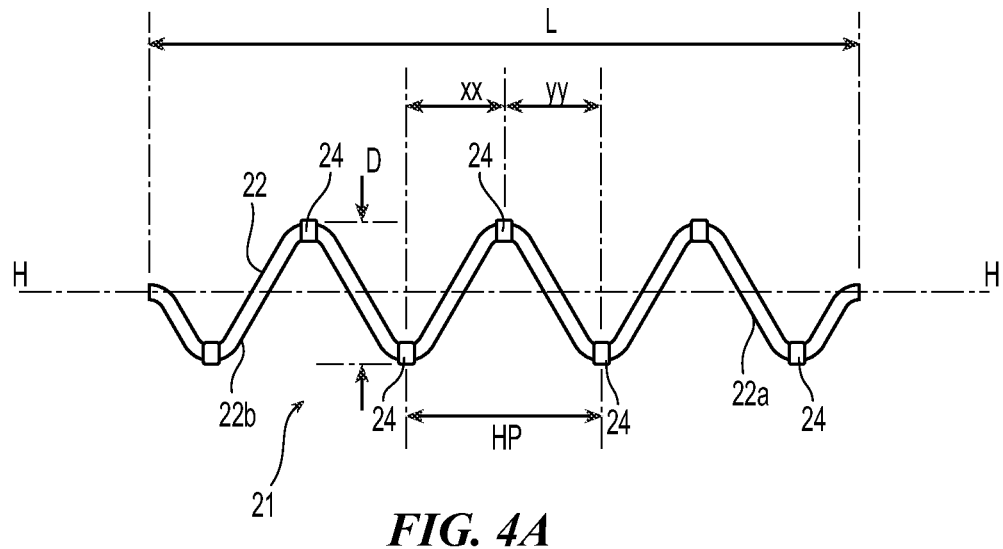
FIG. 4A is a plan view of a treatment assembly for use in a treatment device in accordance with an embodiment of the technology.

As best seen in FIG. 3B, in the deployed state, the support structure 22 defines a maximum axial length of the therapeutic assembly 21 that is approximately equal to or less than a renal artery length 54 of a main renal artery (i.e., a section of a renal artery proximal to a bifurcation). Because this length can vary from patient to patient, it is envisioned that the deployed helical-shaped support structure 22 may be fabricated in different sizes (e.g., with varying lengths L and/or diameters D as shown in FIG. 4A) that may be appropriate for different patients. Referring to FIGS. 3B and 3C, in the deployed state, the helical-shaped therapeutic assembly 21 provides for circumferentially discontinuous contact between the energy delivery elements 24 and the inner wall 55 of the renal artery RA. That is, the helical path may comprise a partial arc (i.e., <360°), a complete arc (i.e., 360°) or a more than complete arc (i.e., >360°) along the inner wall of a vessel about the longitudinal axis of the vessel. In some embodiments, however, the arc is not substantially in one plane normal to the central axis of the artery, but instead preferably defines an obtuse angle with the central axis of the artery.

A. The Helical Structure

Figure 4B:
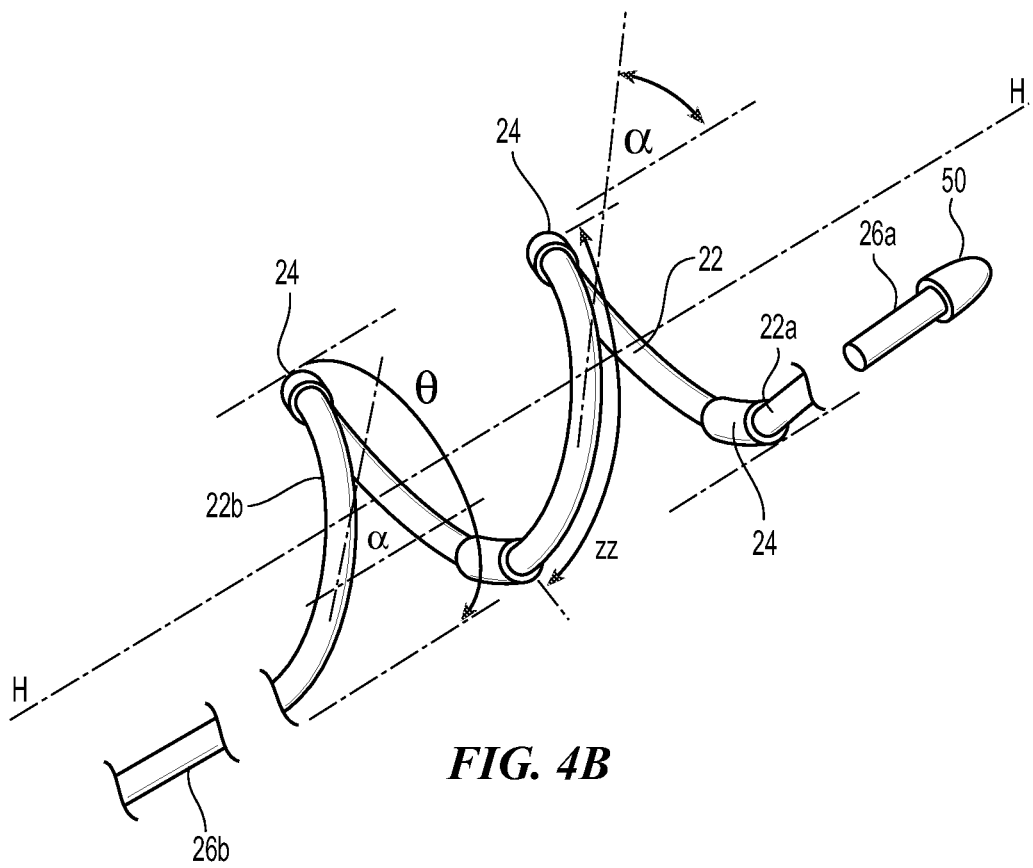
FIG. 4B is an isometric view of the treatment assembly of FIG. 4A.

FIG. 4A is a plan view of an embodiment of a therapeutic or treatment assembly 21 for use with a treatment device (e.g., treatment device 12) in accordance with an embodiment of the technology, and FIG. 4B is an isometric view of the therapeutic assembly 21 of FIG. 4A. The energy delivery elements 24 depicted in FIGS. 4A and 4B are merely for illustrative purposes, and it will be appreciated that the treatment assembly 21 can include a different number and/or arrangement of energy delivery elements 24.

As shown in FIGS. 4A and 4B, a helix may be characterized, at least in part, by its overall diameter D, length L, helix angle α (an angle between a tangent line to the helix and its axis), pitch HP (longitudinal distance of one complete helix turn measured parallel to its axis), and number of revolutions (number of times the helix completes a 360° revolution about its axis).

In particular, the deployed or expanded configuration of the helix may be characterized by its axial length L along the axis of elongation in free space, e.g., not restricted by a vessel wall or other structure. As the helical support structure 22 radially expands from its delivery state, its diameter D increases and its length L decreases. That is, when the helical structure deploys, a distal end 22a moves axially towards the proximal end 22b (or vice versa). Accordingly, the deployed length L is less than the unexpanded or delivery length. In certain embodiments, only one of the distal end portion 22a or the proximal end portion 22b of the support structure 22 is fixedly coupled to the elongated shaft 16 or an extension thereof. In other embodiments, the support structure 22 may be transformed to its deployed or expanded configuration by twisting the distal and proximal end portions 22a and 22b relative to one another.

Referring to FIG. 4B, the deployed helically-shaped support structure 22 optionally comprises a distal extension 26a distal to the helical portion that is relatively straight and may terminate with an atraumatic (e.g., rounded) tip 50. The distal extension 26a including the tip 50 may reduce the risk of injuring the blood vessel as the helical structure is expanding and/or as a delivery sheath is retracted, and may facilitate alignment of the helical structure in a vessel as it expands. In some embodiments, the distal extension 26a is generally straight (but flexible) and has a length of less than about 40 mm (e.g., between 2 mm and 10 mm). The tip 50 can be made from a polymer or metal that is fixed to the end of the structural element by adhesive, welding, crimping, over-molding, and/or solder. In other embodiments, the tip 50 may be made from the same material as the structural element and fabricated into the tip 50 by machining or melting. In other embodiments, the distal extension 26a may have a different configuration and/or features. For example, in some embodiments the tip 50 may comprise an energy delivery element or a radiopaque marker. Further, the distal extension 26a is an optional feature that may not be included in all embodiments.

The helical structure may also optionally have a proximal extension 26b that is relatively straight compared to the helically shaped region of the support structure 22. The proximal extension 26b, for example, may be an extension of the support structure 22 and may have a length between 0 mm and 40 mm (e.g., between about 2 and 10 mm). Alternatively, the proximal extension 26b may be comprised of a separate material (e.g., a polymer fiber) with more flexibility than the rest of the support structure 22. The proximal extension 26b is configured to provide a flexible connection between the helical region of the support structure 22 and the distal end of the elongated shaft 16 (FIG. 1). This feature is expected to facilitate alignment of the deployed helical support structure 22 with the vessel wall by reducing the force transferred from the elongated shaft 16 to the helical region of the helical structure 22. This may be useful, for example, when the elongated shaft is biased toward a side of the vessel wall or if the elongated shaft moves relative to the vessel wall allowing the helical structure to remain positioned.

Referring back to FIGS. 4A and 4B together (and with reference to FIGS. 3A and 3B), the dimensions of the deployed helically-shaped structure 22 are influenced by its physical characteristics and its configuration (e.g., expanded vs. unexpanded), which in turn may be selected with renal artery geometry in mind. For example, the axial length L of the deployed helical structure may be selected to be no longer than a patient's renal artery (e.g., the length 54 of renal artery RA of FIGS. 3A and 3B). For example, the distance between the access site and the ostium of the renal artery (e.g., the distance from a femoral access site to the renal artery is typically about 40 cm to about 55 cm) is generally greater than the length of a renal artery from the aorta and the most distal treatment site along the length of the renal artery, which is typically less than about 7 cm. Accordingly, it is envisioned that the elongated shaft 16 (FIG. 1) is at least 40 cm and the helical structure is less than about 7 cm in its unexpanded length L. A length in an unexpanded configuration of no more than about 4 cm may be suitable for use in a large population of patients and provide a long contact area when in an expanded configuration and, in some embodiments, provide a long region for placement of multiple energy delivery elements; however, a shorter length (e.g., less than about 2 cm) in an unexpanded configuration may be used in patients with shorter renal arteries. The helical structure 22 may also be designed to work with typical renal artery diameters. For example, the diameter 52 (FIG. 3A) of the renal artery RA may vary between about 2 mm and about 10 mm. In a particular embodiment, the placement of the energy delivery elements 24 on the helical structure 22 may be selected with regard to an estimated location of the renal plexus RP relative to the renal artery RA.

In another specific embodiment, a section or support structure of the therapeutic assembly 21, when allowed to fully deploy to an unconstrained configuration (i.e., outside of the body as shown in FIGS. 4A and 4B), comprises a helical shape having a diameter D less than about 15 mm (e.g., about 12 mm, 10 mm, 8 mm, or 6 mm); a length L less than or equal to about 40 mm (e.g., less than about 25 mm, less than about 20 mm, less than about 15 mm); a helix angle α of between about 20° and 75° (e.g., between about 35° and 55°); a range of revolutions between 0.25 and 6 (e.g., between 0.75 and 2, between 0.75 and 1.25); and a pitch HP between about 5 mm and 20 mm (e.g., between about 7 mm and 13 mm). In another example, the therapeutic assembly 21 may be configured to expand radially from its delivery state with a diameter about its central axis being approximately 10 mm to a delivery state in which the energy delivery elements 24 are in contact with the artery wall. The foregoing dimensions/angles are associated with specific embodiments of the technology, and it will be appreciated that therapeutic assemblies configured in accordance with other embodiments of the technology may have different arrangements and/or configurations.

In some embodiments, the deployed helically-shaped support structure 22 may be generally cylindrical (i.e., a helical diameter can be generally consistent along a majority of its length). It is also contemplated, however, that the structure 22 may have variations such as a conical helical shape, a tapered structural element, clockwise or counterclockwise pathway, consistent or varied pitch.

In one embodiment, the support structure 22 can include a solid structural element, e.g., a wire, tube, coiled or braided cable. The support structure 22 may be formed from biocompatible metals and/or polymers, including polyethylene terephthalate (PET), polyamide, polyimide, polyethylene block amide copolymers, polypropylene, or polyether ether ketone (PEEK) polymers. In some embodiments, the support structure 22 may be electrically nonconductive, electrically conductive (e.g., stainless steel, nitinol, silver, platinum, nickel-cobalt-chromium-molybdenum alloy), or a combination of electrically conductive and nonconductive materials. In one particular embodiment, for example, the support structure 22 may be formed of a pre-shaped material, such as spring temper stainless steel or nitinol. Furthermore, in particular embodiments, the structure 22 may be formed, at least in part, from radiopaque materials that are capable of being fluoroscopically imaged to allow a clinician to determine if the treatment assembly 21 is appropriately placed and/or deployed in the renal artery. Radiopaque materials may include, for example, barium sulfate, bismuth trioxide, bismuth subcarbonate, powdered tungsten, powdered tantalum, or various formulations of certain metals, including gold and platinum, and these materials may be directly incorporated into structural elements 22 or may form a partial or complete coating on the helical structure 22.

Generally, the helical structure 22 may be designed to apply a desired outward radial force to the renal artery wall 55 (FIGS. 3A and 3B) when inserted and expanded to contact the inner surface of the renal artery wall 55 (FIGS. 3A and 3B). The radial force may be selected to avoid injury from stretching or distending the renal artery RA when the helical structure 22 is expanded against the artery wall 55 within the patient. Radial forces that may avoid injuring the renal artery RA yet provide adequate stabilization force may be determined by calculating the radial force exerted on an artery wall by typical blood pressure. For example, a suitable radial force may be less than or equal to about 300 mN/mm (e.g., less than 200 mN/mm). Factors that may influence the applied radial force include the geometry and the stiffness of the support structure 22. In one particular embodiment, the support structure 22 is about 0.003-0.009 inch (0.08-0.23 mm) in diameter. Depending on the composition of the support structure 22, the structural element diameter may be selected to facilitate a desired conformability and/or radial force against the renal artery when expanded. For example, a support structure 22 formed from a stiffer material (e.g., metal) may be thinner relative to a support structure 22 formed from a highly flexible polymer to achieve similar flexibilities and radial force profiles. The outward pressure of the helical support structure 22 may be assessed in vivo by an associated pressure transducer.

In addition, certain secondary processes, including heat treating and annealing may harden or soften the fiber material to affect strength and stiffness. In particular, for shape-memory alloys such as nitinol, these secondary processes may be varied to give the same starting material different final properties. For example, the elastic range or softness may be increased to impart improved flexibility. The secondary processing of shape memory alloys influences the transition temperature, i.e., the temperature at which the structure exhibits a desired radial strength and stiffness. In embodiments that employ shape memory properties, such as shape memory nitinol, this transition temperature may be set at normal body temperature (e.g., around 37° C.) or in a range between about 37° C. and 45° C. In other embodiments that comprise super elastic nitinol, a transition temperature can be well below body temperature, for example below 0° C. Alternatively, the helical structure may be formed from an elastic or super elastic material such as nitinol that is thermally engineered into a desired helical shape. Alternatively, the helical structure 22 may be formed from multiple materials such as one or more polymers and metals.

Referring back to FIGS. 3B and 3C together, it should be understood that the support structure 22 of the treatment assembly 21, when not inserted into a patient, is capable of deploying to a maximum diameter that is larger than the diameter in its delivery state. Further, the helically-shaped structure 22 may be sized so that the maximum diameter is larger than the lumen diameter 52 of the renal artery RA. When inserted into a patient and transformed to the deployed state, however, the helically-shaped structure 22 expands radially to span the renal artery lumen and, at its largest circumferential section, is approximately or slightly less than (e.g., in embodiments in which the energy delivery elements 24 fill some of the space) the diameter 52 of the renal artery RA. A slight amount of vessel distension may be caused without undue injury and the structure 22 may expand such that its largest circumferential section is slightly more than the diameter 52 of the renal artery RA, or such that one or more energy delivery elements 24 are slightly pressed into the wall 55 of the renal artery RA. A helically-shaped assembly or array that causes slight and non-injurious distension of an artery wall 55 may advantageously provide stable contact force between the energy delivery elements 24 and the artery wall 55 and/or hold the energy delivery elements 24 in place even as the artery moves with respiratory motion and pulsing blood flow. Because this diameter 52 of the renal artery RA varies from patient to patient, the treatment assembly 21 may be capable of assuming a range of diameters between the delivery diameter and the maximum diameter.

As provided above, one feature of the deployed therapeutic assembly 21 in the helical configuration is that the energy delivery elements 24 associated with the helical structure may be placed into stable contact with a vessel wall to reliably create consistent lesions. Further, multiple energy delivery elements 24 may be placed along the helical structure with appropriate spacing to achieve a desired lesion configuration within the target vessel. Another feature of several embodiments of the therapeutic assembly 21 having the helical configuration described above is that the assembly may be expanded to fit within a relatively wide range of different vessel diameters and/or with various tortuosities.

B. Size and Configuration of the Energy Delivery Elements

It should be understood that the embodiments provided herein may be used in conjunction with one or more energy delivery elements 24. As described in greater detail below, the deployed helically-shaped structure carrying the energy delivery elements 24 is configured to provide a therapeutic energy delivery to the renal artery without any repositioning. Illustrative embodiments of the energy delivery elements 24 are shown in FIGS. 5A-5D. The energy delivery elements 24 associated with the helical structure 22 may be separate elements or may be an integral part of the helical structure 22. In some patients, it may be desirable to use the energy delivery element(s) 24 to create a single lesion or multiple focal lesions that are spaced around the circumference of the renal artery. A single focal lesion with desired longitudinal and/or circumferential dimensions, one or more full-circle lesions, multiple circumferentially spaced focal lesions at a common longitudinal position, spiral-shaped lesions, interrupted spiral lesions, generally linear lesions, and/or multiple longitudinally spaced discrete focal lesions at a common circumferential position alternatively or additionally may be created. In still further embodiments, the energy delivery elements 24 may be used to create lesions having a variety of other geometric shapes or patterns.

Depending on the size, shape, and number of the energy delivery elements 24, the formed lesions may be spaced apart around the circumference of the renal artery and the same formed lesions also may be spaced apart along the longitudinal axis of the renal artery. In particular embodiments, it is desirable for each formed lesion to cover at least 10% of the vessel circumference to increase the probability of affecting the renal plexus. Furthermore, to achieve denervation of the kidney, it is considered desirable for the formed lesion pattern, as viewed from a proximal or distal end of the vessel, to extend at least approximately all the way around the circumference of the renal artery. In other words, each formed lesion covers an arc of the circumference, and each of the lesions, as viewed from an end of the vessel, abut or overlap adjacent or other lesions in the pattern to create either an actual circumferential lesion or a virtually circumferential lesion. The formed lesions defining an actual circumferential lesion lie in a single plane perpendicular to a longitudinal axis of the renal artery. A virtually circumferential lesion is defined by multiple lesions that may not all lie in a single perpendicular plane, although more than one lesion of the pattern can be so formed. At least one of the formed lesions comprising the virtually circumferential lesion is axially spaced apart from other lesions. In a non-limiting example, a virtually circumferential lesion can comprise six lesions created in a single helical pattern along the renal artery such that each lesion spans an arc extending along at least one sixth of the vessel circumference such that the resulting pattern of lesions completely encompasses the vessel circumference when viewed from an end of the vessel. In other examples, however, a virtually circumferential lesion can comprise a different number of lesions. It is also desirable that each lesion be sufficiently deep to penetrate into and beyond the adventitia to thereby affect the renal plexus. However, lesions that are too deep (e.g., >5 mm) run the risk of interfering with non-target tissue and tissue structures (e.g., a renal vein) so a controlled depth of energy treatment is also desirable.

As shown in FIGS. 4A and 4B, energy delivery elements 24 may be distributed on the helical structure 22 in a desired arrangement. For example, the axial distances between the energy delivery elements 24 may be selected so that the edges of the lesions formed by individual energy delivery elements 24 on the renal artery wall 55 are overlapping or non-overlapping. One or both of the axial distances xx or yy may be about 2 mm to about 1 cm. In a particular embodiment, the axial distances xx or yy may be in the range of about 2 mm to about 5 mm. In another embodiment, the energy delivery elements 24 may be spaced apart about 30 mm. In still another embodiment, the energy delivery elements 24 are spaced apart about 11 mm. In yet another embodiment, the energy delivery elements 24 are spaced apart about 17.5 mm. Further, the axial distance xx may be less than, about equal to, or greater than the axial distance yy.

Figure 4C:
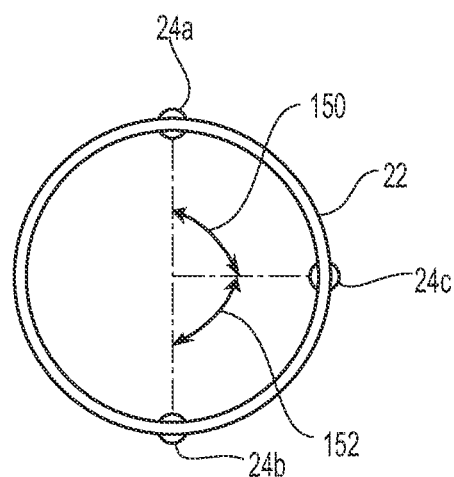
FIG. 4C is an end view of the helical structure of FIG. 4B showing the angular offset of energy delivery elements in a treatment assembly in accordance with an embodiment of the technology.

Spacing of energy delivery elements 24 may be characterized by a helical length distance zz, that is, the distance between energy delivery elements along the path of the helical structure 22. The helical length distance zz may be chosen based on the size of lesions created by energy delivery elements 24 so the lesions either overlap or do not overlap. In some embodiments, the energy delivery elements 24 are both longitudinally and circumferentially offset from one another. FIG. 4C, for example, is an end view of the helical structure 22 showing the angular offset or separation of the energy delivery elements 24 from one another around the circumference of the deployed helical structure 22. In particular, energy delivery element 24c is offset from energy delivery element 24a by angle 150 and offset from energy delivery element 24b by angle 152. The offset angles may be selected such that, when energy is applied to the renal artery via energy delivery elements 24a, 24b, and 24c, the lesions may or may not overlap circumferentially.

Figure 4D:
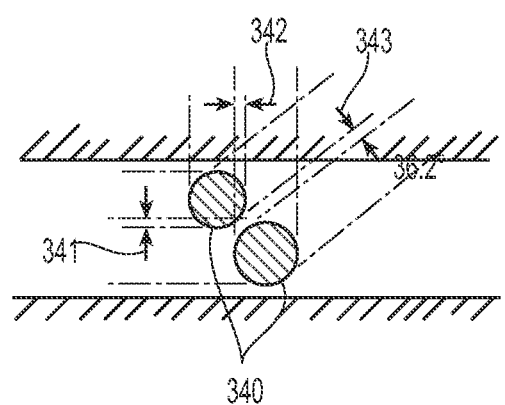
FIG. 4D is a side view of a vessel with lesions prophetically formed by a treatment assembly that circumferentially and longitudinally overlap but do not overlap along a helical path.

FIG. 4D is a side view of a vessel with formed lesions 340 that circumferentially and/or longitudinally overlap, but do not overlap along a helical path. More specifically, lesions 340 can be formed by energy delivery elements 24 to have a circumferential overlap 341 as viewed from one end of the vessel (e.g., FIG. 4C) and/or a longitudinal overlap 342, but may not produce a helical length overlap, instead forming a helical length gap 343. For example, energy delivery elements 24 may take the form of electrodes for applying an electrical field of RF energy to a vessel wall and be configured to produce lesions that are about 5 mm in diameter with the electrodes spaced apart by helical length distance of about 6 to 7 mm. Depending on the number and positioning of the energy delivery elements 24, a helical lesion pattern with any suitable number of turns may be formed. As such, the treatment device 12 may employ a single energy application to form a complex lesion pattern. It should be noted that the embodiments illustrated in FIGS. 4A-4C are exemplary, may be schematic in nature, may not correlate exactly to one another, and are shown only for the purposes of clarifying certain aspects of the technology. As such, the number and spacing of energy delivery elements 24 are different in each of FIGS. 4A-4C, and lesions formed by the illustrated embodiments may not create a sufficiently overlapping pattern to achieve a virtually circumferential lesion as described above, particularly when applying energy in only one deployment of the treatment assembly 21 without repositioning.

Referring back to FIG. 3B, the individual energy delivery elements 24 are connected to energy generator 26 (FIG. 1) and are sized and configured to contact an internal wall of the renal artery. In the illustrated embodiment, the energy delivery element 24 may be operated in a monopolar or unipolar mode. In this arrangement, a return path for the applied RF electric field is established, e.g., by an external dispersive electrode (shown as element 38 in FIGS. 1 and 2), also called an indifferent electrode or neutral electrode. The monopolar application of RF electric field energy serves to ohmically or resistively heat tissue in the vicinity of the electrode. The application of the RF electrical field thermally injures tissue. The treatment objective is to thermally induce neuromodulation (e.g., necrosis, thermal alteration or ablation) in the targeted neural fibers. The thermal injury forms a lesion in the vessel wall. Alternatively, a RF electrical field may be delivered with an oscillating or pulsed intensity that does not thermally injure the tissue whereby neuromodulation in the targeted nerves is accomplished by electrical modification of the nerve signals.

The active surface area of the energy delivery element 24 is defined as the energy transmitting area of the element 24 that may be placed in intimate contact against tissue. Too much contact area between the energy delivery element and the vessel wall may create unduly high temperatures at or around the interface between the tissue and the energy delivery element, thereby creating excessive heat generation at this interface. This excessive heat may create a lesion that is circumferentially too large. This may also lead to undesirable thermal application to the vessel wall. In some instances, too much contact can also lead to small, shallow lesions. Too little contact between the energy delivery element and the vessel wall may result in superficial heating of the vessel wall, thereby creating a lesion that is too small (e.g., <10% of vessel circumference) and/or too shallow.

The active surface area of contact (ASA) between the energy delivery element 24 and the inner vessel wall (e.g., renal artery wall 55) has great bearing on the efficiency and control of the generation of a thermal energy field across the vessel wall to thermally affect targeted neural fibers in the renal plexus. While the ASA of the energy delivery element is important to creating lesions of desirable size and depth, the ratio between the ASA and total surface area (TSA) of the energy delivery element 24 and electrode 46 is also important.

The ASA to TSA ratio influences lesion formation in two ways: (1) the degree of resistive heating via the electric field, and (2) the effects of blood flow or other convective cooling elements such as injected or infused saline. For example, an RF electric field causes lesion formation via resistive heating of tissue exposed to the electric field. The higher the ASA to TSA ratio (i.e., the greater the contact between the electrode and tissue), the greater the resistive heating, e.g., the larger the lesion that is formed. As discussed in greater detail below, the flow of blood over the non-contacting portion of the electrode (TSA minus ASA) provides conductive and convective cooling of the electrode, thereby carrying excess thermal energy away from the interface between the vessel wall and electrode. If the ratio of ASA to TSA is too high (e.g., more than 50%), resistive heating of the tissue may be too aggressive and not enough excess thermal energy is being carried away, resulting in excessive heat generation and increased potential for stenotic injury, thrombus formation and undesirable lesion size. If the ratio of ASA to TSA is too low (e.g., 10%), then there is too little resistive heating of tissue, thereby resulting in superficial heating and smaller and shallower lesions. In a representative embodiment, the ASA of the energy delivery elements 24 contacting tissue may be expressed as $$0.25 TSA \leq ASA \leq 0.50 TSA$$

An ASA to TSA ratio of over 50% may still be effective without excessive heat generation by compensating with a reduced power delivery algorithm and/or by using convective cooling of the electrode by exposing it to blood flow. As discussed further below, electrode cooling can be achieved by injecting or infusing cooling liquids such as saline (e.g., room temperature saline or chilled saline) over the electrode and into the blood stream.

Various size constraints for an energy delivery element 24 may be imposed for clinical reasons by the maximum desired dimensions of the guide catheter, as well as by the size and anatomy of the renal artery lumen itself. In some embodiments such as those shown in FIGS. 13 and 25, the maximum outer diameter (or cross-sectional dimension for non-circular cross-section) of the energy delivery element 24 may be the largest diameter encountered along the length of the elongated shaft 16 distal to the handle assembly 34. As previously discussed, for clinical reasons, the maximum outer diameter (or cross-sectional dimension) of the energy delivery element 24 is constrained by the maximum inner diameter of the guide catheter through which the elongated shaft 16 is to be passed through the intravascular path 14. Assuming that an 8 French guide catheter (which has an inner diameter of approximately 0.091 inch (2.31 mm)) is, from a clinical perspective, the largest desired catheter to be used to access the renal artery, and allowing for a reasonable clearance tolerance between the energy delivery element 24 and the guide catheter, the maximum diameter of the electrode 46 is constrained to about 0.085 inch (2.16 mm). In the event a 6 French guide catheter is used instead of an 8 French guide catheter, then the maximum diameter of the energy delivery element 24 is constrained to about 0.070 inch (1.78 mm), e.g., about 0.050 inch (1.27 mm). In the event a 5 French guide catheter is used, then maximum diameter of the energy delivery element 24 is constrained to about 0.053 inch (1.35 mm).

Based upon these constraints and the aforementioned power delivery considerations, the energy delivery element 24 may have an outer diameter of from about 0.049 to about 0.051 inch (1.24 mm-1.30 mm). The energy delivery elements 24 also may have a minimum outer diameter of about 0.020 inch (0.51 mm) to provide sufficient cooling and lesion size. In some embodiments, the energy delivery element 24 may have a length of about 1 mm to about 3 mm. In some embodiments in which the energy delivery element 24 is a resistive heating element, the energy delivery element 24 have a maximum outer diameter from about 0.049 to 0.051 inch (1.24 mm-1.30 mm) and a length of about 10 mm to 30 mm. One embodiment of energy delivery elements 24, for example, provides for a multiple array of 4-6 electrodes disposed about a support structure (e.g., a tubular structure). The energy delivery elements 24, for example, may be gold electrodes or alternatively, platinum, platinum-iridium, or another suitable material. In one particular embodiment, the electrodes may measure about 0.030 inch ID×0.0325 OD inch×0.060 inch in length (0.76 mm×0.83 mm×1.52 mm). In still another particular embodiment, the electrodes may measure 0.029 inch ID×0.033 inch OD×0.060 inch length (0.72 mm×0.83 mm×1.52 mm). In yet another particular embodiment, the electrodes may measure 0.038 inch ID×0.042 inch OD×0.060 inch length (0.97 mm×1.07 mm×1.52 mm). Moreover, the electrodes may be appropriately electrically insulated from the support structure with the supply wire array of each of the electrodes jacketed in a polymer so as to provide for a compact packaged electrode array assembly about the support structure 22.

Figure 8A:
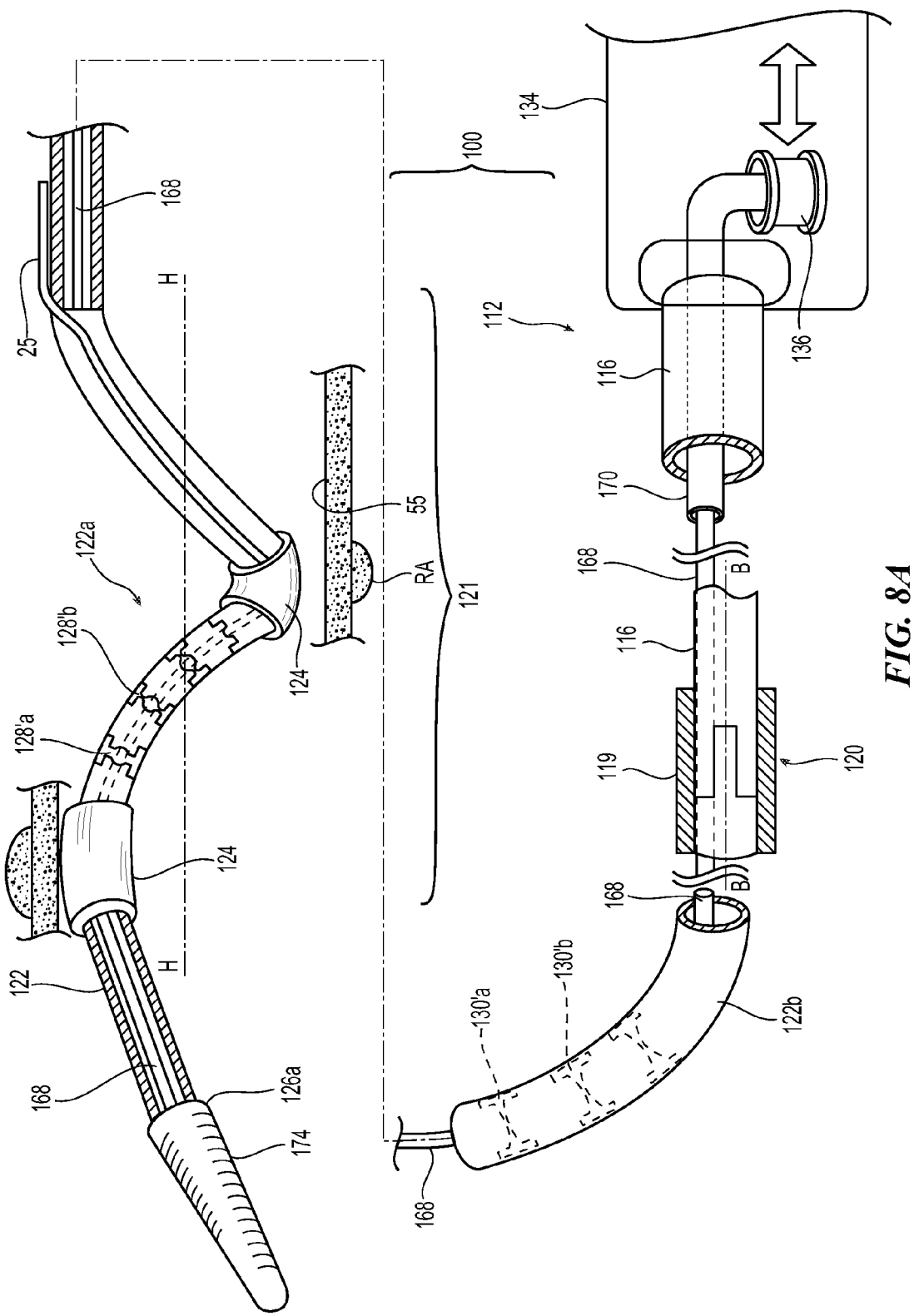
FIG. 8A is a broken perspective view in partial section of a treatment device including the slot pattern of FIG. 6I configured in accordance with an embodiment of the technology.

In other embodiments, the outer diameter of the treatment device 12 may be defined by the one or more energy delivery elements 24 and may be further defined by elements such as e.g., control wire 168 as shown in FIG. 8A. For example, particular embodiments may be used with an 8 French guide catheter and may comprise energy delivery element(s) 24 with a diameter between about 0.049 to 0.053 inch (1.24 mm to 1.35 mm) and a control wire with a diameter between about 0.005 to 0.015 inch (0.13 mm to 0.38 mm) in diameter. In other embodiments, however, the arrangement and/or dimensions of the energy delivery elements 24 and/or control wire may vary.

Figure 5E:
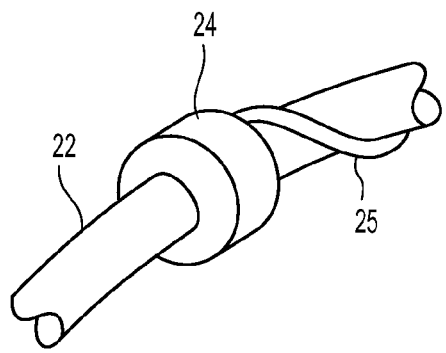
FIG. 5E illustrates an embodiment of a treatment assembly in which the support structure is electrically conductive and serves as the energy delivery element.
Figure 5E:
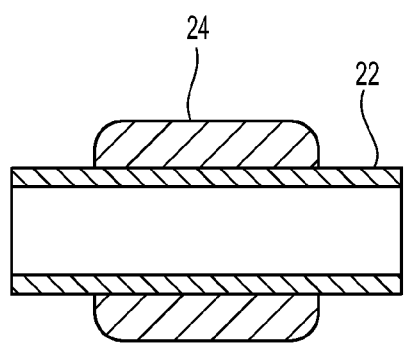
Figure 5E:
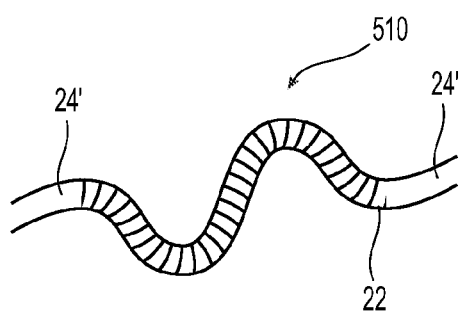
Figure 5E:
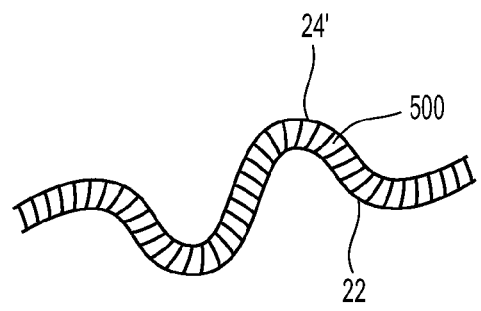
Figure 5E:
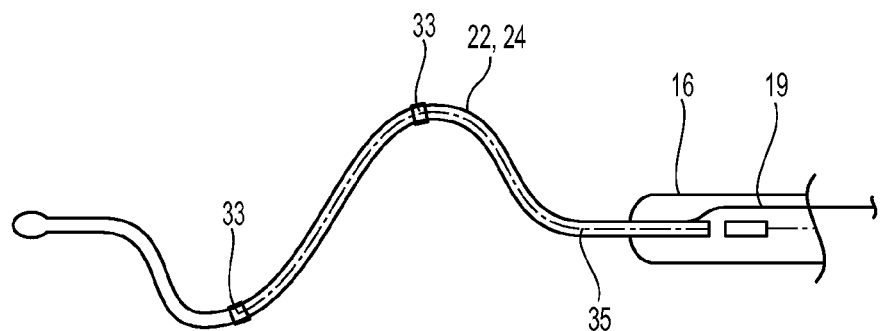

In certain embodiments, the helical structure 22 may be formed of an electrically conductive material. For example, the helical structure 22 may be made from nitinol wire, cable, or tube. As shown in FIG. 5E, wire leads 19 may connect the helical structure 22 to energy generator 26. The helical structure 22 forms a contact region with the renal artery wall and acts as the energy delivery element 24. In this configuration, the helical structure 22 is capable of producing a continuous helical lesion. A helical structure 22 that is configured to be an energy delivery element 24 may optionally comprise sensors 33 positioned on, in, and/or proximate to the helical structure 22 and may be electrically connected to supply wires 35.

In other embodiments, the electrically conductive helical structure 22 is insulated at least in part. That is, the conductive helical structure is partially covered with an electrically insulating material and the uncovered portions of the helical structure 22 serve as one or more conductive energy delivery elements 24. The energy delivery elements 24 may be any size, shape, or number, and may be positioned relative to one another as provided herein.

Energy delivery element 24 may be configured to deliver thermal energy, i.e., to heat up and conduct thermal energy to tissue. For example, energy delivery elements may be an electrically resistive element such as a thermistor or a coil made from electrically resistive wire so that when electrical current is passed through the energy delivery element heat is produced. An electrically resistive wire may be for example an alloy such as nickel-chromium with a diameter for example between 48 and 30 AWG. The resistive wire may be electrically insulated for example with polyimide enamel.

In certain embodiments, the energy delivery elements 24 may be angularly repositioned relative to the renal artery during treatment. Referring back to FIGS. 1 and 2, for example, this angular repositioning may be achieved by compressing the therapeutic assembly 21 and rotating the elongated shaft 16 of the treatment device 12 via the handle assembly 34. In addition to the angular or circumferential repositioning of the energy delivery elements 24, the energy delivery elements 24 optionally may also be repositioned along the lengthwise or longitudinal dimension of the renal artery. This longitudinal repositioning may be achieved, for example, by translating the elongated shaft 16 of treatment device 12 via handle assembly 34, and may occur before, after, or concurrent with angular repositioning of the energy delivery elements 24. With reference to FIG. 3B, repositioning the energy delivery elements 24 in both the longitudinal and angular dimensions places the energy delivery elements 24 in contact with the interior wall 55 of the renal artery RA at a second treatment site for treating the renal plexus RP. In operation, energy may then be delivered via the energy delivery elements 24 to form a second focal lesion at this second treatment site. For embodiments in which multiple energy delivery elements 24 are associated with the helical structure, the initial treatment may result in two or more lesions, and repositioning may allow additional lesions to be created.

In certain embodiments, the lesions created via repositioning of the helically-shaped support structure 22 are angularly and longitudinally offset from the initial lesion(s) about the angular and lengthwise dimensions of the renal artery RA, respectively. The composite lesion pattern created along the renal artery RA by the initial energy application and all subsequent energy applications after any repositioning of the energy delivery element(s) 24 may effectively result in a discontinuous lesion (i.e., it is formed from multiple, longitudinally and angularly spaced treatment sites).

In an alternative embodiment, the energy delivery element 24 may be in the form of an electrically conductive wire. As shown in FIG. 5D, for example, a conductive wire 500 may be wound about the helical structure 22 to form a coiled electrode 24'. The coiled electrode 24' may provide increased surface area for delivering energy. For example, the coiled electrode 24' may form a generally continuous helical lesion in a single energy application. The coiled electrode 24' may be wound in any manner about the helical structure 22, depending on the desired lesion. For example, the coiled electrode 24' may form a continuous path along a length of the helix or the coiled structure may form one or more short discrete electrodes separated by non-conducting sections. In other embodiments, portions of the coiled electrode 24' may be positioned on the helical structure to come in contact with the vessel wall when the helical structure is expanded, while other portions of the coiled electrode 24' may be positioned away from the vessel wall when the helical structure is expanded to allow lesions to be discontinuous. Further, in such an arrangement, regions of the coiled electrode 24' that do not contact the renal artery may contribute to cooling of the energy delivery elements 24', as described in greater detail below. The positioning and number of conductive portions forming the energy delivery elements 24' may be selected according to a desired lesion pattern.

In the embodiments shown in FIGS. 5A and 5B, energy delivery elements 24 preferably comprise metal electrodes with rounded ends and a lumen. The nitinol helical support structure 22 is preferably electrically insulated (e.g., with PET) and the electrodes 24 are mounted over the insulation. Supply wires 25 connect the electrodes to an energy source (not shown) and deliver energy (e.g., RF electrical current) to the electrodes 24. The rounded ends reduce mechanical irritation to the vessel wall and provide a more consistent current density when energy is delivered compared to electrodes with square or sharper ends. The energy delivery elements 24 may alternatively comprise other forms as noted, such as a coil electrode 24' described above with reference to FIG. 5D. In another embodiment, the structural element 510 that forms the helical structure 22 may be the energy delivery element 24' itself, as seen, for example in FIG. 5C.

III. Selected Embodiments Of Renal Denervation Systems

The representative embodiments provided herein include features that may be combined with one another and with the features of other disclosed embodiments. In an effort to provide a concise description of these embodiments, not all features of an actual implementation are described in the specification. It should be appreciated that in the development of any such actual implementation, as in any engineering or design project, numerous implementation-specific decisions should be made to achieve the developers' specific goals, such as compliance with system-related and business-related constraints, which may vary from one implementation to another.

Figure 6A:
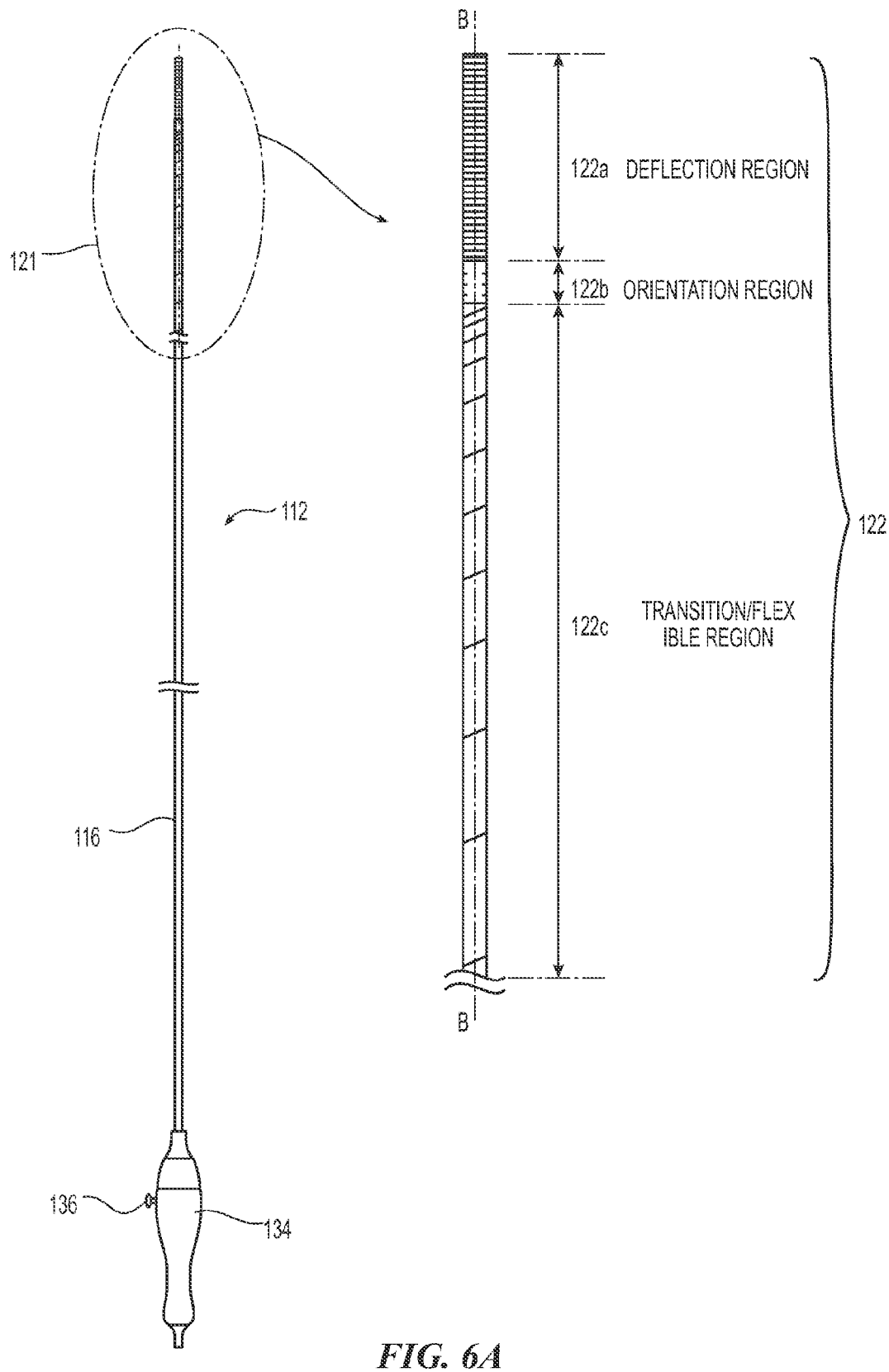
FIG. 6A illustrates an embodiment of a treatment device including an elongated shaft having different mechanical and functional regions configured in accordance with an embodiment of the technology.

FIG. 6A illustrates an embodiment of a treatment device 112 including an elongated shaft 116 having different mechanical and functional regions configured in accordance with an embodiment of the technology. The elongated shaft 116 of the treatment device 112, for example, includes a distal region with a therapeutic or treatment assembly 121 for delivery and deployment at a renal artery site for treatment and, in particular, for renal denervation. Disposed at a proximal end of the elongated shaft 116 is a handle assembly 134 for manipulation of the elongated shaft 116 and the therapeutic assembly 121. More specifically, the handle assembly 134 is configured with an actuator 136 (schematically shown) to provide for remote operation of a control member (e.g., control wire 168 of FIG. 6E or 8A) for controlling or transforming the therapeutic assembly 121 between a delivery state and a deployed state. Further details regarding suitable handle assemblies may be found, for example, in U.S. patent application Ser. No. 12/759,641, "Handle Assemblies for Intravascular Treatment Devices and Associated System sand Methods" to Clark et al., which is incorporated herein by reference in its entirety.

The treatment device 112 is configured to deliver the therapeutic assembly 121 to a treatment site in a delivery (e.g., low-profile) state in which the assembly 121 is substantially linear (e.g., straight) such that energy delivery elements (not shown) carried by a support structure 122 of the treatment assembly 121 are substantially axially aligned along the support member 122. Once located at the treatment site within the renal artery, the handle assembly 134 is operated for actuation of a control member that transforms the therapeutic assembly 121 from the delivery state to a deployed state. In one embodiment, for example, the control member comprises a control wire 168 (FIG. 8A) disposed within an internal lumen of the tubular support structure 122. One end of the control wire 168 may be affixed at or near the distal end of the support structure 122, and the opposite end of the control wire 168 terminates within the handle assembly 134. As mentioned previously, the handle assembly 134 is configured for manipulating the control wire 168 to transform the therapeutic assembly 121 between the delivery and the deployed states. The tension in the control wire 168 provides for a proximally and axially directed force that acts on the support structure 122. Under the influence of the tension force in the control wire 168 and, in operation within a patient under the influence of a radial constraint of the patient's renal arterial wall, the support structure 122 deforms so as to deploy into the helical geometry to bring the energy delivery elements into stable contact with the wall of the renal artery.

To provide for the desired deformation upon deployment, the support structure 122 may be a tubular member having a plurality of slots, cuts, through holes, and/or openings selectively formed or disposed about the support structure 122. The tubular support structure 122 may have a number of features generally similar to the features of support structure 22 described above. For example, the support structure 122 may be formed from biocompatible metals and/or polymers, including PET, polyamide, polyimide, polyethylene block amide copolymer, polypropylene, or PEEK polymers, and the slots are preferably laser cut into the tubular structure in a desired configuration. In particular embodiments, the support structure 122 may be electrically nonconductive, electrically conductive (e.g., stainless steel, nitinol, silver, platinum nickel-cobalt-chromium-molybdenum alloy), or a combination of electrically conductive and nonconductive materials. In one particular embodiment, the support structure 122 may be formed of a pre-shaped material, such as spring temper stainless steel or nitinol. Moreover, in some embodiments the support structure 122 may be formed, at least in part, from radiopaque materials that are capable of being imaged fluoroscopically to allow a clinician to determine if the support structure 122 is appropriately placed and/or deployed in the renal artery. Radiopaque materials may include barium sulfate, bismuth trioxide, bismuth subcarbonate, powdered tungsten, powdered tantalum, or various formulations of certain metals, including gold, platinum, and platinum-iridium, and these materials may be directly incorporated into the support structure 122 or may form a partial or complete coating of the support structure 122.

The location, orientation and/or configuration of the slots, cuts, through holes, and/or openings formed or disposed about the support structure 122 define the deformation of the structure. Moreover, the slots, cuts, through holes, and/or openings can be varied along the tubular structure 122 so as to define varying regions of deformation along the structure. In the embodiment illustrated in FIG. 6A, for example, the tubular structure 122 includes a distal deflection region 122a, an intermediate orientation region 122b proximal to the distal deflection region 122a, and a transition or flexible region 122c proximal to the orientation region 122b. As will be described in greater detail below, the deflection region 122a is configured to have a substantially helical geometry upon deployment. The orientation region 122b is configured to locate or bias the deflection region 122a away from a longitudinal axis B of the elongated shaft 116 and toward a wall of the renal artery. The transition region 122c is configured to provide flexibility to the treatment device 112 as the elongated shaft 112 is advanced through the sometimes tortuous intravascular path from the percutaneous access site to the targeted treatment site within the respective renal artery (as described above with reference to FIG. 2). Further details regarding various mechanical and functional aspects of the different regions of the treatment device 112 are described below.

Figure 6B:
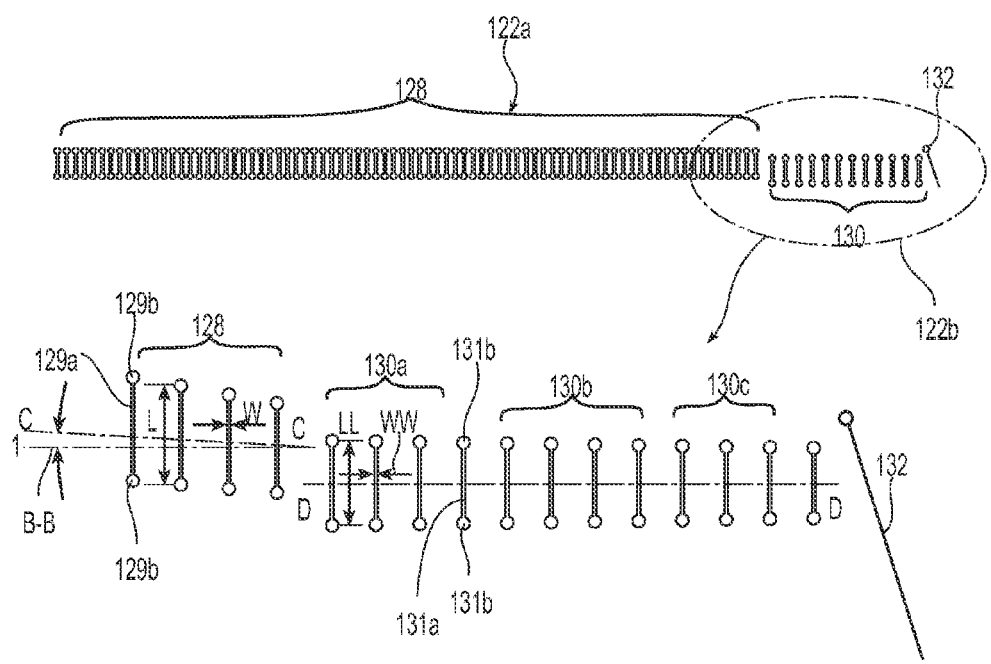
FIG. 6B is a plan view of a slot pattern for use in the treatment device of FIG. 6A.

FIG. 6B is a plan view of a slot pattern configured in accordance with one embodiment of the technology. Referring to FIGS. 6A and 6B together, for example, the deflection region 122a may be defined by a plurality of substantially equal length transverse slots 128 arranged along the support structure 122 in a spiral fashion. The orientation region 122b may be defined by a plurality of axially spaced transverse slots 130 in which at least two slots differ in length. Further, as best seen in FIG. 6A, the orientation region 122b can have a smaller axial length than the deflection region 122a. The transition region 122c is located proximally of the orientation region 122b and has an axial length greater than each of the deflection region 122a and the orientation region 122b. In the illustrated embodiment, the transition region 122c can include a continuous spiral cut or slit 132 having a varying pitch along the support structure 122. In one embodiment, for example, the pitch of the spiral cut 132 can increase proximally along the elongated shaft 116. Further details regarding various mechanical and functional aspects of the regions of the treatment device 112 are described below.

Figure 6C:
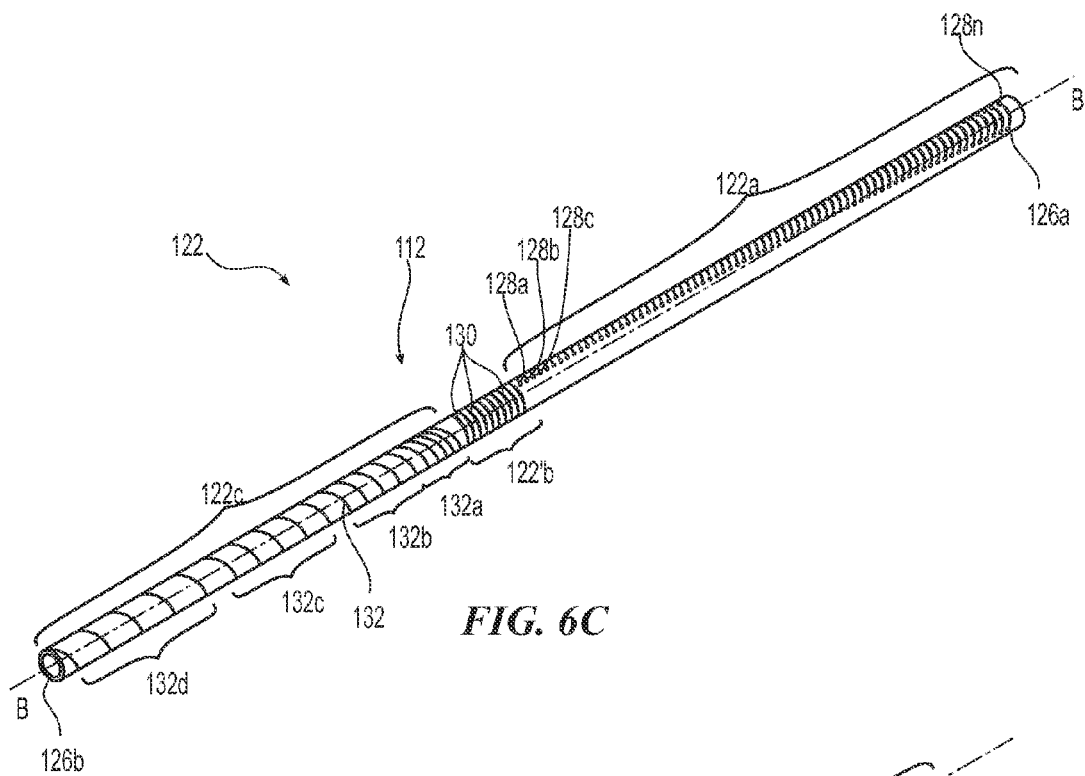
FIG. 6C is a perspective view of a distal portion of the treatment device of FIG. 6A in a delivery state (e.g., low-profile or collapsed configuration) outside a patient in accordance with an embodiment of the technology.
Figure 6D:
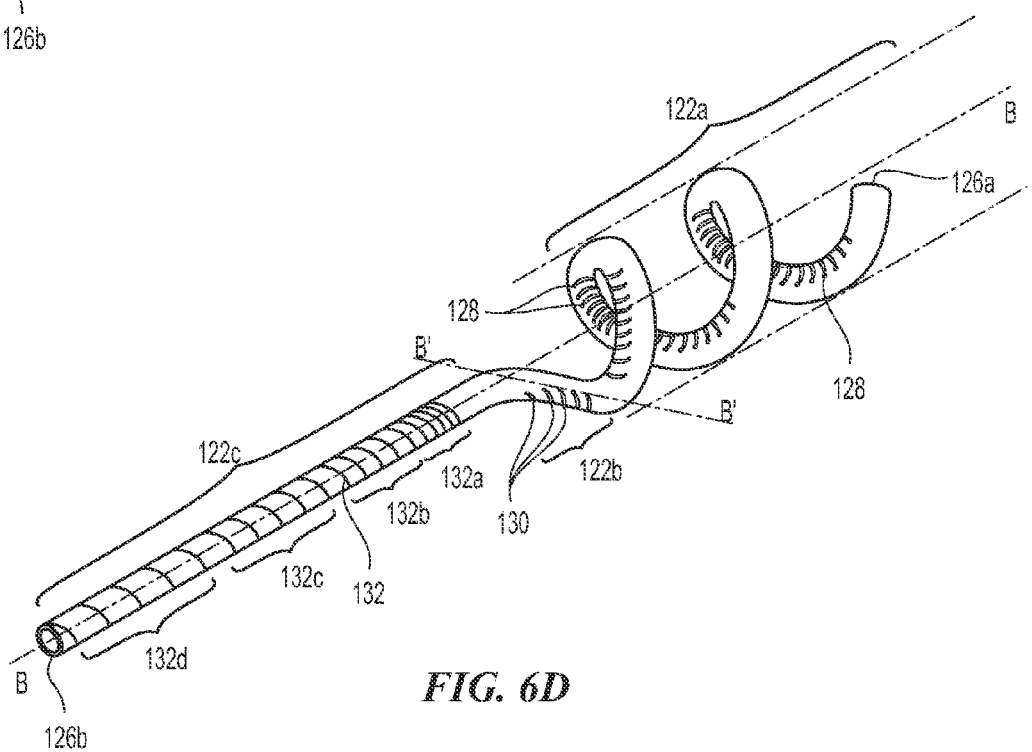
FIG. 6D is a perspective view of the treatment device of FIG. 6C in a deployed state (e.g., expanded configuration) outside a patient.

FIG. 6C is a perspective view of the treatment device 112 including the support structure 122 in a delivery state (e.g., low-profile or collapsed configuration) outside of a patient in accordance with an embodiment of the present technology, and FIG. 6D is a perspective view of the support structure 122 in a deployed state (e.g., expanded configuration). For ease of understanding, the support structure 122 in FIGS. 6C and 6D is shown without energy delivery elements disposed about the support structure 122.

Referring to FIGS. 6C and 6D together, the support structure 122 comprises a tubular member having a central lumen to define a longitudinal axis B-B. As described above, the support structure 122 includes a proximal generally flexible transition region 122c, an intermediate orientation region 122b, and a distal deflection region 122a. The support structure 122 is selectively transformable between the delivery state (FIG. 6C) and the deployed state (FIG. 6D) by application of a force having at least a proximally directed axial component and preferably applied at or near the distal end 126a to transform distal deflection region 122a and intermediate orientation region 122b. In one embodiment, for example, an axial force applied at or near the distal end 126a directed at least partially in the proximal direction deflects the distal deflection region 122a of the support structure 122 such that it forms the helically-shaped support structure such as is shown in FIG. 6D (e.g., within the renal artery) to bring one or more energy delivery elements (not shown) into contact with the inner wall of the renal artery.

The Deflection Region

Figure 6E:
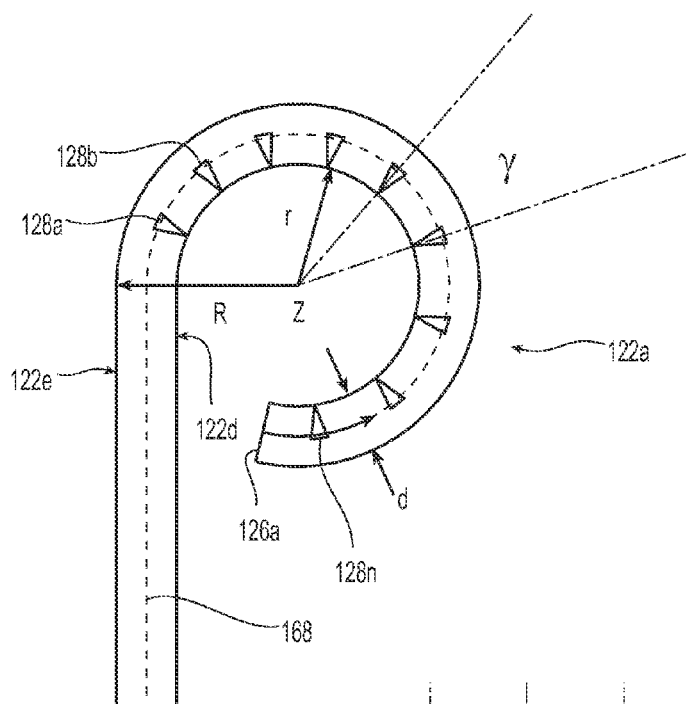
FIG. 6E is a partially schematic plan view of a distal region of the support structure of FIG. 6A in a generally helically-shaped deployed state.

As mentioned above, to provide the support structure 122 with the desired deflection and deployment configuration, the deflection region 122a includes a plurality of slots 128a, 128b, 128c, . . . 128n. Again, the plurality of slots 128a-128n are selectively formed, spaced, and/or oriented about the longitudinal axis B-B such that the distal deflection region 122a deflects in a predictable manner to form a helical geometry in the deployed state within the renal artery. Outside of the renal artery or other lumen that may radially constrain deflection of the distal region 122a, the distal region 122a may define a non-helical geometry in its fully expanded configuration, such as, for example, a substantially circular geometry as shown in FIG. 6E. As shown therein, the control wire 168 is disposed in the central lumen of the support structure 122, and is anchored at or near the distal end 126a. When the control wire 168 is placed under tension in the proximal direction, at least a portion of the deflection region 122a (in the absence of any restriction in the radial direction) deflects from the substantially straight shape of FIG. 6C to form the substantial circular shape of FIG. 6E. More specifically, referring to FIGS. 6C-6E together, a portion of the deflection region 122a deflects such that the deflection slots 128a-n deform and close or approximately close (as shown schematically in FIG. 6E) and provide contact between the edges of the support structure 122 framing a central region in each slot 128. Further details regarding the configuration of the slots are described below.

The deflection region 122a is arranged to deflect about a center of curvature Z to define a first radius of curvature r with respect to a first surface 122d of the support member 122, and a second radius of curvature R with respect to a second surface 122e. The second radius of curvature R is greater than the first radius of curvature r with the difference being the width or diameter d of the support member 122 measured at its outer surface. Under a radial constraint of, for example, the inner wall of a renal artery, the deflection region 122a deforms to define a substantially helical deployed shape (as depicted in FIG. 6D) instead of the substantial circular shape defined in the absence of radial constraint (as depicted in FIG. 6E). Thus, the proportions of the substantially helical deployed shape (e.g., the diameter and pitch of the helix) can vary according to the inner diameter of the lumen (e.g., the renal artery lumen) within which the deflection region 122a is deformed.

Figure 6F:
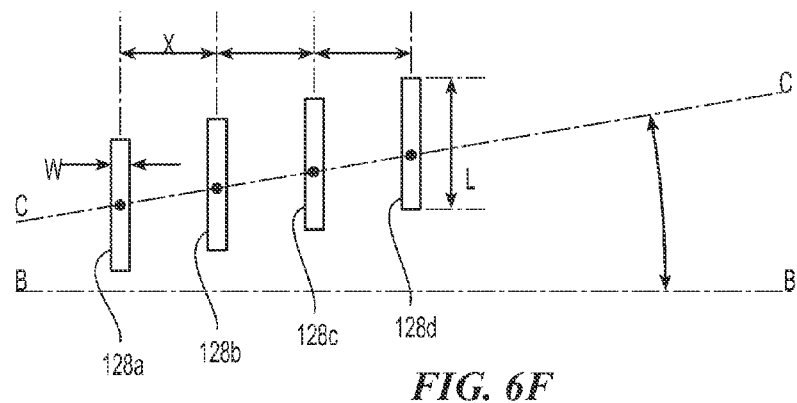
FIG. 6F is a partially schematic plan view of a distal portion of a treatment device of in a polygon-shaped deployed state in accordance with another embodiment of the technology.

The arrangement and configuration of the slots 128a-128n (FIG. 6C) further define the geometry of the deflectable distal region 122a. FIG. 6F, for example, schematically illustrates a slot pattern for slots 128 in accordance with one embodiment of the technology to illustrate the slot spacing and orientation about the deflection region 122a of the support member 122. Although only four slots 128a-d are shown in FIG. 6F, it will be appreciated that the deflection region 122a can have any number of desired slots 128. Referring to FIGS. 6E and 6F together, the centers of the slots 128 are disposed and spaced along a progressive axis C-C. The progressive axis C-C defines a progressive angle θ with the longitudinal axis B-B of the support structure 122 (FIG. 6A) to define an angular spacing of y about the center of curvature Z (FIG. 6E) in the unconstrained deployed state. The centers of the slots 128a-128d are shown as substantially equidistantly spaced at a distance x. Alternatively, however, the center spacing between the slots may vary (x1, x2, etc.) along the progressive axis C-C. Each slot 128 further defines a maximum arc length L about the longitudinal axis B-B and a maximum slot width W in the direction of the longitudinal axis B-B.

The total number of slots 128 in the region 122a under deflection multiplied by the slot width W populated in a specific length defines the first radius of curvature r in the deflected portion of the deflection region 122a (when placed in an unconstrained deployed state). In one particular embodiment, for example, each slot ma have a width W ranging from about 0.0005 to 0.010 inch (0.01 to 0.25 mm) and a slot arc length L of about 0.0005 to 0.010 inch (0.01 to 0.25 mm) so as to define a first radius of curvature r in an unconstrained deflected state that ranges between about 3.5 to 6 mm (7 to 12 mm diameter). Minimizing the first radius of curvature r at a maximum application of axial force through the deflection region 122a of the support member 122 defines the flexibility of the deflection region 122a. Accordingly, the smaller the first radius of curvature r, the greater the flexibility; the greater the first radius of curvature r, the greater the stiffness. Thus, the flexibility and/or stiffness of the deflection region 122a of the support member 122 can be defined by selecting the number and/or width of slots of the distal region 122a. In one embodiment, for example, the deflection region 122a can include approximately 2 to 100 slots, with each having a slot width W ranging from about 0.0005 to 0.010 inch (0.01 to 0.25 mm) and a slot arc length L of about 0.0005 to 0.010 inch (0.01 to 0.25 mm) so as to define a first radius of curvature r in an unconstrained deflected state that ranges between about 3.5 to 6 mm (7 to 12 mm diameter).

Figure 6G:
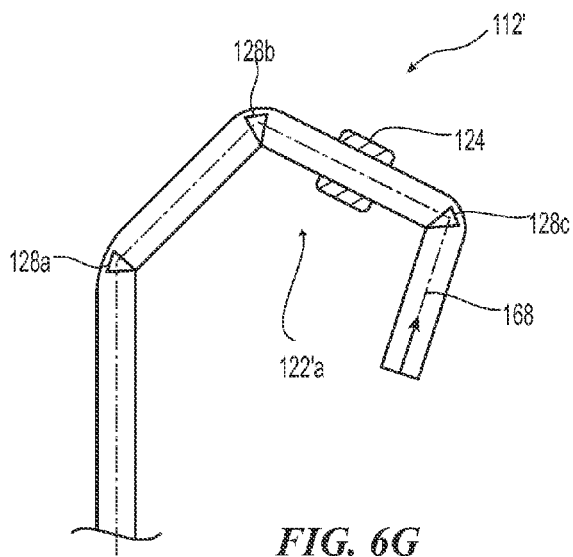
FIG. 6G is a plan view of a slot pattern for use in the treatment device of FIG. 6A in accordance with another embodiment of the technology.

Because the first radius of curvature r of the deflection region 122a is directly related to the number of slots 128, the number of slots 128 can be few in number so as to provide for a non-continuous radius of curvature in a segment of the deflection region 122a such that the segment is substantially polygonal. FIG. 6G, for example, is a schematic plan view of a treatment device 112' configured in accordance with another embodiment of the technology. A deflection region 122'a of the treatment device 112' may include a low or reduced number of deflection slots 128 (e.g., three slots 128a-c are shown) such that the deflection region 122'a defines a substantially polygonal geometry when under a tension load at its distal end (i.e., from control wire 168). In other embodiments, a different number of slots 128 may be used to selectively form a desired geometry for the treatment device 112'.

Referring back to FIGS. 6B and 6C and as noted previously, the deflection region 122a is defined by a plurality of deflection slots 128 in which each slot 128 extends substantially transverse to the longitudinal axis B-B of the support structure 122 with the slots 128 being of substantially similar arc length. Moreover, with reference to FIG. 6F, the centers of the slots 128 of the deflection region 122a are generally spaced apart along a progressive axis CC that is skewed from the longitudinal axis BB such that the slots 128 of the deflection region 122a progress in a generally spiral fashion along the support structure 122 in the axial direction (as best seen in FIG. 6C). The plurality of slots 128 of the deflection region 122a are selectively formed, spaced, and/or oriented about the longitudinal axis B-B such that the deflection region 122a deflects or deforms in a predictable manner so as to preferably form a helical geometry when in a deployed state (e.g., within the renal artery).

Referring again to FIG. 6B, for example, the deflection region 122a includes a pattern of deflection slots 128 arranged in accordance with one embodiment of the technology to illustrate the slot spacing and orientation about the support member 122 (FIG. 6A). The centers of the deflection slots 128 are disposed and spaced along progressive axis C-C. The progressive axis C-C defines a progressive angle $\theta_1$ with the longitudinal axis B-B of the support structure 122 (FIG. 6A). The progressive angle $\theta_1$ defines and, more particularly, directly corresponds to a pitch angle of the helical geometry defined by the support structure 122 when in a deployed state. The progressive angle $\theta_1$ can range from, for example, about zero degrees (0°) to about six degrees) (6°), e.g., one-half degree, (0.5°, two degrees (2°), etc. The centers of the deflection slots 128 are shown as substantially equidistantly spaced apart. In other embodiments, however, the center spacing between slots 128 may vary along the progressive axis C-C. The total number of slots 128 defining the deflection region 122a can be from about 2 to 100 slots (e.g., about 80 slots). In one particular embodiment, the total axial length of the deflection region 122a is about one inch (2.54 cm). In other embodiments, however, the deflection region 122a can have a different number of slots 128 and/or the slots can have different dimensions or arrangements relative to each other.

In one embodiment, each of the deflection slots 128 comprises a substantially rectangular central region 129a that extends generally perpendicular to and about the central longitudinal axis B-B of the shaft 116. The elongate lateral walls of the central region 129a define a slot width W therebetween (e.g., about 0.0015 inch (0.038 mm)) to define a maximum gap that may be closed when the slot 128 deforms during deflection of region 122a. Each slot 128 further comprises lateral regions 129b in communication or contiguous with the central region 129a. In one embodiment, the lateral regions 129b are substantially circular and have a diameter (e.g., 0.0060 inch (0.15 mm)) to define regions for stress relief at the ends of slots 128. The spacing between the centers of the substantially circular lateral regions 129b define an arc length L (e.g., about 0.040 inch (1.02 mm)) about the longitudinal axis of the structure 122. In some embodiments, these lateral regions 129b may be formed as elliptical cuts on a non-perpendicular angle relative to the longitudinal axis B-B of the support structure 122, 122', 122".

Figure 6H:
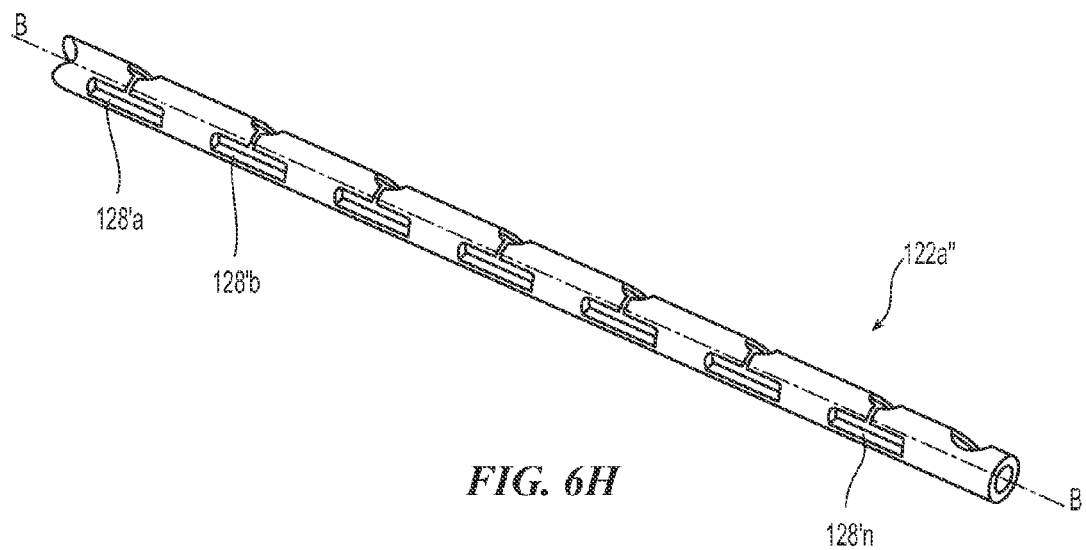
FIG. 6H is a perspective view of a support structure for use in a treatment device configured in accordance with another embodiment of the technology.
Figure 6I:
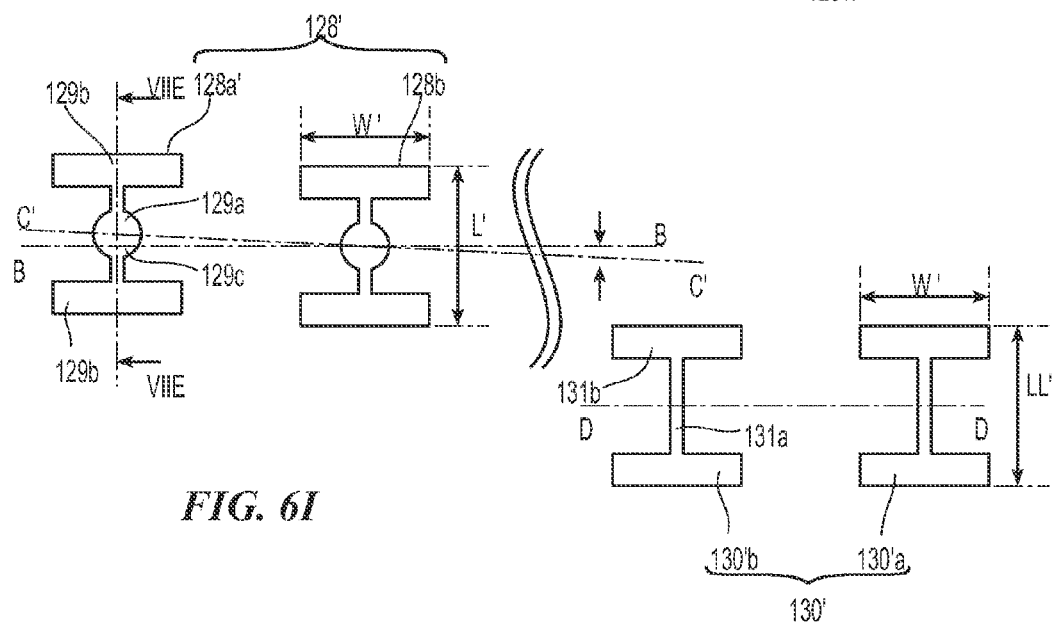
FIG. 6I is a plan view of an embodiment of a slot pattern for use in the support structure of FIG. 6H.

Alternate configurations of the deflection slots are possible. For example, the deflection slots can be more specifically formed to provide a desired flexibility and deflection in the deflection region 122a of the support member 122. FIGS. 6H and 6I, for example, illustrate a deflection region 122a" having deflection slots 128' configured in accordance with another embodiment of the technology. In this embodiment, the deflection slots 128' extend substantially transverse to the progressive axis C-C and are substantially symmetrical about the progressive axis C-C. The slots 128', for example, can be generally "I-shaped" and include a central region 129a extending perpendicular to the progressive axis C-C with two enlarged lateral regions 129b disposed about the central slot region 129a. Further, the walls of the support structure 122" forming the perimeter of each of the lateral regions 129b define a substantially rectangular geometry preferably extending substantially parallel to the longitudinal axis B-B of the support structure 122" with the corners of the rectangular-shaped openings being radiused. The central region 129a of the slots 128' can include a substantially circular cut-out region 129c formed in communication with the lateral regions 129b. Alternatively, in some embodiments the central region 129c of the slots 128' may be generally rectangular and not include a circular cut-out.

As best seen in FIG. 6I, the distal slots 128' extend about the longitudinal axis B-B of the support structure 122" at an arc length L' of, for example, less than about 0.05 inch (1.27 mm), e.g., about 0.04 inch (1.02 mm). The lateral regions 129b define the maximum width W' of the deflection slot 128' to be, for example, about 0.03 inch (0.76 mm). The circular portion 129c of central region 129a is contiguous with or in communication with the lateral regions and includes a central circular cut-out 129c having a diameter of e.g., about 0.01 inch (0.25 mm). The central region 129a defines a minimum width of, e.g., about 0.02 inch (0.51 mm) in the longitudinal direction of the support structure. In one particular embodiment, the total number of slots 128' in the distal region is less than 30 slots (e.g., 25 slots), the slot spacing is about 0.03-0.04 inch (0.76-1.02 mm), and the slots are equally spaced apart in the distal deflection region 122". In other embodiments, however, the distal region may have a different number of slots and/or the slots may have a different arrangement (e.g., different dimensions, different or non-equal spacing between slots, etc.).

Figure 6J:
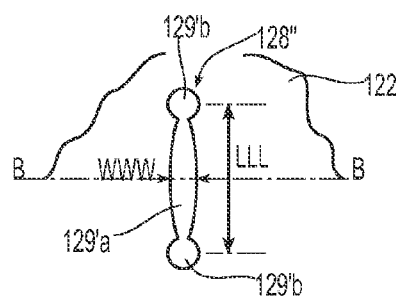
FIG. 6J is a plan view of a slot pattern for use with a treatment device configured in accordance with an embodiment of the technology.

Alternate slot, cut, and/or opening configurations can provide desired flexibility, stress-relief or other performance characteristics. FIG. 6J, for example, is an alternative slot arrangement 128" that can be used, for example, in either the deflection region 122a or the orientation region 122b (described in greater detail below) of the support structure 122. The illustrative slot 128" includes a central region 129'a that extends substantially perpendicular and about the longitudinal axis B-B of the support structure 122. The opposed lateral walls of the central region 129'a are generally arcuate, each defining a radius of curvature (e.g., about 0.06 inch (1.52 mm)) with a maximum gap WWW therebetween (e.g., about 0.005 inch (0.13 mm)) to define the maximum slot gap that may be partially or fully closed during deflection of the support structure 122. Further, disposed about the longitudinal axis B-B of the support structure 122 are lateral regions 129'b in communication or contiguous with the central region 129'a. The lateral regions 129'b are substantially circular and each have a diameter (e.g., 0.005 inch (0.13 mm)) to define regions for stress relief. The spacing between the centers of the curved lateral regions 129'b define a length LLL (e.g., about 0.04 inch (1.02 mm)) about the longitudinal axis B-B of the support structure 122. These lateral regions 129'b may be formed, for example as elliptical cuts on a non-perpendicular angle relative to a longitudinal axis of the shaft.

Figure 6K:
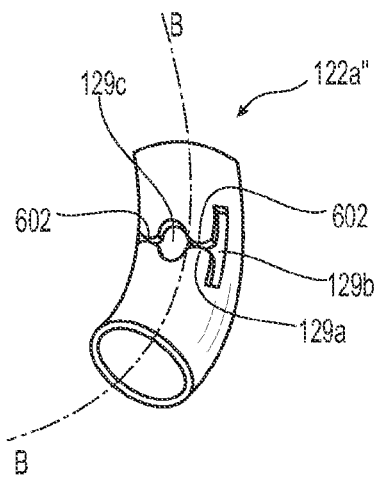
FIGS. 6K and 6L illustrate deformed slots of the support structure of FIG. 6H in a deployed state in accordance with an embodiment of the technology.
Figure 6L:
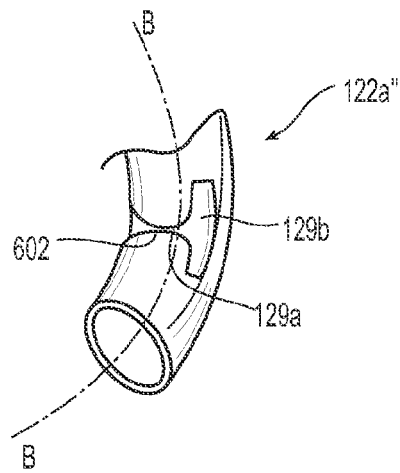
Figure 6M:
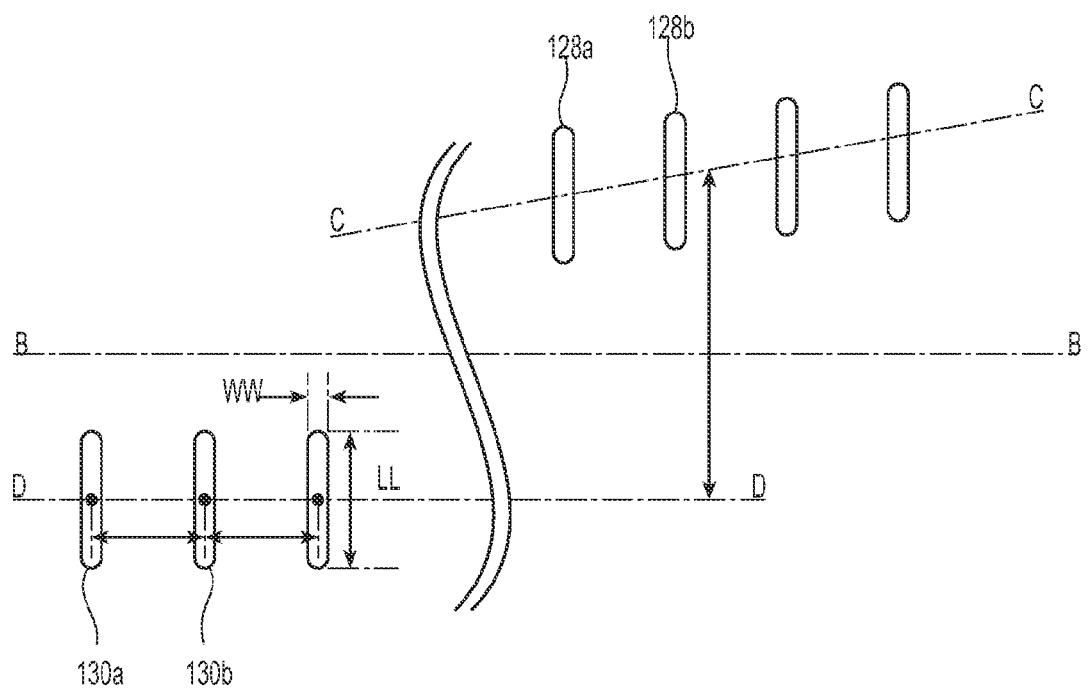
FIG. 6M is a plan view of a slot pattern for use with a treatment device configured in accordance with an embodiment of the technology.

The configuration of a slot in the deflection region 122a and/or orientation region 122b of the elongated shaft can impact the flexibility of the support structure 122. For example, as shown in FIGS. 6K and 6L, the inclusion (or absence) of the circular cut-out 129c in the central region 129a of a slot 128, 128', 128" can vary the number of contact points between the sidewalls of the slots disposed about the bisecting axis of the slot. FIG. 6K, for example, illustrates a portion of the distal region 122a" in a deflected or bent configuration. The central circular cut-out 129c provides for two contact points 602 between the sidewalls of central region 129a—one point of contact between each of the lateral regions 129b and the central circular cut-out 129c. In contrast and with reference to FIG. 6L, the absence of a central circular cut-out 129c provides for a single contact point 602 between the walls of the central region 129c when along a deflected portion of the distal region 122".

It should also be noted that, in order to facilitate fabrication of the support members 122, 122', 122", the deflection slots 128, 128', 128" described above may be formed perpendicular or generally perpendicular to either the longitudinal axis B-B or the progressive axis C-C without impairing the ability of the support member 122, 122', 122" to form the desired helical geometry when in a deployed state.

Further, as described above with reference to FIG. 6E, when support structure 122 is transformed from the delivery state to the deployed state, slots 128, 128", 128''' are deformed such that the walls defining central regions 129a, 129"a (as shown, for example, in FIGS. 6B, 6I, and 6J) approach each other to narrow the corresponding gap widths W, WW, WWW up to and including fully closing the gap wherein one or more pairs of opposing contact points touch each other (as shown schematically in FIG. 6E and described above with reference to FIGS. 6K and 6L).

The Orientation Region

Referring back again to FIGS. 6A-6D and as discussed previously, disposed proximally of the deflection region 122a is the orientation region 122b defined by a plurality of orientation slots 130. It may be desirable to control the orientation of the helical axis relative to the longitudinal axis B-B of the support structure 122. For example, in a therapeutic assembly incorporating the support structure 122, it may be desirable to direct the therapeutic assembly in a selected direction away from the longitudinal axis B-B such that at least a portion of the deflection region 122a is laterally off-set from the proximal end 126b of the support structure 122 and/or a distal end of the elongated shaft 116. As best seen in FIG. 6D, for example, the orientation region 122b can include orientation slots or openings 130 that are formed, spaced and/or oriented to provide for an orientation axis B-B that is skewed (e.g., from about 45 degrees) (45° to about 90 degrees)(90°) relative to the longitudinal axis B-B and orients the helically shaped geometry of the deflection region 122a adjacent the renal artery wall with the helical axis directed axially along the renal artery.

The orientation slots 130 can have a variety of different arrangements/configurations. Referring to FIG. 6B (and with reference to FIG. 6M), for example, the centers of orientation slots 130 are disposed and spaced along an orientation axis D-D that is radially offset from the progressive axis C-C (e.g., by about 90° about the longitudinal axis B-B of the support structure 122). The orientation axis D-D may extend generally parallel to the longitudinal axis B-B or, alternatively, may be skewed at a selected angle relative to the longitudinal axis B-B (as described in greater detail below with reference to FIG. 6N). In the illustrated embodiment, the centers of the orientation slots 130 are shown as substantially equidistantly spaced apart. In other embodiments, however, the spacing between the individual slots 130 may vary along the orientation axis D-D. Each slot 130 defines a maximum arc length LL about the longitudinal axis B-B and a maximum slot width WW in the direction of the longitudinal axis B-B.

Referring to FIG. 6B, in one embodiment the orientation slots 130 can include groups of slots of varying arc length LL about the longitudinal axis B-B. For example, the orientation slots 130 can include a first group of orientation slots 130a having a first arc length, a second group of orientation slots 130b having a second arc length less than the first arc length of the first group of orientation slots 130a, and a third group of orientation slots 130c having a third arc length less than the second arc length of group 130b. For example, in one particular embodiment, the first group of orientation slots 130a has an arc length of about 0.038 inch (0.97 mm), the second group of orientation slots 130b has an arc length of about 0.034 inch (0.86 mm), and the third group of orientation slots 130c has an arc length of about 0.03 inch (0.76 mm). In other embodiments, however, the orientation slots 130 may have different sizes and/or arrangements relative to each other. For example, in some embodiments one or more groups of orientation slots 130 may have different slot widths (in addition to, or in lieu of, varying arc lengths).

In one embodiment, the total number of slots 130 defining the orientation region 122b is less than 20 slots (e.g., about 5 to 15 slots, about 6 to 12 slots, etc.) equally spaced over the orientation region 122b. Further, in one particular embodiment, the total axial length of the orientation region 122b is about 0.2 to 0.25 inch (5.08 to 6.35 mm). In other embodiments, the orientation region 122b may have a different number of slots and/or a different arrangement and/or dimensions.

Alternate configurations of the orientation slots are possible. For example, Referring back again to the pattern illustrated in FIG. 6I, orientation slots 130' may be substantially elongated defining a preferably maximum arc length LL' about the longitudinal axis B-B and a maximum slot width WW in the direction of the longitudinal axis B-B. In one particular embodiment, for example, each orientation slot 130' has a width W' ranging from about 0.0005 to 0.010 inch (0.01 mm to 0.03 mm) and a slot arc length LL' of about 0.0005 to 0.010 inch (0.01 mm to 0.03 mm) so as to define a first radius of curvature r in an unconstrained deflected state that ranges between about 7 to 12 mm. In other embodiments, however, the orientation slots 130' may have other dimensions and/or arrangements.

In the illustrated embodiment, the orientation slots 130' extend generally perpendicular to the orientation axis D-D and are substantially symmetrical about the orientation axis D-D. The orientation slots 130' are generally "I-shaped" having a central region 131a extending perpendicular to the orientation axis D-D with two enlarged lateral regions 131b disposed about the central slot region 131a for stress relief. In this embodiment, the walls of the support structure 122" forming the perimeter of each of the lateral regions 131b can define, for example, a substantially rectangular geometry extending substantially parallel to the longitudinal axis B-B of the support structure 122" with the corners of the rectangular-shaped openings being radiused (not shown). Further, central regions 131a of the individual orientation slots 130' may be generally rectangular, or may have another suitable shape.

Each of the orientation slots 130' depicted in FIG. 6I can include a substantial rectangular central region 131a that extends substantially perpendicular and about the longitudinal axis B-B of the support structure 122. The elongate lateral walls of the central region 131a define a gap therebetween (e.g., about 0.0015 inch (0.038 mm)) to define the maximum closing gap of the slot during deflection of the structure 122. Each slot 130' can also include lateral regions 131b disposed about the longitudinal axis B-B and in communication or contiguous with the central region 131a. The lateral regions 131b define a substantially rectangular geometry preferably extending substantially parallel to the longitudinal axis B-B of the support structure 122" with the corners of the rectangular-shaped openings being radiused to define regions for stress relief. The spacing between the centers of the substantially rectangular lateral regions 131b define an arc length L (e.g., about 0.04 inch (1.02 mm)) about the longitudinal axis B-B of the support structure 122". Alternatively, lateral regions 131b may be formed as elliptical cuts on a non-perpendicular angle relative to the longitudinal axis B-B of the support structure 122, 122', 122".

In some embodiments, the total number of slots 130' in the orientation region is generally less than ten slots, e.g., five slots, the slot spacing can be, e.g., about 0.03 to 0.04 inch (0.76 mm to 1.02 mm), and the slots 130' can be equally spaced apart. Further, in some embodiments the orientation axis D-D can be generally parallel to the longitudinal axis B-B and radially offset from the progressive axis C-C at a minimum arc length distance of, e.g., about 0.01 inch (0.25 mm) over an angle ranging from about 50° to less than 90° about the longitudinal axis B-B of the support structure 122".

Figure 6N:
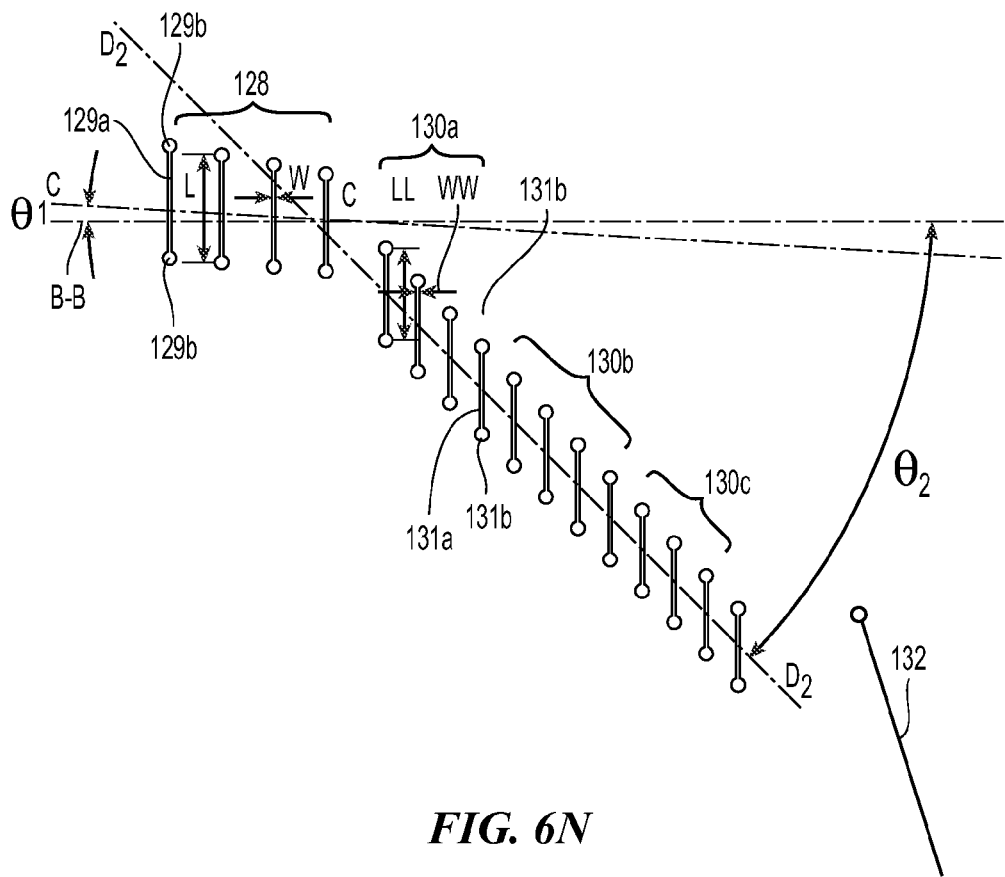
FIG. 6N is a plan view of a slot pattern for use with a treatment device configured in accordance with an embodiment of the technology.
Figure 6O:
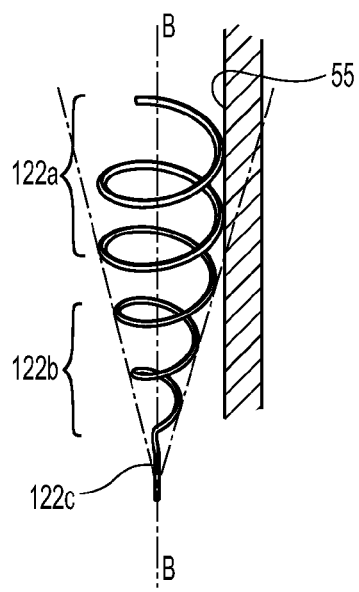
FIG. 6O is a schematic illustration of a portion of a treatment device having a support structure including the slot pattern of FIG. 6N in a deployed state within a renal artery of a patient.

In yet another embodiment, the orientation slots 130 may be disposed along an orientation axis that is substantially skewed with respect to the longitudinal axis B-B. FIG. 6N, for example, is a plan view of a slot pattern configured in accordance with another embodiment of the technology. In this embodiment, the orientation slots 130 are disposed on an orientation axis $D_2$-$D_2$ that may be skewed relative to the longitudinal axis B-B by an angle $\theta_2$ ranging from, e.g., about 0 degrees (0°) to about 45 degrees (45°). The angled orientation axis $D_2$-$D_2$ provides for an orientation region 122b having a tapered helical geometry upon deployment of the support structure 122. FIG. 6O, for example, is a schematic illustration of a portion of a treatment device having a support structure including the slot pattern of FIG. 6N in a deployed state within a renal artery of a patient.

The Flexible/Transition Region

Referring again to FIG. 6A, disposed proximally of the orientation region 122b is the flexible or transition region 122c. As noted above, the flexible region 122c can include, for example, the transitional helical or spiral slit or cut 132 having a variable pitch over its length. The variable pitch of the spiral cut 132 along the length of the flexible region 122c provides the support structure 122 with variable flexibility along the length of the elongated shaft 116. In one embodiment, for example, the transitional cut 132 extends over an axial length of, e.g., about 170 mm initiating proximal to the orientation region 122b. In other embodiments, however, the transitional cut 132 may have a different length.

As illustrated in FIGS. 6C and 6D, in some embodiments the pitch of the transition cut 132 may vary over the length of the transition cut to define multiple, different transition regions (four transition regions 132a, 132b, 132c, and 132d are shown in FIG. 6C). More specifically, in one embodiment, the cut 132 defines a first transitional portion 132a having a first pitch by forming, e.g., five revolutions about the tubular support structure 122 at a spacing of 0.02 inch (0.51 mm) and transitions to a second transitional portion 132b having a second pitch defined by, e.g., five revolutions at a spacing of 0.040 inch (1.02 mm). The cut 132 continues to define a third transitional portion 132a having a third pitch defined by, e.g., ten revolutions at a spacing of 0.06 inch (1.52 mm) and transitions to a fourth pitch defined by, e.g., twenty revolutions at a spacing of 0.08 inch (2.03 mm). It should be appreciated in the above example that, considering each sequential transitional portion 132 in order from the distal end to the proximal end of transition region 122c, the slit pitch spacing increases and the flexibility of tubular support structure 122 decreases.

The transitional cut 132 may have a generally constant width of, e.g., about 0.0005 inch (0.01 mm) over its length, or the width of the transitional cut 132 may vary over its length. The transitional cut 132 can also include at each end a substantially circular void contiguous with or in communication with the transitional cut. In other embodiments, however, the transitional cut 132 can have a different arrangement and/or different dimensions. For example, rather than having stepwise increases in pitch, the transitional cut 132 may have a continuously increasing pitch from the distal end to the proximal end of transition region 122c.

Figure 7A:
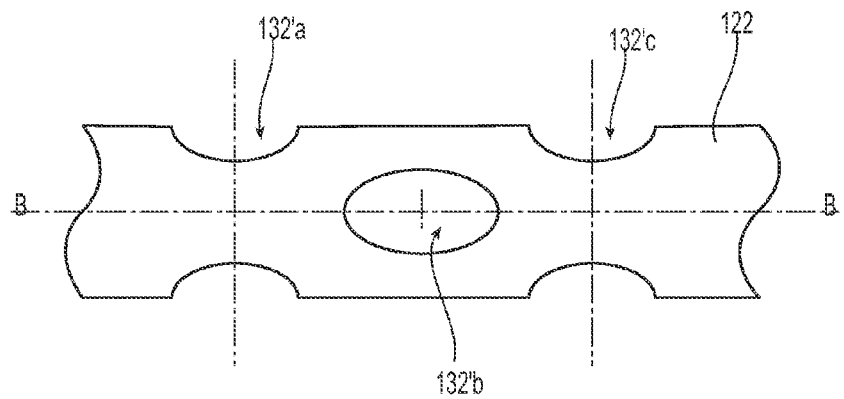
FIG. 7A is a plan view of a hole pattern for use with a treatment device configured in accordance with an embodiment of the technology.
Figure 7B:
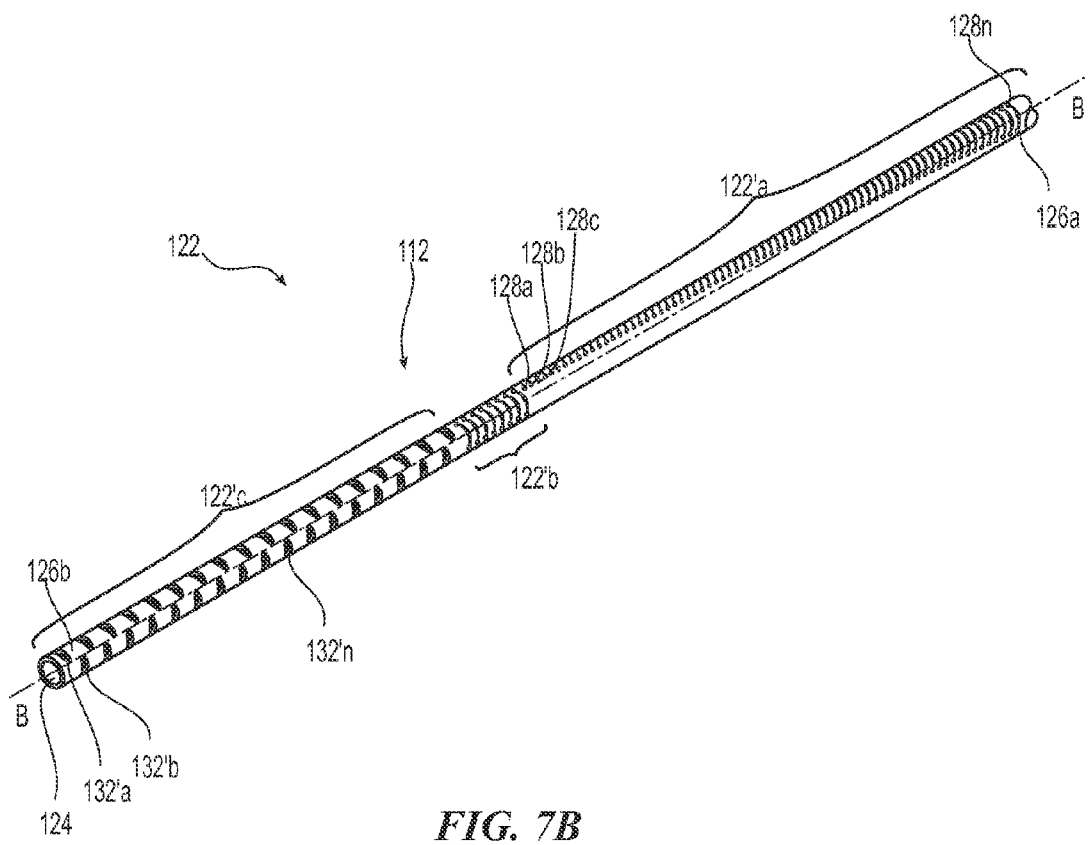
FIG. 7B is a perspective view of a distal portion of a treatment device including a flexible region having the hole pattern of FIG. 7A in a delivery state outside a patient.

Alternate slot, cut and/or opening configurations can provide for the desired flexibility, stress-relief or other performance characteristics in the flexible region 122c in lieu of the transition cut 132. In some embodiments, for example, opening or apertures may be selectively formed in the elongated shaft 116 to provide the desired flexibility. The individual openings or apertures of the flexible region 122c can, for example, have centers disposed along an axis that extends parallel to the central longitudinal axis B-B of the support structure 122. FIGS. 7A and 7B, for example, illustrate the support structure 122 with an alternate arrangement for the flexible region 122c, having through holes or openings 132'a, 132'b, 132'c that each extend through the tubular support structure 122. The openings 132', for example, can be alternately disposed on axes that are angularly spaced from one another about the longitudinal axis B-B of the support structure 122. In the illustrated embodiment, for example, opening 132'b is angularly disposed at 90° relative to the axially adjacent openings 132'a and 132'c. In other embodiments, however, the openings 132' may have a different arrangement.

FIG. 8A is a broken perspective view in partial section of a treatment device 100 including a catheter having an elongated shaft 116 with a distal region 120 having a support structure 122 for delivery and deployment of a therapeutic or treatment assembly 121 at a target treatment site in a lumen and, in particular, for performing renal denervation within a renal artery. Disposed at a proximal end of the elongated shaft 116 is a handle assembly 134, shown schematically, for manipulation of the elongated shaft 116 and the therapeutic assembly 121. More specifically, the handle assembly 134 is configured to provide for remote operation of a control member 168 (e.g., a control wire) for controlling or transforming the therapeutic assembly 121 between a delivery state and a deployed state (shown in FIG. 8A).

The system 100 is configured to deliver the therapeutic assembly 121 to the treatment site in a delivery state (not shown) in which the therapeutic assembly 121 is substantially linear (e.g., straight) such that the energy delivery elements 124 are substantially axially aligned along the support member 122. Energy supply wires 25 may be disposed along an outer surface of the support member 122 and coupled to each of the energy delivery elements 124 for supplying treatment energy to the respective energy delivery elements 124. Once located at the treatment site within the renal artery, actuation of the control member 168 that transforms the therapeutic assembly 121 from the delivery state to the deployed state as shown. In the illustrated embodiment, the control wire 168 is disposed within the tubular support structure 122. One end of the control member 168 may be affixed at or near the distal end 126a of the support structure 122 (e.g., terminating in a tip member 174). The opposite end of the control member 168 can terminate within the handle assembly 134 and be operably coupled to an actuator for transforming the therapeutic assembly 121 between the delivery and the deployed state.

The tension in the control member 168 can provide a proximal and/or axially directed force to the distal end 126a of the support structure 122. For example, under the influence of the tension force in the control member 168, the distal region 122b of the support structure 122 deflects. The distal deflection region 122a preferably include a plurality of slots 128 (only two are shown as 128'a and 128'b). As described above, the slots 128'a and 128'b are disposed along a progressive axis. The slots 128'a and 128'b formed in the distal region 122a of the support structure bias the deflection of the distal region 122a so as to form one or more curved portions, each having a radius of curvature preferably defined by the number of deflection slots 128, the individual slot width, slot configuration, and/or slot arrangement. As the distal region 122a continues to deflect, it radially expands placing one or more of the spaced-apart energy elements 124 into contact with the inner wall 55 of the renal artery. The support structure 122, when subject to the tension of the control wire 168 and the radial constraints of the vessel wall 55, is configured to form a substantially helical shape so as to axially space and radially offset the energy delivery elements 124 from one another. Moreover, because the deflection region 122a of the support structure 122 is configured to form a helical geometry within the renal artery when under a tension load, the treatment assembly 121 is not expected to radially overload the wall 55 of the renal artery. Rather, the support structure 122 deforms to form the helix under a continuously increasing tension load.

As discussed above, the progressive angle of the axis (e.g., progressive axis C-C) along which the deflection slots 128, 128', 128" are disposed defines the helical angle of the resulting deployed arrangement. In one embodiment, an amount of tension to fully deploy the therapeutic assembly 121 is typically less than, for example, about 1.5 lbf (pound-force) (0.68 kgF) applied at the distal end 126a of the therapeutic assembly 121, e.g., between about 1 lbf (0.45 kgF) to about 1.5 lbf (0.68 kgF). In the helically shaped deployed state of FIG. 8A, the slots 128' are disposed along the interior surface of the helix with the supply wires 25 for the energy delivery elements 24 disposed on an outer surface of the helix so as to form a "spine" of the assembly. The supply wires 25 can extend along the length of the treatment device 112 to an appropriately configured energy generator (not shown).

The support structure 122 of the therapeutic assembly 121 includes a proximal portion that defines an orientation region 122b of the assembly for locating the therapeutic assembly adjacent to the wall of the renal artery. As shown in FIG. 8A, the proximal region of the support structure 122 includes a plurality of orientation slots 130'. In operation, upon actuation of the handle assembly 134 to place the control wire 168 under tension, the orientation region 122b deflects in a radially outward direction within the renal artery to locate the therapeutic assembly 121 into contact with the arterial wall 55. More specifically, the slots 130' deform under the tension force so as to deflect the orientation region 122b radially outward from the longitudinal axis B-B of the support structure 122. In the fully deployed state, the resultant helical geometry of the therapeutic assembly 121 at the distal end of the support structure 122 is preferably offset from the longitudinal axis B-B at the proximal end of the support structure 122 such that the helical axis H-H and the longitudinal axis B-B of the support structure 122 are non-coaxial. The axes H-H, B-B may be parallel to one another or, alternatively, skewed with respect to one another.

The proximal end of the support structure 122 can be coupled to a separate member forming the elongated shaft 116 of the device 112. Alternatively, the support structure 122 and the elongated shaft 116 may be a single unitary member that extends proximally from the distal end 126a into the handle assembly 134. In one embodiment, the tubular support structure 122 is formed from a metallic shape-memory material (e.g., nitinol). Further, in one embodiment the support structure 122 can have an axial length of less than five inches (12.7 cm) and, more specifically, about two inches (5.08 cm); an outer diameter of about 0.020 inch (0.57 mm) and, more specifically, ranging between about 0.016 inch (0.41 mm) to about 0.018 inch (0.46 mm); a tubular wall thickness of less than 0.005 inch (0.13 mm) and, more particularly, about 0.003 inch (0.08 mm). In several embodiments, the elongated shaft 116 can be formed from stainless steel metal tubing having an outer diameter of, e.g., about 0.020 (0.57 mm) to about 0.060 inch (1.52 mm). In coupling the proximal support structure 122 to the elongated shaft 116, a joint 119 may be provided therebetween to provide the desired transfer of torque from the elongated shaft 116 to the support structure 122 when navigating to the treatment site. More specifically, each end of the support structure 122 and the elongated shaft 116 may respectively include mating notches that permit the ends of the tubular members to interlock with one another as shown in the joint assembly 120. In some embodiments, disposed about the joint 119 is a stainless steel sleeve that is crimped about the juncture to provide additional support to the joint 119.

As noted above, the control member 168 can be a control rod or wire that extends the axial length of the catheter device 112 from at or near the distal end 126a of the support structure 122 to the handle assembly 134. The control wire 168 can be comprised of ultra high molecular weight (UHMW) fiber, such as for example high strength, gel-spun fiber sold under the trademark SPECTRA or other sufficiently strong polyethylene fiber. Alternatively, nitinol, a para-aramid synthetic fiber sold under the trademark KEVLAR, or other mono- or multi-filament types can be used provided they are compatible with the application and can transfer the tensile force to the distal end of the therapeutic assembly 121 over the length of the treatment device 112.

Figure 8B:
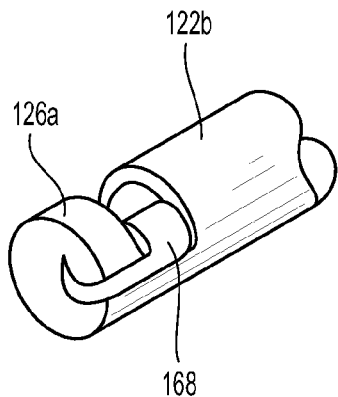
FIGS. 8B-8D illustrate various configurations of a distal end of a support structure configured in accordance with embodiments of the present technology.
Figure 8C:
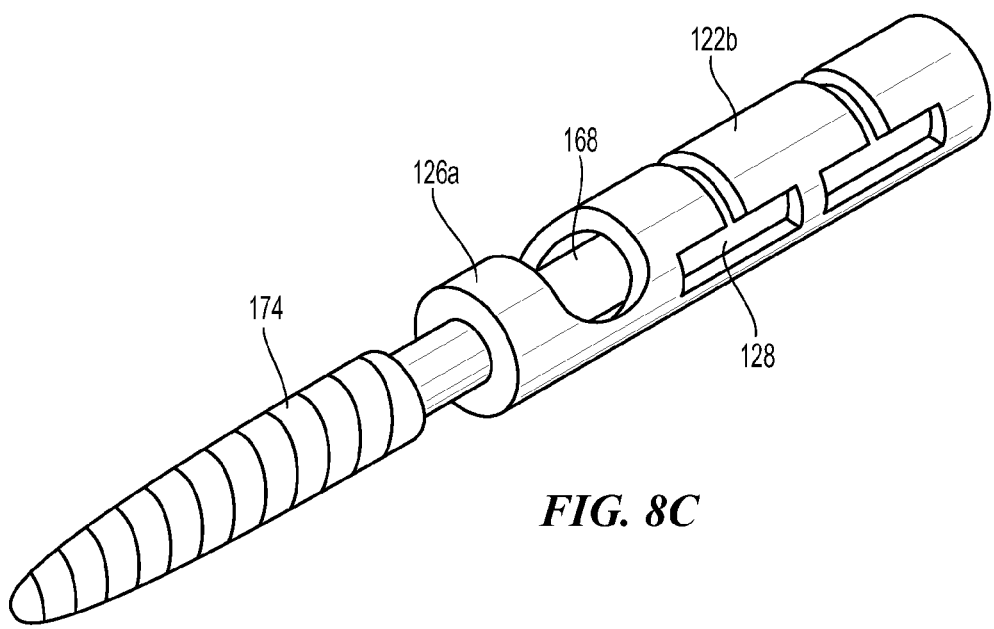
Figure 8D:
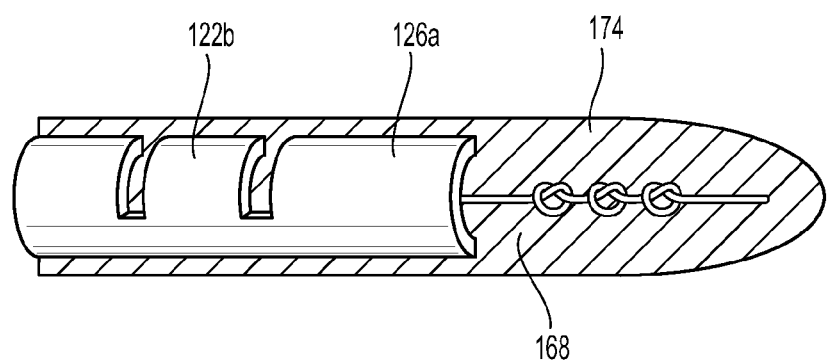

To provide the desired tensile force at the distal end of the therapeutic assembly 121, the control wire 168 may be anchored at or near the distal end 126a of the support structure 122. FIGS. 8B-8D, for example, illustrate various anchoring configurations for the control wire 168. More specifically, as shown in FIG. 8B, the distal end 126a of the support structure includes a slot adjacent the axial opening to tie and anchor the control wire 168 therethrough. In an alternate anchoring arrangement shown in FIG. 8C, the control wire 168 extends through the axial opening at the distal end 126a. The control wire 168 can be encased in a coil 174 material to stop the control wire 168 from sliding proximally into the distal portion of the support structure 122. FIG. 8D illustrates another tip 174 configured in accordance with an embodiment of the disclosure. In this arrangement, the control wire 168 can be tripled-knotted to provide an enlarged surface of the control wire 168 on which to coat the polymer material that is formed into a tip.

Referring back to FIG. 8A, the control wire 168 can extend through the elongated shaft 116 to the handle assembly 134. In operation of the handle assembly 134 to tension and release the control wire 168 when transforming the therapeutic assembly between deployed and delivered states, friction occurs between the moving control wire 168 and the interior of the relatively stationary elongated shaft. One embodiment of the control wire 168 assembly is configured to minimize the friction contact between the control wire 168 and the interior of the elongated shaft 116. For example, as shown in FIG. 8A, a sleeve 170 can be disposed and bound to the control wire 168 to provide a relatively low-friction outer surface. The sleeve 170 preferably has axial length that is less than that of the elongated shaft 116 and, more preferably, covers a substantially proximal portion of the control wire 168 within the elongated shaft 116. During operation of the handle assembly 134 to tension and release the control wire 168, the tubular sleeve 170 is configured to move with the control wire 168 and acts as a bearing surface against the interior of the elongated shaft 116, thereby reducing friction between the control wire 168 and the elongated shaft 116.

In several embodiments, a control member may be configured to be outside of the support structure of the treatment assembly that carries the energy delivery elements. For example, the support structure of the treatment assembly may instead be externally wound or wrapped around the control member. In such arrangements, the control member engages a portion of the support structure to apply a force that converts the support structure and the treatment assembly between its delivery and deployed state.

Figure 9A:
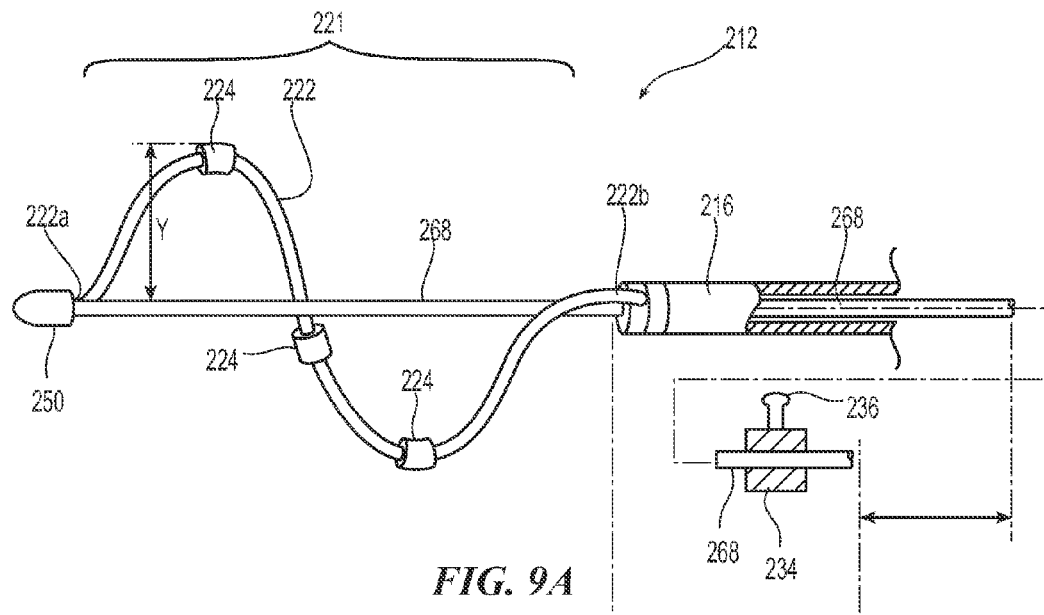
FIG. 9A illustrates a treatment device configured in accordance with an embodiment of the present technology in a deployed state (e.g., expanded configuration) outside a patient.
Figure 9B:
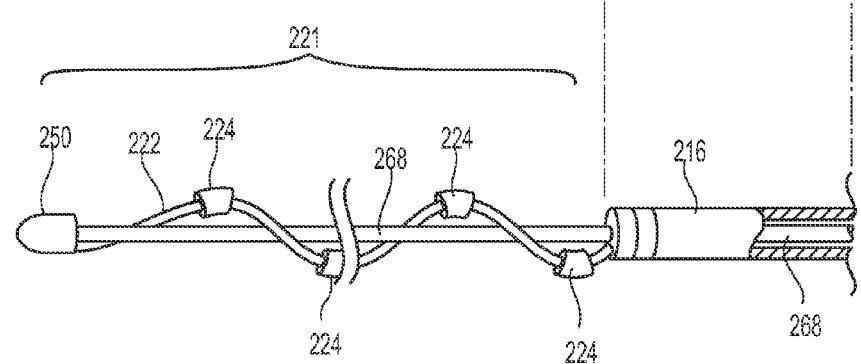
FIG. 9B illustrates the treatment device of FIG. 9A in a delivery state (e.g., low-profile or collapsed configuration).

FIGS. 9A and 9B, for example, illustrate a distal portion of a treatment device 212 configured in accordance with further embodiments of the present technology. More specifically, FIGS. 9A and 9B illustrate a treatment assembly 221 having a tubular support structure 222 helically wrapped about a control member 268 with a plurality of energy delivery elements 224 disposed about the support structure 222. The support structure 222 can include a number of features generally similar to the support structures 22 and 122 described above.

In the illustrated embodiment, a distal region or portion 222a of the support structure 222 terminates in an end piece (e.g., a conical or bullet-shaped tip 250) or, alternatively, a collar, shaft, or cap. The tip 250 can include a rounded distal portion to facilitate atraumatic insertion of the treatment device 212 into a renal artery. A proximal region or portion 222b of the support structure 222 is coupled to and affixed to an elongated shaft 216 of the treatment device 212. The elongated shaft 216 defines a central passageway for passage of a control member 268. The control member 268 may be, for example, a solid wire made from a metal or polymer. The control member 268 extends from the elongated shaft 216 and is affixed to the distal region 222a of the support structure 222 at the tip 250. Moreover, the control member 268 slidably passes through the elongated shaft 216 to an actuator 236 in a handle assembly 234.

In this embodiment, the control member 268 is configured to move distally and proximally through the elongated shaft 216 so as to move the distal region 222a of the support structure 222 accordingly. Distal and proximal movement of the distal region 222a respectively lengthen and shorten the axial length of the helix of the support structure 222 so as to transform the treatment assembly 221 between a delivery (FIG. 9B) and deployed state (FIG. 9A) such that the energy delivery elements 224 move a radial distance Y to engage the walls of the renal artery (not shown).

Figure 9C:
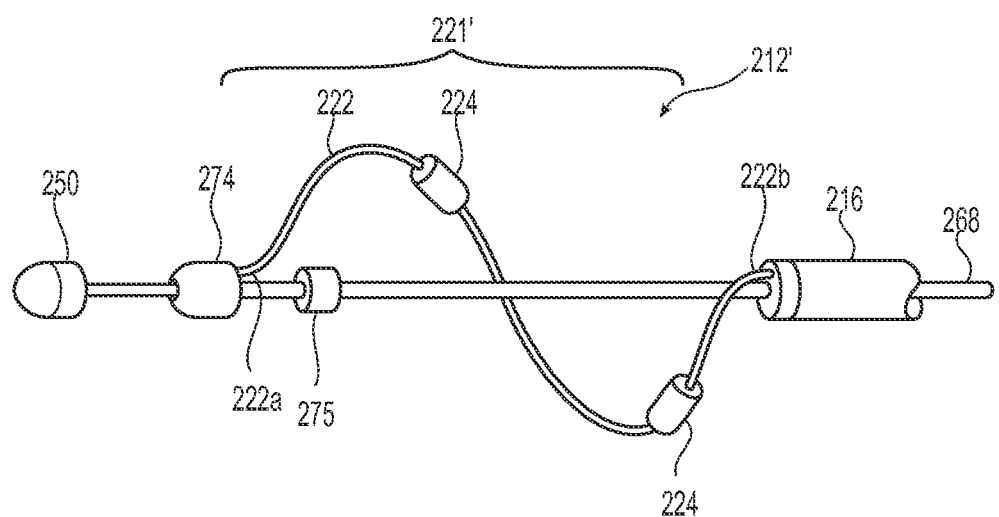
FIG. 9C illustrates another embodiment of a treatment device configured in accordance with an embodiment of the present technology in a deployed state.

In an alternate embodiment, the treatment assembly may not be affixed to a control member at the distal region of the tubular support structure. FIG. 9C, for example, illustrates another embodiment of a treatment device 212' and treatment assembly 221' having a helical shaped support structure 222 with a plurality of energy delivery elements 224 disposed about the helical support structure 222. A distal end region 222a of the support structure 222 is coupled to a collar element 274 that includes a passage sized and shaped to slidably accommodate the control member 268 that terminates at an end piece 250. In this embodiment, the control member 268 comprises control wire that extends from the elongated shaft 216 and moves distally and proximally through the elongated shaft 216 and the collar element 274. A stopper member 275 can be connected to the control wire 268 proximal to the collar element 274.

The control wire 268 facilitates the expansion and/or contraction of the helical support structure 222 when it is pulled or pushed to shorten or lengthen the helical support structure 222. For example, pulling (i.e., an increase in tension) of the control wire 268 may trigger expansion of the helical structure 222, while pushing (i.e., an increase in compression) of the control wire 268 may lengthen the helical support structure 222 to a compressed configuration. In some embodiments, helical structure 222 has elastic or super-elastic properties such that when force is removed the helical structure 222 elastically returns to a relaxed state. Force may be applied by the end piece 250 or the stopper member 275 to transform the treatment assembly 221' between the delivery and deployed states. For example, the control wire 268 may be pushed distally such that the stopper member 275 engages and distally moves the collar element 274 so as to lengthen the support structure 222 and reduce its diameter placing it in a delivery state. Alternatively, the control wire 268 may be pulled proximally to cause end piece 250 to engage and proximally move the collar element 274 so as to shorten the helical support structure 222 and increase its diameter, thereby placing it in a deployed state.

When the helical support structure 222 has a pre-formed helical shape memory, the helical support structure 222 elastically expands to its pre-formed shape when the collar element 274 is not engaged with either the stopper member 275 or the end piece 250. In this way the helical support structure 222 may expand to contact the inner wall of the renal artery with a relatively consistent force. Furthermore, in some embodiments the force exerted in the renal arterial wall by the pre-formed helical structure 222 may be less dependent on the operator's control at the handle assembly 234 (FIG. 9A).

Figure 9D:
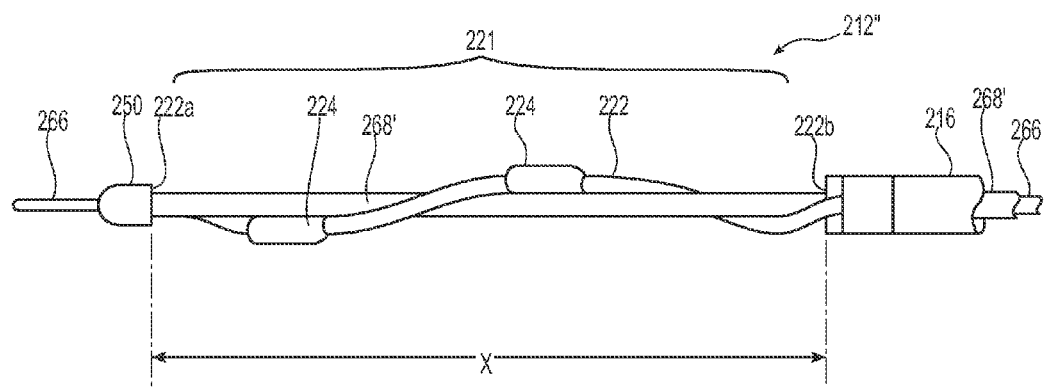
FIG. 9D illustrates yet another embodiment of a treatment device in a delivery state.
Figure 9E:
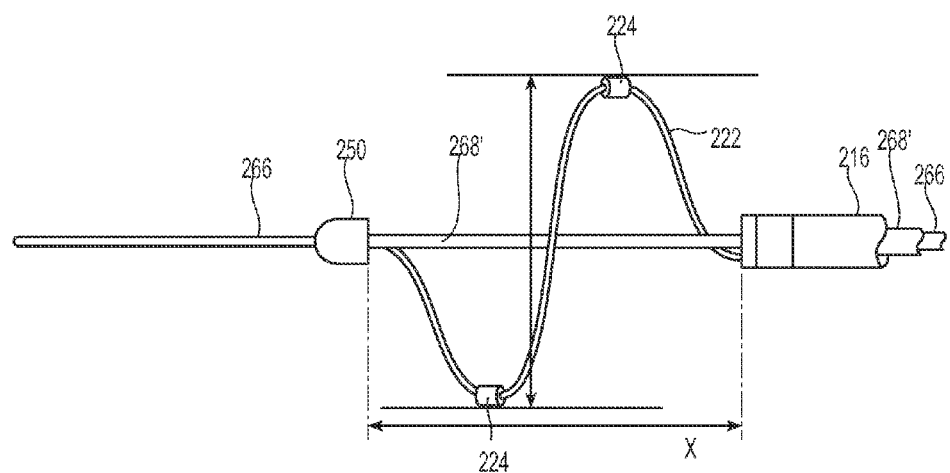
FIG. 9E illustrates the device of FIG. 9D in a deployed state.

FIGS. 9D and 9E illustrate another embodiment of a treatment device 212". In this embodiment, control member 268' comprises a hollow tube defining an internal passage for a guide wire 266 to facilitate insertion of the treatment assembly 221 through an intravascular path to a renal artery. Accordingly, the treatment device 212" is configured for an OTW or RX delivery as described herein. The control member 268' defines an internal lumen extending through the control member and composed of, for example, a polyimide tube with wall thickness less than about 0.003 inch (0.08 mm) (e.g., about 0.001 inch (0.02 mm)) and a lumen with a diameter of less than about 0.015 inch (0.38 mm) (e.g., about 0.014 inch (0.36 mm)). In addition to engaging and tracking along the guide wire 266, the device 212" transforms the configuration of the treatment assembly 221 between the delivery state and the deployed state in a manner similar to that of treatment device 212 shown and described with respect to FIGS. 9A and 9B.

Figure 10A:
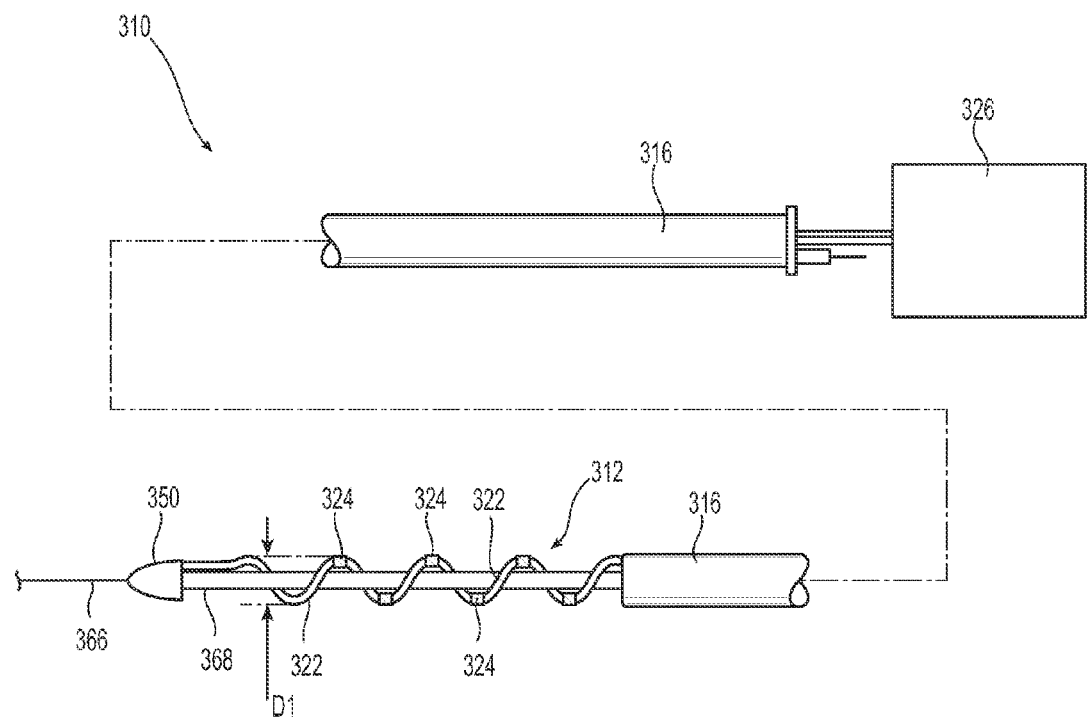
FIG. 10A is broken plan view of another treatment device in a delivery state outside a patient in accordance with an embodiment of the technology.
Figure 10B:
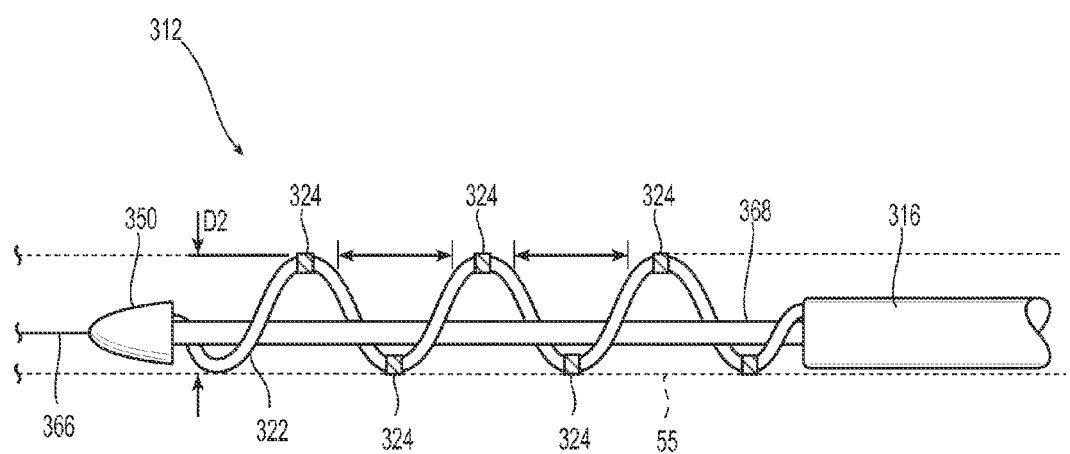
FIG. 10B is a detailed view of a distal portion of the device of FIG. 10A in a deployed state.

FIGS. 10A and 10B are side views of another embodiment of a treatment device 310 having an OTW configuration and including a tubular control member 368 defining a guide wire lumen that extends substantially the entire length of the device. The control member 368 is configured to slidably receive a guide wire 366 such that the treatment device 310 may be tracked over the guide wire 366 using over-the-wire techniques. The control member 368 is slidably disposed within an elongated shaft 316. In one embodiment, the control member 368 is allowed to slide relative to the elongated shaft 316 within a thin-walled sleeve (not shown) that is attached to an inner surface of the elongated shaft 316 using thermal or adhesive bonding methods. The thin-walled sleeve may be formed out of a polymeric material such as, but not limited to, polyimide. In other embodiments, however, the treatment device 310 may not include the sleeve.

The treatment device 310 also includes a treatment assembly 312 extending between a distal portion of the elongated shaft 316 and a distal portion of the control member 368. The treatment assembly 312 is deployable at a target location within the vasculature and includes multiple (e.g., six) energy delivery elements 324 (e.g., electrodes) for delivering energy from an energy generator 326 to a vessel wall. In some embodiment, the energy delivery elements or electrodes 324 may be equally spaced apart along the length of the support structure 322. In other embodiments, however, the number and/or arrangements of the energy delivery elements 324 may vary. The axial length of the support structure 322 can be between, e.g., about 17 mm to 20 mm. In other embodiments, however, the support structure 322 may have a different length so long as the structure sufficiently supports the number of electrodes in a desired electrode spacing pattern.

The energy delivery elements 324 may be a series of separate band electrodes spaced along that support structure 322. Band or tubular electrodes may be used in some embodiments, for example, because they have lower power requirements for ablation as compared to disc or flat electrodes. In other embodiments, however, disc or flat electrodes are also suitable for use. In still another embodiment, electrodes having a spiral or coil shape may be utilized. In one embodiment, the individual energy delivery elements 324 may have a length ranging from approximately 1-5 mm, and the spacing between each of the energy delivery elements 324 may range from approximately 1-10 mm. In other embodiments, however, the energy delivery elements 324 may have different dimensions and/or arrangements.

The energy delivery elements 324 may be formed from any suitable metallic material (e.g., gold, platinum, an alloy of platinum and iridium, etc.). In one embodiment, for example, energy delivery elements 324 may be 99.95% pure gold with an inner diameter that ranges between about 0.025 inch (0.64 mm) and 0.030 inch (0.76 mm), and an outer diameter that ranges between about 0.030 inch (0.76 mm) and 0.035 inch (0.89 mm). Electrodes of smaller or larger dimensions, i.e., diameter and length, are also suitable for use herein.

Each energy delivery element or electrode 324 is electrically connected to the generator 326 by a conductor or wire (not shown) extending through a lumen of the elongated shaft 316. Each electrode 324 may be welded or otherwise electrically coupled to the distal end of its energy supply wire and each wire can extend through the elongated shaft 316 for the entire length of shaft such that a proximal end thereof is coupled to the generator 326.

The support structure 322 may comprise a shape memory component that extends at least the length of the assembly 312. Shape memory support structure 322 is utilized to deploy or transform the treatment assembly 312 from a delivery state shown in FIG. 10A (i.e., a substantially straightened form) to a deployed state shown in FIG. 10B (i.e., a preset spiral or helical form). More particularly, the shape memory component of support structure 322 may be constructed from a shape memory material that is pre-formed or pre-shaped into the deployed state. Certain shape memory materials have the ability to return to a predefined or predetermined shape when subjected to certain thermal conditions. When shape memory materials, such as nickel-titanium (nitinol) or shape memory polymers or electro-active polymers, are at a relatively low temperature, items formed therefrom may generally be deformed quite easily into a new shape that they retain until exposed to a relatively higher transformation temperature, which in embodiments hereof is above a normal body temperature of 37° C., that then returns the items to the predefined or predetermined shape they held prior to the deformation. In some embodiments, support structure 322 may be formed from such a shape memory material, inserted into the body in a deformed, low profile straightened state, and returned to a "remembered" preset shape once shape memory support structure 322 is exposed to a transformation temperature in vivo. Thus, shape memory support structure 322 has at least two stages of size or shape, a generally straightened or stretched-out coil configuration of a sufficiently low profile for delivery to the treatment site as shown in FIG. 10A and a spiral or helical configuration that places energy delivery elements 324 into contact with a vessel wall 55, which is shown as a dashed line in FIG. 10B. The delivery state may also be achieved by mechanically straightening shape memory support structure 322 by the operator or via a tensioning device. Referring to FIG. 10A, in one embodiment a delivery diameter D1 of shape memory support structure 322 may be between about 1 and 2 mm to accommodate delivery to a target vessel, such as a renal artery.

The treatment assembly 312 may also include an insulating component (not shown) that functions to electrically isolate shape memory support structure 322 from the energy delivery element 324. The insulating component, for example, can include a tubular sheath defining a lumen that is formed from an electrically insulative material, such as polyethylene block amide copolymer. In an embodiment, the insulating component may have an outer diameter of approximately 0.027 inch (0.69 mm) and an inner diameter of approximately 0.023 inch (0.59 mm). The insulating component is configured to house shape memory support structure 322 as well as housing wires to provide additional protection thereto, and electrodes 324 are attached to or disposed around insulating component. A distal end of the insulating component may be attached to a distal end of guide wire shaft 368 by any suitable method such as an adhesive, a sleeve, or other mechanical method. In one embodiment depicted in FIG. 10A, the distal end of the insulating component is preferably attached to the distal end of guide wire shaft 368 via a cyanoacrylate adhesive and a polymer sleeve surrounds and holds together the distal ends to form a tapered distal tip 350 of the treatment assembly 312. In other embodiments, however, the insulating component may have a different arrangement relative to the treatment assembly 312.

Both shape memory support structure 322 and the insulating component preferably extend along the length treatment assembly 312 and proximally extend into the distal end of the shaft 316, e.g., at least one or two centimeters, such that the proximal end of shape memory support structure 322 is sufficiently removed from the energy delivery elements 324 to avoid any thermal effects therefrom.

As the shape memory support structure 322 of the treatment assembly 312 assumes the deployed configuration, the distal end of the insulating component proximally retracts such that the treatment assembly 312 radially expands into contact with vessel wall, since the distal end of the insulating component is coupled to distal end of inner tubular shaft 368. The control member 368 also slightly proximally retracts within elongated shaft 316 in order to allow deployment of the treatment assembly 312.

In each of the previously described embodiments of the treatment or therapeutic devices, the control member is configured as a wire, tubular shaft or other inner member that applies a force at or near the distal end of the support structure to alter the configuration of the therapeutic assembly between a delivery state and a deployed state. In other embodiments, however, an actuating force may be applied at or near the proximal end of the therapeutic assembly to transform the configuration of the assembly.

FIGS. 11A and 11B, for example, illustrate an embodiment of a treatment device 612 configured to apply a deforming force to a proximal end of the treatment assembly. The treatment device 612 includes a tubular elongated shaft 616 having a proximal end coupled to a handle assembly 634 and a distal end coupled to a treatment assembly 621. The illustrated treatment assembly 621 includes a tubular support structure 622 carrying a plurality of energy delivery elements 624. Energy supply wires (omitted for clarity) extend internally or externally along the support structure 622 to provide a treatment energy to the energy delivery elements 624. A proximal end 622b of the support structure 622 is disposed within and affixed to the distal end of the tubular elongated shaft 616. The support structure 622 defines a preferably helical shape wrapped about a tubular control member 668 having an internal lumen for passage of a guide wire 666 that can extend distally beyond the treatment assembly 621 and proximally beyond the handle assembly 634. Accordingly, the treatment device 612 is configured for an over-the-wire delivery. The support structure distal end 622a is coupled to a distal region of the tubular control member 668. The control member 668 extends proximally into the elongated shaft 616 and is affixed to an internal surface of the handle assembly 634. Accordingly, the distal end 622a of the support structure 622 can remain at a fixed distance from the handle assembly 634.

The elongated shaft 616 extends proximally into the handle assembly 634, and is coupled to an actuator 636. In one embodiment, the actuator 636 provides for linear displacement or direct longitudinal translation of the elongated shaft 616. The actuator 636 is shown schematically as a slider-in-groove assembly. In operation, proximal translation of the actuator 636 translates the axial shaft 616 proximally with respect to handle assembly 634 and thus to inner member 668. The distal end of the elongated shaft 616 applies a tension force to the affixed proximal end 622b of the support structure 622. Because the distal end 622a of the support structure 622 is affixed to the control member 668, proximal translation of the proximal end 622a of the support structure 622 elongates the structure so as to place the treatment assembly 612 in a low profile delivery state (FIG. 11A). Distal translation of the actuator 636 results in compressing the support structure 622 axially so as to place the treatment assembly 612 into a deployed state (as best seen in FIG. 11B).

Figure 11C:
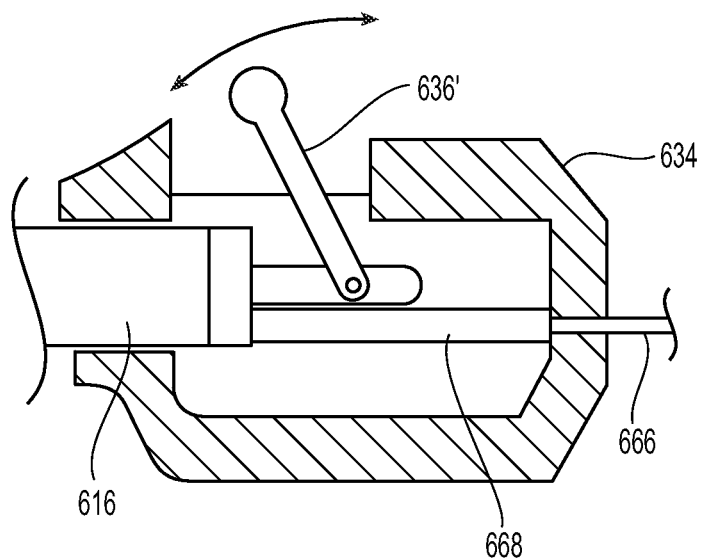
FIG. 11C is a longitudinal cross-sectional view of a handle assembly for use in the device of FIG. 11A in accordance with an embodiment of the present technology.
Figure 11D:
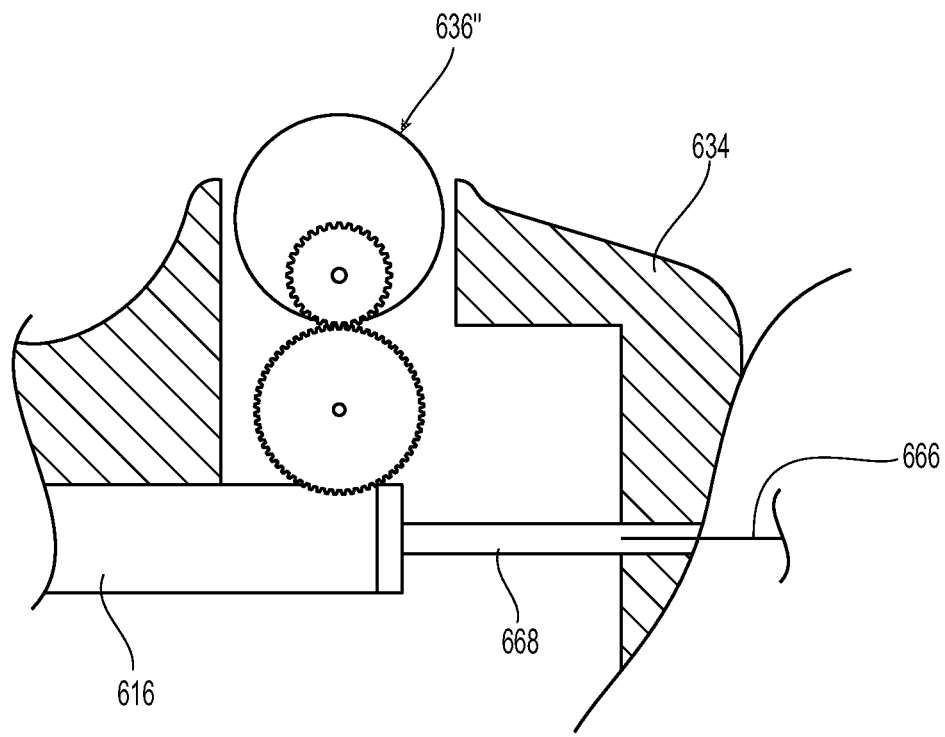
FIG. 11D is a longitudinal cross-sectional view of another handle assembly for use in the device of FIG. 11A in accordance with an embodiment of the present technology.

Alternate configurations of the handle assembly 634 can provide the desired axial translation of the elongated shaft 616. FIG. 11C, for example, illustrates an alternate arrangement of the handle assembly 634 that provides for a pivot-type actuator 636' to axially translate the elongated shaft 616. The actuator 636' can include a pivot connection to the elongated shaft 616. Accordingly, angular rotation of actuator 636' about the pivot connection linearly translates the elongated shaft 616. The amount of angular rotation of the actuator 636' can be controlled by the distance between elongated shaft 616 and the pivot point. FIG. 11D illustrates another alternate configuration of the handle assembly 634 including a gear-type actuator 636" to linearly translate the elongated shaft 616. In one embodiment, for example, the actuator 636" includes a knob or thumb roller connected to a small gear. The elongated shaft 616 may be connected to a larger gear engaged with the a small gear such that the small gear rotates, which in turn rotates the larger gear and translates the elongated shaft 616. The difference in gear sizes allows a small roller rotation to create a large translation of the elongated shaft 616.

In the previously described embodiments of the treatment device, the treatment assembly of the devices was altered between a delivery state and a deployed state by pushing or pulling on either a proximal end or a distal end of the support structure depending upon the configuration. It should be understood that the treatment device may be configured for selectively applying a force at or near either the proximal or the distal end of the support structure such that a clinician may select the end for relevant movement depending, for example, the constraints around the supporting structure.

Figure 12A:
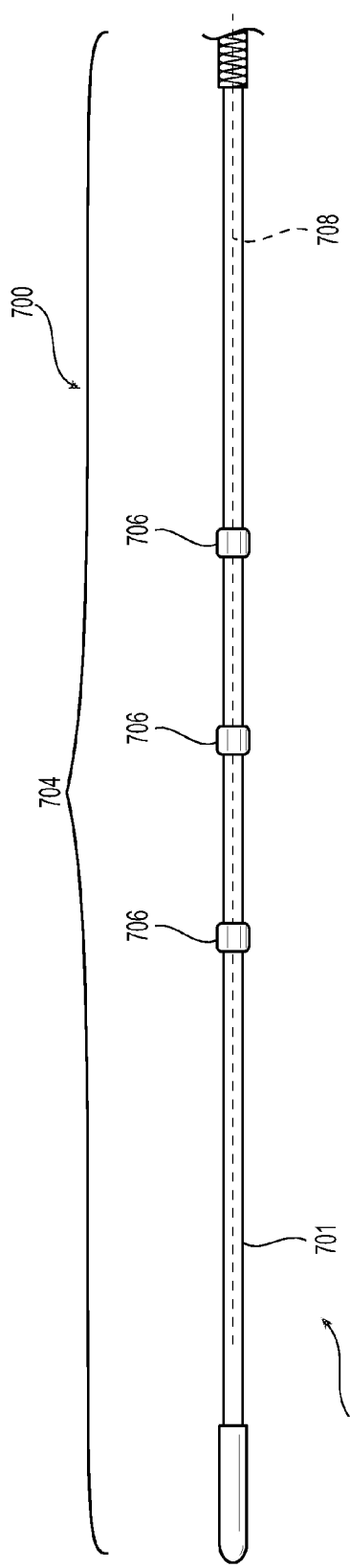
FIG. 12A is a side view of a distal portion of a treatment device in a delivery state (e.g., low-profile or collapsed configuration) outside a patient in accordance with an embodiment of the present technology.
Figure 12B:
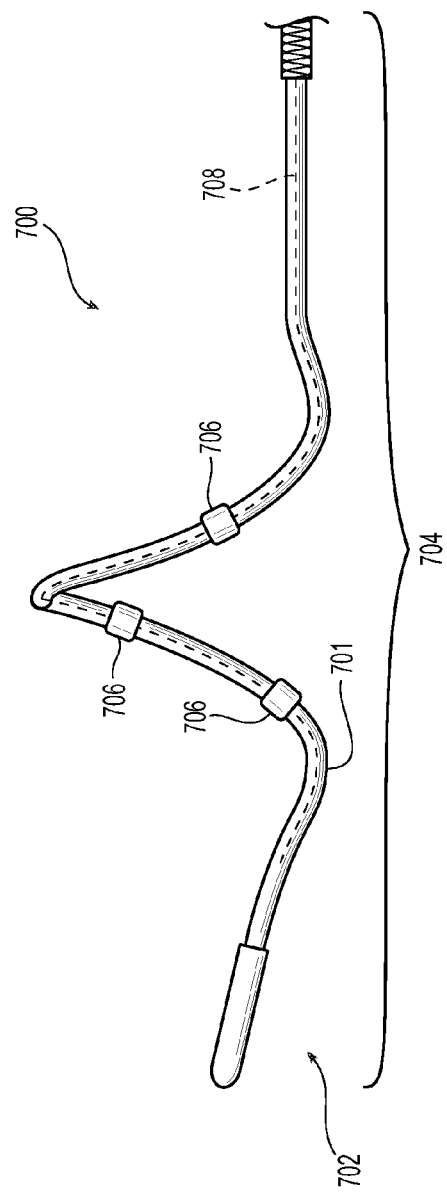
FIG. 12B is a side view of the distal portion of the treatment device of FIG. 12B in a deployed state (e.g., expanded configuration) outside the patient.

In several alternate configurations, the treatment assembly can be movable between the delivery and deployed states by either inserting or retracting a control member (e.g., an insertion member, stylet, pre-shaped member, etc.) into a distal treatment section or portion of a tubular support structure. FIGS. 12A and 12B, for example, are side perspective views of a portion of a treatment device 700 configured in accordance with an additional embodiment of the technology. More specifically, FIG. 12A illustrates the treatment device 700 in a delivery state (e.g., low-profile or collapsed configuration) outside a patient, and FIG. 12B illustrates the treatment device 700 in a deployed state (e.g., expanded configuration). Referring to FIGS. 12A and 12B together, the treatment device 700 includes an elongated shaft 701 having a distal portion 702, and a treatment section 704 at the distal portion 702. The treatment device 700 also includes a plurality of energy delivery elements 706 carried by the treatment section 704. The treatment device 700 further includes a control member 708 (shown schematically in broken lines) coupled to the treatment device 700 and slidably moveable relative to the treatment section 704. As will be described in greater detail below, the treatment section 704 or the control member 708 comprises a pre-formed helical shape, and the other of the treatment section 704 and the control member 708 comprises a substantially straight shape. The treatment section 704 and the control member 708 are movable relative to one another to alter the treatment device 700 between a low-profile delivery state (FIG. 12A) and an expanded delivery state having the pre-formed helical shape (FIG. 12B). For purposes of illustration, control member 708 is shown in both FIGS. 12A and 12B. As described in greater detail below, in various embodiments, the control member 708 may be either inserted into or withdrawn from the treatment section 704 to alter the treatment device 700 between the delivery and deployed states.

For example, in one embodiment described below, the control member 708 can include a stylet, stiffening mandrel, straightening member, or a procedural guide wire extending along at least a portion of the length of the treatment device 700 and configured to straighten a pre-shaped helical treatment section 704 of the treatment device 700 during delivery. More specifically, the control member 708 facilitates the expansion and/or contraction of the treatment section 704 when the control member 708 is pulled or pushed, respectively, relative to the treatment section 704. In another embodiment, a pre-shaped control member (e.g., stylet or pre-shaped member) can provide a helical shape to a relatively flexible, distal portion 702 of the treatment device 700.

Figure 13A:
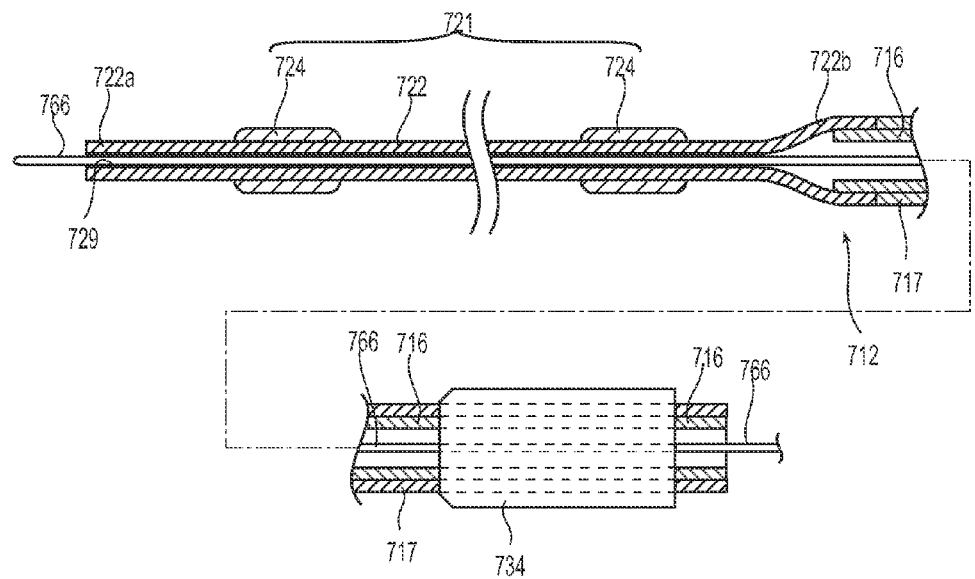
FIG. 13A is a broken side view in part section of a treatment device in a delivery state in accordance an embodiment of the present technology.

FIGS. 13A-15B are directed to various embodiments of treatment devices including features generally similar to the treatment device 700 described above with reference to FIGS. 12A and 12B. FIGS. 13A and 13B, for example, are cross-sectional views of a treatment device 712 including a treatment section or assembly 721 having a plurality of energy delivery elements 724 carried by a relatively flexible tubular support structure 722 defining a central lumen 729. The tubular support structure 722 includes a distal end 722a having an axial opening for passage of a guide wire 766 (FIG. 13A) extending through the lumen 729. The tubular support structure 722 has a proximal end 722b coupled to or affixed to the distal end of a tubular elongated shaft 716. The elongated shaft 716 defines a central lumen for housing the guide wire 766. Accordingly, the present configuration provides for an over-the-wire delivery from an access site in which the guide wire 766 is initially inserted to a treatment site (e.g., within a renal artery), and the treatment device 712 is installed over the guide wire 766. Inserting the substantially straight and linear guide wire 766 through the flexible tubular support structure 722 maintains the tubular support structure 722 in a normally straight shape so as to place the treatment assembly 721 into a low profile delivery state for delivery to the treatment site in the renal artery. The guide wire 766 may be of a constant stiffness along its length or may have a variable stiffness or flexibility along its length so as to provide increased flexibility, for example, in the proximal to distal direction.

Once the treatment device 712 is delivered over guide wire 766 to a desired position within the renal artery, the guide wire 766 is refracted completely from treatment device 712 and an elongate control member 768 (FIG. 13B) is inserted at a proximal end of the device 712 and advanced distally through the elongated shaft 716 into the central lumen 729 of the tubular support structure 722. The distal region of the control member 768 can have a pre-set deployed shape (e.g., a helical shape) when unconstrained to define the deployed state of the treatment assembly 721. The control member 768 may be made from a super-elastic nitinol material having a pre-set or pre-formed helical shape. Alternatively, the control member can be made from a shape-memory material.

Figure 13B:
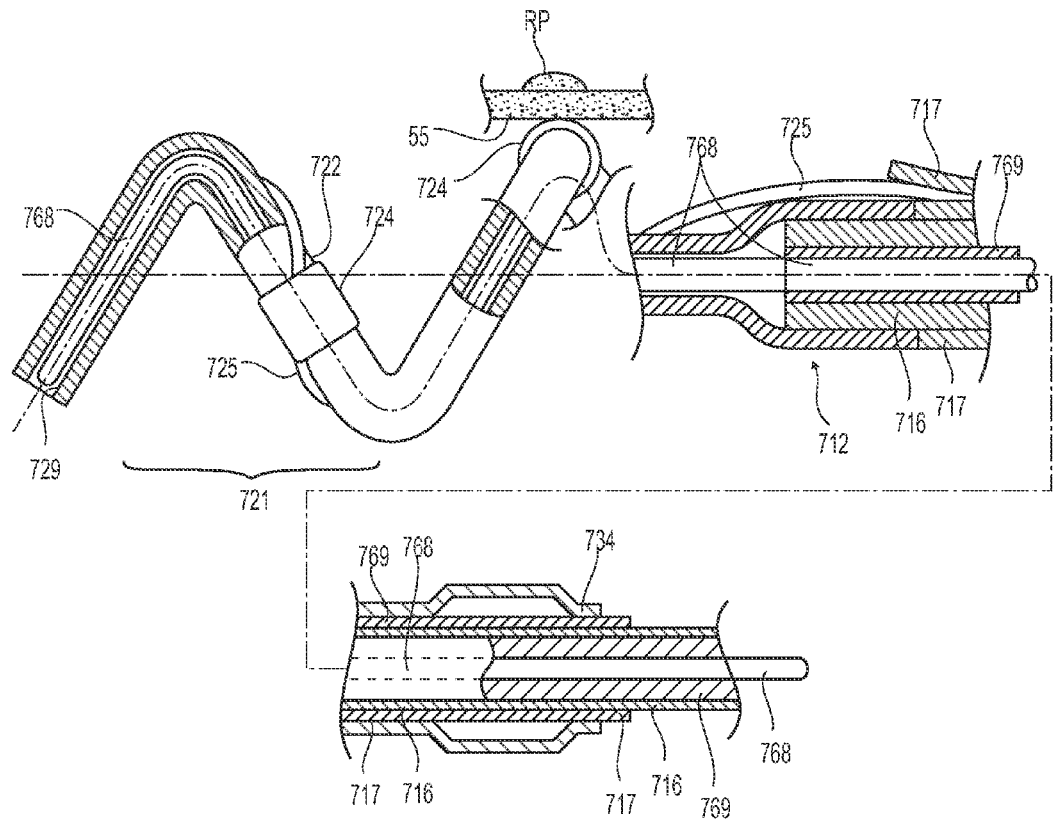
FIG. 13B is a broken side view in part section of the embodiment of FIG. 13A in a deployed state within a renal artery.

The control member 768 is sufficiently elastic so as to be straightened for insertion at the proximal end of the device, for example, at the handle 734. The control member 768 may be inserted directly into the elongated shaft 716. Alternatively, the control member 768 may be first housed inside of a more rigid insertion tube 769 (FIG. 13B) to straighten out the control wire 768 and facilitate insertion of the control member 768 into the catheter device 712. In this embodiment, the treatment assembly 721 can be inserted into the proximal end of the elongated shaft 716 and, once located at the treatment site within the renal artery, the insertion tube 769 can be retracted to allow the control member 768 to deploy. As shown in FIG. 13B, the control member 768 imparts a force on the tubular support structure 722, thereby deforming it in to an expanded helical configuration and deploying the treatment assembly 721 to locate the energy delivery elements 724 against the wall of the renal artery.

In a particular embodiment, a plurality of electrical delivery elements 724 are configured as multiple electrodes 724 mounted onto a flexible, somewhat distensible tube 722 (e.g., a tube made of polyethylene block amide copolymer such as PEBAX® 5533D, or a lower durometer material). In other embodiments, the tubular support structure 722 may be constructed from other polymers, e.g., PET, polyamide, polyimide, PEBAX, polypropylene, or PEEK polymers that provide the desired flexibility. In one embodiment, the tubular support structure 722 has an inner diameter of about 0.03 inch (0.76 mm) and an outer diameter of about 0.04 inch (1.02 mm) and a length of about 4 cm. The electrodes 724 can be cylindrical electrodes and, in one embodiment, can have an inner diameter of about 0.042 inch (1.07 mm), an outer diameter of about 0.046 inch (1.17 mm), and a length of about 1 mm. The electrodes 724 can be spaced between 3 to 5 mm apart and bonded to the tubular support structure 722 using an adhesive. Electrode conductive power supply wires 725 can extend proximally along and outside the tubular support structure 722.

In several embodiments, the proximal end 722b of the flexible support structure 722 with the electrodes 724 is placed over the distal end of tubular elongated shaft 716 and bonded in place. The elongated shaft 716, for example, can include a polyamide tube. In one embodiment, the shaft 716 has an inner diameter about of 0.025 inch (0.64 mm) and an outer diameter of about 0.03 inch (0.76 mm) with a length of about 100 cm. In other embodiments, the elongated shaft has an inner diameter of 0.026 inch (0.66 mm) and an outer diameter of 0.028 inch (0.71 mm) and/or other suitable dimensions. An outer tubular jacket 717 can surround the shaft 716 and abut or overlap the proximal end 722a of the tubular support structure 722.

The control member 768 for deploying the treatment assembly 721 can include, for example, a nitinol wire pre-shaped with a helical configuration over the distal region of the control member 768. In one embodiment, the control member 768 has a diameter of about 0.015 inch (0.38 mm) and tapers distally to a tip having a diameter of 0.008 inch (0.20 mm). Several different diameters of pre-shaped control members 768 can be made to accommodate different diameter renal arteries with each having a diameter ranging from about 4.0 mm to about 8.0 mm. The control member 768 can have a shape memory transformation temperature that is slightly above body temperature (e.g., austenite finish temperature $A_f=42°$ C.). The control member 768 is more pliable at temperatures below the $A_f$, and therefore the helical region can be straightened manually with relative ease. Accordingly, the control member 768 can then be inserted directly into the proximal end of the catheter without the need for the "rigid insertion tube 769." Once the distal region of the control member 768 is positioned within the tubular support structure 722 surrounded by the multiple electrodes 824, raising the temperature of the shape memory control member 768 above the $A_f$ will allow it to assume the helical configuration, deform the tubular support structure 722 and press the electrodes 724 into the arterial wall allowing the tissue ablation to occur. Once the ablation is completed and the energy source 26 turned off, the surrounding blood flow can cool the electrodes 724 and the control member 768 below the $A_f$, allowing the control member 768 to become more pliable for removal from the catheter. Those skilled in the art will understand that various methods can be used to heat the control member 768 to transform its shape.

In the embodiment illustrated in FIG. 13B, the control member 768 is disposed in the optional insertion tube 769. The insertion tube 769 can be made from a variety of materials including braided polyimide, PEEK, and/or stainless steel and can have dimensions such that the insertion tube 769 can slide easily through the elongated shaft 716. The pre-shaped control member 768 has a total axial delivery length that is greater that then the axial length of the insertion tube 769 such that the guide wire 766 can be advanced and retracted from the proximal end of the catheter device 712.

In the above described embodiments that use the flexible tubular support structure 722 and the insertion tube 769 for delivery and deployment of the therapeutic assembly, the guide wire is completely removed from the tubular support structure 722 before insertion of the pre-shaped control member 768 because there is only a single lumen in the elongated shaft of the catheter for receiving the guide wire 766 and the control member 768. Further embodiments of treatment devices, however, include for an elongated shaft with multiple lumens to provide multiple passageways in which to hold a control member, a guide wire, supply wires, and/or an injectable fluid (e.g., contrast, medicine, or saline). Accordingly, such treatment devices provide for an over-the-wire delivery and deployment of a treatment assembly with an insertable member without the need to remove the guide wire completely from the catheter.

Figure 14A:
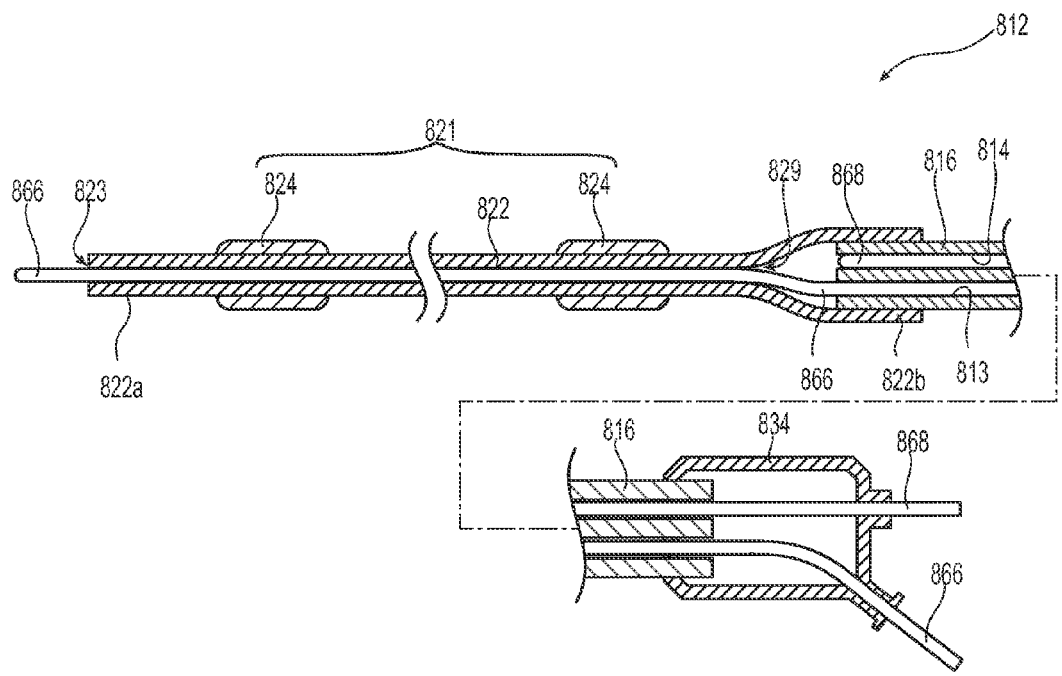
FIG. 14A is a broken longitudinal cross-sectional view of another embodiment of a treatment device in a delivery state in accordance an embodiment of the present technology.
Figure 14B:
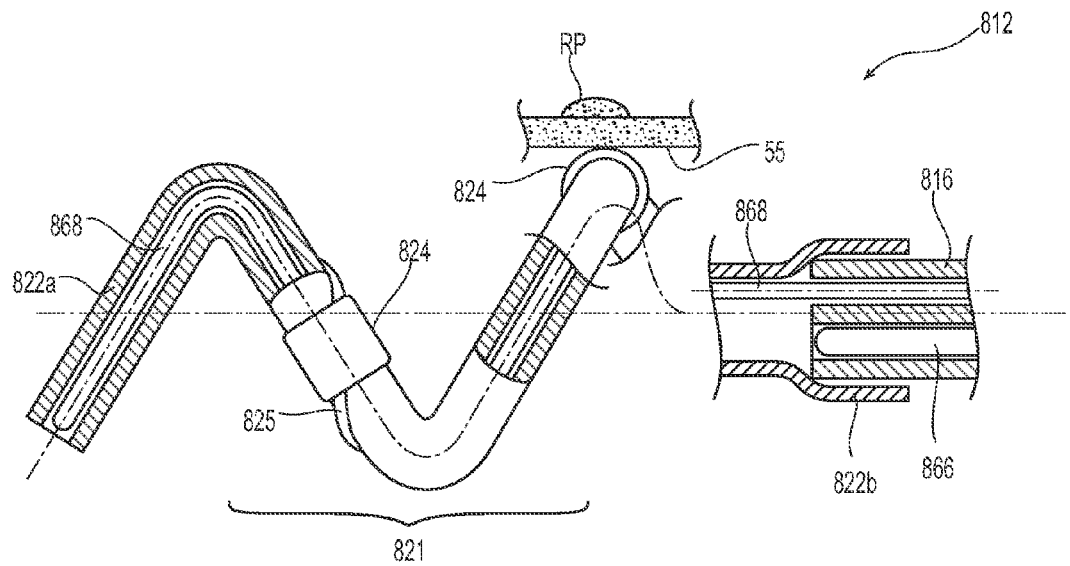
FIG. 14B is a broken side view in part section of the embodiment of FIG. 14A in a deployed state within a renal artery.

FIGS. 14A and 14B, for example, are broken longitudinal cross-sectional views of a treatment device 812 configured in accordance with another embodiment of the present technology. As shown in FIG. 14A, the treatment device 812 includes a treatment assembly 821 having a plurality of energy delivery elements 824 carried by a relatively flexible tubular support structure 822 defining a central lumen 829. The tubular support structure 822 includes a distal end 822a having an axial opening 823 for passage of a guide wire 866 extending through the central lumen 829. The tubular support structure 822 has a proximal end 822b coupled or affixed to the distal end of an elongated tubular shaft 816. The elongated shaft 816 can define a first internal lumen 813 for housing the guide wire 866. The guide wire 866 exits proximally from a conventional hub/luer fitting located, for example, at the handle 834. Accordingly, the illustrated configuration provides for an OTW delivery from the access site to the treatment site. Inserting the substantially straight guide wire 866 through the flexible tubular support structure 822 straightens the tubular support structure 822 so as to place the treatment assembly 821 into a low profile delivery state for delivery to the treatment site in the renal artery.

The tubular shaft 816 further includes a second internal lumen 814 for housing a control member 868 for deployment of the treatment assembly 821. The tubular shaft 816 may have multiple lumens to hold the shape insertion members, supply wires, and/or an injectable fluid (e.g., contrast, medicine, or saline). FIGS. 14A and 14B show the two lumens 813, 814 formed within the integral tubular shaft 816. Alternatively, the first and second lumens 813 and 814 can be defined by separate tubular shafts disposed within the outer tubular shaft 816. Within the second internal lumen 814 of the tubular shaft 816, the control member 868 can be maintained in a substantially linear configuration. Once the treatment device 812 is placed in a desired position within a renal artery, the guide wire 866 can be refracted from the tubular support structure 822 into the first lumen 813, and the control member 868 can be advanced distally into the central lumen 829 of the tubular support structure 822. Because each of the control member 868 and the guide wire 866 have independent lumens in which they reside, the guide wire 866 needs only be retracted a sufficient distance proximally to exit the tubular support structure 822 of the treatment assembly 821 so as to allow the control member 868 to fill the support structure 822 and deploy the treatment assembly 821. In several embodiments, for example, the guide wire 866 can be retracted 10-20 cm (e.g., about 15 cm) to clear the tubular support structure 822 for deployment of the treatment assembly 821.

The control member 868 can have a pre-set deployed shape that defines a helical shape when unconstrained to define the deployed state of the treatment assembly 821. The control member 868 may be made from a super-elastic nitinol material having a pre-set helical shape. Once located within the support structure 822, the elastic control member 868 can impart a force on the tubular support structure 822 deforming it in to an expanded helical configuration (e.g., as shown in FIG. 14B), so as to deploy the treatment assembly 821 and locate the energy delivery elements 824 against the wall of the renal artery.

Figure 14C:
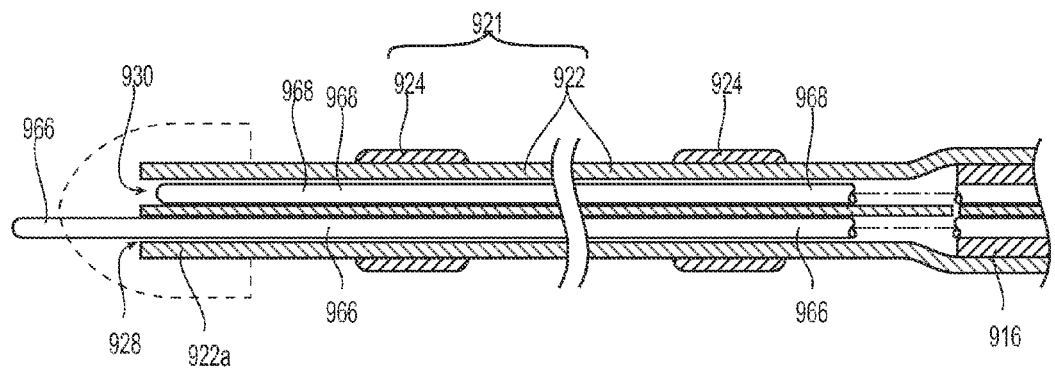
FIG. 14C is a longitudinal cross-sectional view of a distal portion of another embodiment of a treatment device in a delivery state in accordance an embodiment of the present technology.
Figure 14D:
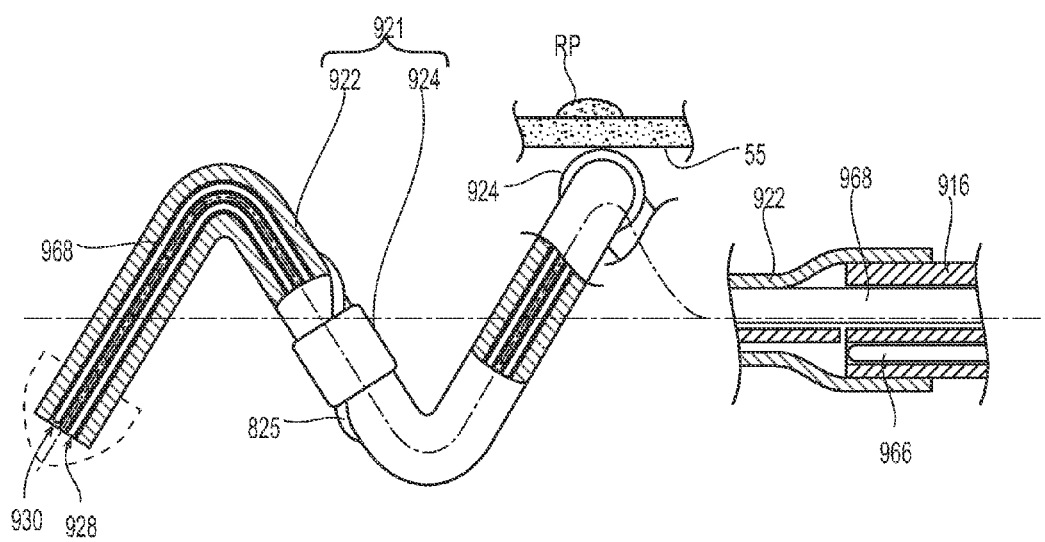
FIG. 14D is a broken longitudinal cross-sectional view of the embodiment of FIG. 14C in a deployed state within a renal artery.

In other embodiments of the device with the multi-lumen elongated shaft, a tubular support structure can include at least two or more independent lumens or passageways. For example, FIGS. 14C and 14D illustrate a treatment device 912 including a treatment assembly 921 with a plurality of energy delivery elements 924. A tubular support structure 922 defines at least two internal lumens. A first lumen 928 can include an axial opening at its distal end and can be adapted to accept a guide wire 966 having a diameter of less than about 0.015 inch (0.38 mm) for insertion and retraction from the first lumen 928. Accordingly, the support structure 922 can be delivered into a renal artery using an OTW approach as discussed above. In other embodiments, the distal end 922a of the tubular support structure 922 may terminate in a rounded distal tip to facilitate atraumatic insertion of the treatment device into the renal artery. A second lumen 930 is adapted to hold a deployment member 968 having a pre-set distal region defining a helical shape in a deployed state.

The therapeutic assembly 921 can be placed into a low-profile delivery state (e.g., as shown in FIG. 14C) by inserting the guide wire 966 through the first lumen 928 of the support structure 922 for delivery to a renal artery. The substantially linear guide wire 966 can overcome the pre-set helical shape in the flexible deployment member 968 to maintain the therapeutic assembly 921 in the delivery state. The guide wire 966 may be of a constant stiffness along its length or, alternatively, may have a variable stiffness or flexibility along its length so as to provide increased stiffness, for example, in the proximal to distal direction. Once the treatment assembly 921 is positioned at the target treatment site in the renal artery, the therapeutic assembly 921 can be deployed by retracting the guide wire 966 out of the first lumen 928 of the support structure 922 such that it is generally located within the elongated shaft 916 (e.g., within one of the plurality of lumens formed within the elongated shaft 916). With the guide wire 966 removed from the support structure 922, the deployment member 968 can impart a deforming force on the tubular support structure 922 that deforms it to the helical shape so as to deploy the therapeutic assembly 921 (e.g., as shown in FIG. 14D). Accordingly, the guide wire 966 provides a control member to alter the therapeutic assembly between the delivery and the deployed states. Optionally, the first lumen 928 may be used to deliver a fluid distally, such as saline to cool the energy delivery element 924 during energy delivery.

In another embodiment, the deployment member 968 may be retractable to control the delivery and deployment states of the treatment assembly 921 and the guide wire 966 or other straightening stylet can remain in the first lumen 928 during deployment. In such an arrangement, the guide wire 966 can be sufficiently rigid to place the treatment assembly 921 in the low profile configuration for delivery, yet flexible enough to allow the deployment member 968 to impart a force on the assembly 921 to place the support structure 922 and the treatment assembly 921 in the deployment configuration.

Figure 15A:
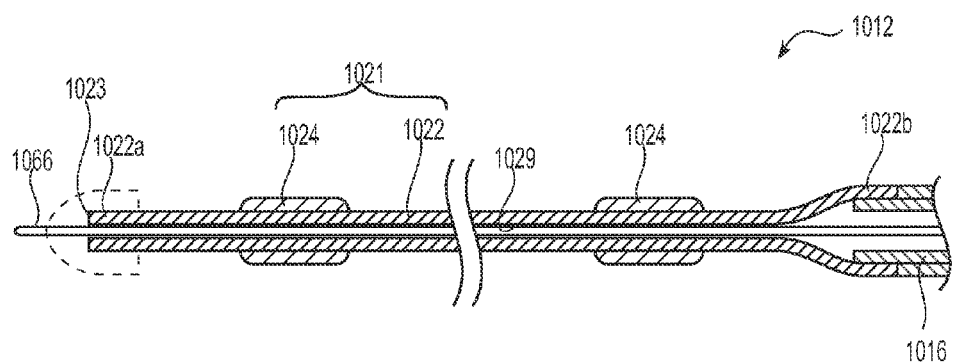
FIG. 15A is a longitudinal cross-sectional view of a distal portion of another embodiment of a treatment device in a delivery state in accordance an embodiment of the present technology.
Figure 15B:
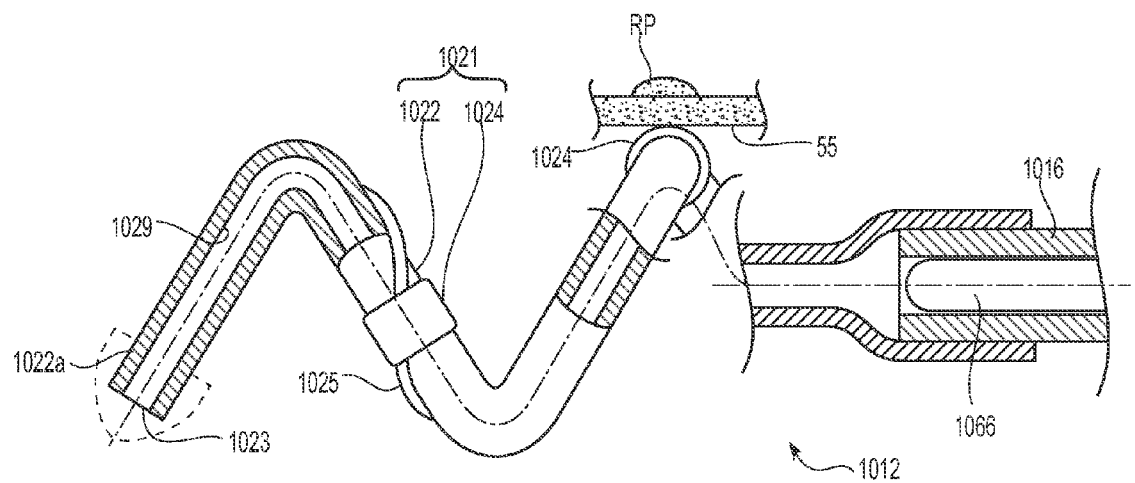
FIG. 15B is a broken side view in part section of the embodiment of FIG. 15A in a deployed state within a renal artery.

FIGS. 15A and 15B illustrate still another embodiment a treatment device 1012 that allows a guide wire 1066 to remain at least partially inserted in an elongated shaft 1016 during treatment. As shown in FIG. 15A, the treatment device 1012 includes a single lumen in each of a tubular support structure 1022 and the elongated shaft 1016. The treatment device 1012 includes a treatment assembly 1021 having a plurality of energy delivery elements 1024 mounted to the tubular support structure 1022 defining a single central lumen 1029. The support structure 1022 may be covered with an electrical insulator, e.g., with a heat shrink tube of a polymer such as PET. The tubular support structure 1022 may also include a distal end 1022a having an axial opening 1023 to allow the guide wire 1066 to project beyond the distal end 1022a. In some embodiments, the distal end 1022a may terminate in a rounded distal portion (e.g., as shown in broken lines). The tubular support structure 1022 can have a proximal end 1022b coupled to the distal end of the elongated shaft 1016. The central lumen 1029 of the support structure 1022 can extend through the elongated shaft 1016 to receive the guide wire 1066 and allow for an OTW delivery. In operation, inserting the substantially straight guide wire 1066 through the tubular support structure 1022 straightens the tubular support structure 1022 so as to place the treatment assembly 1021 into a low-profile delivery state (e.g., as shown in FIG. 15A) for delivery to the treatment site in the renal artery.

The tubular support member 1022 may be made from an elastic or super elastic material, e.g., nitinol tubing or polymer-composite tubing including braided or coiled filaments of nitinol. In several embodiments, the support structure 1022 can have an inner diameter less than or equal to about 0.015 inch (0.38 mm), e.g., about 0.010 inch (0.25 mm), and a wall thickness of less than about 0.005 inch (0.13 mm), e.g., about 0.003 inch (0.76 mm). The tubular support structure 1022 may also be made from a shape-memory material, e.g., nitinol having a pre-formed helical deployed shape. As an alternative to using a pre-formed shape, the tubular support structure 1022 may includes a pre-shaped inner member (e.g., inner tubing) or an outer frame structure (not shown) that biases the tubular support structure 1022 into the helical deployment configuration.

With the guide wire 1066 disposed in the central lumen 1029, the guide wire 1066 imparts a straightening force on the tubular support structure 1022 so as to define the low profile or collapsed delivery configuration shown in FIG. 15A. The guide wire 1066 may be of a constant stiffness along its length or, alternatively, may have a variable stiffness or flexibility along its length so as to provide increased flexibility (e.g., in the proximal to distal direction). To deploy the treatment assembly 1021, the guide wire 1066 can be retracted proximally into the elongated shaft 1016 so as to remove the guide wire 1066 from the support structure 1022. As shown in FIG. 15B, in the absence of a straightening force, the support structure 1022 can deploy into a helical configuration. Accordingly, the guide wire 1066 acts as a control member for altering the configuration of the treatment assembly 1021 between the delivery and the deployed states.

Figure 16A:
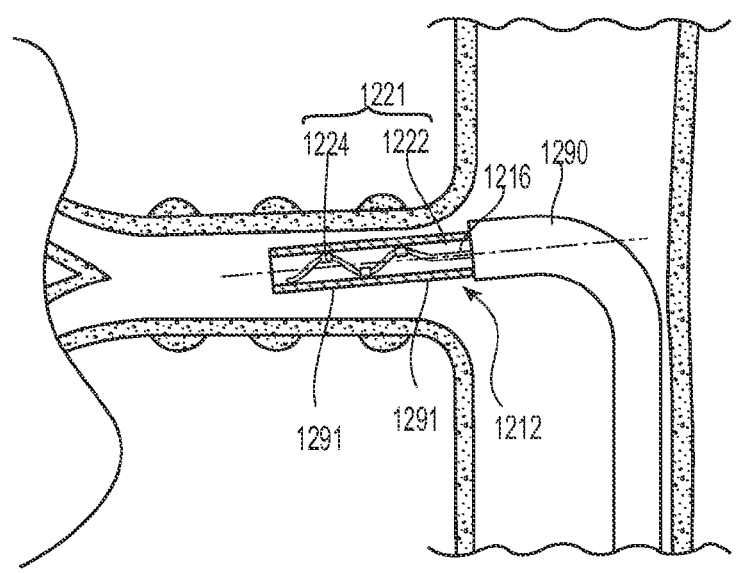
FIG. 16A is a cross-sectional view of one embodiment a treatment device in a delivery state within a patient's renal artery in accordance an embodiment of the present technology.
Figure 16B:
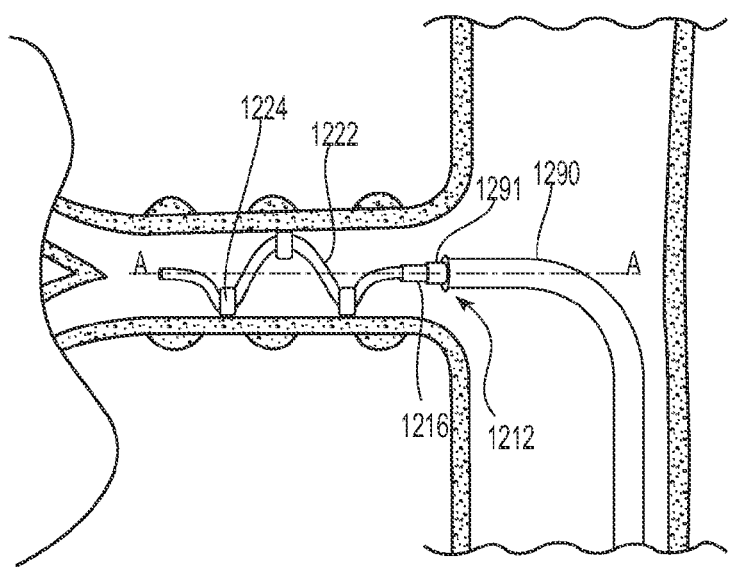
FIG. 16B is a cross-sectional view of one embodiment a treatment device in a deployed state within a patient's renal artery in accordance an embodiment of the present technology.

Although the embodiments of the treatment or catheter devices previously described include an arrangement of the treatment assembly and a control member to place the assembly in a low-profile delivery state, the catheter devices may further include an external sheath that can be disposed and retracted over the treatment assembly to alter its delivery and deployed configurations. For example, as shown in FIGS. 16A and 16B, a treatment device 1212 can be used in conjunction with a delivery sheath 1291 that forms a sheath around a treatment assembly 1221 and an elongated shaft 1216. As noted, in certain embodiments, it may be advantageous to use a guide catheter 1290 of a particular size to facilitate insertion of the treatment device 1221 through the femoral artery. A delivery sheath 1291 may be used in conjunction with the guide catheter 1290 to gain access to a renal artery and deliver a contained expandable helical structure 1222. Alternatively, the delivery sheath 1291 may be used in conjunction with a guide wire (not shown) as described previously. When used in conjunction with the guide catheter 1290, a working length of the elongated shaft 1216 may be about 40 cm to about 125 cm. If, for example, a 55 cm length guide catheter is used, then this working length may be about 70 cm to about 80 cm. If a 90 cm length guide catheter 1290 is used, then this working length may be about 105 cm to about 115 cm. In a representative embodiment where no guide catheter 1290 is used, then this working length may be about 40 cm to about 50 cm. In still other embodiments, a variety of other different dimensions and/or arrangements may be used.

In the depicted embodiment, the treatment assembly 1221 includes a helical structure 1222 that may be held in a low profile delivery configuration by the delivery sheath 1291. Removal of the delivery sheath 1291 allows the helical support structure 1222 to deploy and place the energy delivery elements 1224 into contact with the wall of the renal artery. The deployment of the support structure 1222 may be passive (e.g., the structure has a pre-set deployed shape) or active (e.g., the deployment is facilitated by a pre-shaped stylet or a tension wire). Regardless of the type of expansion, the helical support structure 1222 may by coupled to a control member (e.g., a control wire) that compresses the helical structure prior to removal or repositioning of the treatment device 1212. In particular embodiments, depending on the placement and number of energy delivery elements 1224, the helical support structure 1222 may be progressively repositioned within the renal artery to provide a plurality of locations for energy delivery. FIG. 16B shows the embodiment of a catheter with a helical structure 1222 of FIG. 16A with the delivery sheath 1291 retracted allowing the helical structure 22 to elastically expand to its deployed configuration in a renal artery. It should be noted that, in FIG. 16A, the sheath 1291 and treatment assembly 1221 are drawn oversized for clarity.

In one particular embodiment, a sheath can be used to hold the components of the treatment assembly together, particularly as the device is navigated through to the treatment site within the renal artery. With reference to FIGS. 9A and 9B, the treatment assembly 221 can include a spine or support structure 222 of nitinol material with a plurality of electrodes 224 disposed thereabout. The nitinol support structure 222 can be helically wrapped about a braided polyamide inner member 268. In the delivery state of the treatment assembly 221 of FIG. 9B, the support structure 222 may lie adjacent to the inner member 268 over its length. In order to minimize substantial separation between the support structure 222 and the inner member 268 when the treatment assembly 221 is bent or curved during delivery, a sheath can be disposed over the treatment assembly 221. Sheaths may also be employed with the treatment assemblies described above with reference to FIGS. 10A-11B and other suitable treatment assemblies described herein.

A sheath may also be used to support a treatment assembly in its delivery configuration, even when the treatment assembly has a shape-forming insertion member disposed in the lumen of the flexible tubular support structure. For example, with reference to FIGS. 13A and 13B, a sheath (not shown) can be disposed over support structure 722. Upon retraction of the guide wire 766 and insertion of a control member 768 into the lumen of the support structure 722, the sheath prevents the treatment assembly 721 from deploying to its fullest transverse dimension. To permit the assembly 721 to deploy completely to the desired helical configuration, the sheath can be retracted. Alternatively or in addition, the tubular support structure 722 is preferable stiff enough to allow for guidable insertion to the treatment site without the use of the stylet or shaping member, but flexible enough to take on the shape of the inserted control member 768 once the sheath is withdrawn. Further, in the alternative or in addition to, the insertable control member 768 can be sheathed to minimize or eliminate the premature deployment of the treatment assembly upon insertion of the control member. Accordingly, once the sheath is removed, the insertion member 768 can expand to its full deployment configuration.

In still further embodiments with reference to FIGS. 13A and 13B, the stylet 768 is positioned in the distal end treatment assembly 721 of the device 712 while the device is at the treatment site (e.g., within the renal artery). In this embodiment, for example, the stylet 768 is sheathed in a low-profile configuration during insertion by insertion tube 769. The insertion tube 769 is removed from the pre-formed stylet 768 after insertion, allowing the stylet 768 to take its helical shape in the manner described above. In this embodiment, the stylet 768 can provide structure and a desired level of rigidity to the device 712 to help guide and position the device 712 during delivery and then give it the desired helical arrangement upon deployment.

In some of the over-the-wire embodiments of the treatment catheter device described above, the guide wire is described as extending within the elongated shaft of the catheter from at least the distal end of the treatment assembly to a location proximal of the handle assembly. In order to disengage the catheter from the guide wire requires retracting the full length of the guide wire proximally from the access site. Accordingly, the guide wire axial length may be greater than that of the catheter elongated shaft and its distal treatment assembly. To provide for an operation and manipulation of a shorter guide wire, and in particular to minimize the retraction distance to disengage the catheter from the guide wire, it may be desirable to have a treatment catheter device that provides for a rapid-exchange configuration. The rapid exchange examples described below with reference to FIGS. 17A-17E may also be used with any of the treatment devices described herein that employ a guide wire and OTW delivery techniques.

Figure 17A:
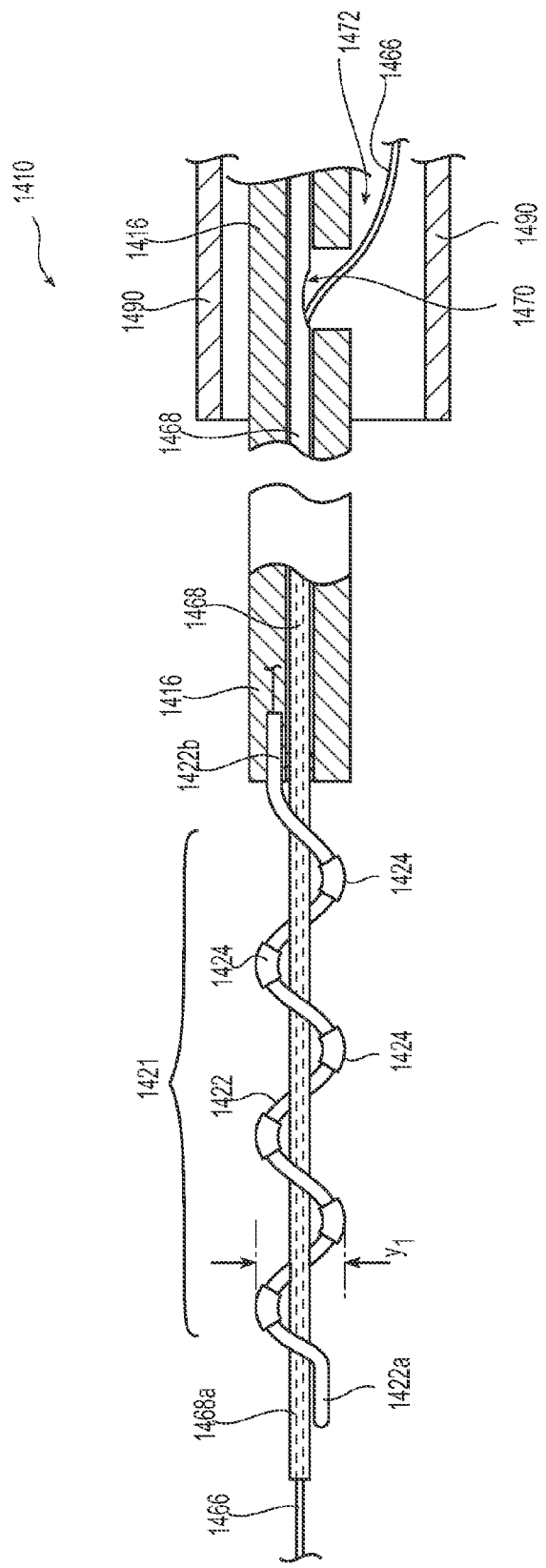
FIG. 17A is a broken side view in part section of a distal portion a rapid-exchange type of a treatment device configured in accordance an embodiment of the present technology.

FIG. 17A, for example, is a broken side view in part section of a distal portion of a treatment device 1410 with a rapid exchange configuration in accordance with an embodiment of the technology. The treatment device 1410 includes a treatment assembly 1421 helically disposed about a tubular control member 1468 that defines an internal lumen for passage over a guide wire 1466. The tubular control member 1468 extends proximally within the elongated shaft 1416 of the treatment device 1410, which is shown at least partially disposed within a guide catheter 1490. To provide for a rapid exchange configuration in which the guide wire 1466 extends at least partially parallel to and externally to the elongated shaft 1416, the tubular control member 1468 includes an opening 1470 proximal to the treatment assembly 1421, but distal of a handle assembly (not shown) for exit of the guide wire 1466. The elongated shaft 1416 also preferably includes an opening 1472 for exit of the guide wire 1466 and passage into the guide catheter 1490. Because the guide wire 1466 does not need to extend proximally through the elongated shaft 1416 to the handle assembly (not shown), its overall length can be reduced.

Figure 17B:
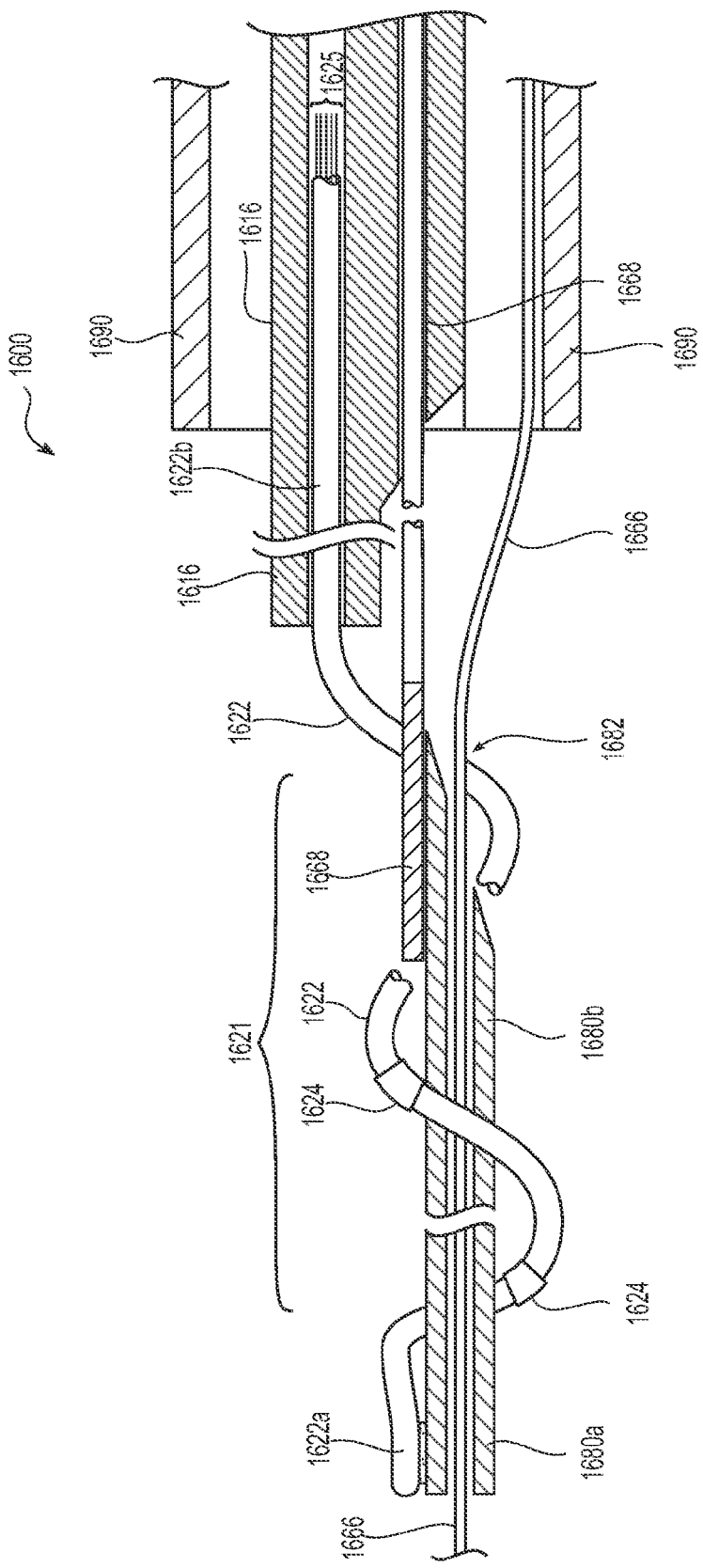
FIG. 17B is a broken side view in part section of a distal portion of a rapid-exchange type of a treatment device in a delivery state in accordance an embodiment of the present technology.
Figure 17C:
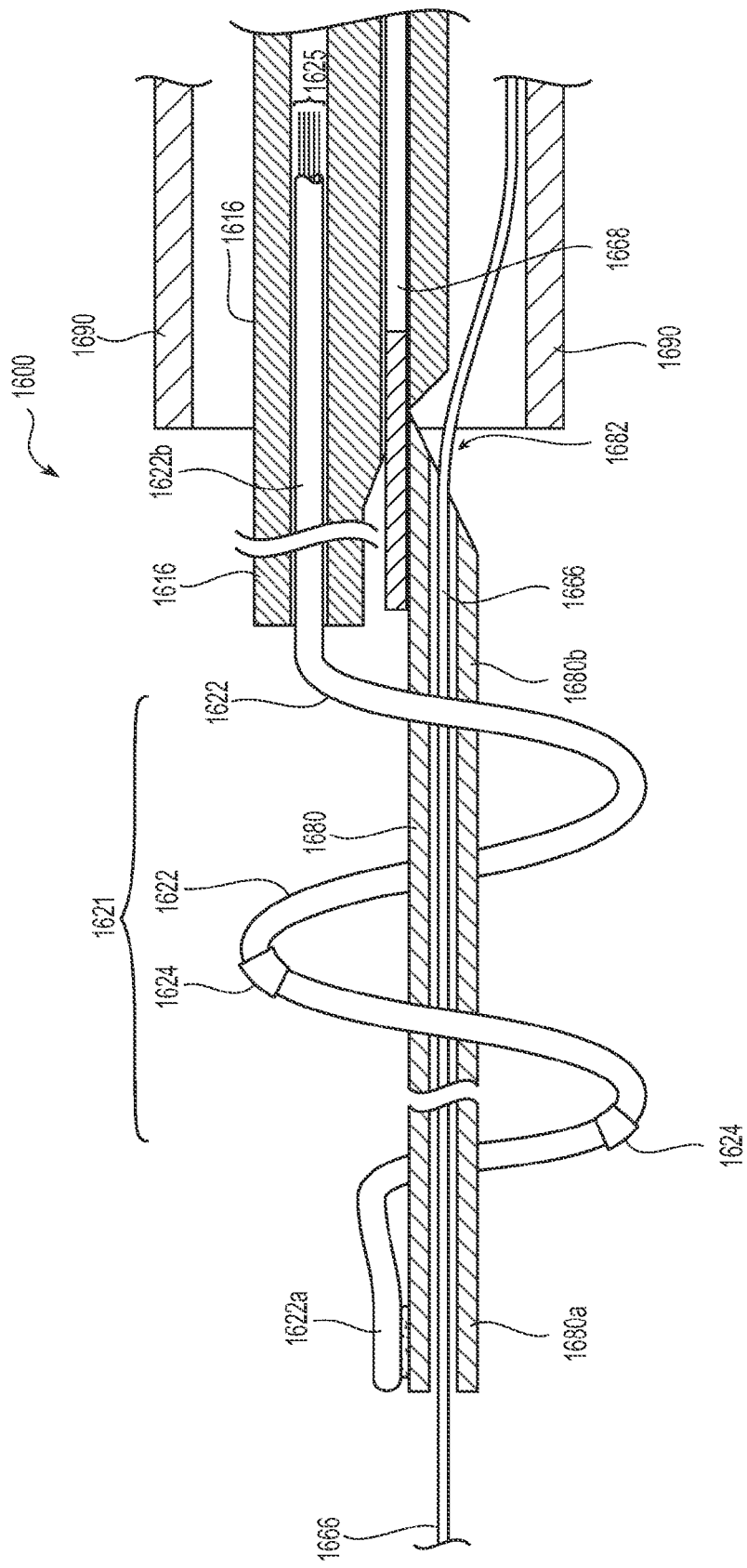
FIG. 17C is a broken side view of a distal portion of the treatment device of FIG. 17B in a deployed state.

FIGS. 17B and 17C illustrate another embodiment of a treatment device 1600 with a rapid exchange configuration in accordance with another embodiment of the technology. More specifically, FIG. 17B is a broken side view in part section of a distal portion the treatment device 1600 in a delivery state, and FIG. 17C is a broken side view of the treatment device 1600 in a deployed state. Referring to FIGS. 17B and 17C together, the treatment device 1600 includes a treatment assembly 1621 having a tubular support structure 1622 with a plurality of energy delivery elements 1624 disposed about the support structure 1622. The support structure 1622 extends proximally within at least a portion of the elongated shaft 1616 of the treatment device 1600. Energy supply wires 1625 preferably extend within the tubular support structure 1622 to provide energy from an external generator source (not shown) to each of the energy delivery elements 1624. The tubular support structure 1622 extends distally about a tubular member 1680 in a spiral or helical manner and terminates along an outer surface of the tubular member 1680 and is preferably bonded at a distal region 1680*a* of the tubular member 1680.

The tubular member 1680 provides the treatment assembly 1621 with an inner member disposed within the helix defined by the support structure 1622 that can be used to control the distal region of the support structure 1622 to alter the support structure 1622 of the treatment assembly 1621 between a delivery and a deployed configuration. The treatment device 1600 further includes a control member 1668 coupled to a proximal region of the tubular member 1680 for pushing distally and pulling proximally the inner member 1680 so as to move respectively the distal end 1622*a* of the tubular support structure 1622 in the distal and proximal directions with respect to the distal end of the shaft 1616. Distal movement of the distal end 1622*a* of the support structure 1622 lengthens an axial length of the helical shaped support structure 1622 and places the treatment assembly 1621 in the delivery configuration (as seen in FIG. 17B). Likewise, proximal movement of the distal end 1622*a* of the support structure 1622 shortens an axial length of the helical shaped support structure 1622 to place the treatment assembly 1621 in the deployed configuration shown in FIG. 17C. In one embodiment, the control member 1668 may be configured as a push-pull rod. For example, the push-pull rod can extend axially within the elongated shaft 1616 and, in some embodiments, within an independent lumen in the elongated shaft 1616 separate from a lumen carrying power supply wires 1625 for the treatment assembly 1621.

The tubular inner member 1680 defines a internal lumen for passage of a guide wire 1666. Accordingly, the tubular inner member 1680 includes an axial opening at a distal end region 1680*a* for passage of the guide wire 1666. The proximal end region 1680*b* of the tubular inner member 1680 is configured for a proximal passage and exit of the guide wire 1666. The proximal region 1680*b* may terminate, for example, in an oblique elongated opening 1682 for exiting of the guide wire 1666. In some embodiments, the proximal region 1680*b* of the inner member 1680 may be affixed to the distal end of the push-pull member 1668 such that the push-pull member 1668 can control the axial distance between the guide wire exit 1682 and the elongated shaft 1668. Further, in some embodiments the distal end of the push-pull member 1668 may include a taper or angled end to increase the cross-sectional area of the push-pull member 1668 for bonding to the inner tubular member 1680. Because the arrangement of the inner member 1680 and the push-pull member 1668 maintains the guide wire exit opening external to the elongated shaft 1616, the arrangement provides for a rapid exchange configuration.

In particular, the guide wire exit opening 1682 provides that the guide wire 1666 can extend parallel and external to the elongated shaft 1616. Thus, manipulation of the guide wire 1666 does not require that the guide wire 1666 extend proximally within the full length of the elongated shaft 1616 and beyond, for example, through a handle assembly. Accordingly, in some embodiments the guide wire length 1666 may have a reduced length, e.g., about 180 cm. Moreover, to the extent it may be desired to disengage the treatment assembly 1621 from the guide wire 1666, the guide wire 1666 need only be retracted an amount sufficient to proximally retract the distal end of the guide wire from the guide wire exit opening 1682.

In one embodiment, the elongated shaft 1616 is configured to engage the proximal region of the inner tubular member 1680 in the deployed configuration of the treatment assembly 1621. More specifically, the distal region of the elongated shaft 1616 is formed so as to form a mating fit with the external portion of the proximal end 1680b of the tubular member 1680 in the deployed configuration. As shown in FIG. 17C, the push-pull member 1668 is fully retracted so as to deploy the treatment assembly 1621. The retraction of the push-pull member 1668 locates the proximal end 1680b adjacent the distal end of elongated shaft 1616. The distal end of the elongated shaft 1616 preferably includes a taper such that the internal lumen for the energy supply wires 1625 and the linear portion of the tubular support structure 1622 extend distally beyond the internal lumen which houses the push-pull member 1668. The taper (e.g., skived or oblique notch) at the distal end of the elongated shaft 1616 is sized and shaped to receive the proximal end 1680b of the inner tubular member when located adjacent the elongated shaft 1616.

In one embodiment, the treatment assembly 1621 may have a maximum delivery length ranging from, for example, about 8 mm to about 50 mm, e.g., about 15 mm to about 50 mm. In a deployed configuration, the treatment assembly 1621 may have a maximum axial length of, e.g., about 45 mm. The tubular member 1680 may have an axial length ranging from about 2-50 cm. with an opening 1682 having an axial length of, e.g., about 2-8 mm. The push-pull rod 1668 may be configured to alter the axial distance between the distal end of the elongated shaft 1616 and the opening 1682 of the inner tubular member 1680 over a distance of, e.g., 1 mm to about 30 mm. The elongated shaft 1616 and the guide wire 1666 may extend parallel to one another within a surrounding guide catheter 1690. The catheter device 1612 can be configured such that the opening 1682 is located inside or outside the guide catheter 1690.

Figure 17D:
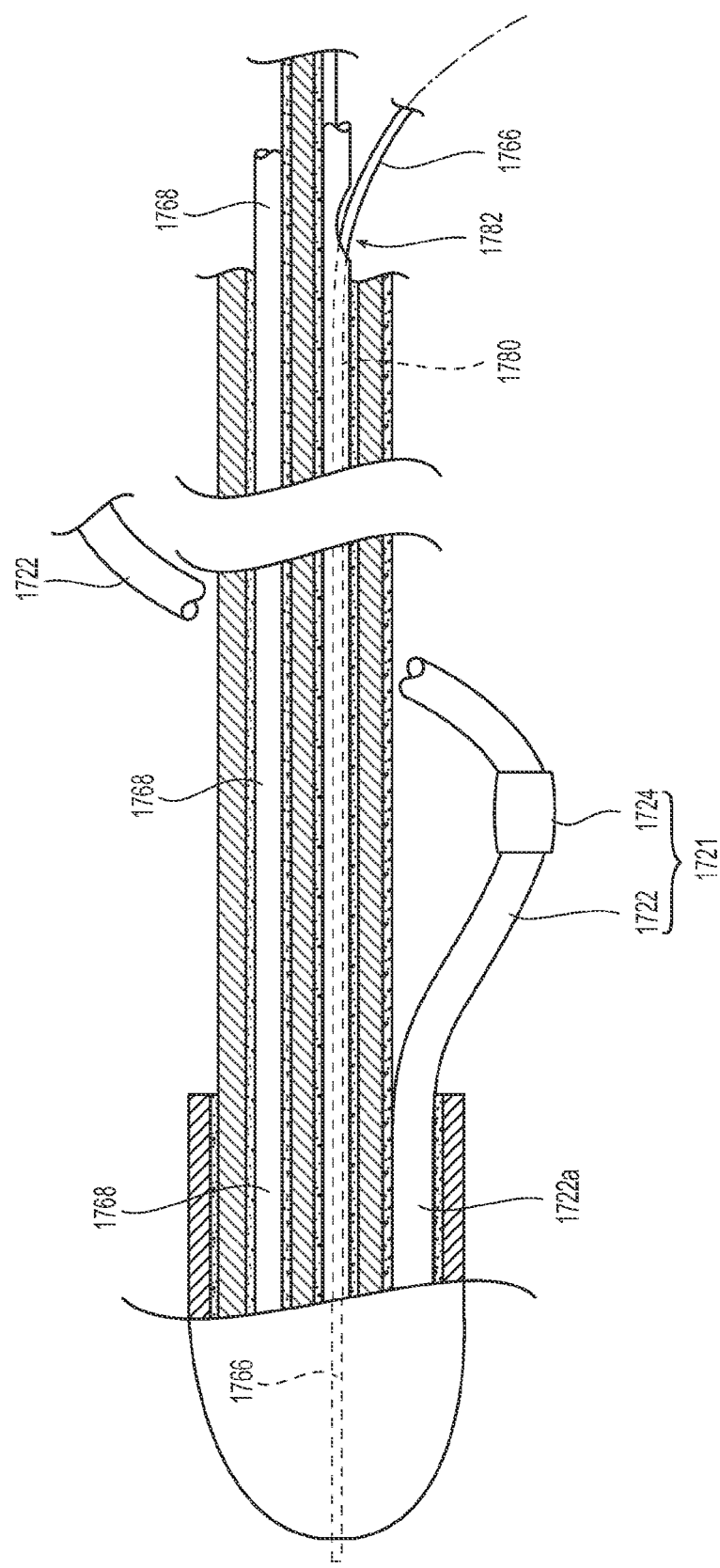
FIG. 17D is a broken side view in part section of a distal portion of another rapid-exchange type of a treatment device in accordance an embodiment of the present technology.

An alternate embodiment of the treatment device 1710 is shown in FIG. 17D. In this embodiment, the treatment assembly 1721 includes a tubular support structure 1722 having a proximal portion that extends proximally into the elongated shaft to carry the energy supply wires for the energy delivery elements 1724 disposed about the support structure 1722. Extending parallel to the proximal portion of the tubular support structure 1722 are a control member 1768 that includes a push-pull rod. Also preferably extending parallel to the push-pull control member 1768 is a tubular member 1780 defining an internal lumen for passage of a guide wire 1766. Each of the distal end region 1722a of the support structure 1722 and the pull-push rod member 1768 is preferably affixed to the tubular member 1780 such that axial movement of the push-pull member 1768 moves the distal end of the tubular support structure 1722 and the tubular member 1780 along the guide wire 1766. The tubular support structure 1722 is preferably helically wrapped about the tubular member 1780 such that the tubular member 1780 is internal to the helix defined by the support member 1722. The distal and proximal movement of the distal region 1722a respectively extends and reduces the axial length of the helical tubular support structure 1722 to place the treatment assembly 1721 in the delivery and deployed configurations. Proximal of the treatment assembly 1721, distal of the handle assembly along the tubular member 1780 is an opening 1782 to provide for a rapid exchange configuration.

Because the push-pull member 1768 and the distal end 1722a of the tubular support structure are affixed to the tubular member 1780, the tubular support structure 1722 cannot be rotated about the tubular member 1780 and its axial opening through which the guide wire passes. Accordingly, to provide for a distal end 1722a that rotates about the guide wire lumen of the member 1780, the push-pull member 1768 and the distal end 1722a of the tubular support member 1722a are coupled to but separable from the tubular member 1780 as seen for example, in FIG. 17E. More specifically the tubular member 1780 is preferably detachable or independently rotatable with respect to the tubular support structure 1722 and the push-pull member 1768. Accordingly, a rotatable distal region of the treatment assembly 1721 is rotatable about the guide wire 1766. Moreover, because the distal region of the treatment assembly 1721 is rotatable about the tubular member 1780, the proximal guide wire exit 1782 can remain fixed relative to the treatment assembly 1721 such that the rapid exchange configuration does not interfere with rotation of the treatment assembly.

Figure 17E:
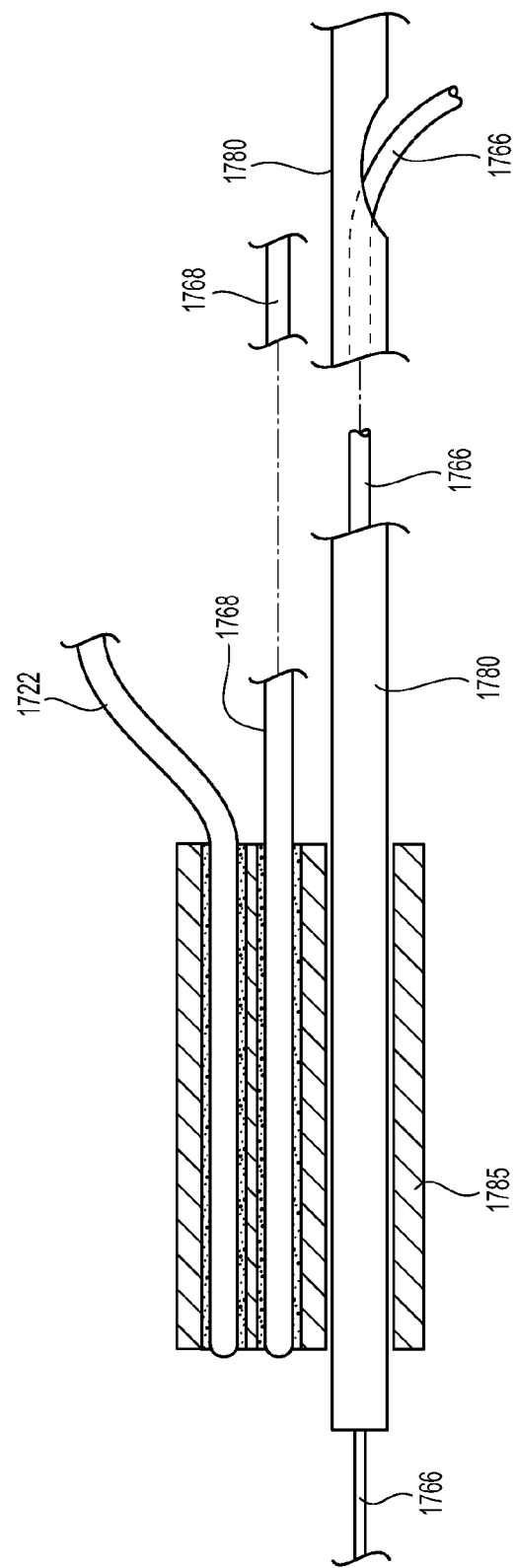
FIG. 17E is a broken side view in part section of a distal portion of yet another embodiment of a rapid-exchange type of a treatment device in accordance an embodiment of the present technology.

In the embodiment shown in FIG. 17E, a sleeve 1785 is provided to which the distal end of the tubular support structure 1722 and the push-pull member 1768 are affixed. The sleeve 1785 further defines an internal passage for slidably receiving the member 1780. The sleeve 1785 provides for a tip assembly of the treatment assembly which axially slides and rotates about the tubular member 1780. The configuration further provides rotation of the support structure 1722 and the push-pull member 1768 of the assembly relative to the tubular member 1780 while maintaining the preferably generally helical shape without the support structure 1722 "wrapping up" around the tubular member 1780 and losing the desired shape/configuration while manipulating the treatment assembly within the vessel.

IV. Applying Energy To Tissue Via The Energy Delivery Element

Referring back to FIG. 1, the energy generator 26 may supply a continuous or pulsed RF electric field to the energy delivery elements 24. Although a continuous delivery of RF energy is desirable, the application of RF energy in pulses may allow the application of relatively higher energy levels (e.g., higher power), longer or shorter total duration times, and/or better controlled intravascular renal neuromodulation therapy. Pulsed energy may also allow for the use of a smaller electrode.

Although many of the embodiments described herein pertain to electrical systems configured for the delivery of RF energy, it is contemplated that the desired treatment may be accomplished by other means, e.g., by coherent or incoherent light; direct thermal modification (e.g., with a heated or cooled fluid or resistive heating element or cryogenic applicator); microwave; ultrasound (including high intensity focused ultrasound); diode laser; radiation; a tissue heating fluid; and/or a cryogenic refrigerant.

As previously discussed, energy delivery may be monitored and controlled via data collected with one or more sensors, such as temperature sensors (e.g., thermocouples, thermistors, etc.), impedance sensors, pressure sensors, optical sensors, flow sensors, chemical sensors, etc., which may be incorporated into or on the energy delivery elements 24, the support structure 22, and/or in/on adjacent areas on the distal portion 20. A sensor may be incorporated into the energy delivery element(s) 24 in a manner that specifies whether the sensor(s) are in contact with tissue at the treatment site and/or are facing blood flow. The ability to specify sensor placement relative to tissue and blood flow is highly significant, since a temperature gradient across the electrode from the side facing blood flow to the side in contact with the vessel wall may be up to about 15° C. Significant gradients across the electrode in other sensed data (e.g., flow, pressure, impedance, etc.) also are expected.

The sensor(s) may, for example, be incorporated on the side of one or more energy delivery elements 24 that contact the vessel wall at the treatment site during power and energy delivery or may be incorporated on the opposing side of one or more energy delivery elements 24 that face blood flow during energy delivery, and/or may be incorporated within certain regions of the energy delivery elements 24 (e.g., distal, proximal, quandrants, etc.). In some embodiments, multiple sensors may be provided at multiple positions along the electrode or energy delivery element array and/or relative to blood flow. For example, a plurality of circumferentially and/or longitudinally spaced sensors may be provided. In one embodiment, a first sensor may contact the vessel wall during treatment, and a second sensor may face blood flow.

Additionally or alternatively, various microsensors may be used to acquire data corresponding to the energy delivery elements 24, the vessel wall and/or the blood flowing across the energy delivery elements 24. For example, arrays of micro thermocouples and/or impedance sensors may be implemented to acquire data along the energy delivery elements 24 or other parts of the treatment device. Sensor data may be acquired or monitored prior to, simultaneous with, or after the delivery of energy or in between pulses of energy, when applicable. The monitored data may be used in a feedback loop to better control therapy, e.g., to determine whether to continue or stop treatment, and it may facilitate controlled delivery of an increased or reduced power or a longer or shorter duration therapy.

V. Blood Flow Around The Energy Delivery Elements

Non-target tissue may be protected by blood flow within the respective renal artery that serves as a conductive and/or convective heat sink that carries away excess thermal energy. For example, referring to FIGS. 1 and 18 together, since blood flow is not blocked by the elongated shaft 16, the helically-shaped therapeutic assembly 21, and the energy delivery elements 24 it carries, the native circulation of blood in the respective renal artery serves to remove excess thermal energy from the non-target tissue and the energy delivery element. The removal of excess thermal energy by blood flow also allows for treatments of higher power, where more power may be delivered to the target tissue as thermal energy is carried away from the electrode and non-target tissue. In this way, intravascularly-delivered thermal energy heats target neural fibers located proximate to the vessel wall to modulate the target neural fibers, while blood flow within the respective renal artery protects non-target tissue of the vessel wall from excessive or undesirable thermal injury.

It may also be desirable to provide enhanced cooling by inducing additional native blood flow across the energy delivery elements 24. For example, techniques and/or technologies may be implemented by the clinician to increase perfusion through the renal artery or to the energy delivery elements 24 themselves. These techniques include positioning partial occlusion elements (e.g., balloons) within upstream vascular bodies such as the aorta, or within a portion of the renal artery to improve flow across the energy delivery element.

Figure 18:
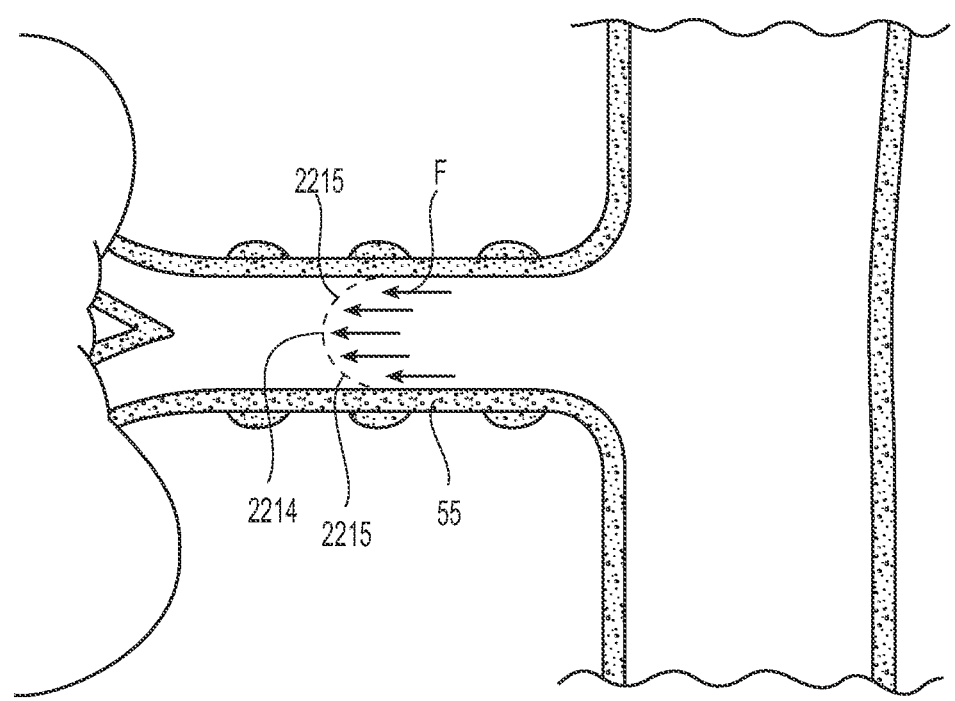
FIG. 18 is an illustration of theoretical blood flow in a renal artery in accordance with an embodiment of the technology.

FIG. 18, for example, illustrates hypothetical blood flow in a renal artery. Blood flow (F) is thought to be laminar, e.g., to exhibit a gradient of flow rates such that in an area closest to the center of the artery, e.g., area 2214, the blood flow F may be faster relative to areas closer to the renal artery wall 55, e.g., areas 2215. Accordingly, the blood flow F nearest the location of the energy delivery elements 24 is relatively slow. Because cooling of the energy delivery elements 24 is mediated by blood flow, improved cooling may be achieved by redirecting the blood flow F in the renal artery so that the blood flowing around the energy delivery elements 24 is relatively faster.

Figure 19A:
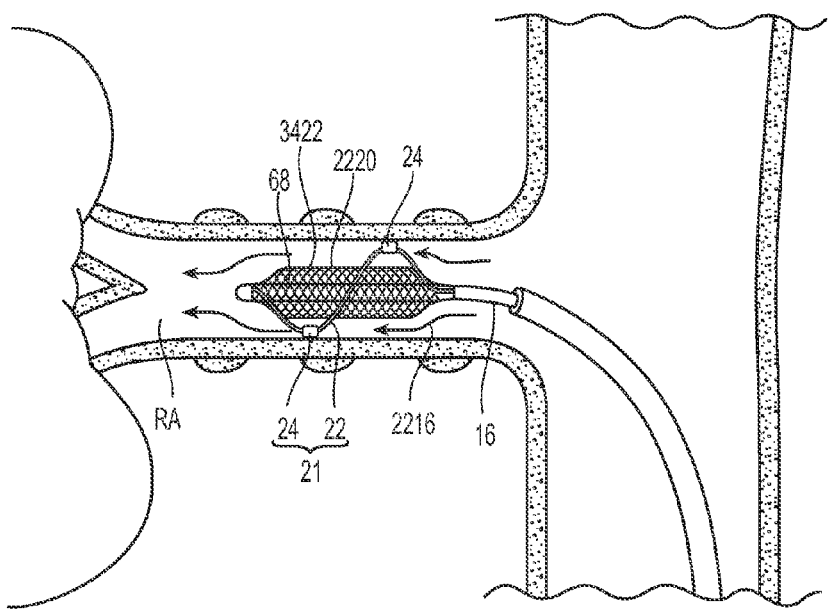
FIG. 19A is a cross-sectional view of a treatment assembly including a fluid redirecting element within a renal artery in accordance with an embodiment of the present technology.

FIG. 19A illustrates an embodiment in which a fluid redirecting element 2220 is positioned within the center of the renal artery. Accordingly, the flowing blood, represented by arrows 2216, including faster flowing blood, is redirected towards the energy delivery elements 24. The fluid redirecting element may be any biocompatible material, such as a polymer, that is positioned to encourage blood flow towards the energy delivery elements 24 carried by a mesh structure 3422.

Figure 19B:
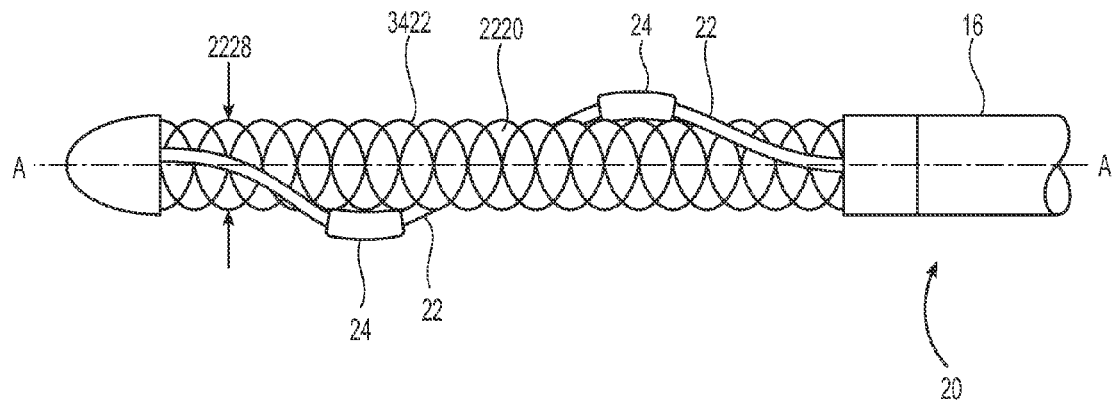
FIG. 19B is a side view of a support structure with a schematic illustration of a fluid redirecting element in a delivery state (e.g., low-profile or collapsed configuration) outside a patient in accordance with an embodiment of the present technology.

Referring to FIGS. 19A and 19B together, the fluid redirecting element 2220 may extend from the distal end region 20 of the elongated shaft 16, generally along the axis A-A of the elongated shaft 16. For embodiments in which a guide wire (not shown) is used, the fluid redirecting element 2220 may include an integral passage (not shown) of an inner member sized and shaped to accommodate the guide wire. In addition, in some embodiments, an axial length of the fluid redirecting element 2220 may be at least 25%, at least 50%, or at least 75% of an axial length of the mesh structure 2220 in the expanded configuration. In any case, in order to maximize redirected blood flow, the fluid redirecting element 2220 may extend at least far enough into the mesh structure 3422 so that an imaginary axis through the energy delivery elements 24 and orthogonal to the axis A-A intersects the fluid redirecting element 2220. The diameter 2228 of the fluid redirecting element 2220 may be expandable such that in its unexpanded state it is generally compatible with insertion, repositioning, and removal of the mesh structure 3422 and in its expanded state it is configured to redirect blood flow toward areas closer to the renal artery wall, e.g., areas 2215. As shown in FIG. 19B, in a collapsed configuration, the mesh structure 3422 may conform to the shape of the fluid redirecting element 2220. The diameter 2228 may be slightly larger than, about equal to, or less than a diameter of the elongated shaft 16. In one embodiment, the diameter 2228 may be less than about 2.18 mm.

In addition, or as an alternative, to passively utilizing blood flow as a heat sink, active cooling may be provided to remove excess thermal energy and protect non-target tissues. For example, a thermal fluid infusate may be injected, infused, or otherwise delivered into the vessel in an open circuit system. Thermal fluid infusates used for active cooling may, for example, include (room temperature or chilled) saline or some other biocompatible fluid. The thermal fluid infusate(s) may, for example, be introduced through the treatment device 12 via one or more infusion lumens and/or ports. When introduced into the bloodstream, the thermal fluid infusate(s) may, for example, be introduced through a guide catheter at a location upstream from the energy delivery elements 24 or at other locations relative to the tissue for which protection is sought. The delivery of a thermal fluid infusate in the vicinity of the treatment site (via an open circuit system and/or via a closed circuit system) may, for example, allow for the application of increased/higher power treatment, may allow for the maintenance of lower temperature at the vessel wall during energy delivery, may facilitate the creation of deeper or larger lesions, may facilitate a reduction in treatment time, may allow for the use of a smaller electrode size, or a combination thereof.

Accordingly, treatment devices configured in accordance with embodiments of the technology may include features for an open circuit cooling system, such as a lumen in fluid communication with a source of infusate and a pumping mechanism (e.g., manual injection or a motorized pump) for injection or infusion of saline or some other biocompatible thermal fluid infusate from outside the patient, through elongated shaft 16 and towards the energy delivery elements 24 into the patient's bloodstream during energy delivery. In addition, the distal end region 20 of the elongated shaft 16 may include one or more ports for injection or infusion of saline directly at the treatment site.

VI. Use Of The System

A. Intravascular Delivery, Deflection and Placement of the Treatment Device

As mentioned previously, any one of the embodiments of the treatment devices described herein may be delivered using OTW or RX techniques. When delivered in this manner, the elongated shaft 16 includes a passage or lumen accommodating passage of a guide wire. Alternatively, any one of the treatment devices 12 described herein may be deployed using a conventional guide catheter or pre-curved renal guide catheter (e.g., as shown in FIGS. 3A and 3B). When using a guide catheter, the femoral artery is exposed and cannulated at the base of the femoral triangle, using conventional techniques. In one exemplary approach, a guide wire is inserted through the access site and passed using image guidance through the femoral artery, into the iliac artery and aorta, and into either the left or right renal artery. A guide catheter may be passed over the guide wire into the accessed renal artery. The guide wire is then removed. Alternatively, a renal guide catheter, which is specifically shaped and configured to access a renal artery, may be used to avoid using a guide wire. Still alternatively, the treatment device may be routed from the femoral artery to the renal artery using angiographic guidance and without the need of a guide catheter.

When a guide catheter is used, at least three delivery approaches may be implemented. In one approach, one or more of the aforementioned delivery techniques may be used to position a guide catheter within the renal artery just distal to the entrance of the renal artery. The treatment device is then routed via the guide catheter into the renal artery. Once the treatment device is properly positioned within the renal artery, the guide catheter is retracted from the renal artery into the abdominal aorta. In this approach, the guide catheter should be sized and configured to accommodate passage of the treatment device. For example, a 6 French guide catheter may be used.

In a second approach, a first guide catheter is placed at the entrance of the renal artery (with or without a guide wire). A second guide catheter (also called a delivery sheath) is passed via the first guide catheter (with or without the assistance of a guide wire) into the renal artery. The treatment device is then routed via the second guide catheter into the renal artery. Once the treatment device is properly positioned within the renal artery the second guide catheter is retracted, leaving the first guide catheter at the entrance to the renal artery. In this approach the first and second guide catheters should be sized and configured to accommodate passage of the second guide catheter within the first guide catheter (i.e., the inner diameter of the first guide catheter should be greater than the outer diameter of the second guide catheter). For example, a 8 French guide catheter may be used for the first guide catheter, and 5 French guide catheter may be used for the second guide catheter.

In a third approach, a renal guide catheter is positioned within the abdominal aorta, just proximal to the entrance of the renal artery. The treatment device 12 as described herein is passed through the guide catheter and into the accessed renal artery. The elongated shaft makes atraumatic passage through the guide catheter, in response to forces applied to the elongated shaft 16 through the handle assembly 34.

B. Control of Applied Energy

1. Overview

Referring back to FIG. 1, a treatment administered using the system 10 constitutes delivering energy through the energy delivery elements or electrodes 24 to the inner wall of a renal artery for a predetermined amount of time (e.g., 120 sec). Multiple treatments (e.g., 4-6) may be administered in both the left and right renal arteries to achieve the desired coverage. A technical objective of a treatment may be, for example, to heat tissue to a desired depth (e.g., at least about 3 mm) to a temperature that would lesion a nerve (e.g., about 65° C.). A clinical objective of the procedure typically is to neuromodulate (e.g., lesion) a sufficient number of renal nerves (either efferent or afferent nerves of the sympathetic renal plexus) to cause a reduction in sympathetic tone. If the technical objective of a treatment is met (e.g., tissue is heated to about 65° C. to a depth of about 3 mm) the probability of forming a lesion of renal nerve tissue is high. The greater the number of technically successful treatments, the greater the probability of modulating a sufficient proportion of renal nerves, and thus the greater the probability of clinical success.

Throughout the treatment there may be a number of states that are indicative of a possibility that the treatment may not be successful. In certain embodiments, based on indications of these states, the operation of the system 10 may be stopped or modified. For example, certain indications may result in cessation of energy delivery and an appropriate message may be displayed, such as on display 33. Factors that may result in a display message and/or cessation or modification of a treatment protocol include, but are not limited to, indications of an impedance, blood flow, and/or temperature measurement or change that is outside of accepted or expected thresholds and/or ranges that may be predetermined or calculated. A message can indicate information such as a type of patient condition (e.g., an abnormal patient condition), the type and/or value of the parameter that falls outside an accepted or expected threshold, an indication of suggested action for a clinician, or an indication that energy delivery has been stopped. However, if no unexpected or aberrant measurements are observed, energy may continue to be delivered at the target site in accordance with a programmed profile for a specified duration resulting in a complete treatment. Following a completed treatment, energy delivery is stopped and a message indicating completion of the treatment may be displayed.

However, a treatment can be completed without initiating an indication of an abnormal patient condition and yet an event or combination of events could occur that alters (e.g., decreases) the probability of a technically successful treatment. For example, an electrode that is delivering energy could move or be inadvertently placed with insufficient contact between the electrode and the wall of a renal artery, thereby resulting in insufficient lesion depth or temperature. Therefore, even when a treatment is completed without an indication of abnormal patient condition, it may be difficult to evaluate the technical success of the treatment. Likewise, to the extent that indications of abnormal patient conditions may be reported by the system 10, it may be difficult to understand the causes of the abnormal patient conditions (such as temperature and/or impedance values that fall outside of expected ranges).

As noted above, one or more evaluation/feedback algorithms 31 may be provided that are executed on a processor-based component of the system 10, such as one or more components provided with the generator 26. In such implementations, the one or more evaluation/feedback algorithms 31 may be able to provide a user with meaningful feedback that can be used in evaluating a given treatment and/or that can be used in learning the significance of certain types of abnormal patient conditions and how to reduce the occurrence of such conditions. For example, if a particular parameter (e.g., an impedance or temperature value) causes or indicates that treatment did not proceed as expected and (in some instances), may have resulted in a technically unsuccessful treatment, the system 10 can provide feedback (e.g., via the display 33) to alert the clinician. The alert to the clinician can range from a simple notification of unsuccessful treatment to a recommendation that a particular parameter of the treatment (e.g., the impedance value(s) during treatment, placement of the energy delivery elements 24 within the patient, etc.) be modified in a subsequent treatment. The system 10 can accordingly learn from completed treatment cycles and modify subsequent treatment parameters based on such learning to improve efficacy. Non-exhaustive examples of measurements the one or more evaluation/feedback algorithms 31 may consider include measurements related to change(s) in temperature over a specified time, a maximum temperature, a maximum average temperature, a minimum temperature, a temperature at a predetermined or calculated time relative to a predetermined or calculated temperature, an average temperature over a specified time, a maximum blood flow, a minimum blood flow, a blood flow at a predetermined or calculated time relative to a predetermined or calculated blood flow, an average blood flow over time, a maximum impedance, a minimum impedance, an impedance at a predetermined or calculated time relative to a predetermined or calculated impedance, a change in impedance over a specified time, or a change in impedance relative to a change in temperature over a specified time. Measurements may be taken at one or more predetermined times, ranges of times, calculated times, and/or times when or relative to when a measured event occurs. It will be appreciated that the foregoing list merely provides a number of examples of different measurements, and other suitable measurements may be used.

2. Control of Applied Energy

With the treatments disclosed herein for delivering therapy to target tissue, it may be beneficial for energy to be delivered to the target neural structures in a controlled manner. The controlled delivery of energy will allow the zone of thermal treatment to extend into the renal fascia while reducing undesirable energy delivery or thermal effects to the vessel wall. A controlled delivery of energy may also result in a more consistent, predictable and efficient overall treatment. Accordingly, the generator 26 desirably includes a processor including a memory component with instructions for executing an algorithm 30 (see FIG. 1) for controlling the delivery of power and energy to the energy delivery device. The algorithm 30, a representative embodiment of which is depicted in FIG. 3, may be implemented as a conventional computer program for execution by a processor coupled to the generator 26. A clinician using step-by-step instructions may also implement the algorithm 30 manually.

The operating parameters monitored in accordance with the algorithm may include, for example, temperature, time, impedance, power, blood flow, flow velocity, volumetric flow rate, blood pressure, heart rate, etc. Discrete values in temperature may be used to trigger changes in power or energy delivery. For example, high values in temperature (e.g., 85° C.) could indicate tissue desiccation in which case the algorithm may decrease or stop the power and energy delivery to prevent undesirable thermal effects to target or non-target tissue. Time additionally or alternatively may be used to prevent undesirable thermal alteration to non-target tissue. For each treatment, a set time (e.g., 2 minutes) is checked to prevent indefinite delivery of power.

Impedance may be used to measure tissue changes. Impedance indicates the electrical property of the treatment site. In thermal inductive embodiments, when an electric field is applied to the treatment site, the impedance will decrease as the tissue cells become less resistive to current flow. If too much energy is applied, tissue desiccation or coagulation may occur near the electrode, which would increase the impedance as the cells lose water retention and/or the electrode surface area decreases (e.g., via the accumulation of coagulum). Thus, an increase in tissue impedance may be indicative of or predictive of undesirable thermal alteration to target or non-target tissue. In other embodiments, the impedance value may be used to assess contact of the energy delivery element(s) 24 with the tissue. For multiple electrode configurations (e.g., when the energy delivery element(s) 24 includes two or more electrodes,) a relatively small difference between the impedance values of the individual electrodes may be indicative of good contact with the tissue. For a single electrode configuration, a stable value may be indicative of good contact. Accordingly, impedance information from the one or more electrodes may be provided to a downstream monitor, which in turn may provide an indication to a clinician related to the quality of the energy delivery element(s) 24 contact with the tissue.

Additionally or alternatively, power is an effective parameter to monitor in controlling the delivery of therapy. Power is a function of voltage and current. The algorithm 30 may tailor the voltage and/or current to achieve a desired power.

Derivatives of the aforementioned parameters (e.g., rates of change) also may be used to trigger changes in power or energy delivery. For example, the rate of change in temperature could be monitored such that power output is reduced in the event that a sudden rise in temperature is detected. Likewise, the rate of change of impedance could be monitored such that power output is reduced in the event that a sudden rise in impedance is detected.

Figure 20:
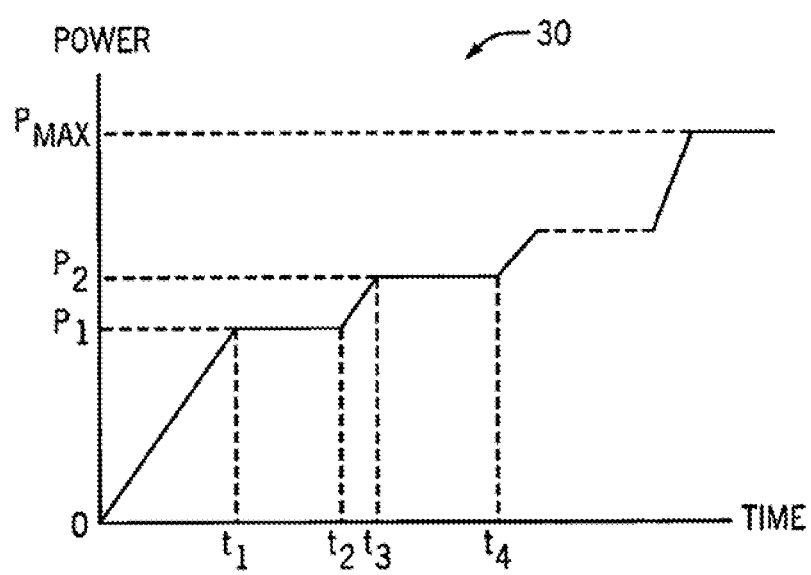
FIG. 20 is a graph depicting an energy delivery algorithm that may be used in conjunction with the system of FIG. 1 in accordance with an embodiment of the technology.

As seen in FIG. 20, when a clinician initiates treatment (e.g., via the foot pedal 32 illustrated in FIG. 1), the control algorithm 30 includes instructions to the generator 26 to gradually adjust its power output to a first power level $P_1$ (e.g., 5 watts) over a first time period $t_1$ (e.g., 15 seconds). The power increase during the first time period is generally linear. As a result, the generator 26 increases its power output at a generally constant rate of $P_1/t_1$. Alternatively, the power increase may be non-linear (e.g., exponential or parabolic) with a variable rate of increase. Once $P_1$ and $t_1$ are achieved, the algorithm may hold at $P_1$ until a new time $t_2$ for a predetermined period of time $t_2-t_1$ (e.g., 3 seconds). At $t_2$ power is increased by a predetermined increment (e.g., 1 watt) to $P_2$ over a predetermined period of time, $t_3$-$t_2$ (e.g., 1 second). This power ramp in predetermined increments of about 1 watt over predetermined periods of time may continue until a maximum power $P_{MAX}$ is achieved or some other condition is satisfied. In one embodiment, $P_{MAX}$ is 8 watts. In another embodiment $P_{MAX}$ is 10 watts. Optionally, the power may be maintained at the maximum power $P_{MAX}$ for a desired period of time or up to the desired total treatment time (e.g., up to about 120 seconds).

In FIG. 20, the algorithm 30 illustratively includes a power-control algorithm. However, it should be understood that the algorithm 30 alternatively may include a temperature-control algorithm. For example, power may be gradually increased until a desired temperature (or temperatures) is obtained for a desired duration (or durations). In another embodiment, a combination power-control and temperature-control algorithm may be provided.

As discussed, the algorithm 30 includes monitoring certain operating parameters (e.g., temperature, time, impedance, power, flow velocity, volumetric flow rate, blood pressure, heart rate, etc.). The operating parameters may be monitored continuously or periodically. The algorithm 30 checks the monitored parameters against predetermined parameter profiles to determine whether the parameters individually or in combination fall within the ranges set by the predetermined parameter profiles. If the monitored parameters fall within the ranges set by the predetermined parameter profiles, then treatment may continue at the commanded power output. If monitored parameters fall outside the ranges set by the predetermined parameter profiles, the algorithm 30 adjusts the commanded power output accordingly. For example, if a target temperature (e.g., 65° C.) is achieved, then power delivery is kept constant until the total treatment time (e.g., 120 seconds) has expired. If a first temperature threshold (e.g., 70° C.) is achieved or exceeded, then power is reduced in predetermined increments (e.g., 0.5 watts, 1.0 watts, etc.) until a target temperature is achieved. If a second power threshold (e.g., 85° C.) is achieved or exceeded, thereby indicating an undesirable condition, then power delivery may be terminated. The system may be equipped with various audible and visual alarms to alert the operator of certain conditions.

The following is a non-exhaustive list of events under which algorithm 30 may adjust and/or terminate/discontinue the commanded power output:

(1) The measured temperature exceeds a maximum temperature threshold (e.g., from about 70 to about 85° C.).

(2) The average temperature derived from the measured temperature exceeds an average temperature threshold (e.g., about 65° C.).

(3) The rate of change of the measured temperature exceeds a rate of change threshold.

(4) The temperature rise over a period of time is below a minimum temperature change threshold while the generator 26 has non-zero output. Poor contact between the energy delivery element(s) 24 and the arterial wall may cause such a condition.

(5) A measured impedance exceeds or falls outside an impedance threshold (e.g., <20 Ohms or >500 Ohms).

(6) A measured impedance exceeds a relative threshold (e.g., impedance decreases from a starting or baseline value and then rises above this baseline value)

(7) A measured power exceeds a power threshold (e.g., >8 Watts or >10 Watts).

(8) A measured duration of power delivery exceeds a time threshold (e.g., >120 seconds).

Advantageously, the magnitude of maximum power delivered during renal neuromodulation treatment in accordance with the present technology may be relatively low (e.g., less than about 15 Watts, less than about 10 Watts, less than about 8 Watts, etc.) as compared, for example, to the power levels utilized in electrophysiology treatments to achieve cardiac tissue ablation (e.g., power levels greater than about 15 Watts, greater than about 30 Watts, etc.). Since relatively low power levels may be utilized to achieve such renal neuromodulation, the flow rate and/or total volume of intravascular infusate injection needed to maintain the energy delivery element and/or non-target tissue at or below a desired temperature during power delivery (e.g., at or below about 50° C., for example, or at or below about 45° C.) also may be relatively lower than would be required at the higher power levels used, for example, in electrophysiology treatments (e.g., power levels above about 15 Watts). In embodiments in which active cooling is used, the relative reduction in flow rate and/or total volume of intravascular infusate infusion advantageously may facilitate the use of intravascular infusate in higher risk patient groups that would be contraindicated were higher power levels and, thus, correspondingly higher infusate rates/volumes utilized (e.g., patients with heart disease, heart failure, renal insufficiency and/or diabetes mellitus).

C. Technical Evaluation of a Treatment

Figure 21:
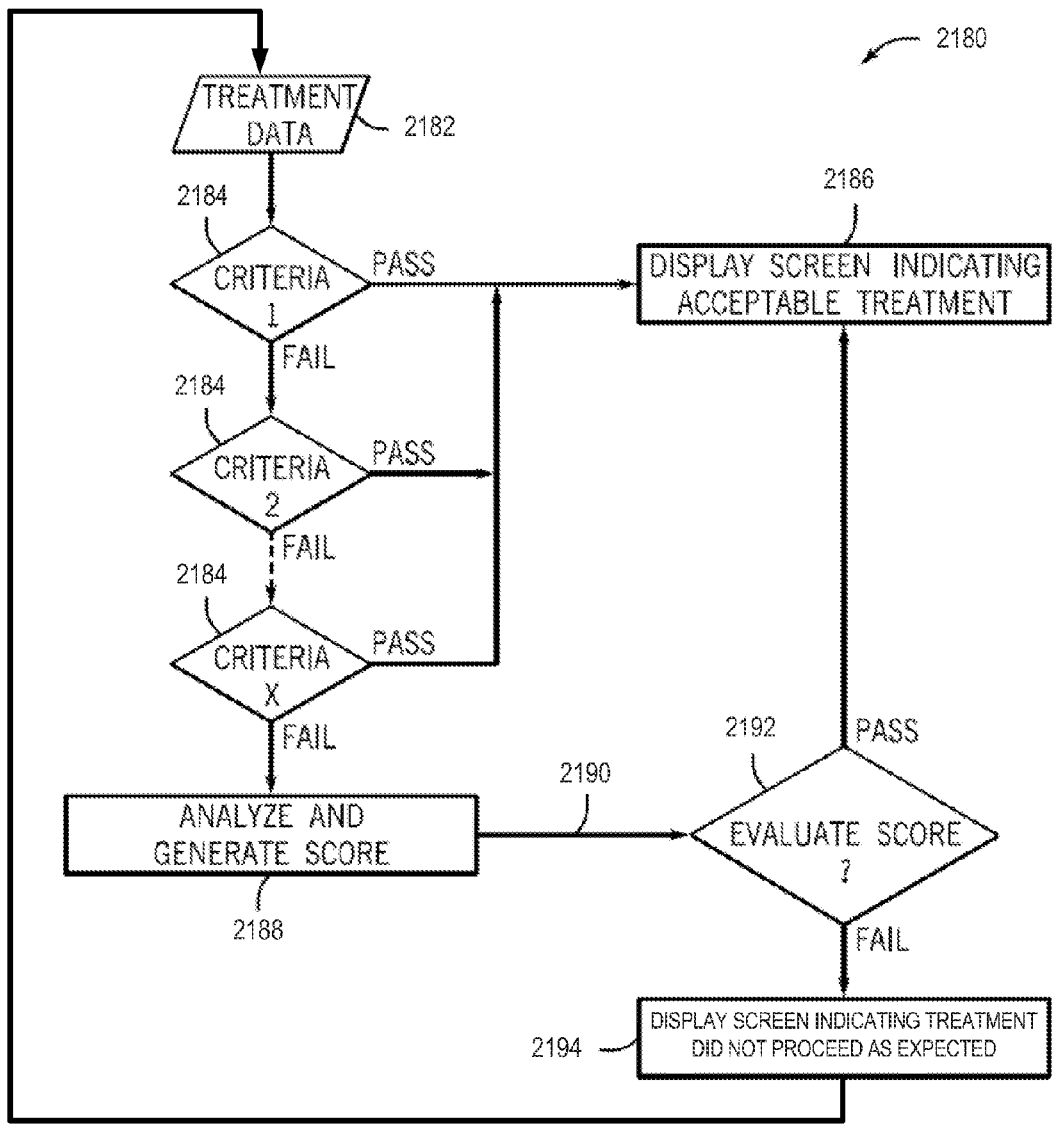
FIGS. 21 and 22 are block diagrams illustrating algorithms for evaluating a treatment in accordance with embodiments of the present technology.

FIG. 21 is a block diagram of a treatment algorithm 2180 configured in accordance with an embodiment of the present technology. The algorithm 2180 is configured to evaluate events in a treatment, determine the probability of technical success of the treatment and display a message accordingly to provide feedback to an operator of the system 10 (or another suitable treatment system). If the treatment is determined to have a predetermined probability of sub optimal technical success, a message indicating that the treatment did not proceed as expected may be displayed. Alternative implementations can categorize a treatment into several ranges of probabilities of success, such as probability of success on a scale of 1 to 5. Similarly, in certain implementations, the algorithm 2180 can evaluate if a treatment belongs in a high probability of success category, a very low probability of success category, or somewhere in between.

Variables that characterize a treatment and that may be used by the algorithm 2180 in evaluating a treatment include, but are not limited to: time (i.e., treatment duration), power, change in temperature, maximum temperature, mean temperature, blood flow, standard deviation of temperature or impedance, change in impedance, or combinations of these or other variables. For example, some or all of the variables may be provided to the algorithm 2180 as treatment data 2182. In this generalized depiction of an algorithm 2180, the treatment data 2180 may be assessed based on a cascade or series of different categories or degrees of criteria 2184. Favorable assessment of the treatment data 2182 in view of one of the criteria 2184 may result in the display (block 2186) of a message indicating the treatment was acceptable or successful. Failure of the treatment data 2182 to be found acceptable in view of a criterion 2184 may result in the treatment data dropping to the next evaluation criterion 2184.

In the depicted embodiment, failure of the treatment data to be found acceptable in view of all of the criteria 2184 may result in an additional evaluation being performed, such as the depicted analysis and scoring step 2188. The output of the analysis and scoring step (e.g., a score 2190) may be evaluated (block 2192). Based on this evaluation 2192, the treatment may be deemed acceptable, and the corresponding screen displayed (block 2186), or not acceptable, and a screen 2194 displayed indicating that treatment did not proceed as expected. In still further embodiments, the algorithm 2180 can include an automatic action (e.g., automatic reduction of the power level supplied to the energy source) in response to an indication that treatment did not proceed as expected.

Figure 22:
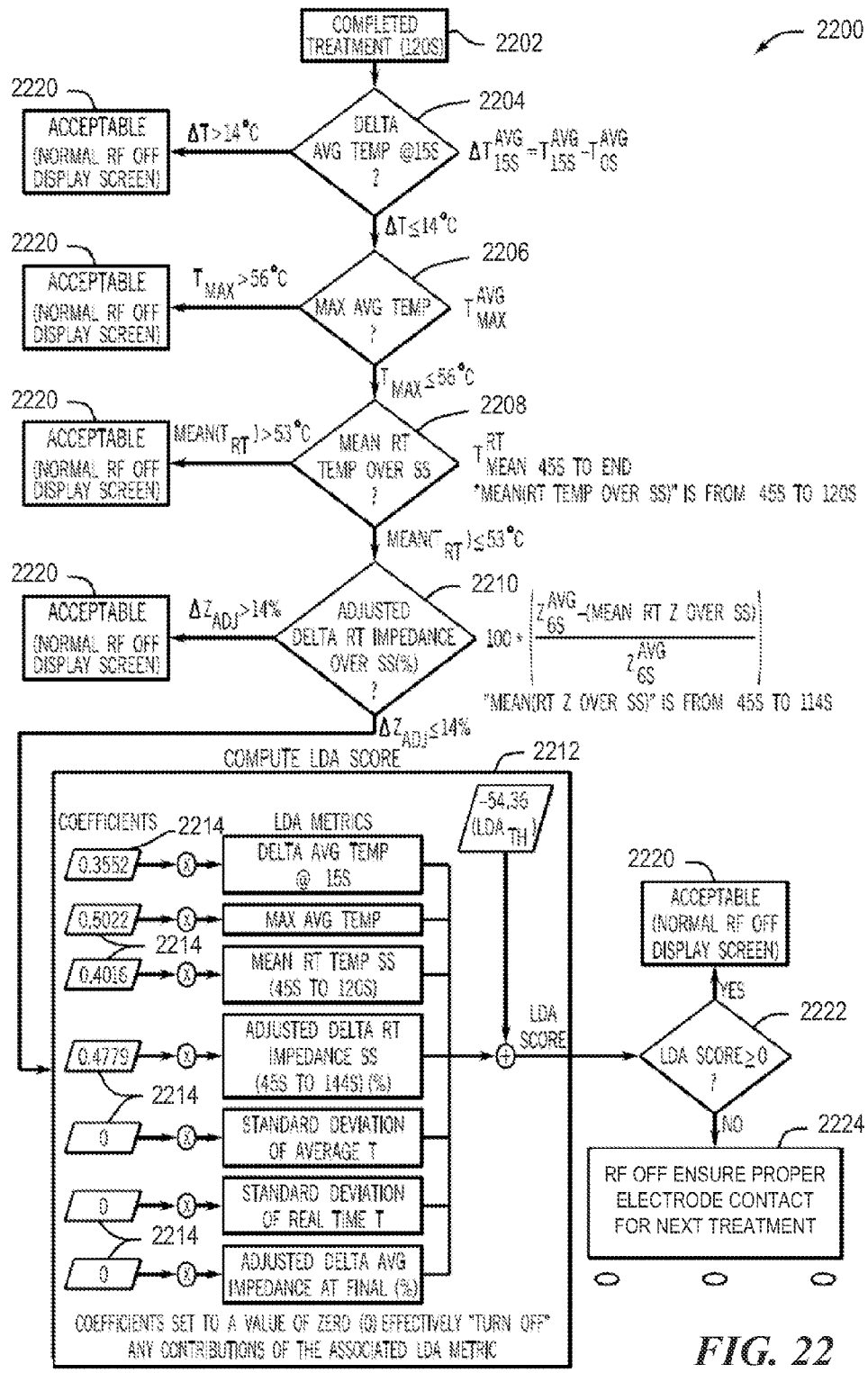

While FIG. 21 depicts a generalized and simplified implementation of a treatment evaluation algorithm, FIG. 22 depicts a more detailed example of one embodiment of a treatment evaluation algorithm 2200. The treatment evaluation algorithm 2200 may be computed following the completion of a treatment (block 2202), which may be 120 seconds long (as depicted) or some other suitable duration, and using data and/or measurements derived over the course of the treatment.

In the depicted embodiment, it is considered likely that the greatest probability of less than ideal treatment occurs when an electrode is not in consistent contact with the vessel wall. Accordingly, decision blocks 2204, 2206, 2208, and 2210 in the flowchart are associated with different criteria and screen out those treatments that appear to have one or more criteria outside a pre-determined range (i.e., do not have a high probability of success) based on observed or measured data 2202 over the course of the completed treatment. In the depicted embodiment, those treatments that are not screened out at decision blocks 2204, 2206, 2208, and 2210 enter a linear discriminant analysis (LDA) 2212 to further evaluate the treatment. In other embodiments, other suitable analyses may be performed instead of the depicted LDA. Values assigned to each step (i.e., evaluation by a respective criterion) and coefficients 2214 used in the LDA can be derived from data collected from several treatments and/or from experience gained from animal studies.

In the depicted embodiment, the first decision block 2204 evaluates the initial temperature response to energy delivery by checking if the change in average temperature in the first 15 seconds is greater than 14° C. In one implementation, average temperature refers to the average over a short amount of time (e.g., 3 seconds), which essentially filters large fluctuations at high frequency caused by pulsatile blood flow. As will be appreciated, a temperature rise in the treatment electrode is a result of heat conducting from tissue to the electrode. If an electrode is not in sufficient contact with a vessel wall, energy is delivered into the blood flowing around it and the temperature of the electrode is not increased as much. With this in mind, if the change in average temperature in the first 15 seconds is greater than, e.g., 14° C., this initial temperature response may indicate sufficient electrode contact, contact force, and/or blood flow rate, at least in the beginning of the treatment and, if no indication that treatment did not proceed as expected is encountered for the remainder of the treatment, there is not a high probability that the treatment was less than optimal or technically unsuccessful. Thus, a positive answer at decision block 2204 results in a "Treatment Complete" message 2220 being displayed. However, if the change in average temperature in the first 15 seconds is less than or equal to, e.g., 14° C., this initial temperature response may indicate that the electrode may not have had sufficient contact with the vessel wall. Thus, a negative answer at decision block 2204 results in proceeding to criteria 2206 for further evaluation.

At decision block 2206 the hottest temperature is evaluated by checking if the maximum average temperature is greater than, e.g., 56° C. A temperature rise above a threshold level (e.g., 56° C.), regardless of duration, may be enough to allow technical success. Thus, a temperature above threshold may be sufficient to indicate successful lesion formation despite the fact that at decision block 2204 the initial rise in temperature did not indicate sufficient contact. For example, the electrode may not have had sufficient contact initially but then contact could have been made at least for enough time to cause the vessel wall to heat up such that the temperature sensor in the electrode reads above 56° C. A positive result at decision block 2206 results in a "Treatment Complete" message 2220 being displayed. However, a negative result at decision block 2206 indicates that the maximum average temperature did not rise enough. The algorithm 2200, therefore, proceeds to decision block 2208 for further evaluation.

At decision block 2208 the mean temperature is evaluated during a period when power is sustained at its maximum amount (i.e., the ramping up period is eliminated from the mean calculation). In one embodiment, this evaluation consists of determining whether the mean real time temperature is above 53° C. during the period from 45 seconds to 120 seconds. In this manner, this criterion checks to determine if temperature was above a threshold for a certain duration. If decision block 2208 yields a positive determination then, despite the fact that the initial temperature response and the maximum average temperature were insufficient to indicate technical success (i.e., decision blocks 2204 and 2206 were failed), the mean temperature during the last 75 seconds indicates sufficient contact for sufficient time. For example, it is possible that a sufficient lesion was made and yet the maximum average temperature measured in the electrode was not greater than 56° C. because there is high blood flow pulling heat from the electrode. Therefore, a positive result at decision block 2208 results in a "Treatment Complete" message 2220 being displayed. However, a negative result at decision block 2208 indicates that the mean real time temperature in the sustained power stage was not sufficient and the algorithm 2200 proceeds to decision block 2210 for further evaluation of the treatment.

At decision block 2210 the change in impedance is evaluated by checking if the percentage of impedance change during a predetermined period of time (e.g., 45 seconds to 114 seconds), is greater than a predetermined value (e.g., 14%) of the initial impedance. The initial impedance is determined as the impedance shortly after the beginning of treatment (e.g., at 6 seconds) to eliminate possible misreadings in impedance measurement prior to this period (e.g., due to contrast injection). As will be appreciated, the impedance of tissue to radiofrequency (RF) electrical current decreases as the tissue temperature increases until the tissue is heated enough to cause it to desiccate at which point its impedance starts to rise. Therefore, a decrease in tissue impedance can indicate a rise in tissue temperature. The percentage change in real time impedance over the sustained power stage may be calculated as follows:

$$\% \, \Delta Z \text{ over } SS = 100 * \left( \frac{Z_{6s}^{avg} - (\text{mean } RT \, Z \text{ over } SS)}{Z_{6s}^{avg}} \right) \quad (1)$$

If decision block 2210 yields a positive determination then, despite the fact that the previous three decision blocks failed to show that there was a sufficient rise in temperature (i.e., decision blocks 2204, 2206, and 2208 were failed), the change in impedance could indicate that tissue was heated sufficiently but the temperature sensor in the electrode did not rise enough. For example, very high blood flow could cause the electrode temperature to remain relatively low even if the tissue was heated. Therefore, a positive result at decision block 2210 results in a "Treatment Complete" message 2220 being displayed. However, a negative result at decision block 2210 results in the algorithm 2200 proceeding to perform a LDA 2212.

At LDA 2212, a combination of events is evaluated along with a rating of importance for each event. In the depicted embodiment, for example, the criteria evaluated at decision blocks 2204, 2206, 2208, 2210 are included in the LDA 2212. In addition, in this implementation, three additional criteria may be included: (1) standard deviation of average temperature (which can provide an indication of the degree of sliding motion caused by respiration); (2) standard deviation of real time temperature (which can provide an indication of variable blood flow and/or contact force and/or intermittent contact); and (3) adjusted change in average impedance at the end of the treatment (which can further characterize change in impedance and provide an indication of change in temperature of tissue). If this analysis determines the combination of variables to have a significant impact on reducing technical success (e.g., a LDA score <0 at decision block 2222) then an "Unexpected Treatment" message 2224 is displayed. Otherwise, a "Treatment Complete" message 2220 is displayed.

It will be appreciated that the various parameters described above are merely representative examples associated with one embodiment of the algorithm 2200, and one or more of these parameters may vary in other embodiments. Further, the specific values described above with respect to particular portions of the treatment may be modified/changed in other embodiments based on, for example, different device configurations, electrode configurations, treatment protocols, etc.

As described above, the algorithm 2200 is configured to evaluate a treatment and display a message indicating that treatment is complete or, alternatively, that treatment did not proceed as expected. Based on the message describing the evaluation of the treatment, the clinician (or the system using automated techniques) can then decide whether further treatments may be necessary and/or if one or more parameters should be modified in subsequent treatments. In the above-described examples, for example, the algorithm 2200 may evaluate a number of situations generally related to poor contact between the electrode and vessel wall to help determine if the treatment was less than optimal. For example, poor contact may occur when an electrode slides back and forth as the patient breaths and the artery moves, when an electrode becomes displaced when a patient moves, when the catheter is moved inadvertently, when a catheter is not deflected to the degree needed to apply sufficient contact or contact force between the electrode and vessel wall, and/or when an electrode is placed in a precarious position. Further, as described above, if a particular parameter or set of parameters may have contributed to or resulted in a less than optimal treatment, the system 10 (FIG. 1) can provide feedback to alert the clinician to modify one or more treatment parameters during a subsequent treatment. Such evaluation and feedback of a treatment is expected to help clinicians learn to improve their placement technique to get better contact and reduce the frequency of technically unsuccessful treatments.

D. Feedback Related to High Temperature Conditions

While the preceding describes generalized evaluation of the technical success of a treatment, another form of feedback that may be useful to an operator of the system 10 (FIG. 1) is feedback related to specific types of patient or treatment conditions. For example, the system 10 may generate a message related to high temperature conditions. In particular, during a treatment while energy is being delivered, tissue temperature may increase above a specified level. A temperature sensor (e.g., thermocouple, thermistor, etc.) positioned in or near the electrode provides an indication of temperature in the electrode and, to some extent, an indication of tissue temperature. The electrode does not heat directly as energy is delivered to tissue. Instead, tissue is heated and the heat conducts to the electrode and the temperature sensor in the electrode. In one implementation, the system 10 may cease energy delivery if the real time temperature rises above a predefined maximum temperature (e.g., 85° C.). In such an event, the system may generate a message indicating the high temperature condition. However, depending on the circumstances, different actions by the clinician may be appropriate.

If tissue becomes too hot, established temperature thresholds can be exceeded. The implications of high tissue temperature are that an acute constriction of the artery or a protrusion of the artery wall could occur. This can happen right away or within a short time (e.g., about 50 seconds to about 100 seconds) after the occurrence of the high temperature is noted and a message is generated. In such an occurrence, the clinician may be instructed to image the treatment site to watch for a constriction or protrusion before starting another treatment.

Figure 23:
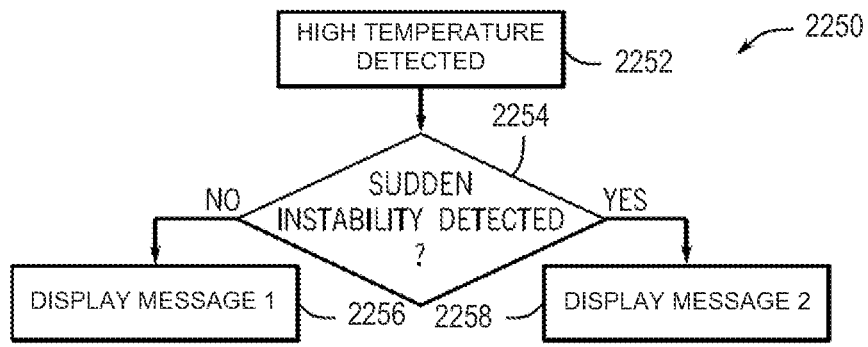
FIG. 23 is a block diagram illustrating an algorithm for providing operator feedback upon occurrence of a high temperature condition in accordance with an embodiment of the present technology.

FIG. 23, for example, is a block diagram illustrating an algorithm 2250 for providing operator feedback when a high temperature condition is detected in accordance with an embodiment of the present technology. In one implementation the algorithm 2250 is executed in response to a high temperature condition (block 2252) and evaluates (decision block 2254) data from the treatment to determine if the high temperature condition involved a situation that included sudden instability or if it did not. Sudden instability can be caused, for example, by sudden movement of the patient or catheter, thereby causing the electrode to be pushed harder (i.e., contact force is increased) into the vessel wall, which could also be accompanied by movement to another location. In the event that sudden instability is not detected at decision block 2254, a first message may be displayed (block 2256), such as an indication that a high temperature has been detected and an instruction to image the treatment site to determine if the site has been damaged. In the event that sudden instability is detected at decision block 2254, an alternative message may be displayed (block 2258) that, in addition to indicating the occurrence of the high temperature and instructing the clinician to image the treatment site, may also indicate the possibility that the electrode may have moved from its original site. Such feedback may prompt the clinician to compare previous images and avoid treating again on either of the original site or the site to which the electrode has moved.

E. Feedback Related to High Impedance

As with high temperature, in certain circumstances the system 10 (FIG. 1) may generate a message related to the occurrence of high impedance. As will be appreciated, impedance to RF current passing from a treatment electrode through the body to a dispersive return electrode can provide an indication of characteristics of the tissue that is in contact with the treatment electrode. For example, an electrode positioned in the blood stream in a renal artery may measure a lower impedance than an electrode contacting the vessel wall. Furthermore, as tissue temperature rises its impedance decreases. However, if the tissue gets too hot it may desicate and its impedance may increase. During a treatment as tissue is gradually heated it is expected that impedance will decrease. A significant rise in impedance can be a result of an undesired situation such as tissue desication or electrode movement. In certain implementations, the system 10 may be configured to cease energy delivery if the real time impedance rise is higher than a predefined maximum change in impedance from the starting impedance.

Figure 24:
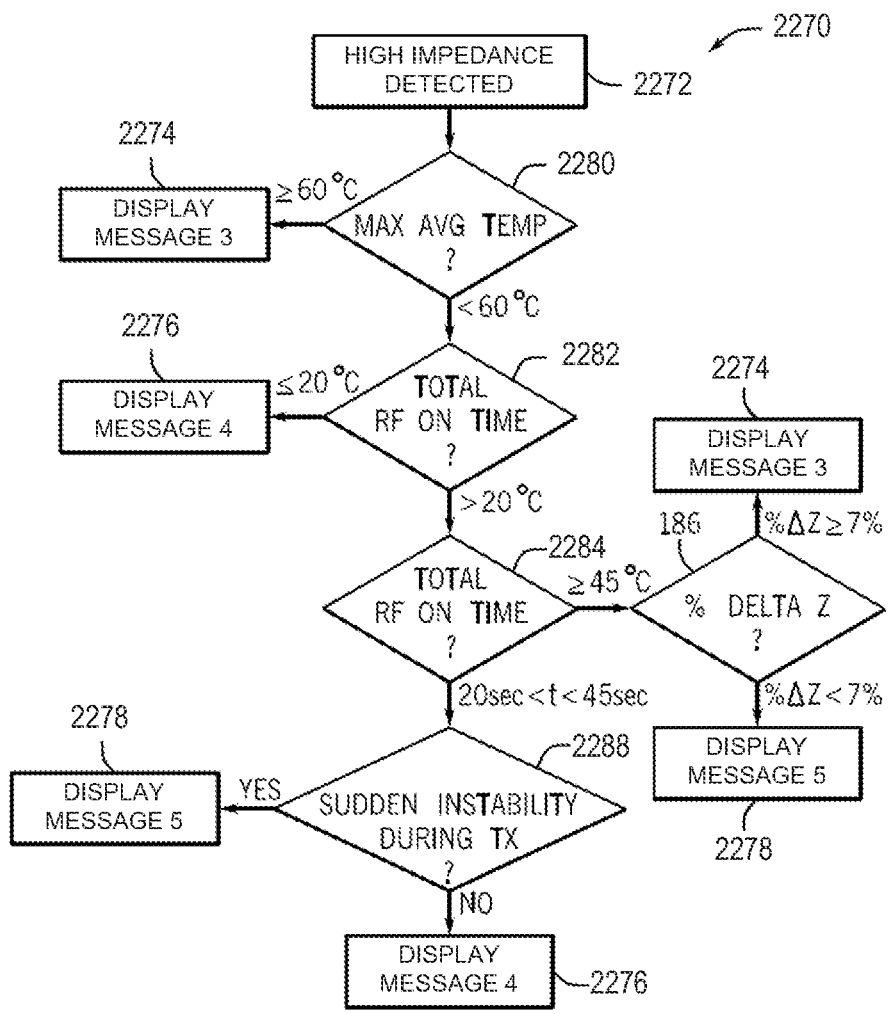
FIG. 24 is a block diagram illustrating an algorithm for providing operator feedback upon occurrence of a high impedance condition in accordance with an embodiment of the present technology.

FIG. 24, for example, is a block diagram illustrating an algorithm 2270 for providing operator feedback upon occurrence of a high impedance condition in accordance with an embodiment of the present technology. In the depicted embodiment, the algorithm 2270 evaluates data from the treatment and determines if detection of a high impedance event (block 2272) was likely to involve a situation in which (a) tissue temperature was high and desiccation was likely, (b) the electrode moved, or (c) there was poor electrode contact or no electrode contact with the vessel wall. The algorithm 170 evaluates the data to determine which, if any, of these three situations occurred and displays one of three messages 2274, 2276, or 2278 accordingly.

In accordance with one embodiment of the algorithm 2270, upon detection of a high impedance (block 2272), the maximum average temperature during the treatment is evaluated (decision block 2280). If this temperature is above a certain threshold (e.g., at or above 60° C.) then the high impedance may be attributed to high tissue temperature resulting in desiccation. In this event, message 2274 may be displayed instructing the clinician to check for a constriction or protrusion (i.e., to image the treatment site) and to avoid treating again in the same location. Conversely, if the temperature is below the threshold (e.g., below 60° C.), the algorithm 2270 proceeds to decision block 2282.

In the depicted embodiment, at decision block 2282, the algorithm 2270 evaluates if the high impedance event occurred early in treatment (e.g., in the first 20 seconds of energy delivery) when power is relatively low. If yes, it is unlikely that tissue temperature was high and more likely that the electrode initially had poor or no contact and subsequently established better contact, causing impedance to jump. In this event message 2276 may be displayed instructing the clinician to attempt to establish better contact and repeat treatment at the same site. However, if the event occurs later in treatment (e.g., more than 20 seconds elapsed), the algorithm 2270 proceeds to decision block 2284.

At decision block 2284, the algorithm 2270 evaluates when the high impedance event occurred during treatment. For example, if the event occurred after a predetermined period of time (e.g., 45 seconds), when the power has reached high levels, the algorithm proceeds to decision block 2286. However, if the event occurred when power is being ramped up and is not at its highest (e.g., between 20 seconds and 45 seconds), the algorithm proceeds to decision block 2288.

At decision block 2286, the algorithm 2270 calculates the percentage change in impedance (%ΔZ) at the time of the high impedance event compared to the impedance at a specified time (e.g., 45 seconds). This is the period when power is sustained at a high level. In one embodiment, the percentage change in impedance is calculated as:

$$\% \Delta Z = 100 * \left| \frac{[(\text{final avg } Z) - (\text{avg } Z @ 45 \text{ sec})]}{(\text{avg } Z @ 45 \text{ sec})} \right| \qquad (2)$$

If %ΔZ is greater than or equal to a predetermined amount (e.g., 7%) then it may be likely that tissue began to desiccate due to high temperature. In this event, message 2274 may be displayed instructing the clinician to check for a constriction or protrusion (i.e., to image the treatment site) and to avoid treating again in the same location. Otherwise, tissue desiccation is less likely and it is more likely that the electrode moved to cause the high impedance event. In this event, message 2278 may be displayed notifying the clinician that the electrode may have moved. In the event the electrode has moved or may have moved, it is unlikely that tissue temperature reached a high level. Accordingly, it is expected that treating in the same location can be done if there are no or limited other locations to perform another treatment.

At decision block 2288, the algorithm 2270 may determine whether a sudden instability occurred. If such instability was present, it is likely that the electrode moved. In this event, message 2278 may be displayed notifying the clinician that the electrode may have moved. As discussed above, the clinician may exhibit caution and avoid treating the original location or the location to which the electrode moved or the clinician may opt to treat in the same location if no other sites or a limited number of sites are available for further treatment. Otherwise, if no sudden instability occurred, it is more likely that the electrode had poor contact. In this event, message 2276 may be displayed instructing the clinician to attempt to establish better contact and that treating the same site is safe.

The same objective of detecting high impedance conditions can be achieved using alternate measurements and calculations. For example, in a further embodiment of the algorithm 2270, temperature and impedance data is taken for a sample time interval (e.g., 20 seconds). At a shorter time interval (e.g., every 1.5 seconds), the standard deviation of the impedance and temperature data is calculated. A first standard temperature for an interval is calculated as the standard deviation of the temperature divided by the standard deviation of the temperature at the initial time interval. If the standard deviation of the impedance measurements is greater than or equal to a pre-determined value (e.g., 10 Ohms), and the first standard temperature is greater than a pre-determined threshold (e.g., 3), then the algorithm 2270 can display message 2276, indicating poor electrode contact. However, if the standard deviation of the impedance measurement is outside the acceptable range, but the first standard temperature is within the acceptable range, then message 2278 will be displayed to alert the clinician that there is electrode instability.

In accordance with a further embodiment of the algorithm 2270, the impedance of two or more electrodes 24 (e.g., positioned on the treatment region 22 of the catheter 12 of FIG. 1) can each provide an independent impedance reading. During delivery of the therapeutic assembly 22 to the treatment site (e.g., within the renal artery), the impedance readings of the electrodes 24 are typically different due to the anatomy of the vasculature, as the catheter 12 will conform to the path of least resistance, often bending at vasculature curves to only contact one wall of the renal artery. In some embodiments, once the therapeutic assembly 22 is in position for treatment, the therapeutic assembly 22 can be expanded circumferentially to contact the entire circumferential surface of a segment of the renal artery wall. This expansion can place multiple electrodes 24 in contact with the renal artery wall. As the therapeutic assembly 22 is expanded into the treatment configuration and the electrodes 24 make increased contact with the renal artery wall, the impedance values of the individual electrodes 24 can increase and/or approach the same value. With good, stable contact, fluctuations of impedance values also reduce as described above. The energy generator 26 can continually or continuously monitor the individual impedance values. The values can then be compared to determine when contact has been effectively made, as an indication of successful treatment. In further embodiments, a moving average of impedance can be compared to a pre-determined range of variability of impedance values with limits set to guide stability measures.

F. Feedback Related to Vasoconstriction

In further embodiments, the system 10 may generate a message related to the occurrence of vasoconstriction. In particular, while treatment is being delivered, blood vessels may contract to a less-than-optimal diameter. Constricted blood vessels can lead to reduced blood flow, increased treatment site temperatures, and increased blood pressure. Vasoconstriction can be measured by sampling the amplitude (the "envelope") of real-time temperature data. The current envelope can be compared to a previous envelope sample taken (e.g., 200 ms prior). If the difference between the current envelope and the previous time point envelope is less than a pre-determined value (e.g., less than −0.5° C., or, in other words, there is a less than a 0.5 degree reduction in the present envelope value compared to the envelope value at the previous time point), then measurements are taken at a future time point (e.g., in 5 seconds). If the difference in average temperature at the future time point and the current time point is more than a given temperature threshold (e.g., more than 1° C.), then an algorithm 2500 may determine that an undesirably high level of constriction exists, and can cease/alter energy delivery. In such an event, the system 10 may generate a message indicating the high constriction condition. However, depending on the circumstances, different actions by the clinician may be appropriate.

Figure 25:
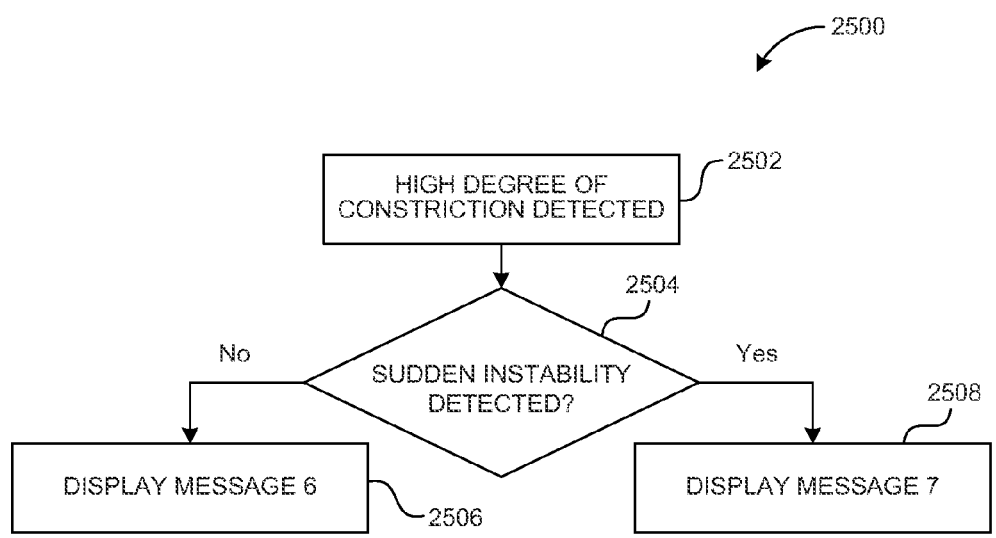
FIG. 25 is a block diagram illustrating an algorithm for providing operator feedback upon occurrence of a high degree of vessel constriction in accordance with an embodiment of the present technology.

FIG. 25, for example, is a block diagram illustrating an algorithm 2500 for providing operator feedback when a high degree of vessel constriction is detected in accordance with an embodiment of the present technology. In one implementation, the algorithm 2500 is executed in response to a high constriction level (e.g., vessels constricted at or below a certain diameter) (Block 2502) and evaluates (decision block 2504) data from the treatment to determine if the high constriction level involved a situation that included sudden instability or if it did not. An indication of sudden instability can indicate that the electrode 24 moved.

In the event that sudden instability is not detected at decision block 2504, a first message may be displayed (block 2506), such as an indication that a high constriction level has been detected and an instruction to a clinician to reduce treatment power. In further embodiments, the energy level may be automatically altered in response to the detected constriction level. In the event that sudden instability is detected at decision block 2504, an alternative message may be displayed (block 2508) that, in addition to indicating the occurrence of the high constriction level and instructions to the clinician, may also indicate the possibility that the electrode 24 may have moved from its original site. Such feedback may prompt the clinician to alter or cease treatment.

G. Feedback Related to Cardiac Factors

1. Feedback Related to Abnormal Heart Rate

Like other physiological conditions mentioned above, in certain circumstances the system 10 may generate a message related to the occurrence of an abnormal heart rate. In particular, while treatment is being delivered, heart rate may exceed or fall below desirable conditions (e.g., temporary procedural or chronic bradycardia). Instantaneous heart rate can be determined by measuring real-time temperature and impedance. More specifically, a real-time temperature reading can be filtered, for example, between 0.5 Hz and 2.5 Hz using a second order Butterworth filter. Local maxima of the filtered signal are determined. The local maxima are the detected peaks of the real-temperature signal. The instantaneous beat rate is the interval between the peaks, as the signal peaks correspond to the periodic change in the cardiac cycle.

In one implementation, the system 10 may cease/alter energy delivery if the heart rate falls outside a desirable range. In such an event, the system may generate a message indicating the adverse heart rate condition. However, depending on the circumstances, different actions by the clinician may be appropriate.

Figure 26A:
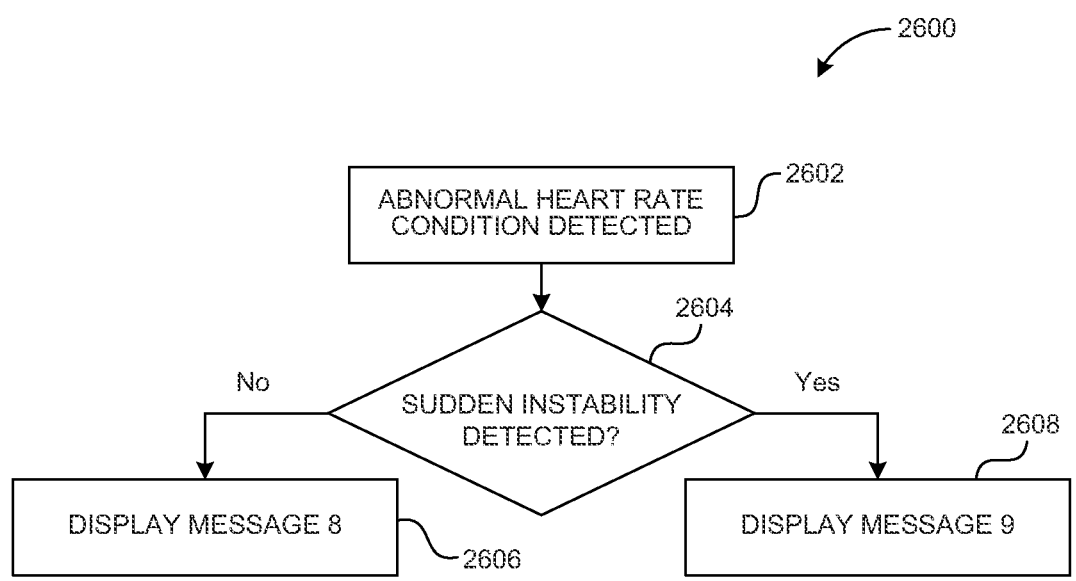
FIG. 26A is a block diagram illustrating an algorithm for providing operator feedback upon occurrence of an abnormal heart rate condition in accordance with an embodiment of the present technology.

FIG. 26A, for example, is a block diagram illustrating an algorithm 2600 for providing operator feedback/instructions upon detection of an abnormal heart rate condition in accordance with an embodiment of the present technology. In one implementation, for example, the algorithm 2600 may be executed in response to an abnormal heart rate condition (e.g., above or below a pre-determined threshold) (Block 2602). At decision block 2604, the algorithm 2600 evaluates data from the treatment to determine if the detected abnormal heart rate condition involved a situation that included sudden instability. An indication of sudden instability can indicate that the electrode moved.

In the event that sudden instability is not detected at decision block 2604, a first message may be displayed to the clinician (block 2606), such as an indication that an abnormal heart rate has been detected and an instruction to the clinician to reduce treatment power. In further embodiments, the energy level may be automatically altered in response to the detected adverse heart rate. In the event that sudden instability is detected at decision block 2604, an alternative message may be displayed (block 2608) that, in addition to indicating the occurrence of the abnormal heart rate and instructions to the clinician, may also indicate the possibility that the electrode may have moved from its original site. Such feedback may prompt the clinician to alter or cease treatment.

2. Feedback Related to Low Blood Flow

The system 10 may also be configured to generate a message related to low blood flow conditions. For example, if blood flow falls below a certain level during treatment (or if vessels are undesirably narrow), the convective heat removed from the electrode 24 and tissue surface is reduced. Excessively high tissue temperatures can lead to the negative outcomes described above, such as thrombosis, charring, unreliable lesion size, etc. Reducing power from the generator 26 to prevent the tissue from reaching an unacceptable temperature can lead to insufficient lesion depth, and nerves may not be heated to sufficient ablation temperatures. An algorithm can be used to measure blood flow or the loss of heat to the blood stream. In one embodiment, blood flow can be measured with a flow meter or a Doppler sensor placed in the renal artery on a separate catheter or on the treatment catheter 12. In another embodiment, heat loss or thermal decay can be measured by delivering energy (e.g., RF energy) to raise a blood, tissue, or substrate temperature. The energy can be turned off and the algorithm can include monitoring the temperature as a gauge of thermal decay. A rapid thermal decay may represent sufficient blood flow, while a gradual thermal decay may represent low blood flow. For example, in one embodiment, the algorithm 2610 can indicate a low blood flow if the slope of real-time temperature measurements over the starting temperature exceeds a preset threshold (e.g., 2.75) and the average temperature is greater than a preset temperature (e.g., 65° C.). In further embodiments, thermal decay and/or blood flow can be characterized by measuring temperature oscillations of an electrode delivering RF or resistive heat. At a given temperature or power delivery amplitude/magnitude, a narrow oscillation range may indicate a relatively low thermal decay/blood flow.

Figure 26B:
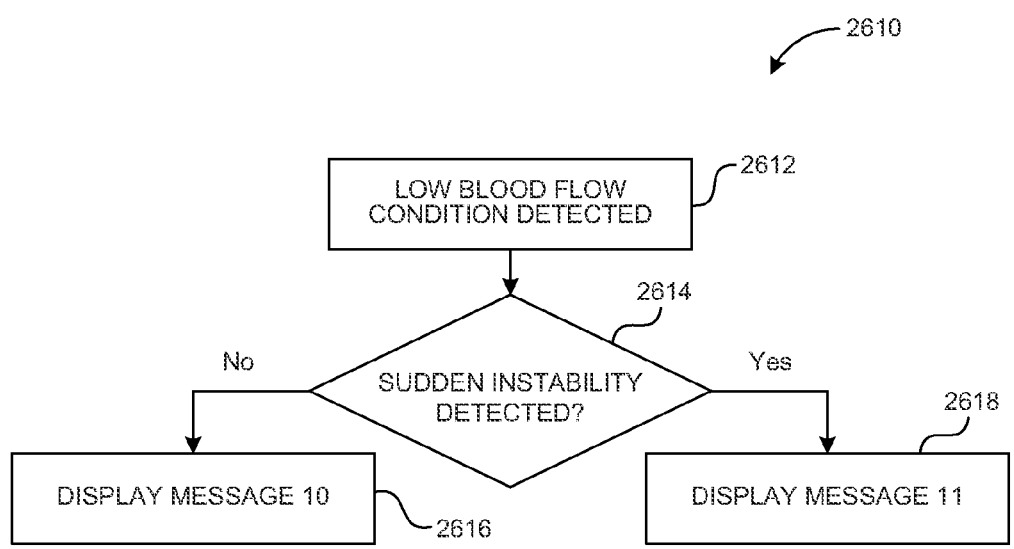
FIG. 26B is a block diagram illustrating an algorithm for providing operator feedback upon occurrence of a low blood flow condition in accordance with an embodiment of the present technology.

FIG. 26B, for example, is a block diagram illustrating an algorithm 2610 for providing operator feedback/instructions upon occurrence of a low blood flow condition in accordance with an embodiment of the present technology. In one implementation, the algorithm 2610 is executed in response to a detected low blood flow condition (e.g., flow below a predetermined threshold) (Block 2612). At block 2614, the algorithm 2610 evaluates data from the treatment to determine if the low blood flow condition involved a situation that included sudden instability. In the event that sudden instability is not detected at decision block 2614, a first message may be displayed (block 2616), such as an indication that low blood flow has been detected and an instruction to a clinician to reduce treatment power. In the event that sudden instability is detected, an alternative message may be displayed (block 2618) that, in addition to indicating the occurrence of low blood flow and instructions to the clinician, may also indicate the possibility that the electrode may have moved from its original site. As noted above, such feedback may prompt the clinician to alter or cease treatment.

In further embodiments, if blood flow or thermal decay values are lower than a typical or pre-determined threshold, the energy delivery algorithm 2610 can include automatically altering one or more conditions or characteristics of treatment or of the catheter to improve blood flow. For example, in one embodiment, the algorithm 2610 can respond to a low blood flow by pulsing the energy provided to the energy delivery element 264 rather than providing continuous energy. This may allow the lower blood flow to more adequately remove heat from the tissue surface while still creating a sufficiently deep lesion to ablate a nerve.

In another embodiment, the algorithm 2610 can include responding to a low blood flow by cooling the electrodes, as described in further detail in International Patent Application No. PCT/US2011/033491, filed Apr. 26, 2011, and U.S. patent application Ser. No. 12/874,457, filed Aug. 30, 2010. The foregoing applications are incorporated herein by reference in their entireties.

In a further embodiment, the algorithm 2610 can respond to a low blood flow by requiring a manual increase of blood flow to the region. For example, a non-occlusive balloon can be inflated in the abdominal aorta, thereby increasing pressure and flow in the renal artery. The balloon can be incorporated on the treatment catheter or on a separate catheter.

H. Feedback Display

Figure 27A:
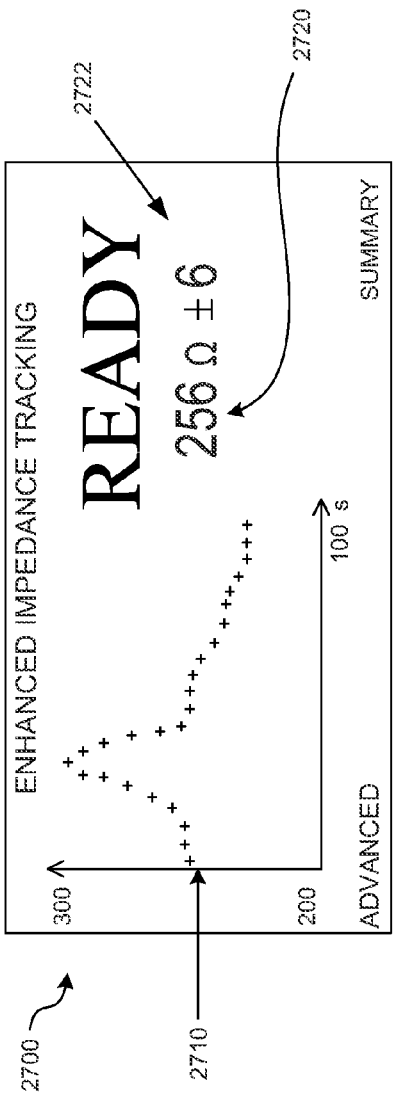
FIGS. 27A and 27B are screen shots illustrating representative generator display screens configured in accordance with aspects of the present technology.
Figure 27B:
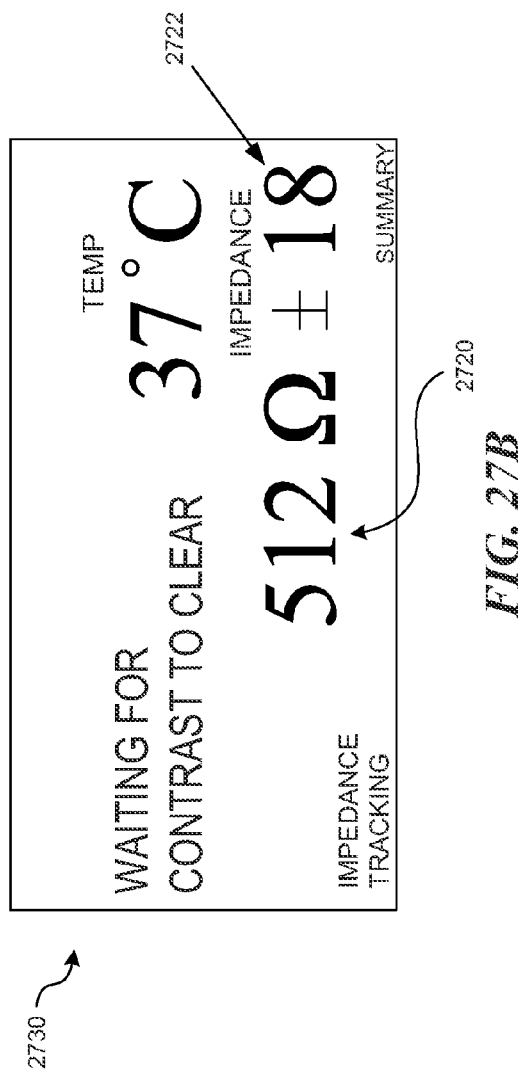

FIGS. 27A and 27B are screen shots illustrating representative generator display screens configured in accordance with aspects of the present technology. FIG. 27A, for example, is a display screen 2700 for enhanced impedance tracking during treatment. The display 2700 includes a graphical display 2710 that tracks impedance measurements in real time over a selected period of time (e.g., 100 seconds). This graphical display 2710, for example, can be a dynamic, rolling display that is updated at periodic intervals to provide an operator with both instantaneous and historical tracking of impedance measurements. The display 2710 can also includes an impedance display 2720 with the current impedance as well as a standard deviation indication 2722 for the impedance. In one embodiment, the standard deviation indication 2722 is configured to flash when this value is greater than 10. Such an indication can alert the operator of a contrast injection that is affecting the measurement or that the electrode may be unstable. Further information about contrast injection indications are described below.

FIG. 27B, for example, is another representative display screen 2730 with additional information for an operator. In this example, the display screen 2730 is configured to alert the operator of a contrast injection and that the system is waiting for contrast to clear before commencing (e.g., disable RF for approximately 1 to 2 seconds until contrast clears). In another embodiment, the display screen 2730 may be configured to provide other alert messages (e.g., "POSSIBLE UNSTABLE ELECTRODE," etc.). The additional information provided in the display screens 2710 and 2730 described above is expected to improve contact assessment prior to RF ON, and improve treatment efficiency and efficacy.

The additional information described above with reference to FIGS. 27A and 10B can be generated based on the algorithms described herein, or other suitable algorithms. In one embodiment, for example, an algorithm can continuously check for contrast injection/stability during pre-RF ON. If the electrode is stable and there is no contrast for >1 second, the baseline impedance Z is set equal to the average impedance Z over 1 second. In one particular example, the real time impedance is compared with two standard deviations of the mean impedance value within a one second window. In another specific example, the real time impedance may be compared with a fixed number (e.g., determine if the standard deviation is greater than 10). In still other examples, other arrangements may be used.

If the real time impedance measurement is within this range, no message is displayed. However, if the real time impedance is not within two standard deviations of the mean, the electrode may not stable (i.e., drifting, moving, etc.) and one or both of the message(s) described above with reference to FIGS. 27A and 27B may be displayed to the user (e.g., "WAITING FOR CONTRAST TO CLEAR," "POSSIBLE UNSTABLE ELECTRODE"). By way of example, for contrast injection detection, in addition to the standard deviation of the impedance, the algorithm may be configured to factor in the standard deviation of a real time temperature measurement to look for excursions of the real time temperature below a starting body temperature. The exact value for the temperature excursion cut off can vary. In one particular example, the system is configured such that if there is an increase in impedance (e.g., standard deviation >10) accompanied by a drop in real time temperature, the system will flag a Contrast Detected event leading to the "WAITING FOR CONTRAST TO CLEAR" message to be displayed to the operator. In other examples, however, other algorithms and/or ranges may be used to determine contrast injection events and/or the stability of the electrode. Further, in some embodiments the system may modify/adjust various treatment parameters based on detected conditions without displaying such messages to the clinician.

Figure 28:
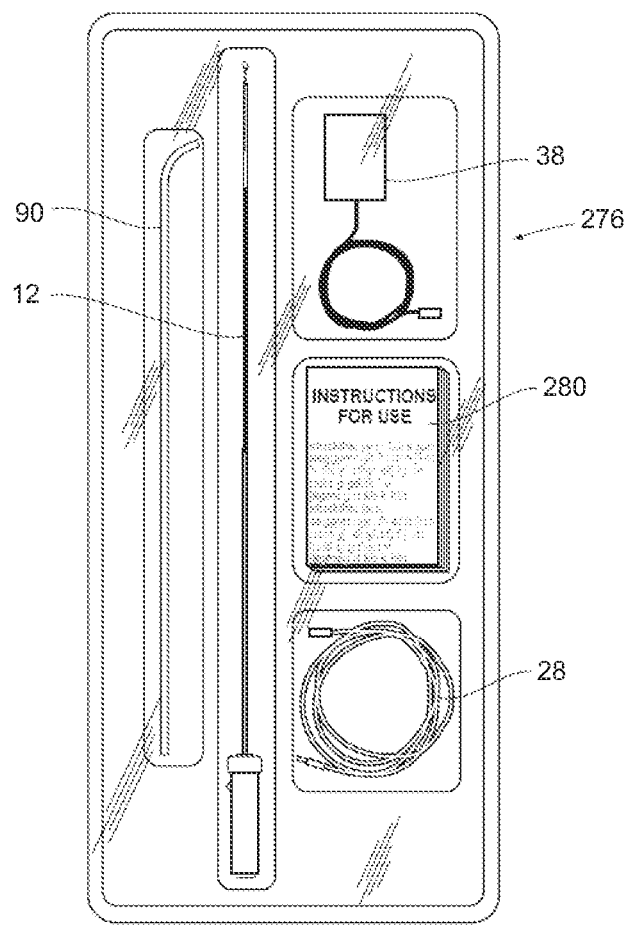
FIG. 28 is an illustration of a kit containing packaged components of the system of FIG. 1 in accordance with an embodiment of the technology.

VII. Prepackaged kit for distribution, transport and sale of the disclosed apparatuses and Systems As shown in FIG. 28, one or more components of the system 10 shown in FIG. 1 may be packaged together in a kit 276 for convenient delivery to and use by the customer/clinical operator. Components suitable for packaging include, the treatment device 12, the cable 28 for connecting the treatment device 12 to the energy generator 26, the neutral or dispersive electrode 38, and one or more guide catheters (e.g., a renal guide catheter). Cable 28 may also be integrated into the treatment device 12 such that both components are packaged together. Each component may have its own sterile packaging (for components requiring sterilization) or the components may have dedicated sterilized compartments within the kit packaging. This kit may also include step-by-step instructions 280 for use that provide the operator with technical product features and operating instructions for using the system 10 and treatment device 12, including all methods of insertion, delivery, placement, and use of the treatment device 12 disclosed herein.

VIII. Additional Clinical Uses Of The Disclosed Technology

Although certain embodiments of the present techniques relate to at least partially denervating a kidney of a patient to block afferent and/or efferent neural communication from within a renal blood vessel (e.g., renal artery), the apparatuses, methods and systems described herein may also be used for other intravascular treatments. For example, the aforementioned catheter system, or select aspects of such system, may be placed in other peripheral blood vessels to deliver energy and/or electric fields to achieve a neuromodulatory affect by altering nerves proximate to these other peripheral blood vessels. There are a number of arterial vessels arising from the aorta which travel alongside a rich collection of nerves to target organs. Utilizing the arteries to access and modulate these nerves may have clear therapeutic potential in a number of disease states. Some examples include the nerves encircling the celiac trunk, superior mesenteric artery, and inferior mesenteric artery.

Sympathetic nerves proximate to or encircling the arterial blood vessel known as the celiac trunk may pass through the celiac ganglion and follow branches of the celiac trunk to innervate the stomach, small intestine, abdominal blood vessels, liver, bile ducts, gallbladder, pancreas, adrenal glands, and kidneys. Modulating these nerves in whole (or in part via selective modulation) may enable treatment of conditions including, but not limited to, diabetes, pancreatitis, obesity, hypertension, obesity related hypertension, hepatitis, hepatorenal syndrome, gastric ulcers, gastric motility disorders, irritable bowel syndrome, and autoimmune disorders such as Crohn's disease.

Sympathetic nerves proximate to or encircling the arterial blood vessel known as the inferior mesenteric artery may pass through the inferior mesenteric ganglion and follow branches of the inferior mesenteric artery to innervate the colon, rectum, bladder, sex organs, and external genitalia. Modulating these nerves in whole (or in part via selective modulation) may enable treatment of conditions including, but not limited to, GI motility disorders, colitis, urinary retention, hyperactive bladder, incontinence, infertility, polycystic ovarian syndrome, premature ejaculation, erectile dysfunction, dyspareunia, and vaginismus.

While arterial access and treatments received have been provided herein, the disclosed apparatuses, methods and systems may also be used to deliver treatment from within a peripheral vein or lymphatic vessel.

IX. Additional Discussion of Pertinent Anatomy and Physiology

The following discussion provides further details regarding pertinent patient anatomy and physiology. This section is intended to supplement and expand upon the previous discussion regarding the relevant anatomy and physiology, and to provide additional context regarding the disclosed technology and the therapeutic benefits associated with renal denervation. For example, as mentioned previously, several properties of the renal vasculature may inform the design of treatment devices and associated methods for achieving renal neuromodulation via intravascular access, and impose specific design requirements for such devices. Specific design requirements may include accessing the renal artery, facilitating stable contact between the energy delivery elements of such devices and a luminal surface or wall of the renal artery, and/or effectively modulating the renal nerves with the neuromodulatory apparatus.

A. The Sympathetic Nervous System

The Sympathetic Nervous System (SNS) is a branch of the autonomic nervous system along with the enteric nervous system and parasympathetic nervous system. It is always active at a basal level (called sympathetic tone) and becomes more active during times of stress. Like other parts of the nervous system, the sympathetic nervous system operates through a series of interconnected neurons. Sympathetic neurons are frequently considered part of the peripheral nervous system (PNS), although many lie within the central nervous system (CNS). Sympathetic neurons of the spinal cord (which is part of the CNS) communicate with peripheral sympathetic neurons via a series of sympathetic ganglia. Within the ganglia, spinal cord sympathetic neurons join peripheral sympathetic neurons through synapses. Spinal cord sympathetic neurons are therefore called presynaptic (or preganglionic) neurons, while peripheral sympathetic neurons are called postsynaptic (or postganglionic) neurons.

At synapses within the sympathetic ganglia, preganglionic sympathetic neurons release acetylcholine, a chemical messenger that binds and activates nicotinic acetylcholine receptors on postganglionic neurons. In response to this stimulus, postganglionic neurons principally release noradrenaline (norepinephrine). Prolonged activation may elicit the release of adrenaline from the adrenal medulla.

Once released, norepinephrine and epinephrine bind adrenergic receptors on peripheral tissues. Binding to adrenergic receptors causes a neuronal and hormonal response. The physiologic manifestations include pupil dilation, increased heart rate, occasional vomiting, and increased blood pressure. Increased sweating is also seen due to binding of cholinergic receptors of the sweat glands.

The sympathetic nervous system is responsible for up- and down-regulating many homeostatic mechanisms in living organisms. Fibers from the SNS innervate tissues in almost every organ system, providing at least some regulatory function to things as diverse as pupil diameter, gut motility, and urinary output. This response is also known as sympathoadrenal response of the body, as the preganglionic sympathetic fibers that end in the adrenal medulla (but also all other sympathetic fibers) secrete acetylcholine, which activates the secretion of adrenaline (epinephrine) and to a lesser extent noradrenaline (norepinephrine). Therefore, this response that acts primarily on the cardiovascular system is mediated directly via impulses transmitted through the sympathetic nervous system and indirectly via catecholamines secreted from the adrenal medulla.

Science typically looks at the SNS as an automatic regulation system, that is, one that operates without the intervention of conscious thought. Some evolutionary theorists suggest that the sympathetic nervous system operated in early organisms to maintain survival as the sympathetic nervous system is responsible for priming the body for action. One example of this priming is in the moments before waking, in which sympathetic outflow spontaneously increases in preparation for action.

1. The Sympathetic Chain

Figure 29:
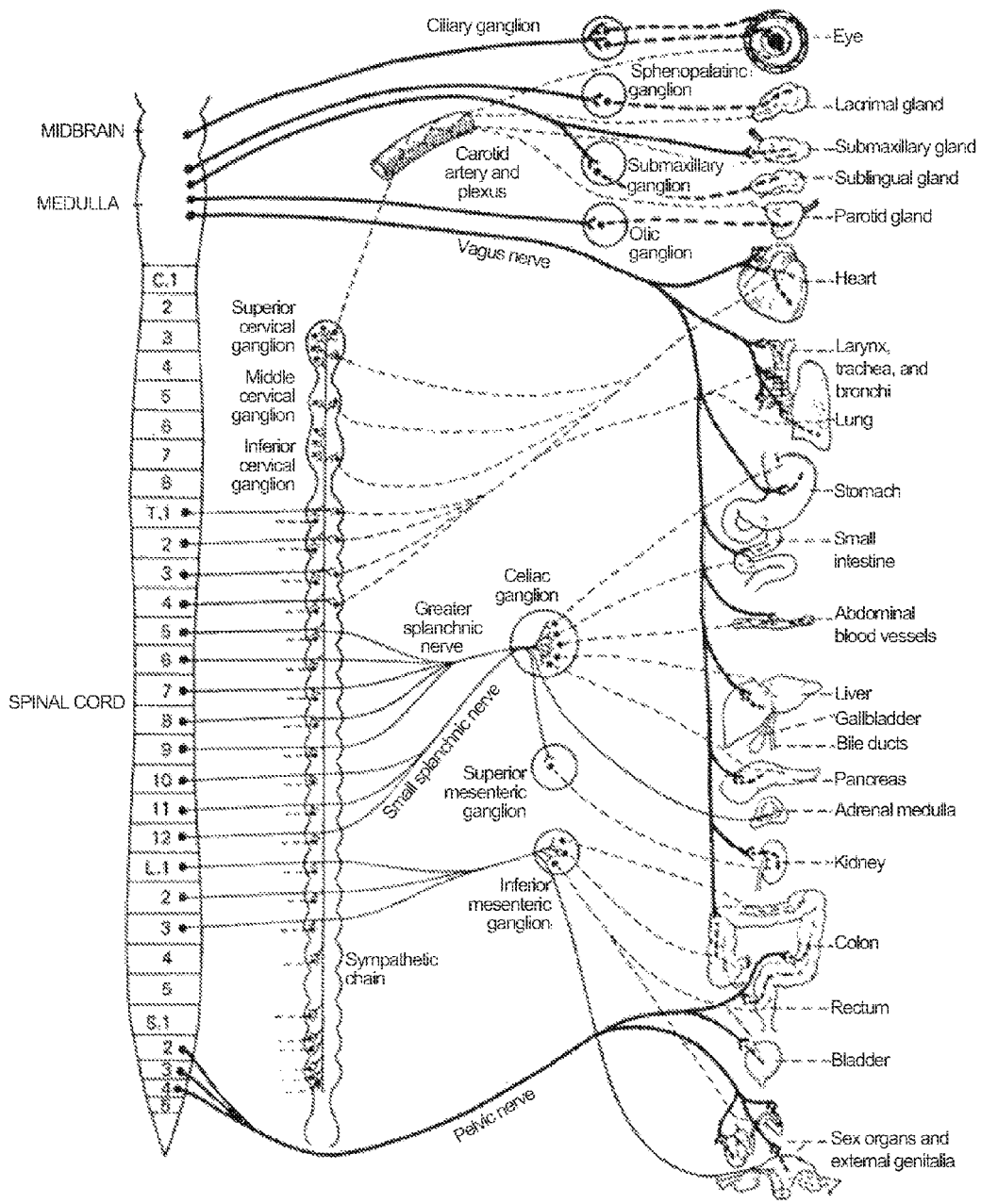
FIG. 29 is a conceptual illustration of the sympathetic nervous system (SNS) and how the brain communicates with the body via the SNS.

As shown in FIG. 29, the SNS provides a network of nerves that allows the brain to communicate with the body. Sympathetic nerves originate inside the vertebral column, toward the middle of the spinal cord in the intermediolateral cell column (or lateral horn), beginning at the first thoracic segment of the spinal cord and are thought to extend to the second or third lumbar segments. Because its cells begin in the thoracic and lumbar regions of the spinal cord, the SNS is said to have a thoracolumbar outflow. Axons of these nerves leave the spinal cord through the anterior rootlet/root. They pass near the spinal (sensory) ganglion, where they enter the anterior rami of the spinal nerves. However, unlike somatic innervation, they quickly separate out through white rami connectors which connect to either the paravertebral (which lie near the vertebral column) or prevertebral (which lie near the aortic bifurcation) ganglia extending alongside the spinal column.

In order to reach the target organs and glands, the axons should travel long distances in the body, and, to accomplish this, many axons relay their message to a second cell through synaptic transmission. The ends of the axons link across a space, the synapse, to the dendrites of the second cell. The first cell (the presynaptic cell) sends a neurotransmitter across the synaptic cleft where it activates the second cell (the postsynaptic cell). The message is then carried to the final destination.

In the SNS and other components of the peripheral nervous system, these synapses are made at sites called ganglia. The cell that sends its fiber is called a preganglionic cell, while the cell whose fiber leaves the ganglion is called a postganglionic cell. As mentioned previously, the preganglionic cells of the SNS are located between the first thoracic (T1) segment and third lumbar (L3) segments of the spinal cord. Postganglionic cells have their cell bodies in the ganglia and send their axons to target organs or glands.

The ganglia include not just the sympathetic trunks but also the cervical ganglia (superior, middle and inferior), which sends sympathetic nerve fibers to the head and thorax organs, and the celiac and mesenteric ganglia (which send sympathetic fibers to the gut).

2. Innervation of the Kidneys

Figure 30:
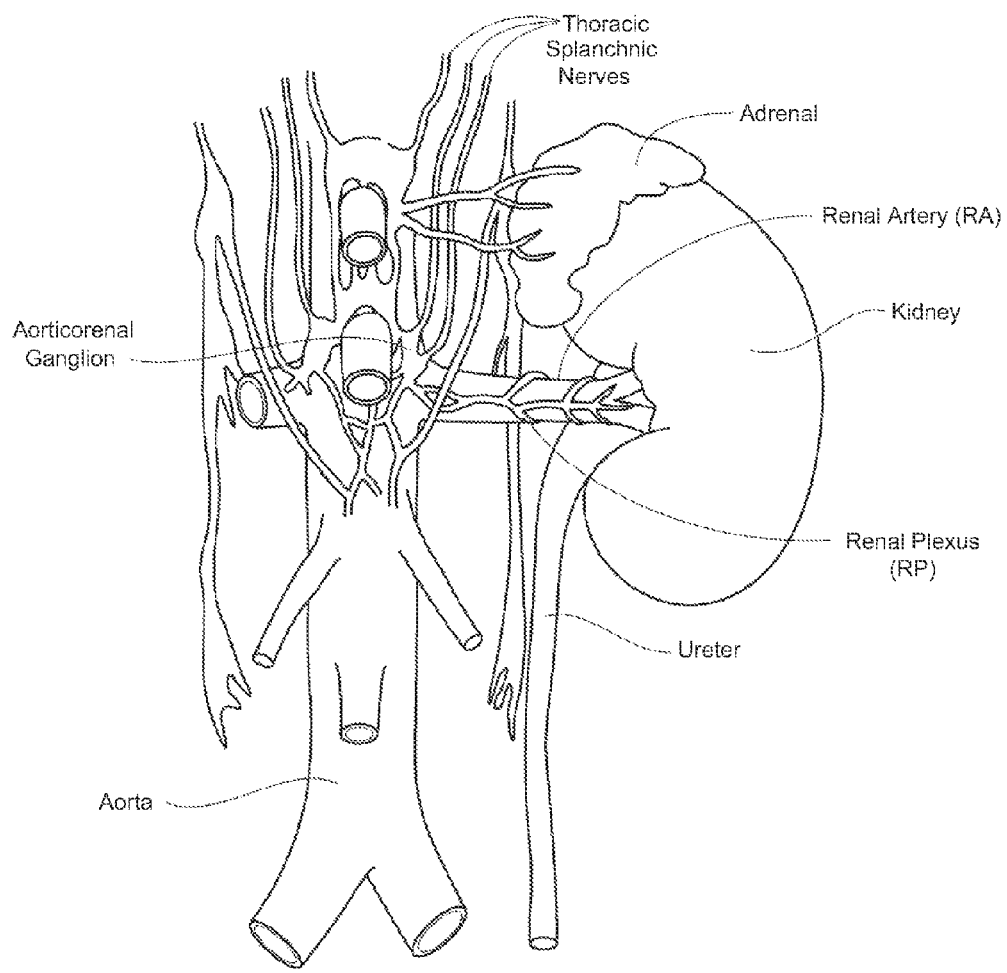
FIG. 30 is an enlarged anatomic view of nerves innervating a left kidney to form the renal plexus surrounding the left renal artery.

As FIG. 30 shows, the kidney is innervated by the renal plexus RP, which is intimately associated with the renal artery. The renal plexus RP is an autonomic plexus that surrounds the renal artery and is embedded within the adventitia of the renal artery. The renal plexus RP extends along the renal artery until it arrives at the substance of the kidney. Fibers contributing to the renal plexus RP arise from the celiac ganglion, the superior mesenteric ganglion, the aorticorenal ganglion and the aortic plexus. The renal plexus RP, also referred to as the renal nerve, is predominantly comprised of sympathetic components. There is no (or at least very minimal) parasympathetic innervation of the kidney.

Preganglionic neuronal cell bodies are located in the intermediolateral cell column of the spinal cord. Preganglionic axons pass through the paravertebral ganglia (they do not synapse) to become the lesser splanchnic nerve, the least splanchnic nerve, first lumbar splanchnic nerve, second lumbar splanchnic nerve, and travel to the celiac ganglion, the superior mesenteric ganglion, and the aorticorenal ganglion. Postganglionic neuronal cell bodies exit the celiac ganglion, the superior mesenteric ganglion, and the aorticorenal ganglion to the renal plexus RP and are distributed to the renal vasculature.

3. Renal Sympathetic Neural Activity

Messages travel through the SNS in a bidirectional flow. Efferent messages may trigger changes in different parts of the body simultaneously. For example, the sympathetic nervous system may accelerate heart rate; widen bronchial passages; decrease motility (movement) of the large intestine; constrict blood vessels; increase peristalsis in the esophagus; cause pupil dilation, piloerection (goose bumps) and perspiration (sweating); and raise blood pressure. Afferent messages carry signals from various organs and sensory receptors in the body to other organs and, particularly, the brain.

Hypertension, heart failure and chronic kidney disease are a few of many disease states that result from chronic activation of the SNS, especially the renal sympathetic nervous system. Chronic activation of the SNS is a maladaptive response that drives the progression of these disease states. Pharmaceutical management of the renin-angiotensin-aldosterone system (RAAS) has been a longstanding, but somewhat ineffective, approach for reducing over-activity of the SNS.

As mentioned above, the renal sympathetic nervous system has been identified as a major contributor to the complex pathophysiology of hypertension, states of volume overload (such as heart failure), and progressive renal disease, both experimentally and in humans. Studies employing radiotracer dilution methodology to measure overflow of norepinephrine from the kidneys to plasma revealed increased renal norepinephrine (NE) spillover rates in patients with essential hypertension, particularly so in young hypertensive subjects, which in concert with increased NE spillover from the heart, is consistent with the hemodynamic profile typically seen in early hypertension and characterized by an increased heart rate, cardiac output, and renovascular resistance. It is now known that essential hypertension is commonly neurogenic, often accompanied by pronounced sympathetic nervous system overactivity.

Activation of cardiorenal sympathetic nerve activity is even more pronounced in heart failure, as demonstrated by an exaggerated increase of NE overflow from the heart and the kidneys to plasma in this patient group. In line with this notion is the recent demonstration of a strong negative predictive value of renal sympathetic activation on all-cause mortality and heart transplantation in patients with congestive heart failure, which is independent of overall sympathetic activity, glomerular filtration rate, and left ventricular ejection fraction. These findings support the notion that treatment regimens that are designed to reduce renal sympathetic stimulation have the potential to improve survival in patients with heart failure.

Both chronic and end stage renal disease are characterized by heightened sympathetic nervous activation. In patients with end stage renal disease, plasma levels of norepinephrine above the median have been demonstrated to be predictive for both all-cause death and death from cardiovascular disease. This is also true for patients suffering from diabetic or contrast nephropathy. There is compelling evidence suggesting that sensory afferent signals originating from the diseased kidneys are major contributors to initiating and sustaining elevated central sympathetic outflow in this patient group; this facilitates the occurrence of the well known adverse consequences of chronic sympathetic over activity, such as hypertension, left ventricular hypertrophy, ventricular arrhythmias, sudden cardiac death, insulin resistance, diabetes, and metabolic syndrome.

(i) Renal Sympathetic Efferent Activity

Sympathetic nerves to the kidneys terminate in the blood vessels, the juxtaglomerular apparatus and the renal tubules. Stimulation of the renal sympathetic nerves causes increased renin release, increased sodium (Na+) reabsorption, and a reduction of renal blood flow. These components of the neural regulation of renal function are considerably stimulated in disease states characterized by heightened sympathetic tone and clearly contribute to the rise in blood pressure in hypertensive patients. The reduction of renal blood flow and glomerular filtration rate as a result of renal sympathetic efferent stimulation is likely a cornerstone of the loss of renal function in cardio-renal syndrome, which is renal dysfunction as a progressive complication of chronic heart failure, with a clinical course that typically fluctuates with the patient's clinical status and treatment. Pharmacologic strategies to thwart the consequences of renal efferent sympathetic stimulation include centrally acting sympatholytic drugs, beta blockers (intended to reduce renin release), angiotensin converting enzyme inhibitors and receptor blockers (intended to block the action of angiotensin II and aldosterone activation consequent to renin release) and diuretics (intended to counter the renal sympathetic mediated sodium and water retention).

However, the current pharmacologic strategies have significant limitations including limited efficacy, compliance issues, side effects and others.

(ii) Renal Sensory Afferent Nerve Activity

Figure 31A:
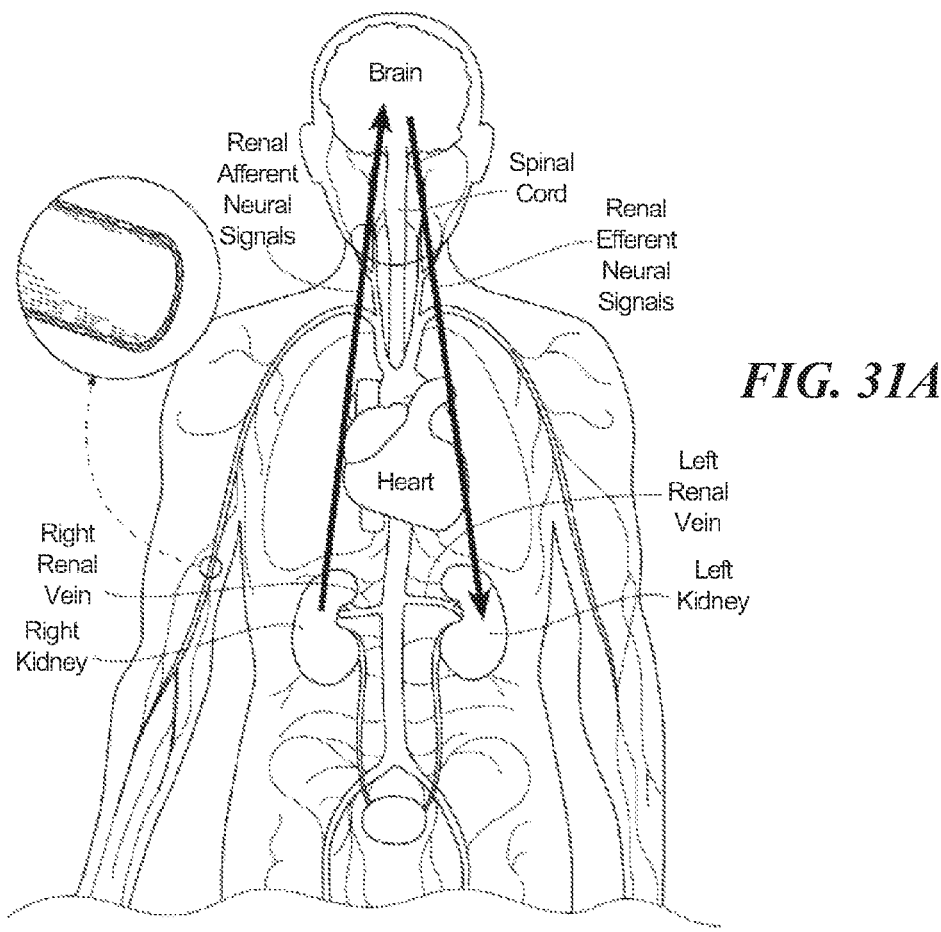
FIGS. 31A and 31B provide anatomic and conceptual views of a human body, respectively, depicting neural efferent and afferent communication between the brain and kidneys.
Figure 31B:
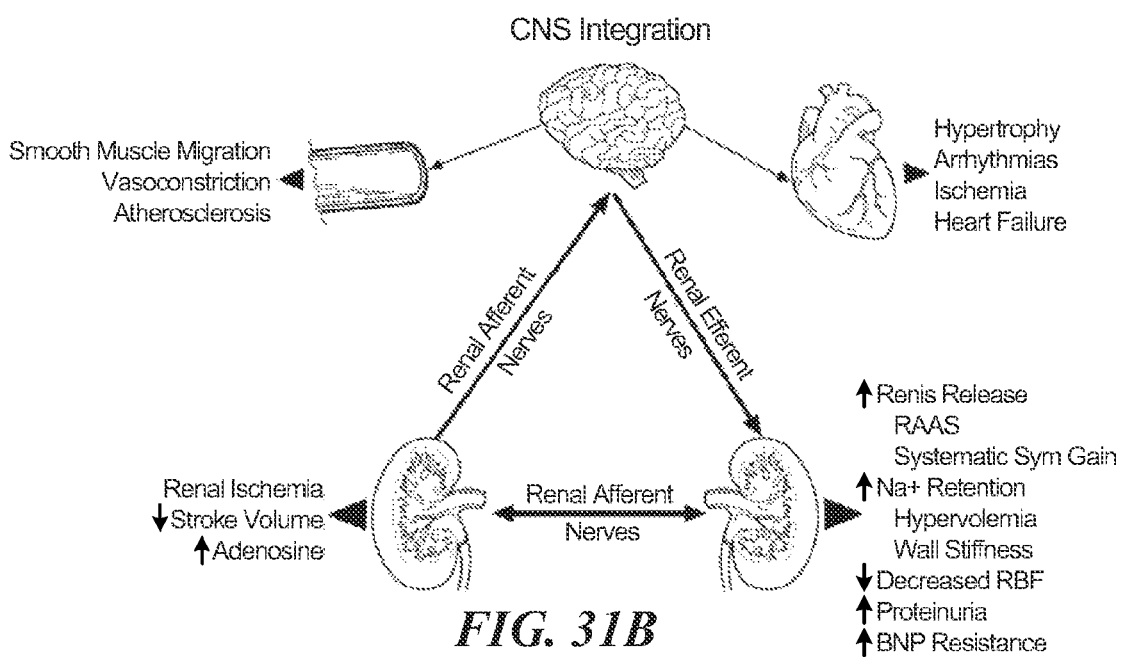

The kidneys communicate with integral structures in the central nervous system via renal sensory afferent nerves. Several forms of "renal injury" may induce activation of sensory afferent signals. For example, renal ischemia, reduction in stroke volume or renal blood flow, or an abundance of adenosine enzyme may trigger activation of afferent neural communication. As shown in FIGS. 31A and 31B, this afferent communication might be from the kidney to the brain or might be from one kidney to the other kidney (via the central nervous system). These afferent signals are centrally integrated and may result in increased sympathetic outflow. This sympathetic drive is directed towards the kidneys, thereby activating the RAAS and inducing increased renin secretion, sodium retention, volume retention and vasoconstriction. Central sympathetic over activity also impacts other organs and bodily structures innervated by sympathetic nerves such as the heart and the peripheral vasculature, resulting in the described adverse effects of sympathetic activation, several aspects of which also contribute to the rise in blood pressure.

The physiology therefore suggests that (i) modulation of tissue with efferent sympathetic nerves will reduce inappropriate renin release, salt retention, and reduction of renal blood flow, and that (ii) modulation of tissue with afferent sensory nerves will reduce the systemic contribution to hypertension and other disease states associated with increased central sympathetic tone through its direct effect on the posterior hypothalamus as well as the contralateral kidney. In addition to the central hypotensive effects of afferent renal denervation, a desirable reduction of central sympathetic outflow to various other sympathetically innervated organs such as the heart and the vasculature is anticipated.

B. Additional Clinical Benefits of Renal Denervation

As provided above, renal denervation is likely to be valuable in the treatment of several clinical conditions characterized by increased overall and particularly renal sympathetic activity such as hypertension, metabolic syndrome, insulin resistance, diabetes, left ventricular hypertrophy, chronic end stage renal disease, inappropriate fluid retention in heart failure, cardio-renal syndrome, and sudden death. Since the reduction of afferent neural signals contributes to the systemic reduction of sympathetic tone/drive, renal denervation might also be useful in treating other conditions associated with systemic sympathetic hyperactivity. Accordingly, renal denervation may also benefit other organs and bodily structures innervated by sympathetic nerves, including those identified in FIG. 29. For example, as previously discussed, a reduction in central sympathetic drive may reduce the insulin resistance that afflicts people with metabolic syndrome and Type II diabetics. Additionally, patients with osteoporosis are also sympathetically activated and might also benefit from the down regulation of sympathetic drive that accompanies renal denervation.

C. Achieving Intravascular Access to the Renal Artery

Figures 32A, 32B:
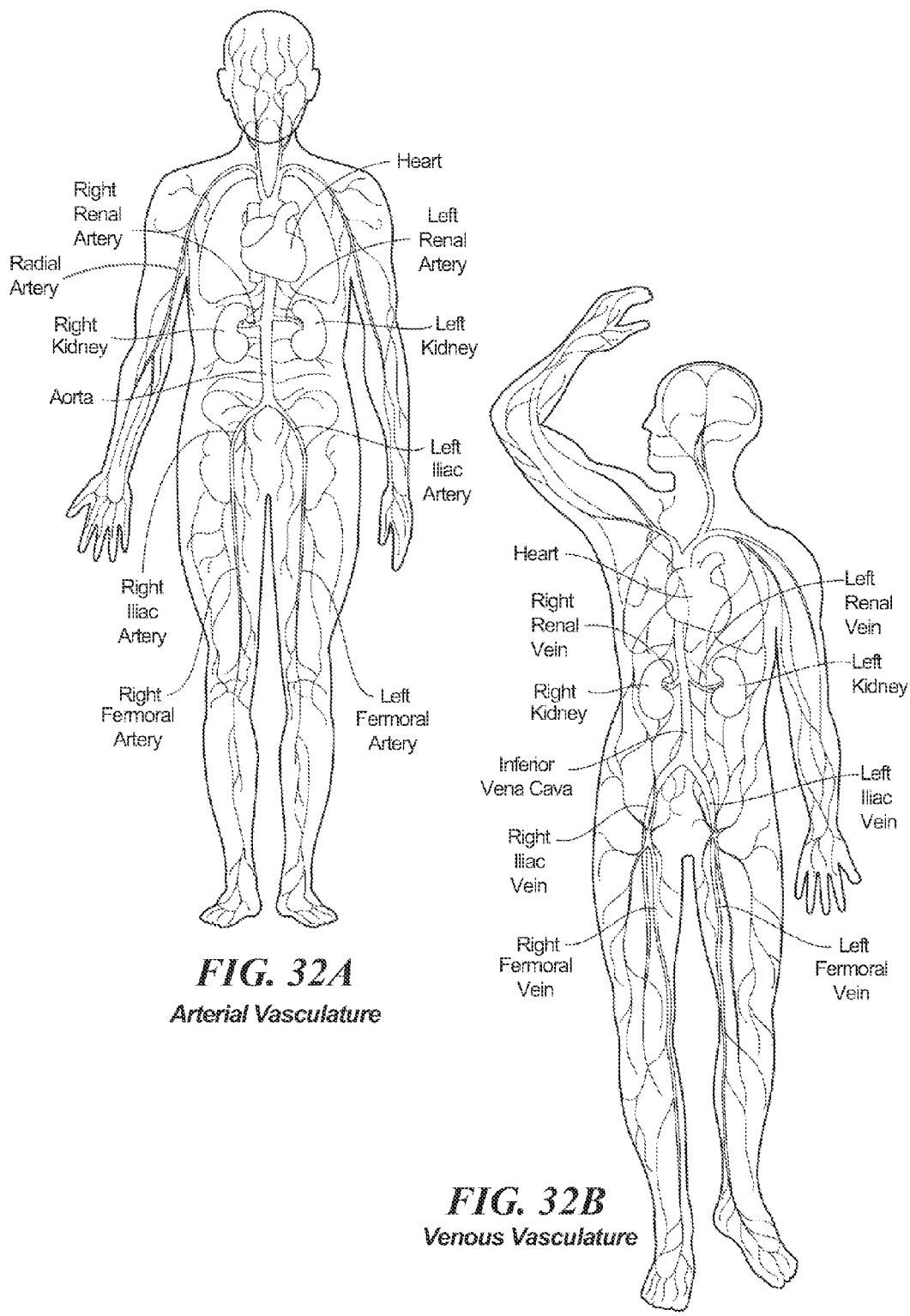
FIGS. 32A and 32B are, respectively, anatomic views of the arterial and venous vasculatures of a human.

In accordance with the present technology, neuromodulation of a left and/or right renal plexus RP, which is intimately associated with a left and/or right renal artery, may be achieved through intravascular access. As FIG. 32A shows, blood moved by contractions of the heart is conveyed from the left ventricle of the heart by the aorta. The aorta descends through the thorax and branches into the left and right renal arteries. Below the renal arteries, the aorta bifurcates at the left and right iliac arteries. The left and right iliac arteries descend, respectively, through the left and right legs and join the left and right femoral arteries.

As FIG. 32B shows, the blood collects in veins and returns to the heart, through the femoral veins into the iliac veins and into the inferior vena cava. The inferior vena cava branches into the left and right renal veins. Above the renal veins, the inferior vena cava ascends to convey blood into the right atrium of the heart. From the right atrium, the blood is pumped through the right ventricle into the lungs, where it is oxygenated. From the lungs, the oxygenated blood is conveyed into the left atrium. From the left atrium, the oxygenated blood is conveyed by the left ventricle back to the aorta.

As will be described in greater detail later, the femoral artery may be accessed and cannulated at the base of the femoral triangle just inferior to the midpoint of the inguinal ligament. A catheter may be inserted percutaneously into the femoral artery through this access site, passed through the iliac artery and aorta, and placed into either the left or right renal artery. This comprises an intravascular path that offers minimally invasive access to a respective renal artery and/or other renal blood vessels.

The wrist, upper arm, and shoulder region provide other locations for introduction of catheters into the arterial system. For example, catheterization of either the radial, brachial, or axillary artery may be utilized in select cases. Catheters introduced via these access points may be passed through the subclavian artery on the left side (or via the subclavian and brachiocephalic arteries on the right side), through the aortic arch, down the descending aorta and into the renal arteries using standard angiographic technique.

D. Properties and Characteristics of the Renal Vasculature

Since neuromodulation of a left and/or right renal plexus RP may be achieved in accordance with the present technology through intravascular access, properties and characteristics of the renal vasculature may impose constraints upon and/or inform the design of apparatus, systems, and methods for achieving such renal neuromodulation. Some of these properties and characteristics may vary across the patient population and/or within a specific patient across time, as well as in response to disease states, such as hypertension, chronic kidney disease, vascular disease, end-stage renal disease, insulin resistance, diabetes, metabolic syndrome, etc. These properties and characteristics, as explained herein, may have bearing on the efficacy of the procedure and the specific design of the intravascular device. Properties of interest may include, for example, material/mechanical, spatial, fluid dynamic/hemodynamic and/or thermodynamic properties.

As discussed previously, a catheter may be advanced percutaneously into either the left or right renal artery via a minimally invasive intravascular path. However, minimally invasive renal arterial access may be challenging, for example, because as compared to some other arteries that are routinely accessed using catheters, the renal arteries are often extremely tortuous, may be of relatively small diameter, and/or may be of relatively short length. Furthermore, renal arterial atherosclerosis is common in many patients, particularly those with cardiovascular disease. Renal arterial anatomy also may vary significantly from patient to patient, which further complicates minimally invasive access. Significant inter-patient variation may be seen, for example, in relative tortuosity, diameter, length, and/or atherosclerotic plaque burden, as well as in the take-off angle at which a renal artery branches from the aorta. Apparatus, systems and methods for achieving renal neuromodulation via intravascular access should account for these and other aspects of renal arterial anatomy and its variation across the patient population when minimally invasively accessing a renal artery.

In addition to complicating renal arterial access, specifics of the renal anatomy also complicate establishment of stable contact between neuromodulatory apparatus and a luminal surface or wall of a renal artery. When the neuromodulatory apparatus includes an energy delivery element, such as an electrode, consistent positioning and appropriate contact force applied by the energy delivery element to the vessel wall are important for predictability. However, navigation is impeded by the tight space within a renal artery, as well as tortuosity of the artery. Furthermore, establishing consistent contact is complicated by patient movement, respiration, and/or the cardiac cycle because these factors may cause significant movement of the renal artery relative to the aorta, and the cardiac cycle may transiently distend the renal artery (i.e., cause the wall of the artery to pulse.

Even after accessing a renal artery and facilitating stable contact between neuromodulatory apparatus and a luminal surface of the artery, nerves in and around the adventia of the artery should be safely modulated via the neuromodulatory apparatus. Effectively applying thermal treatment from within a renal artery is non-trivial given the potential clinical complications associated with such treatment. For example, the intima and media of the renal artery are highly vulnerable to thermal injury. As discussed in greater detail below, the intima-media thickness separating the vessel lumen from its adventitia means that target renal nerves may be multiple millimeters distant from the luminal surface of the artery. Sufficient energy should be delivered to or heat removed from the target renal nerves to modulate the target renal nerves without excessively cooling or heating the vessel wall to the extent that the wall is frozen, desiccated, or otherwise potentially affected to an undesirable extent. A potential clinical complication associated with excessive heating is thrombus formation from coagulating blood flowing through the artery. Given that this thrombus may cause a kidney infarct, thereby causing irreversible damage to the kidney, thermal treatment from within the renal artery should be applied carefully. Accordingly, the complex fluid mechanics and thermodynamic conditions present in the renal artery during treatment, particularly those that may impact heat transfer dynamics at the treatment site, may be important in applying energy (e.g., heating thermal energy) and/or removing heat from the tissue (e.g., cooling thermal conditions) from within the renal artery.

The neuromodulatory apparatus should also be configured to allow for adjustable positioning and repositioning of the energy delivery element within the renal artery since location of treatment may also impact clinical efficacy. For example, it may be tempting to apply a full circumferential treatment from within the renal artery given that the renal nerves may be spaced circumferentially around a renal artery. In some situations, full-circle lesion likely resulting from a continuous circumferential treatment may be potentially related to renal artery stenosis. Therefore, the formation of more complex lesions along a longitudinal dimension of the renal artery via the mesh structures described herein and/or repositioning of the neuromodulatory apparatus to multiple treatment locations may be desirable. It should be noted, however, that a benefit of creating a circumferential ablation may outweigh the potential of renal artery stenosis or the risk may be mitigated with certain embodiments or in certain patients and creating a circumferential ablation could be a goal. Additionally, variable positioning and repositioning of the neuromodulatory apparatus may prove to be useful in circumstances where the renal artery is particularly tortuous or where there are proximal branch vessels off the renal artery main vessel, making treatment in certain locations challenging. Manipulation of a device in a renal artery should also consider mechanical injury imposed by the device on the renal artery. Motion of a device in an artery, for example by inserting, manipulating, negotiating bends and so forth, may contribute to dissection, perforation, denuding intima, or disrupting the interior elastic lamina.

Blood flow through a renal artery may be temporarily occluded for a short time with minimal or no complications. However, occlusion for a significant amount of time should be avoided because to prevent injury to the kidney such as ischemia. It could be beneficial to avoid occlusion all together or, if occlusion is beneficial to the embodiment, to limit the duration of occlusion, for example to 2-5 minutes.

Based on the above described challenges of (1) renal artery intervention, (2) consistent and stable placement of the treatment element against the vessel wall, (3) effective application of treatment across the vessel wall, (4) positioning and potentially repositioning the treatment apparatus to allow for multiple treatment locations, and (5) avoiding or limiting duration of blood flow occlusion, various independent and dependent properties of the renal vasculature that may be of interest include, for example, (a) vessel diameter, vessel length, intima-media thickness, coefficient of friction, and tortuosity; (b) distensibility, stiffness and modulus of elasticity of the vessel wall; (c) peak systolic, end-diastolic blood flow velocity, as well as the mean systolic-diastolic peak blood flow velocity, and mean/max volumetric blood flow rate; (d) specific heat capacity of blood and/or of the vessel wall, thermal conductivity of blood and/or of the vessel wall, and/or thermal convectivity of blood flow past a vessel wall treatment site and/or radiative heat transfer; (e) renal artery motion relative to the aorta induced by respiration, patient movement, and/or blood flow pulsatility: and (f) as well as the take-off angle of a renal artery relative to the aorta. These properties will be discussed in greater detail with respect to the renal arteries. However, dependent on the apparatus, systems and methods utilized to achieve renal neuromodulation, such properties of the renal arteries, also may guide and/or constrain design characteristics.

As noted above, an apparatus positioned within a renal artery should conform to the geometry of the artery. Renal artery vessel diameter, $D_{RA}$, typically is in a range of about 2-10 mm, with most of the patient population having a $D_{RA}$ of about 4 mm to about 8 mm and an average of about 6 mm. Renal artery vessel length, $L_{RA}$, between its ostium at the aorta/renal artery juncture and its distal branchings, generally is in a range of about 5-70 mm, and a significant portion of the patient population is in a range of about 20-50 mm. Since the target renal plexus is embedded within the adventitia of the renal artery, the composite Intima-Media Thickness, IMT, (i.e., the radial outward distance from the artery's luminal surface to the adventitia containing target neural structures) also is notable and generally is in a range of about 0.5-2.5 mm, with an average of about 1.5 mm. Although a certain depth of treatment is important to reach the target neural fibers, the treatment should not be too deep (e.g., >5 mm from inner wall of the renal artery) to avoid non-target tissue and anatomical structures such as the renal vein.

An additional property of the renal artery that may be of interest is the degree of renal motion relative to the aorta, induced by respiration and/or blood flow pulsatility. A patient's kidney, which located at the distal end of the renal artery, may move as much as 4" cranially with respiratory excursion. This may impart significant motion to the renal artery connecting the aorta and the kidney, thereby requiring from the neuromodulatory apparatus a unique balance of stiffness and flexibility to maintain contact between the thermal treatment element and the vessel wall during cycles of respiration. Furthermore, the take-off angle between the renal artery and the aorta may vary significantly between patients, and also may vary dynamically within a patient, e.g., due to kidney motion. The take-off angle generally may be in a range of about 30°-135°.

X. Conclusion

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments.

From the foregoing, it will be appreciated that specific embodiments of the technology have been described herein for purposes of illustration, but well-known structures and functions have not been shown or described in detail to avoid unnecessarily obscuring the description of the embodiments of the technology. Where the context permits, singular or plural terms may also include the plural or singular term, respectively.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A catheter for treatment of a human patient via renal denervation, the catheter apparatus comprising:
   a handle assembly;
   a tubular elongate shaft extending from a distal end to a proximal end slidably disposed within the handle assembly;
   an elongate control member slidably disposed within the tubular elongate shaft and having—
      a proximal end protruding from the elongate shaft proximal end and fixedly attached within the handle assembly; and
      a distal region protruding from the elongate shaft distal end and extending along a central axis; and
   a helical support structure having—
      a plurality of energy delivery elements carried thereon including at least a first energy delivery element and a second energy delivery element axially and radially spaced from one another about the control member;
      a delivery state and a deployed state;
      a proximal end coupled to the elongate shaft distal end; and
      an elongate form wrapped about the control member distal region; and
      a distal end coupled to the control member distal region such that the support structure distal end remains at a fixed distance from the handle assembly;
   wherein—
   proximal movement of the elongate shaft relative to the control member places the helical support structure in the delivery state; and
   distal movement of the elongate shaft relative to the control member places the helical support structure in the deployed state.

2. The catheter of claim 1 wherein the support structure comprises an elongate tube.

3. The catheter of claim 1 wherein the elongate shaft proximal end is coupled to an actuator cooperatively associated with the handle assembly such that manual operation of the actuator effects axial translation of the elongate shaft relative to the control member.

4. The catheter of claim 3 wherein the actuator is a slider-in-groove type, a pivot type, or a gear type.

5. The catheter of claim 1 wherein the control member comprises a tubular member defining a central lumen, and the central lumen is configured to receive a guide wire.

6. The catheter of claim 1 wherein the control member comprises a stylet.

* * * * *